United States Patent [19]

Aquino et al.

[11] Patent Number: 5,859,007
[45] Date of Patent: Jan. 12, 1999

[54] CCK OR GASTRIN MODULATING BENZO [B][1,4] DIAZEPINES DERIVATIVES

[75] Inventors: Christopher Joseph Aquino, Long Beach, Wash.; Marcus Brackeen, Durham, N.C.; Milana Dezube, Chapel Hill, N.C.; Brad Richard Henke, Cary, N.C.; Gavin Charles Hirst, Marlboro, Mass.; Peter Walter Jeffs, Chapel Hill, N.C.; Tanya Momtahen, Raleigh, N.C.; Elizabeth Ellen Sugg, Durham, N.C.; Edward Martin Suh, Chapel Hill, N.C.; Timothy Mark Willson, Durham, N.C.

[73] Assignee: Glaxo Wellcome Inc., Research Triangle Park, N.C.

[21] Appl. No.: 722,051

[22] PCT Filed: Apr. 13, 1995

[86] PCT No.: PCT/EP95/01336

§ 371 Date: Nov. 14, 1996

§ 102(e) Date: Nov. 14, 1996

[87] PCT Pub. No.: WO95/28391

PCT Pub. Date: Oct. 26, 1995

[30] Foreign Application Priority Data

Apr. 15, 1994 [GB] United Kingdom ............ 9407467
Oct. 14, 1994 [GB] United Kingdom ............ 9420700

[51] Int. Cl.$^6$ .................... A01N 43/62; C07D 243/12
[52] U.S. Cl. ............................ 514/221; 540/518
[58] Field of Search ................ 540/518; 514/221

[56] References Cited

U.S. PATENT DOCUMENTS

| | | | |
|---|---|---|---|
| 4,001,408 | 1/1977 | Rossi ................. | 424/244 |
| 4,988,692 | 1/1991 | Gasc et al. ........... | 514/221 |
| 5,206,234 | 4/1993 | Bock et al. .......... | 514/213 |
| 5,585,376 | 12/1996 | Finch et al. ......... | 514/221 |
| 5,637,697 | 6/1997 | Finch et al. ......... | 540/518 |
| 5,641,775 | 6/1997 | Finch et al. ......... | 514/221 |

FOREIGN PATENT DOCUMENTS

| | | | |
|---|---|---|---|
| 0284256 | 9/1988 | European Pat. Off. | A61K 31/55 |
| A0284256 | 9/1988 | European Pat. Off. | |
| 0376849 | 7/1990 | European Pat. Off. | C07D 243/12 |
| A0376849 | 7/1990 | European Pat. Off. | |
| WO 93/14074 | 7/1993 | WIPO | |
| A9424149 | 10/1994 | WIPO | |
| 94/25445 | 11/1994 | WIPO | |
| 95/03285 | 2/1995 | WIPO | |
| WO 95/03284 | 2/1995 | WIPO | |
| 95/28419 | 10/1995 | WIPO | |

*Primary Examiner*—Mukund J. Shah
*Assistant Examiner*—Tamthom T. Ngo
*Attorney, Agent, or Firm*—Gardiner F. H. Smith; Shah R. Makujina; Robert H. Brink

[57] ABSTRACT

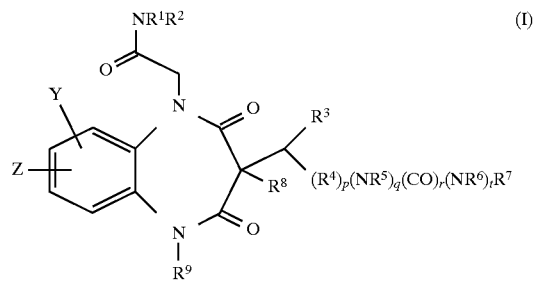

Benzo[b][1,4]diazepine compounds of formula (I), where $R^1$ is selected from $C_1$–$C_6$alkyl, $C_3$–$C_6$cycloalkyl, phenyl, or substituted phenyl; $R^2$ is selected from $C_3$–$C_6$alkyl, $C_3$–$C_6$cycloalkyl, $C_3$–$C_6$alkenyl, benzyl, phenyl$C_1$–$C_3$alkyl of substituted phenyl; or $NR^1R^2$ together form 1,2,3,4-tetrahydroquinoline or benzazepine, mono-, di-, or trisubstituted independently with $C_{1-6}$alkyl $C_{1-6}$alkoxy or halogen substituents; p is an integer 0 or 1; q is an integer 0 or 1; r is an integer 0 or 1; t is an integer 0 or 1, provided that when r is 0 then t is 0; $R^3$, $R^5$, and $R^6$ are independently hydrogen or $C_{1-6}$alkyl; $R^4$ is $C_{1-6}$alkyl or $C_{1-6}$alkenyl; $R^7$ is selected from the group consisting of hydrogen, $C_{1-6}$alkyl, $C_{1-6}$cycloalkyl, $C_{1-6}$alkenyl, phenyl, substituted phenyl, napthyl, heteroaryl, substituted heteroaryl, bicycloheteroaryl or substituted bicycloheteroaryl; or $NR^6R^7$ together form a saturated 5,6, or 7 membered ring optionally interrupted by 1,2,3 or 4 N, S or O heteroatoms, with the proviso that any two O or S atoms are not bonded to each other, m is an integer selected from the group of 0, 1, 2, 3 or 4; $R^8$ and $R^9$ are selected from a variety of substituents; Z is hydrogen or halogen; novel intermediates, a pharmaceutical composition for treating obesity, gall bladder stasis, disorders of pancreatic secretion, methods for such treatment and processes for preparing compounds of formula (I).

16 Claims, No Drawings

CCK OR GASTRIN MODULATING BENZO [B][1,4] DIAZEPINES DERIVATIVES

BACKGROUND OF THE INVENTION

This invention relates to benzo[b][1,4]diazepine derivatives, to processes for their preparation, to pharmaceutical compositions containing them and to their use in medicine. More particularly, it relates to compounds which exhibit agonist activity for CCK-A receptors thereby enabling them to modulate the hormones gastrin and cholecystokinin in mammals.

Cholecystokinin (CCK) is a peptide found in the gastrointestinal tract and the central nervous system. see A. J. Prange et al., *Ann. Reports Med. Chem.* 17, 31, 33 (1982), J. A. Williams, i Biomed Res. 3, 107 (1982) and V. Mutt, *Gastrointestinal Hormones*, G. B. J. Green, Ed., Raven Press, N.Y. CCK has been implicated inter alia as a physiological satiety hormone involved in appetite regulation, see Della-Ferra et al, *Science,* 206, 471 (1979), Saito et al., *Nature,* 289, 599, (1981), G. P. Smith, *Eating and its Disorders*, A. J. Stunkard and E. Stellar, Eds, Raven Press, New York, 67 (1984), as a regulator of gallbladder contraction and pancreatic enzyme secretion, an inhibitor of gastric emptying, and as a neurotransmitter, see A. J. Prange, supra, J. A. Williams, *Biomed Res.,* 3, 107 (1982), J. E. Morley, *Life Sci.* 30, 479, (1982). Gastrin is a peptide involved in gastric acid and pepsin secretion in the stomach, see L. Sandvik, et al., *American J. Physiology,* 260, G925 (1991), C. W. Lin, et al., *American J. Physiology,* 262, G1113, (1992). CCK and gastrin share structural homology in their C-terminal tetrapeptide: Trp-Met-Asp-Phe.

Two subtypes of CCK receptors have been identified, designated as CCK-A and CCK-B, and both have been found in the periphery and central nervous systems. It has recently been reported that CCK-B receptors are similar to the gastrin receptor, see Pisegna, J. R., de Weerth, A., Huppi, K., Wank, S. A., *Biochem. Biophys. Res. Commun.* 189, 296–303 (1992). CCK-A receptors are located predominantly in peripheral tissues including the pancreas, gallbladder, ileum, pyloric sphincter and vagal afferent nerve fibers; CCK-A receptors are found to a lesser extent in the brain, see T. H Moran, et al., *Brain Res.,* 362, 175–179 (1986), D. R. Hill, et al., *Brain Res,* 4545, 101, (1988), D. R. Hill, et al., *Neurosci Lett.,* 89, 133, (1988), R. W. Barret, et al., *Mol. Pharmacol.,* 36, 285, (1989), D. R. Hill, et al., *J. Neurosci,* 10, 1070 (1990), V. Dauge et al., *Pharmacol Biochem Behac.,* 33, 637, (1989), while CCK-B receptors are found predominantly in the brain, see V. J. Lotti and R. S. L Chang, *Proc. Natl. Acad. Sci.* U.S.A., 83, 4923 (1986), J. N. Crawley, *Trends Pharm. Sci.,* 88, 232, (1991).

The literature in the CCK area contains extensive discussion surrounding CCK antagonist activity relating to the increase of food intake and treating oncologic disorders, in particular through the use of 1,4- and 1,5-benzodiazepines, see B. E. Evans, *Drugs of the Future*, 14, 971 (1989), M. A. Silverman, et al., *Am. J. Gastroenterol*, 82, 703 (1987), EPO 0538 945, published Apr. 28, 1993, EPO 0 523 845, published Jan. 20, 1993, EPO 0284 256, published 28 Sep., 1988, and also relating to the regulation of anxiety, arousal, neuroleptic agents, and opioid-induced analgesia, see Lotti, supra, Crawley, supra, Singh, L., et al, *Proc. Natl. Acad. Sci.* U.S.A., 88, 1130 (1991).

On the other hand, CCK agonist activity has been linked to inhibition of food intake in animals and thus weight loss, see Della-Fera, et al, supra, K. E. Asin, et al, *Intl. Conference on Obesity*, abstract pp.40 (1990). It has been suggested that CCK acts in the periphery through vagal fibers and not directly on the brain to produce satiety, see Smith, G. P. and Cushin, B. J., *Neuroscience Abstr.,* 4, 180 (1978), Smith, G. P., Jerome, C., Cushin, B. J., Eterno, R., and Simansky, K. J., *Science,* 212, 687–689, (1981). Compounds having CCK agonist activity have been reported to include peptide analogues, see U.S. Pat. No. 4,490,364, PCT WO 91/19733, published 26 Dec. 1991, K. Shiosaki et al., *J. Med. Chem.,* 33, 2950 (1990).

The compounds of the present invention have been found to have CCK-A agonist activity, and therefore may be useful in part for inhibiting appetite, for inducing long-term weight loss in overweight patients and improving the cardiovascular and non-insulin dependent diabetes problems associated with these overweight conditions, and for treating obesity, gall bladder stasis and disorders of pancreatic secretion.

CCK has been shown to inhibit gastric emptying in humans and is thus useful for treatment of diabetes, particularly early noninsulin-dependent diabetes, through maintenance of the following glucose metabolic indicators at or near normal levels: blood glucose, C-peptide, insulin levels at fasting and during oral glucose tolerance tests, hemoglobin A1C, insulin resistance, GIP levels and CCK levels, see U.S. Pat. No. 5,187,154, which is incorporated herein by reference. The CCK-A agonist compounds of the present invention are therefore useful for treatment of diabetes in humans through stabilization of these glucose metabolic indicators.

DETAILED DESCRIPTION OF THE INVENTION

The present invention thus provides benzo[b][1,4] diazepine of the formula (I):

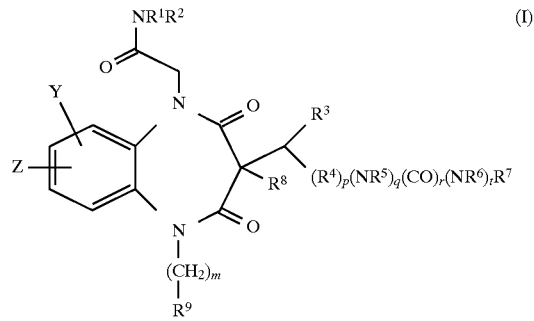

wherein:

$R^1$ is selected from the group consisting of $C_1$–$C_6$ alkyl, $C_3$–$C_7$cycloalkyl, phenyl, or phenyl mono-, di-, or trisubstituted independently with hydroxy, $C_{1-6}$alkyl, $C_{1-6}$alkyl substituted with 1–8 fluorine atoms, $C_{1-6}$alkoxy, $C_{1-6}$alkoxy substituted with 1–8 fluorine atoms, carboxy$C_{1-6}$alkoxy, halo, amino, mono- or di($C_{1-6}$alkyl)amino, —COO($C_{1-4}$alkyl), $C_{1-4}$alkylthio, carboxymethylthio, trifluoromethylsulfonylamino, phenyl$C_{1-6}$alkoxy;

$R^2$ is selected from the group consisting of $C_3$–$C_6$ alkyl, $C_3$–$C_6$cycloalkyl, $C_3$–$C_6$alkenyl, benzyl, phenyl$C_1$–$C_3$alkyl, phenyl mono-, di-, or trisubstituted independently in the ortho or para positions with hydroxy, $C_{1-4}$alkyl, $C_{1-6}$alkoxy, cyano, benzyloxy, pyrrolidino, morpholino, carboxy$C_{1-6}$alkoxy, halo, amino, mono- or di($C_{1-6}$alkyl)amino, —COO($C_{1-4}$alkyl), $C_{1-4}$alkylthio, carboxymethylthio, trifluoromethylsulfonylamino, phenyl$C_{1-6}$alkoxy, $C_{1-4}$alkylsulfonyl or $C_{1-4}$alkylsulfinyl substituents or partially aromatic bicycloheteroaryl; or NR₁R² together form 1,2,3,4-tetrahydroquinoline or benzazepine, mono-, di-, or trisubstituted independently with $C_{1-6}$alkyl, $C_{1-6}$alkoxy or halogen substituents;

p is an integer 0 or 1;

q is an integer 0 or 1;

r is an integer 0 or 1;

t is an integer 0 or 1, provided that when r is 0 then t is 0;

$R^3$, $R^5$ and $R^6$ are independently hydrogen or $C_{1-6}$alkyl;

$R^4$ is $C_{1-6}$alkylene or $C_{2-6}$alkenylene;

$R^7$ is selected from the group consisting of hydrogen, $C_{1-6}$alkyl, $C_{1-6}$cycloalkyl, phenyl, phenyl mono-, di-, or trisubstituted independently with $C_{1-4}$alkyl, hydroxy, $C_{1-6}$alkoxy, halogen, amino, mono- or di($C_{1-6}$alkyl)amino, nitro, carboxy, —COO($C_{1-4}$alkyl), carboxy$C_{1-6}$alkoxy, carboxy$C_{1-4}$alkyl, carboxymethylthio, heteroaryl, mono- or di($C_{1-4}$alkyl)aminoalkyl, or trifluoromethyl, trifluoromethoxy, $C_{1-4}$alkylthio, —SO$_v$($C_{1-4}$alkyl), —SO$_v$NH($C_{1-4}$alkyl), —SO$_v$CF$_3$ or —SO$_v$C$_6$H$_5$, —(CH$_2$)$_v$NO$_2$, —(CH$_2$)$_v$CN, —(CH$_2$)$_v$COOH, —(CH$_2$)$_v$COO($C_{1-4}$alkyl), —(CH$_2$)$_v$SCH$_3$, —(CH$_2$)$_v$SOCH$_3$, —(CH$_2$)$_v$SO$_2$CH$_3$, —(CH$_2$)$_v$CONH$_2$, —SCH$_2$COOH, —CONH(SO$_2$CH$_3$), —CONH(SO$_2$CF$_3$), —(CH$_2$)$_v$N($C_{1-4}$alkyl)$_2$, —(CH$_2$)$_v$NH(SO$_2$CF$_3$), —(CH$_2$)$_v$N(SO$_2$CF$_3$)($C_{1-4}$alkyl), —(CH$_2$)$_v$SO$_2$NHCO($C_{1-4}$alkyl), —(CH$_2$)$_v$SO$_2$N($C_{1-4}$alkyl)CO($C_{1-4}$alkyl), —(CH$_2$)$_v$CONHSO$_2$($C_{1-4}$alkyl), —(CH$_2$)$_v$CON($C_{1-4}$alkyl)SO$_2$($C_{1-4}$alkyl), —(CH$_2$)$_v$NHR$^{10}$ or —(CH$_2$)$_v$OR$^{11}$ substituents, benzyloxy, heteroaryl, heteroaryl mono- or disubstituted independently with halogen, $C_{1-6}$alkyl, hydroxy, nitro, cyano, carboxy, $C_{1-6}$alkoxy, benzyloxy, —COO($C_{1-4}$alkyl), amino, mono- or di($C_{1-6}$alkyl)amino, phenyl or benzyl substituents, napthyl, bicycloheteroaryl, bicycloheteroaryl substituted independently with hydroxy, halogen, carboxyalkyl, acetyl, phenyl, heteroaryl, $C_{1-4}$alkoxy or cyano substituents, or partially aromatic bicycloheteroaryl, provided that when $R^7$ is oxadiazole then $R^8$ is not hydrogen, further provided when p is 1, q is 0, r is 0 and t is 0 then bicycloheteroaryl and substituted bicycloheteroaryl are not 2-indolyl or substituted 2-indolyl, still further provided that when p is 0, q is 1, r is 1 and t is 0 then indolyl and substituted indolyl are bound at the 2 position, even still further provided that when n, p and q are 1 and r is 0 then $R^7$ is not indolyl;

$R^{10}$ is hydrogen, $C_{1-4}$ alkyl, benzyl, —SO$_3$H, —SO$_2$CH$_3$, —SO$_2$CF$_3$, —SO$_2$C$_6$H$_5$, —COO(C$_4$ H$_9$) or —COO(CH$_2$C$_6$H$_5$);

$R^{11}$ is hydrogen, $C_{1-6}$alkyl, $C_{3-6}$cycloalkyl, —CH$_2$C$_6$H$_5$, —CH$_2$COOH, —CH$_2$CONH$_2$, —CH$_2$CONH($C_{1-4}$alkyl), —CH$_2$CON($C_{1-4}$alkyl)$_2$ or

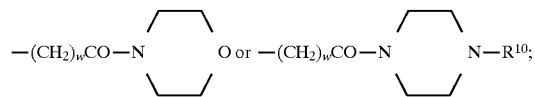

v is an integer selected from the group of 0, 1 or 2; or

NR⁶R⁷ together form a saturated 5, 6, or 7 membered ring optionally interrupted by 1,2,3 or 4N, S or O heteroatoms, with the proviso that any two O or S atoms are not bonded to each other;

w is an integer selected from the group of 0, 1 or 2;

$R^8$ is selected from the group consisting of hydrogen, $C_{1-6}$alkyl, $C_{1-6}$alkoxy, $C_{1-6}$alkoxyC$_{1-6}$alkyl, carboxy$C_{1-6}$alkyl, halogen, amino, cyano, aminoC$_1$–C$_6$ alkyl, mono- or di($C_{1-6}$alkyl)amino, C$_1$–C$_6$alkylamino (C$_1$–C$_6$ alkyl), mono- or di($C_{1-6}$alkyl)aminoamino, $C_{1-6}$alkylmorpholino, $C_{1-6}$alkylpiperidino, $C_{1-6}$alkyletetrahydropyrrolyl, $C_{1-6}$alkylthio, $C_{1-6}$alkylthioC$_{1-6}$alkyl or $C_{1-4}$alkoxycarbonylC$_{1-4}$alkyl, provided that when $R^4$ is ethyl then $R^8$ is not ethyl;

m is an integer selected from the group of 0, 1, 2, 3 or 4;

$R^9$ is selected from the group consisting of hydrogen, $C_1$–$C_6$ alkyl, phenyl or phenyl mono- or disubstituted independently with halogen substituents, or a heteroaryl selected from the group consisting of pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazolyl, pyrrolidinyl, piperidinyl, morpholinyl or thiomorpholinyl, where such heteroaryl may be mono- or di-ortho-substituted independently with halogen, $C_{1-4}$alkyl, nitro, carboxyl, $C_{1-4}$alkoxycarbonyl, $C_{1-4}$alkoxy, $C_{1-4}$alkylthio, amino or mono- or di($C_{1-6}$alkyl)amino substituents;

Y and Z are independently hydrogen or halogen;

or a pharmaceutically acceptable acid-addition or base-addition salt thereof;

heteroaryl in more detail is a five or six membered aromatic ring interrupted with 1, 2, 3 or 4N, O or S heteroatoms, with the proviso that any two O or S heteroatoms are not bonded to each other;

bicycloheteroaryl in more detail is a 9 or 10 membered bicyclo aromatic ring interrupted by 1, 2, 3 or 4N, O or S heteroatoms, with the proviso that any two O or S heteroatoms are not bonded to each other, with the further proviso that bicycloheteroaryl is not 2-quinolinyl;

partially aromatic bicycloheteroaryl in more detail is bicycloheterarylaryl which contains one or more saturated carbon bonds.

When $R^1$ is $C_{3-6}$ alkyl group examples of suitable groups include propyl, isopropyl or t-butyl.

When $R^2$ is phenyl optionally substituted by 1, 2 or 3 groups, examples of suitable $R^2$ groups include phenyl optionally substituted by fluorine, methoxy, methyl, trifluoromethyl, trifluoromethoxy or methylenedioxy. Conveniently there is a single substituent and it is in the 4 position.

When $R^2$ is $C_{3-6}$ cycloalkyl examples of suitable groups include cyclopropyl, cyclobutyl, cyclopentyl or cyclohexyl.

Examples of suitable $R^3$ groups include hydrogen or $C_{1-3}$ alkyl e.g. methyl.

When $R^4$ is an alkylene group examples of suitable groups include methylene, ethylene or propylene.

When $R^4$ is an alkenylene group then it is conveniently ethenylene.

Examples of suitable groups $R^5$ and $R^6$ include hydrogen or $C_{1-3}$ alkyl e.g. methyl.

Examples of suitable groups $R^8$ include hydrogen, $C_{1-3}$ alkyl e.g. methyl or ethyl, $C_{1-3}$ alkoxy e.g. methoxy, $C_{1-3}$ alkoxy-$C_{1-3}$ alkyl e.g. methoxymethyl or carboxymethyl.

Examples of suitable $R^9$ groups include phenyl (optionally substituted by chlorine or fluorine), pyridyl e.g. a 2, 3 or 4 pyridyl group, pyrimidinyl e.g. 2-pyrimidinyl or 5-pyridmidinyl or thiophenyl e.g. 2 or 3 thiophenyl.

When X and Y are halogen these are conveniently fluorine and are preferably at the 7 and/or 8 positions.

When $R^7$ is an optionally substituted phenyl group examples of such groups include phenyl optionally substituted by carboxy, $C_{1-4}$ alkoyxcarbonyl e.g. ethoxycarbonyl or t-butoxycarbonyl, amino or fluorine. When $R^7$ is a napthyl group this may ba a 1 or 2-napthyl group.

When $R^7$ is a heteroaryl group this may be for example a five or six membered ring containing from 1 to 3 heteroatoms selected from O or N. Examples of such groups include oxadiazolyl e.g. 5-phenyl-1,2,4 oxadiazolyl, imidazolyl e.g. 1-phenylimidazolyl-2yl or pyrazolyl e.g. 5-methyl-2H pyrazol-3-yl and its N-benzyl derivative.

When $R^7$ is a bicycloheteroaryl group it may be for example a 6,5 or 6,6 bicyclic system containing 1 to 3 heteroatoms selected from O, N or S. Examples of such groups include indolyl e.g. 2-indolyl or 3-indolyl or N-methylindolyl, indazolyl e.g. indazol-3-yl which may optionally be substituted in the benzene-ring e.g. by fluorine and/or substituted at N-1 by ($C_{1-3}$ alkyl e.g. methyl or benzyl or acetyl) or tetrahydro indazol-3yl, benzofuranyl, benzothienyl, benzoisoxazolyl, benzoimidazolyl, pyrazolopyridinyl or isoxazolopyridinyl.

Conveniently the group $R^1$ is phenyl optionally substituted by a single group selected from fluorine, methoxy, methyl, trifluormethyl, trifluoromethoxy or methylemethoxy and preferably this is at the 4 position. More preferably $R^1$ is phenyl or more especially methoxyphenyl.

Conveniently the group $R^2$ is a $C_{3-6}$ alkyl or $C_{3-6}$ cycloalkyl group and more preferably is isopropyl.

For the group $R^3$ this is conveniently methyl or more preferably hydrogen.

For the group $(R^4)p$ when p is 1 $R^4$ is conveniently methylene, ethylene or ethenylene but more preferably p is zero.

For the groups $R^5$ and $R^6$ these conveniently may be methyl but are preferably hydrogen.

For the group $R^8$ this is conveniently hydrogen, methyl, methoxy, methoxymethyl or carboxymethyl. More preferably $R^8$ is hydrogen, methyl or methoxy.

Conveniently the group $R^9$ is phenyl (optionally substituted by chlorine or fluorine), pyridyl, pyrimidinyl or thienyl. More preferably $R^9$ is phenyl or pyridyl e.g. 3-pyridyl.

Conveniently the group $R^7$ is phenyl (optionally substituted by $C_{1-4}$ alkoxycarbonyl, carboxy, amino or fluorine), naphthyl, a 5 or 6 membered heteroaryl ring containing 1 or 3 heteroatoms selected from O or N or a 6,5 or 6,6 bicycloheterocyclic group containing from 1 to 3 heteroatoms selected from O, N or S, or benzyloxy.

X and Y are conveniently hydrogen or fluorine.

A preferred class of compounds of formula (I) are those wherein r and t are 1 and q is zero. Within this class $R^3$ and $R^6$ are preferably hydrogen and $R^8$ is hydrogen, methyl, ethyl, methoxy, methoxymethyl or carboxymethyl.

A further preferred class of compounds of formula (I) are those wherein q, r and t are zero.

A preferred group of compounds of formula (I) include these wherein $R^1$ is phenyl or 4 methoxyphenyl, $R^2$ is isopropyl, $R^3$ is hydrogen, p and q are zero, $R^6$ is hydrogen, $R^8$ is hydrogen, methyl or methoxy, $R^7$ is phenyl optionally substituted by $C_{1-4}$ alkoxycarbonyl, carboxy, amino or fluorine, $R^9$ is phenyl (optionally substituted by fluorine or chlorine), or pyridyl and X and Y are hydrogen.

A further preferred group of compounds of formula (I) include those wherein q, r and t are zero, $R^1$ is phenyl optionally substituted by methoxy, methyl, fluoro, trifluoromethyl, trifluoromethoxy or methylenedioxy, $R^2$ is $C_{3-6}$ alkyl or $C_{3-6}$ cycloalkyl, $R^3$ is hydrogen, $R^4$ is methylene, ethylene or ethenylene, $R^7$ is phenyl, a 5 or 6 membered heteroaryl group containing from 1 to 3 heteroatoms selected from O or N or a 6,6 or 6,5 bicycloheteraryl group containing from 1 to 3 heteroatoms selected from O, S or N, $R^8$ is hydrogen, methyl or methoxy, $R^9$ is phenyl (optionally substituted by fluorine), pyridyl or thienyl and X and Y are independently hydrogen or fluorine at the 7 or 8 positions. Within this group particular preferred compounds are those wherein $R^1$ is phenyl or 4-methoxyphenyl, $R^2$ is isopropyl, p is zero, $R^9$ is phenyl or pyridyl. More particularly $R^9$ is 3-pyridyl and $R^7$ is indazolyl e.g. indazol-3-yl. Particular groups of compounds of the formula (I) are the following:

1. p is 0.
2. p is 0;

q is 0;

r is 1;

t is 1;

$R^7$ is phenyl or phenyl substituted with carboxy, —COO($C_{1-4}$alkyl), amino or halogen substituents.
3. p is 0;

q is 0;

r is 0;

t is 0;

$R^7$ is napthyl, bicycloheteroaryl or bicycloheteroaryl substituted with $C_{1-6}$alkyl, phenyl or benzyl substituents.
4. $R^1$ is propyl or isopropyl;

$R^2$ is selected from the group consisting of phenyl optionally substituted in the ortho or para positions with $C_{1-6}$alkoxy or amino substituents.
5. $R^1$ is propyl or isopropyl;

$R^2$ is selected from the group consisting of phenyl optionally substituted in the ortho or para positions with $C_{1-6}$alkoxy or amino substituents;

p is an integer 0 or 1;

q is an integer 0 or 1;

r is an integer 0 or 1;

t is an integer 0 or 1, provided that when r is 0 then t is 0;

$R^3$, $R^5$ and $R^6$ are independently hydrogen or $C_{1-3}$alkyl;

$R^4$ is $C_{1-3}$alkylene or $C_{1-3}$alkenylene;

$R^7$ is selected from the group consisting of hydrogen, $C_{1-3}$alkyl, $C_{1-3}$alkenyl, phenyl, phenyl substituted with halogen, amino, carboxy or —COO($C_{1-4}$alkyl) substituents, heteroaryl, heteroaryl substituted with phenyl or benzyl substituents, napthyl, bicycloheteroaryl or bicycloheteroaryl substituted with $C_{1-6}$alkyl, phenyl or benzyl substituents;

$R^8$ is selected from the group consisting of hydrogen, $C_{1-3}$alkyl, $C_{1-3}$alkoxy, $C_{1-3}$alkoxy$C_{1-3}$alkyl or carboxy$C_{1-3}$alkyl;

m is 0 or 1;

$R^9$ is selected from the group consisting of hydrogen, $C_1$–$C_3$alkyl or phenyl, indolyl or indazolyl;

Z is hydrogen.
6. $R^1$ is $C_1$–$C_6$ alkyl;

$R^2$ is selected from the group consisting of phenyl optionally substituted in the ortho or para positions with $C_{1-6}$alkoxy or amino substituents;

p is 1;

q is integer 0;

r is 0;

t is 0;

$R^3$, $R^5$ and $R^6$ are hydrogen;
$R^4$ is methylene;
$R^7$ is bicycloheteroaryl or substituted bicycloheteraryl;
$R^8$ is selected from the group consisting of hydrogen, or $C_{1-3}$alkoxy;
$R^9$ is selected from the group consisting of pyridinyl or pyrimidinyl;
Z is hydrogen.
7. $R^1$ is $C_1$–$C_6$ alkyl;
$R^2$ is selected from the group consisting of phenyl optionally substituted in the ortho or para positions with $C_{1-6}$alkoxy or amino substituents;
p is 0;
q is 0;
r is 0;
t is 0;
$R^3$ is hydrogen;
$R^7$ is indolyl or indazolyl;
$R^8$ is selected from the group consisting of hydrogen, or $C_{1-3}$alkoxy;
$R^9$ is selected from the group consisting of phenyl, pyridinyl or pyrimidinyl;
Z is hydrogen.
8. $R^9$ is phenyl or pyridinyl.
9. $R^7$ is indolyl or indazolyl.

A particularly preferred compound of the invention is 2-[3-(1H-indazol-3-ylmethyl)-2,4-dioxo-5-pyridin-3-yl-2,3,4,5-tetrahydrobenzo(b)[1,4]diazepin-1-yl]-N-isopropyl-N-(4-methoxyphenyl)acetamide and physiologically acceptable salts and enantiomers thereof.

Further preferred compounds of the invention include compounds selected from 2-[3-(1H-Indazol-3-yl)-3-methyl-2,4-dioxo-5-pyridin-3-yl-2,3,4,5-tetrahydrobenzo[b][1,4]diazepin-1-yl]-N-isopropyl-N-(4-methoxyphenyl) acetamide;

N-Isopropyl-2(3 methoxy-2,4-dioxo-5-phenyl-3-phenylcarbamoyl-methyl-2,3,4,5 tetrahydro-benzo[b][1,4]diazepinyl)-N-methoxy-phenyl acetamide;

2-[3-(1H-Indazol-3-yl-methyl)-3-methoxy-2,4-dioxo-5-pyridin-3-yl-2,3,4,5 tetrahydrobenzo[b][1,4]-diazepin-1-yl]-N-isopropyl-N(4-methoxy phenyl)acetamide;

N-Isopropyl-N(4-methoxyphenyl)-2-(3-methyl-2,4-dioxo-5-phenyl 3-phenylcarbamoylmethyl-2,3,4,5 tetrahydro-benzo(b)[1,4]-diazepin-1-yl)acetamide and physiologically acceptable salts and enantiomers thereof.

Suitable pharmaceutically acceptable salts of the compounds of formula (I) include acid addition salts formed with acids, e.g. hydrochlorides, hydrobromides, sulfates, alkyl- or arylsulfonates (methanesulfonates or p-toluenesulfonates), phosphates, acetates, citrates, succinates, lactates, tartrates, fumarates, and maleates; and base salts such as alkali metal salts e.g. sodium salts. The solvates may, for example, be hydrates.

Other salts which are not pharmaceutically acceptable may be useful in the preparation of compounds of formula (I) and these form a further aspect of the invention.

It is to be understood that the present invention encompasses the individual enantiomers of the compounds represented by formula (I) above as well as wholly or partially racemic mixtures thereof. The present invention also covers the individual enantiomers of the compounds represented by formula (I) above as mixtures with diastereoisomers thereof in which one or more of the two stereocenters is inverted.

Also part of the present invention are intermediates used in the various processes of the invention. Examples include intermediates of formula (II):

GENERAL CHEMISTRY PROCEDURES

Compounds of general formula (I) may be prepared by methods known in the art of organic synthesis, as shown in part by the following schemes 1–5. For any of these processes and schemes, it may be necessary and/or desirable to protect sensitive or reactive groups. Protecting groups are employed according to standard methods of organic synthesis (T. W. Green and P. G. M. Watts (1991) *Protecting Groups in Organic Synthesis*, John Wiley & Sons). These groups are removed at a convenient stage of synthesis using methods known from the art. Thus, for example, amino groups may be protected by a group selected from aralkyl (e.g. benzyl), acyl, or sulfonyl, e.g. allylsulfonyl, phthalimide, or tosyl; subsequent removal of the protecting group being effected when desired by hydrolysis or hydrogenolysis as appropriate using standard conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl. e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups may be removed by hydrolysis under acidic or basic conditions. Aralkyl groups such as triphenylmethyl may similarly be removed by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride.

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); mL (microliters); psi (pounds per square inch); M (molar); mM (millimolar); i. v. (intravenous); Hz (Hertz); MHz (megahertz); mol (moles); RT (room temperature); min (minutes); h (hours); mp. (melting point); TLC (thin layer chromatography); HPLC (high pressure liquid chromatography); $T_r$ (retention time); RP (reverse phase); MeOH (methanol); TFA (trifluoroacetic acid); THF (tetrahydrofuran); DMSO (dimethylsulfoxide); EtOAc (ethyl acetate); DCM (dichloromethane); DMF (dimethylformamide); $Et_3N$ (triethylamine); 1,1-carbonyldiimidazole (CDI); isobutyl-chloroformate (iBuCF); N-hydroxysuccinimide (HOSu); N-hydroxybenztriazole (HOBT); ethylcarbodiimide hydrochloride (EDC); bis(2-oxo-3-oxazolidinyl) phosphinic chloride (BOP); tert-butyloxycarbonyl (BOC); dicyclohexylcarbodiimide (DCC); benzyloxycarbonyl (Cbz); $NaHCO_3$ (saturated aqueous sodium bicarbonate). All references to ether are to diethyl ether; brine refers to a saturated aqueous solution of NaCl. Unless otherwise indicated, all temperatures are expressed in °C. (degrees Centigrade). All reactions conducted at room temperature unless otherwise noted.

The $^1$HNMR spectra were recorded on a Varian VXR-300, a Varian Unity-300, or a Varian Unity-400 instrument. Chemical shifts are expressed in parts per million (ppm, d units). Coupling constants are in units of hertz (Hz). Splitting patterns are designated as s, singlet; d, doublet; t, triplet; q, quartet; m, multiplet; br, broad.

Low-resolution mass spectra (MS) were recorded on a JOEL JMS-AX505HA, JOEL SX-102 or a SCIEX-APIiii spectrometers. All mass spectra were taken in the positive ion mode under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid or p-anisldehyde solution. Flash column chromatography was performed on silica gel (230–400 mesh, Merck).

Products were purified by preparative reversed phase high pressure liquid chromatography (RP-HPLC) using either a Waters Model 3000 Delta Prep equipped with a Delta-pak radial compression cartridge ($C_{18}$, 300 A, 15 m, 47 mm×300 mm) or a Pharmacia LKB system using Merck Lobar silica or reverse phase $C_{18}$ columns. Linear gradients were used in all cases and the flow rate was 10–100 mL/minute ($t_0$=5.0 min.). All solvents contained 0.1% TFA. Analytical purity was assessed by RP-HPLC using either a Waters 600E system equipped with a Waters 990 diode array spectrometer (I range 200–400 nM) of a Hewlett Packard series 1050 system equipped with a diode array spectrometer. The stationary phase was either a Vydac $C_{18}$ column (5 m, 4.6 mm×250 mm) or a Rainin $C_{18}$ column (5 m, 4.6 mm×250 mm). The flow rate was 1.0 to 1.5 ml/min. ($t_0$=2.8 or 3.0 min.) and the solvent systems were as described above. Data reported as $T_r$, retention time in minutes (% acetonitrile over time).

The compounds of formula (I) may be prepared by the application of methods known in the art of organic synthesis. Illustrations of such methods are as follows:

Compounds of formula (I) wherein q is zero, r and t are 1 may be prepared by reacting an activated derivative of the acid (II) wherein $R^1$, $R^2$, $R^3$, $R^4$, $R^8$, $R^9$, Z, Y and p have the meanings defined in formula (I) or are protected derivatives thereof

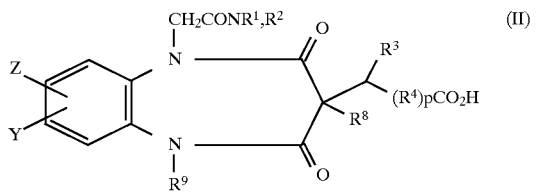

with the amine NHR$^6$R$^7$ wherein $R^6$ and $R^7$ have the meanings defined in formula I or are protected derivatives thereof, followed if necessary or desired by removal of any protecting groups.

Suitable activated derivatives of the acid for use in the reaction include those conventionally used in peptide chemistry and include acid halides, anhydrides including mixed anhydrides and activation with carbodiimides, carbonyldiimidazole, BOP/HOBT, PyBrOP or oxalyl chloride, followed if necessary or desired by removal of any protecting groups. The reaction is conveniently carried out in an aprotic solvent such as N'N-dimethylformamide.

Compounds of formula (I) wherein q, r and t are zero and $R^8$ is hydrogen may be prepared by reacting a compound of formula (III) in which $R^1$, $R^2$, $R^9$, Y and Z have the meanings in formula (I) or are protected derivatives thereof;

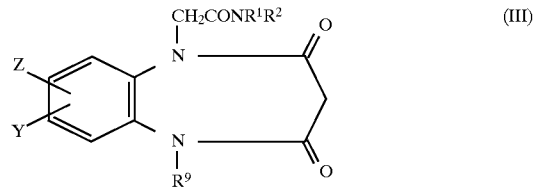

with the halide (IV) wherein $R^7$, $R^4$, $R^3$ and p have the meanings defined in formula (I) and hal is a halogen e.g. bromine.

in an aprotic solvent and in the presence of a strong base, followed if necessary or desired by removal of any protecting groups. Suitable aprotic solvents for use in the reaction include dimethylformamide or tetrahydrofuran.

Suitable bases for use in the reaction include sodium hydride, sodium hexamethyldisilazide or potassium hexamethyldisilazide.

In this reaction it may be desirable to protect any NH groupings and this may be done using conventional protecting groups such as anyl methyl derivative e.g. benzyl or an alkoxycarbonyl derivative e.g. t-butoxycarbonyl grouping. Such protecting groups may also be removed in a conventional manner. Thus the N-benzyl group may be cleared by hydrogenolysis using hydrogen and a palladium catalyst. The t-butoxycarbonyl group may be removed by conventional hydrolysis procedures e.g. with trifluoroacetic acid, hydrogen chloride in dioxane or aqueous potassium carbonate.

Compounds of formula (I) wherein $R^8$ is alkyl, q, r, and t are zero may be prepared by reacting the corresponding compounds of formula (I) wherein $R^8$ is hydrogen and $R^1$, $R^2$, $R^3$, $R^4$, $R^7$, $R^9$, Y, Z and p have the meanings defined in formula (I) or a protected derivative thereof with the alkyl halide $R^8$ hal wherein hal is bromine or iodine; followed if necessary or desired by the removal of any protecting groups.

The reaction is carried out in an aprotic solvent and in the presence of base using the general reactions described above for the preparation of compounds of formula (I) from compounds (III) and (IV).

Compounds of formula (I) in which q and t are zero may be prepared by reacting the diamine (V) in which $R^1$, $R^2$, $R^9$, Y and Z have the meanings given in formula (I) or are protected derivatives thereof;

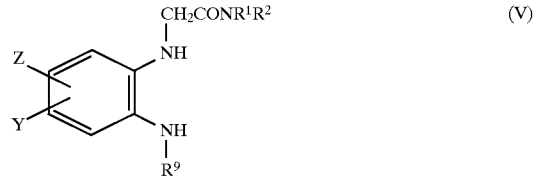

with the diacid chloride (VI).

wherein $R^3$, $R^4$, $R^7$, $R^8$ and r have the meanings defined in formula 1, or are protected derivatives thereof, followed if necessary by removal of any protecting groups. The reaction is conveniently carried out in an aprotic solvent such as an ether e.g. tetrahydrofuran.

Compounds of formula (I) wherein p, q and t are zero and $R^3$ is hydrogen may be prepared by reacting a compound of formula (VII) in which $R^1$, $R^2$, $R^8$, $R^9$, Y and Z have the meaning defined in formula (I).

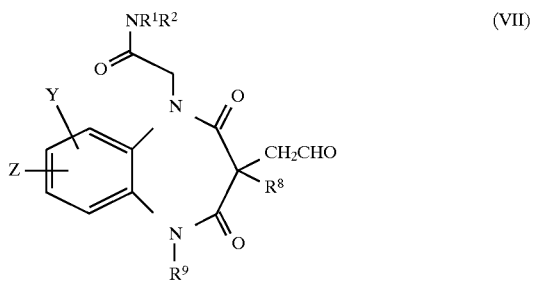

with the compound, $R^7MgBr$ wherein $R^7$ is a group as defined in formula (I) or a protected derivative thereof, followed if necessary by removal of any protecting groups. The reaction is conveniently carried out in an aprotic solvent such as an ether e.g. tetrahydrofuran.

Compounds of formula (I) wherein r and t are zero, q is one and $R^3$ is hydrogen may be prepared by reaction of a compound of formula (VII) with the amine $NR^6R^7$ wherein $R^6$ and $R^7$ have the meanings defined in formula (I) or are protected derivatives thereof under reductive alkylation conditions, followed if necessary by removal of any protecting groups. The reaction is preferably carried out in the presence of an alkanol e.g. methanol and in the presence of sodium cyanoborohydride.

Compounds of formula (I) wherein q, r and t are 1 may be prepared reacting the compound (VIII) wherein $R^1$, $R^2$, $R^3$, $R^4$, $R^5$, $R^8$, $R^9$, Z, Y and p have the meanings defined in formula (I).

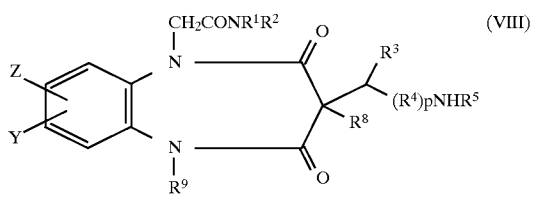

with the amine $HNR^6R^7$ wherein $R^6$ and $R^7$ have the meanings defined in formula (I) or are protected derivatives thereof in the presence of carbonyl diimidazole, followed if necessary by removal of any protecting groups. The reaction is conveniently carried out in an aprotic solvent such as a halohydrocarbon e.g. dichloromethane.

Compounds of formula (I) wherein t is zero, q and r are 1 may be prepared by reacting the compound (VIII) as defined above with an activated derivative of the carboxylic acid $R^7CO_2H$, followed if necessary by removal of any protecting groups. Suitable activated derivatives of the acid include those described above with respect to compound (II).

Compounds of formula (I) may be converted into other compounds of formula (I).

Thus compounds of formula (I) wherein $R^7$ is a phenyl group substituted by an alkoxycarbonyl group may be converted into the corresponding compound wherein $R^7$ is a phenyl group substituted by a carboxy group.

Similarly compounds wherein $R^7$ is an 1-benzylindazolyl group may be converted into the corresponding indazolyl group by hydrogenolysis using hydrogen and a palladium catalyst.

Compounds of formula (I) wherein $R^4$ is an alkenylene group and p is 1 may be reduced to give the corresponding compound wherein $R^4$ is an alkylene group.

Compounds of formula (II) may be prepared by oxidation of the corresponding compound of formula (IX).

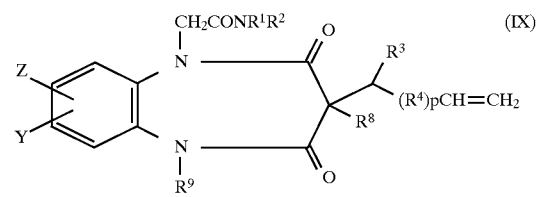

by reaction with ruthenium tetroxide in a solvent such as carbon tetrachloride.

The aldehyde (VIII) may be prepared by oxidation of compound (IX) by reaction with osmium tetroxide and sodium hyperiodate in a suitable solvent such as aqueous dioxan.

Compounds of formula (III) may be prepared by reaction of the diamine (V) with malonyl dichloride in an aprotic solvent such as tetrahydrofuran.

Compounds of formula (IX) may be prepared by reaction of the diamine (V) with the malonyl dichloride (X).

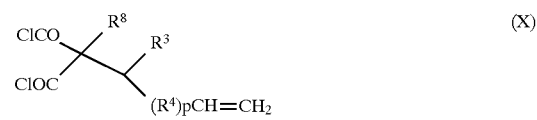

Compounds of formula (IX) wherein $R^8$ is alkyl may also be prepared by alkylation of the corresponding compound of formula (IX) wherein $R^8$ is hydrogen by reaction with the alkylhalide $R^8$ hal in the presence of a suitable base e.g. sodium hexamethyldisilazide.

The diamine (V) may be prepared by reaction of the corresponding compound (XI).

with the bromide $R^1R^2NCOCHBr$ in the presence of a suitable base such as sodium hydride.

Compounds of formula (XI) may be prepared by reaction of 2-fluoronitrobenzene with the amine $R^9NH_2$ in the presence of sodium hydride followed by catalytic reduction of the resultant nitroamine (XII)

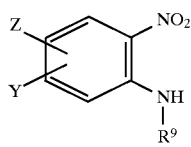

(XII)

using hydrogen and a palladium on charcoal catalyst.

Compounds of formula (III) may be prepared by alkylation of the corresponding compounds of formula (XIII) or (XIV).

The compounds of formula (I) in which there is basic or and acidic center may form salts with physiologically acceptable acids or bases and these may be prepared in a conventional manner.

The compounds of formula (1) contain at least one asymmetric center and the resulting enantiomers may be separated from each other by conventional methods.

The compounds of formula (I) may be prepared by methods known in the art of organic synthesis, an example being shown in Scheme 1:

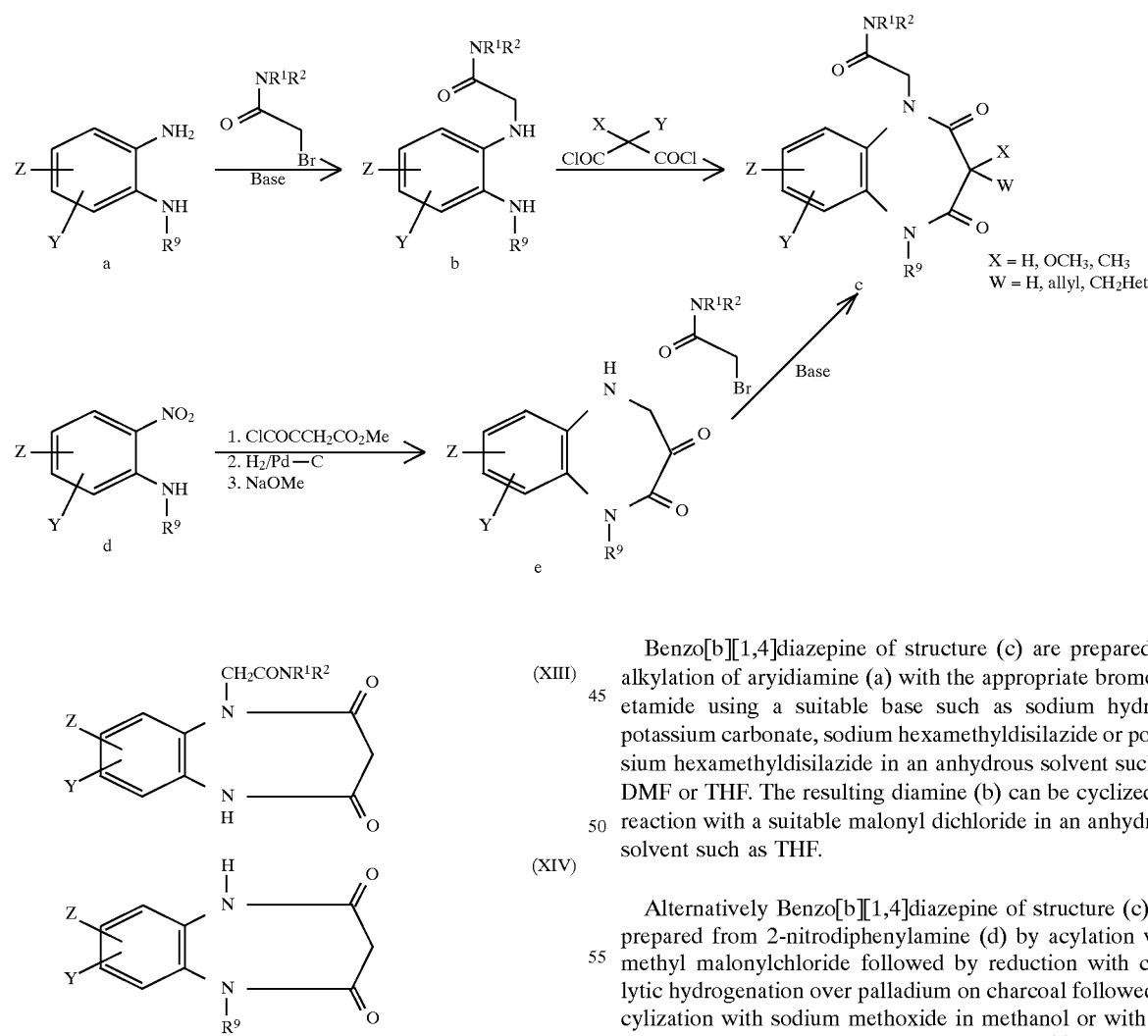

Scheme 1

(XIII)

(XIV)

Thus reaction of compound (XIII) with the appropriate aryl or heteroaryl bromide $R^9Br$ in the presence of copper yields compound (III).

Alternatively reaction of compound (XIV) with the bromide $R^1R^2NCOCH_2Br$ in the presence of a strong base e.g. NaH also yield a compound of formula (III).

The compounds of (XIII) or (XIV) may be prepared by reaction of the appropriate diamine with malonyldichloride.

Benzo[b][1,4]diazepine of structure (c) are prepared by alkylation of aryidiamine (a) with the appropriate bromoacetamide using a suitable base such as sodium hydride, potassium carbonate, sodium hexamethyldisilazide or potassium hexamethyldisilazide in an anhydrous solvent such as DMF or THF. The resulting diamine (b) can be cyclized by reaction with a suitable malonyl dichloride in an anhydrous solvent such as THF.

Alternatively Benzo[b][1,4]diazepine of structure (c) are prepared from 2-nitrodiphenylamine (d) by acylation with methyl malonylchloride followed by reduction with catalytic hydrogenation over palladium on charcoal followed by cylization with sodium methoxide in methanol or with dry HCl in methanol to give the benzodiazepine (e). Alkylation of (e) with the appropriate bromoacetamide using a suitable base such as sodium hydride, potassium carbonate, sodium hexamethyldisilazide or potassium hexamethyldisilazide in an anhydrous solvent such as DMF or THF gives Benzo[b][1,4diazepine of structure (c).

Intermediates useful in the preparation of compounds of formula (I) may be prepared as illustrated in Scheme 2:

Scheme 2

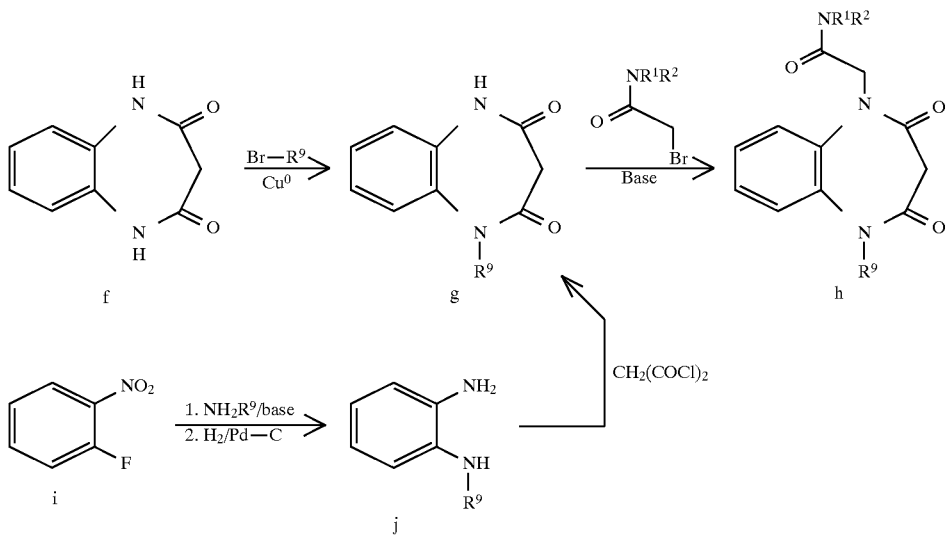

N5-heterosubstituted benzo[b][1,4]diazepine of structure (h) can be prepared by Goldberg reaction of benzodiazepine (f) with a suitable aryl or heteroaryl bromides in the presence of copper metal to give benzodiazepine (g). Alternatively, 2-fluoronitrobenzene can be reacted with a suitable aryl or heteroaryl amines in the presence of sodium hydride, followed by catalytic hydrogenation over palladium on charcoal to give a diamine such as (j). Cyclization of (j) with malonyl dichloride in THF gives benzodiazepine (g). The resulting benzodiazepine (g) can be alkylated with the appropriate bromo acetamide as described in Scheme 1 to give benzo[b][1,4diazepine of structure (h).

Intermediates useful in the preparation of compounds of formula (I) may also be prepared as illustrated in Scheme 3:

Scheme 3

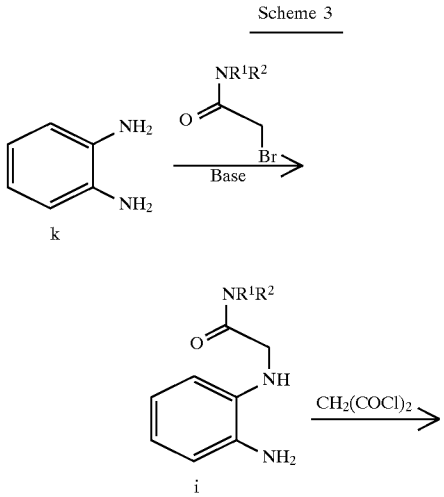

-continued
Scheme 3

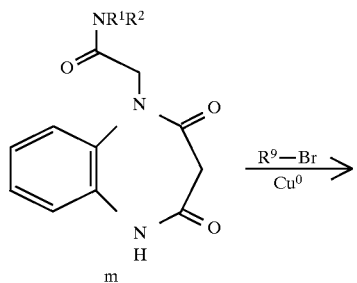

Alkylation of o-diaminobenzene with the appropriate bromoacetamide as described in Scheme 1 gives a diamine such as (i). Cyclization with malonyl dichloride in THF gives a benzo[b][1,4]diazepine (m), which undergoes a Goldberg reaction with a suitable aryl bromide in the presence of copper metal to give 1,5-benzodiazepine such as (n).

The compounds of formula (I) may also be prepared as illustrated in Scheme 4:

Scheme 4

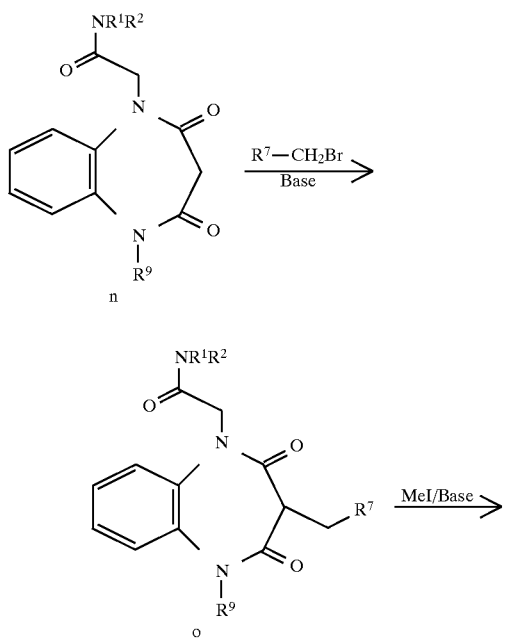

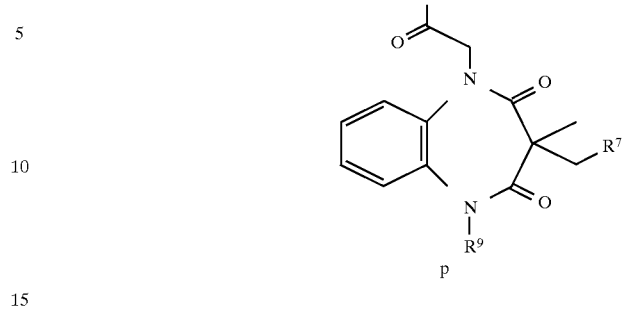

Substitution of C3-methylene benzo[b][1,4]diazepine of structure (n) can be accomplished by alkylation with an aryl or heteroaryl bromomethyl compound using a base such as sodium hydride, potassium carbonate, sodium hexamethyldisilazide or potassium hexamethyldisilazide in an anhydrous solvent such as DMF or THF.

The resulting 1,5-benzodiazepine (o) can additionally be alkylated with methyl iodide using a base such as sodium hydride, potassium carbonate, sodium hexamethyldisilazide or potassium hexamethyldisilazide in an anhydrous solvent such as DMF or THF to give a quaterary C3-benzo[b][1,4] diazepine such as (p).

The compounds of formula (I) may also be prepared as illustrated in Scheme 5:

Scheme 5

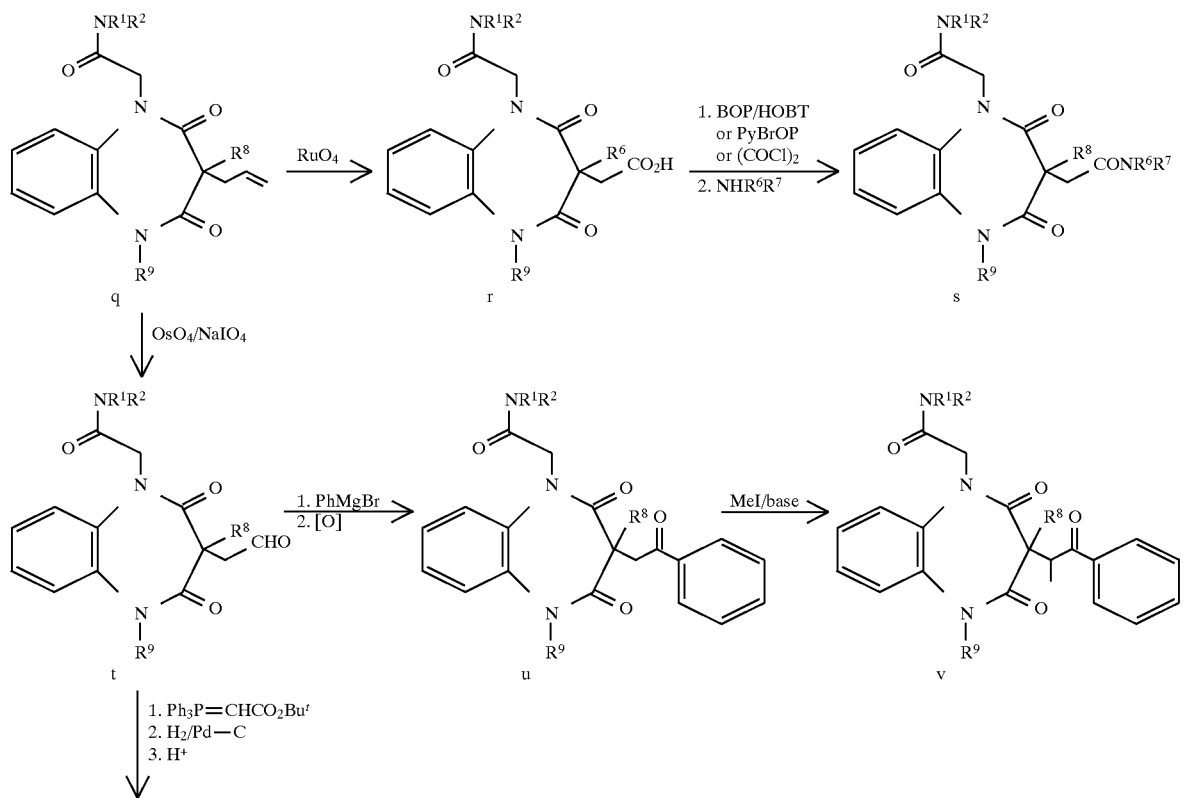

-continued
Scheme 5

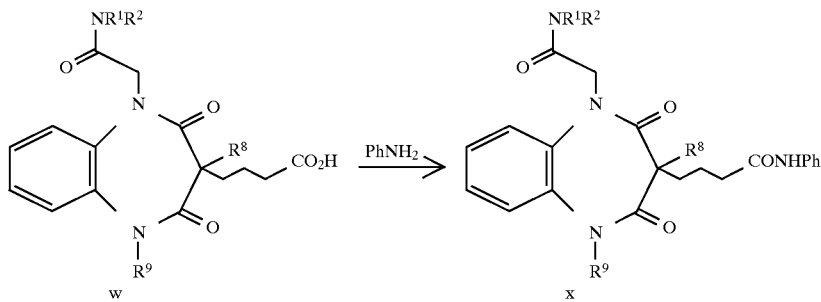

C3-allyl substituted benzo[b][1,4]diazepine such as those of structure (q) can be further substituted by oxidation to a carboxylic acid such as (r) with ruthenium tetroxide in $CCl_4$. The acid (r) can be converted to an amide (s) by reaction with a suitable amine following activation of the acid by an agent such as BOP/HOBT, PyBrOP or oxalyl chloride. Alternatively (q) can be oxidized with $OsO_4/NaIO_4$ in aqueous dioxane to generate aldehyde (t). Reaction of (t) with phenyl magnesium bromide in THF gives ketone (u), which can methylated with methyl iodide and sodium hydride in THF to give ketone (v). Aldehyde (t) can also be homologated to acid (w) by reaction with (tert-butoxycarbonylmethylene) triphenylphosphorane in methylene chloride, followed by catalytic hydrogenation over palladium on charcoal followed by acid hydrolysis. Acid (w) can be converted to an amide (x) by reaction with a suitable amine such an aniline with activation of the acid as detailed in Scheme 5

Alternatively, C3-allyl substituted benzo[b][1,4]diazepine such as (q) can be elaborated alkylation with an aryl or heteroaryl bromomethyl compound using a base such as sodium hydride, potassium carbonate, sodium hexamethyldisilazide or potassium hexamethyldisilazide in an anhydrous solvent such as DMF or THF followed by by oxidation to a carboxylic acid such as (y) with ruthenium tetroxide in $CCl_4$. Acid (y) can be converted to amides (z) by the methods outlined above.

Scheme 6

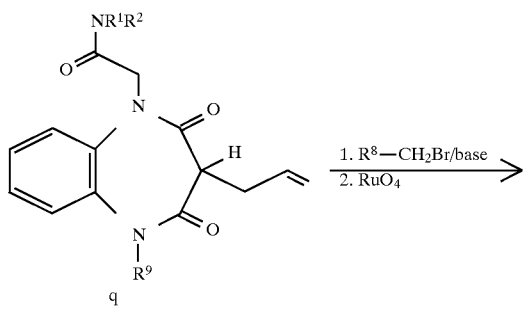

-continued
Scheme 6

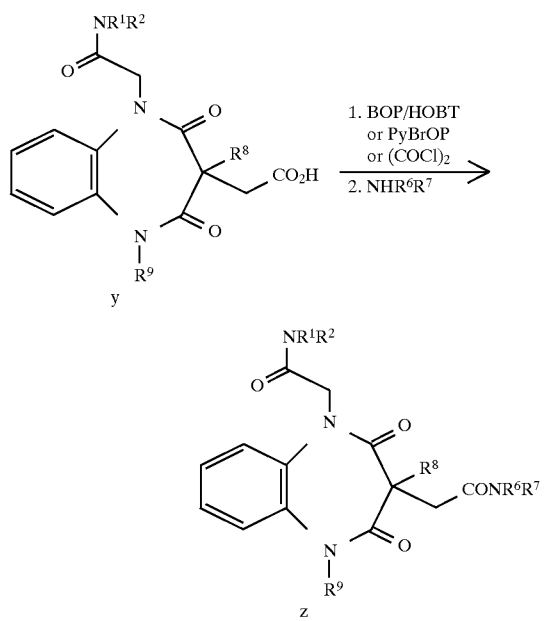

Pharmacology

The efficacy of compounds of the present invention in binding CCK-A and CCK-B and as agonists of CCK-A can be evaluated and measured using pharmacological methods known in the art or as described in detail below based on similarly established methodologies.

1. CCK-A RECEPTOR BINDING ASSAY

Tissue Preparation:

Solutions of 0.3M sucrose and 2.0M sucrose are prepared and chilled overnight at 4° C. On the following day and prior to use, inhibitors are added such that the final concentrations are 0.01% Soybean Trypsin Inhibitor (50 mg/500 ml sucrose) and 100 mM phenylmethysulfonyl fluoride (8.5 mg/500 mL sucrose).

Rats are sacrificed by decapitation using a guillotine. The rat's external abdominal wall is wetted with methanol and fur and skin are removed. The abdomen is opened, the pancreas is carefully dissected out and placed in a 50 mL beaker containing 0.3M sucrose. After all the pancreata are harvested, excess fat and lymph nodes are trimmed off. Pancreatic tissue is divided into approximately 4.0 g aliquots into 30 mL beakers, each containing 1.0 mL of 0.3M sucrose.

In 4° C. cold room, the pancreata are minced with scissors and diluted 1:10 weight:volume with 0.3M sucrose. Aliquots are homogenized in a chilled 40 mL Wheaton dounce with 4 up and down strokes of the "B" pestle followed by 4 up and down strokes of the "A" pestle. Homogenates are filtered through 2 layers of cheesecloth into a chilled 500 mL beaker, then diluted with 2.0M sucrose with stirring to yield a final concentration of 1.3M sucrose homogenate. The resulting 1.3M homogenate is dispensed into 18 thin-walled 36 mL polyallomer tubes on ice (approximately 30 mL homogenate per tube) and each tube is subsequently overlaid with 0.3M sucrose until liquid is approximately 0.5 cm from the top of the tube. The samples are spun in a Sorvall RC70 ultracentrifuge at 27,500 RPM (100,000×g) for 3 hours at 4° C. The interface band is collected into a chilled graduated cylinder, diluted and mixed with cold distilled water to a total volume of 312 mL and spun at 100,000×g for 50 min. at 4° C. The pellets are resuspended in KRH buffer (25 mM HEPES, 104 mM NaCl, 5 mM KCl, 1 mM $KPO_4$, 1.2 mM $MgSO_4$, 2 mM $CaCl_2$, 2.5 mM Glucose, 0.2% BSA, 0.1 mM PMSF, 0.01% STI, pH 7.4 at 4° C.), transferred to a 15 mL Wheaton dounce and homogenized with 4 up and down strokes of the matched "A" (tight) pestle. This homogenate is transferred into 2–27 mL polycarbonate bottles and spun at 100,000×g for 30 min. at 4° C. The pellet is resuspended (1 mL KRH buffer/gm wt of original tissue), transferred to an appropriate size dounce and homogenized with 4 up and down strokes of the matched "A" pestle. 1 mL aliquots are stored at −70° C. in microcentrifuge tubes.

Assay:

Test compounds are diluted in 10×Assay Binding Buffer (200 mM HEPES, 10 mM EGTA, 1.8M NaCl, 50 mM KCL, 50 mM $MgCl_2$, 0.5% BSA, pH 7.4).

50 mL compound+400 mL Assay Binding Buffer+25 mL [$^{125}$I] sulphated CCK-8 labeled with Bolton and Hunter reagent (Amersham, 2000 Cl/mmol)+25 mL prepared rat pancreas membranes are incubated for 30 minutes at 25° C. while shaking gently throughout the incubation.

1 mM L-364718 (final concentration) is used for determination of non-specific binding.

Reaction is stopped using Brandell Cell Harvester, ishing 3× with 3 mL ice-cold (4° C.) assay binding buffer per ish.

Tissues are collected on Whatman GF/B filter papers pre-wet with assay buffer and filter papers counted using a gamma counter.

2. CCK-B RECEPTOR BINDING ASSAY

Tissue Preparation:

Hartley Male Guinea Pigs (250–300 g, Charles River) are sacrificed by decapitation. The brain is removed and placed in 4° C. Buffer (50 mM Tris/HCL, pH 7.4). The cortex is dissected and placed in 4° C. Buffer. The total wet weight of all cortices is determined and the tissues are diluted 1:10 (wt:vol) with Buffer.

The cortex is minced using a Tekmar Tissuemizer then homogenized in Buffer with 5 up and down strokes using a motor driven glass/teflon homogenizer. The preparation is maintained at 4° C. (on ice).

Membranes are pelleted by centrifugation in Sorvall RC5C at 4° C. using a SA 600 rotor spun at 16,000 RPM (47,800×g Maximum). The pellet is saved and the supernatent is discarded. The pellets are combined and resuspended in Buffer at 4° C. using same volume as above and blended as above with 5 up and down strokes of a glass/teflon motor driven homogenizer using the same volume as before. The resulting homogenates are spun at 16,000 RPM (47,800×g Maximum, 36,592×g Average) for 15 minutes at 4° C. Pellets are saved and the supernatents discarded. Pellets are subsequently combined with Buffer to get a final volume of 300 mL and blended using a Tekmar Tissuemizer. Initial protein content is determined by the Biorad protein assay. The volume of suspension is adjusted with buffer, such that the volume adjustment yielded approximately 4.0 mg/mL as a final concentration, confirmed via the Biorad protein assay. The final suspension is transferred as 4.0 mL aliquots into plastic tubes and frozen at −70° C.

Assay:

Skatron filters are soaked in Buffer with 0.1% Bovine Serum Albumin (BSA) for an hour prior to harvesting.

Test compounds are diluted in 10×Assay Binding Buffer (200 mM HEPES, 10 mM EGTA, 1.8M NaCl, 50 mM KCL, 50 mM $MgCl_2$, 0.5% BSA, pH 7.4). [$^{125}$I]-sulfated CCK-8 labeled with Bolton-Hunter reagent (Amersham, 200 Ci/mmol) is diluted.

25 mL 100 mM Bestatin+25 mL 3 mM Phosphoramidon+25 mL test compound+50 mL radioligand+25 mL 10×Assay Binding Buffer+100 mL guinea pig cortex membranes are incubated 150 minutes at room temperature.

For $B_0$ determination, Assay Binding Buffer is substituted for test compound.

For filter binding determination, Assay Binding Buffer is substituted for test compound and guinea pig cortex membranes.

For non-specific binding determination, 1 mM sulphated CCK-8 (Sigma) is substituted for test compound.

Reaction is stopped by filtering using the automated Skatron Cell Harvester. The filters are rinsed using 4° C. Assay Binding Buffer. The filters are subsequently punched, placed in tubes and counted using a gamma counter.

3. GUINEA PIG GALL BLADDER ASSAY

Tissue Preparation:

Gallbladders are removed from guinea pigs sacrificed by cervical dislocation. The isolated gallbladders are cleaned of adherent connective tissue and cut into two rings from each animal (2–4 mm in length). The rings are subsequently suspended in organ chambers containing a physiological salt solution (118.4 mM NaCl, 4.7 mM KCl, 1.2 mM $MgSO_4$, 2.5 mM $CaCl_2$, 1.2 mM $KH_2PO_3$, 25 mM $NaHCO_3$, 11.1 mM dextrose). The bathing solution is maintained at 37° C. and aerated with 95% $O_2$/5% $CO_2$. Tissues are connected via gold chains and stainless steel mounting wires to isometric force displacement transducers (Grass, Model FT03 D). Responses are then recorded on a polygraph (Grass, Model 7E). One tissue from each animal served as a time/solvent control and did not receive test compound.

Assay:

Rings are gradually stretched (over a 120 min. period) to a basal resting tension of 1 gm which is maintained throughout the experiment. During the basal tension adjustment period, the rings are exposed to acetylcholine ($10^{-6}$M) four times to verify tissue contractility. The tissues are then exposed to a submaximal dose of sulfated CCK-8 (Sigma, $3 \times 10^{-9}$M). After obtaining a stable response, the tissues are washed out 3 times rapidly and every 5 to 10 minutes for 1 hour to reestablish a stable baseline.

Compounds are dissolved in dimethylsulfoxide (DMSO) then diluted with water and assayed via a cumulative concentration-response curve to test compound ($10^{-11}$ to $3 \times 10^{-6}$M) followed by a concentration-response curve to sulfated CCK-8 ($10^{-10}$ to $10^{-6}$M) in the presence of the highest dose of the test compound. As a final test, ACH (10 mM) is added to induce maximal contraction. A minimum of three determinations of activity are made for each test compound.

4. 18-HOUR DEPRIVATION-INDUCED FEEDING PARADIGM

Male, Long-Evans rats (Charles River Co., Raleigh, N.C.), weighing 300–375 grams, are acclimated individually for at least a week in hanging, stainless steel mesh cages (17.8×25.4×17.8 cm high) with ad libitum access to water (delivered through automatic drinking spouts at the rear of the cage) and food (Lab Blox, Purina Rodent Laboratory Chow #5001) on a 12-hour light/dark cycle (lights on from 0600–1800 hours, or h) at approximately 22.8° C. Prior to testing, all chow, but not water, is removed at 1600 h. At 0900 h the next morning, rats are weighed. At 0945 h, rats are injected intraperitoneally (i.p.), orally (per os, or p.o.) or through an indwelling, intra-duodenal cannulea with a test compound or vehicle (2 mL/kg) and returned to their home cages. Food is presented at 1000 h. At 1030 h, remaining food and spillage is weighed.

5. MEASUREMENT OF ACID SECRETION IN GASTRIC FISTULA RAT

Gastric fistula rats are prepared according to the methods described by Dimaline, Carter and Barnes (Am. J. Physiol., 251, G615–G618 (1986). Female AH/A rats (200 g) are anaesthetized using a mixture of nitrous oxide, isoflurane and oxygen gas to allow the implantation of a gastric fistula. The abdomen is opened with a midline incision and the stomach exteriorised. A small incision is made in the fundic region of the stomach, along the greater curvature, and the stomach washed clean with 0.9% saline. A titanium cannula is inserted part way into the incision and tied in place with 2/0 gauge suture thread. The cannula is then exteriorised through a stab wound lateral to them midline incision and secured by stitching to the abdominal wall. The midline incision is sutured and the cannula closed with a screw cap to prevent food loss. The rats are then allowed 1 week recovery period before use in secretion experiments. Animals are housed individually in solid bottomed cages containing wood chippings and allowed free access to food and water, in a room with 12 hour light/dark cycle.

18 hours prior to the experiment, rats are placed in grid bottomed cages to prevent coprophagy. Food is removed but the animals are allowed free access to water. At the start of the experiment, each rat is anaesthetized with a mixture of isoflurane, nitrous oxide and oxygen gas and the stomachs washed with 0.9% saline via cannula to remove any remaining food. At the same time, a tail vein cannula is inserted pericutaneously to provide a route for intravenous administration. The rats are then left to recover from the anesthetic in Bollman type restraint cages for the duration of the experiment.

After a 60 minute acclimatization period, gastric secretion is collected every 15 minutes by drainage into pre-weighed pots. During the acclimatization period, a saline infusion (3.5 ml/hour) is given via the tail vein to keep the tubing free from blood clotting and to maintain hydration of the rat.

Collected samples are weighed and the volume of secretions determined. The gastric acid concentration of each 15 minute collection is determined by titration to pH 7.0 with 0.1M NaOH using radiometer auitotitrator equipment, and the total acid secreted per 15 minute period calculated.

Acid secretion is stimulated using a submaximal infusion of pentagastrin ($0.6\ \mu gkg^{-1}h^{-1}$). Once a stable plateau to acid secretion is achieved, test compounds are administered intravenously and acid secretion recorded for a further 180 minutes. Inhibition of acid secretion is expressed as percentage inhibition of pre-test compound secretion levels.

6. MEASUREMENT OF ACID SECRETION IN HEIDENHAIN POUND DOG

Male beagle dogs (10–15 kg) are prepared with a Heidenhain pound by a veterinary surgeon according to the methods described by Emas, Swan and Jacobsen (Methods of Studying Gastric Secretion, Chapter 42, pp. 749–751, Handbook of Physiology, Section 6, Alimentary Canal. Ed: Code CF. Pub: American Physiology Society). Animals are allowed 4 weeks to recover from surgery prior to experimental use. For measurement of acid secretion, dogs are starved overnight, with water ad libitum. Gastric juice is collected from the Heidenhain pouch at 15 min. intervals and total acid output determined by automatic titration to pH 7.0 with 0.1M NaOH. Acid secretion is stimulated using a submaximal intravenous infusion of pentagastrin ($1\ \mu g/kg^{-1}min^{1}$). Once a stable plateau increase in acid secretion is achieved, test compounds are administered by bolus intravenously. Acid secretion is recorded every 15 min. for a further 180 min. Inhibition of acid secretion is expressed as percentage inhibition of plateau acid secretion values.

7. RAT GASTRIC EMPTYING PROTOCOL

Methyl Cellulose (MC) Test Meal

1. Disperse MC in water at 80° C. at a final concentration of 1.5% under continuous stirring. Cool to room temperature.
2. Add Phenol Red (50 mg/100) to solution.
3. Keep solution stirring during entire experiment.

Drug Administration

1. Food deprive animals for 18 hours.
2. Inject test drug/prop. glycol or prop. glycol alone intraperitoneally.
3. After 5 minutes, gavage 1.5 mL of Pheno Red/MC solution Processing Stomachs 1. After 20 minutes, decapitate animal
2. Clamp stomach at the pylorus and cardia ends, and rinse in 0.9% NaCl.
3. Place stomach in 100 mL of 0.1N NaOH, cut into small pieces, and homogenize for 30 seconds.
4. Let settle at room temperature for 60 minutes.
5. In centrifuge tube, add 5 mL of supernatant and 0.5 mL of trichloroacetic acid (29% w/v), and centrifuge at 2,800 rpm for 20 minutes.
6. Decant supernatant, and add 4 mL of 0.5N NaOH and read absorbance at a wavelength of 560 nm.

Calculations

Percent gastric emptying =

$$1 - \frac{(\text{amount of phenol red recovered from test stomach} \times 100)}{\text{average amount of phenol red recovered from standard stomachs}}$$

The standard stomach is determined from the phenol red recovered in stomachs of rats decapitated immediately after intragastric infusion of MC/phenol red.

TABLE 1

Functional activity in isolated guinea pig gallbladder preparation, expressed as % CCK-induced maximal response.

| Example | % Contraction ($3 \times 10^{-5}$M) | %Contraction ($1 \times 10^{-6}$M) |
|---|---|---|
| 1 | 64 | |
| 2 | 94 | |
| 3 | 102 | 75 |
| 4 | 79 | 80 |
| 5 | | 9 |
| 6 | | 7 |
| 7 | | 15 |
| 8 | | 16 |
| 9 | | 31 |
| 10 | | 7 |
| 11 | | 10 |
| 12 | | 19 |
| 13 | | 6 |
| 14 | 64 | |
| 15 | | 54 |
| 16 | 54 | |
| 17 | 55 | 48 |
| 18 | 3 | |
| 19 | 76 | |
| 20 | 66 | |
| 21 | 90 | 80 |
| 22 | 71 | 61 |
| 23 | 50 | |
| 24 | 34 | |
| 25 | | 88 |
| 26 | | 91 |
| 27 | 40 | |
| 28 | | 3 |
| 29 | 85 | 65 |
| 30 | 70 | 75 |
| 32 | | 38 |
| 33 | | 53 |
| 34 | | 47 |
| 35 | | 44 |
| 36 | | 19 |
| 37 | | 46 |
| 38 | | 30 |
| 39 | | 57 |
| 40 | | 10 |
| 41 | | 40 |
| 42 | | 16 |
| 43 | 61 | |
| 44 | 83 | 57 |
| 45 | | 57 |
| 46 | 6 | 6 |
| 47 | | 92 |
| 48 | 75 | |
| 49 | 91 | 75 |
| 50 | 94 | 83 |
| 51 | 83 | 82 |
| 52 | 96 | 70 |
| 53 | 103 | 96 |
| 54 | 43 | 63 |
| 55 | | 21 |
| 56 | 98 | 90 |
| 57 | 134 | 99 |
| 58 | 95 | 80 |
| 59 | 102 | 100 |
| 60 | 81 | 94 |
| 61 | 77 | 63 |
| 62 | 86 | 96 |
| 63 | 96 | 77 |
| 64 | 98 | 67 |
| 65 | 93 | 88 |
| 66 | 116 | 97 |
| 67 | 102 | 78 |
| 68 | 99 | 93 |
| 69 | 92 | 98 |
| 70 | 73 | 66 |
| 71 | 92 | 106 |
| 72 | 93 | 104 |
| 73 | 64 | 58 |
| 74 | 88 | 86 |

TABLE 1-continued

Functional activity in isolated guinea pig gallbladder preparation, expressed as % CCK-induced maximal response.

| Example | % Contraction ($3 \times 10^{-5}$M) | %Contraction ($1 \times 10^{-6}$M) |
|---|---|---|
| 75 | 82 | 102 |
| 76 | 95 | 93 |
| 77 | 120 | 78 |
| 78 | | 43 |
| 79 | 93 | 92 |
| 80 | 73 | 81 |
| 81 | 96 | 97 |
| 82 | 89 | 69 |
| 83 | 97 | 85 |
| 84 | 96 | 96 |

TABLE 1

Functional activity of compounds in CCK-A agonist isolated guinea pig gallbladder preparation assay and in gastric emptying assay.

| | Isolated guinea pig gallbladder: % contraction | rat gastric emptying: % emptying |
|---|---|---|
| Vehicle[A] | — | 66 |
| CCK8[B] | 100 | 0 |
| CCK-8 and CCK-A antagonist[C] | — | 52 |
| CCK-8 and CCK-B antagonist[D] | — | 0 |
| CCK-A agonist 1[E] | 87 | 6 |
| CCK-A agonist 2[F] | 100 | 2.5 |

[A]0.5% methyl cellulose was used as a test vehicle in the gastric emptying assay.
[B]CCK-B is the C-terminal octapeptide of CCK, delivered at 1 $\mu$M in the gallbladder assay, administered intraperitoneally at 30 nmoles/kg in the gastric emptying assay.
[C]CCK-A antagonist is MK-329, see Evans, B. E., et al, Proc. Nat. Acad. Sci. (83), 4918–1922 (1986), administered intraperitoneally at .5 $\mu$moles/kg in the gastric emptying assay.
[D]CCK-B antagonist is L-365,260, see Bock, M. G. et al, J. Med. Chem., (32), 16–23 (1989), administered intraperitoneally at .5 mmoles/kg in the gastric emptying assay.
[E]CCK-A agonist 1 is 2-[3-(1H-Indazol-3-ylmethyl)-2,4-dioxo-5-phenyl-2,3, 4,5-tetrahydro-benzo[b][1,4]diazepin-1-yl]-N-isopropyl-N-(4-methoxy-phenyl)acetamide, delivered at 30 $\mu$M in the gallbladder assay, administered intraperitoneally at 0.1 $\mu$moles/kg in the gastric emptying assay. Example 31 below.
[F]CCK-A agonist 2 is 2-[3-(1H-indazol-3-ylmethyl)-2,4-dioxo-5-(2-pyridinyl) -2,3,4,5-tetrahydro-benzo[b][1,4]diazepin-1-yl]-N-isopropyl-N-(4-methoxy-phenyl)acetamide, delivered at 30 $\mu$M in the gallbladder assay, administered intraperitoneally at 0.1 $\mu$moles/kg in the gastric emptying assay.

While it is possible that, for use in therapy, a compound of the invention may be administered as the raw chemical it is possible to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be acceptable in the sense of being compatable with the other ingredients of the formulation and not deleterious to the recipient thereof. According to another aspect of the invention, there is provided a process for the preparation of a pharmaceutical formulation comprising admixing a compound of formula (I) or a pharmaceutically acceptable salt or solvate thereof with one of more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical, (including buccal and sublingual), vaginal or parental (including intramuscular, sub-cutaneous, intravenous, and directly into the affected joint) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets, or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups, or elixirs, or may be presented as a dry product for constitution with water of other suitable vehicle before use. Such liquid preparations may contain conventional additives such as suspending agents, non-aqueous vehicles (which may include edible oils), or preservatives.

Oral formulations in solid dosage forms such as tablets and capsules for treatment of obesity and its related conditions, for treatment of diabetes and related conditions, for improving gastrointestinal motility, modifying pancreatic enzyme secretions, inducing gallbladder contraction, modifying food intake, inducing satiety and reducing anxiety should be suitable for non-disintegration in the stomach with rapid disintegration in the intestine, i.e. an enteric coating. Examples of enteric coatings utilizing pH dependence for solubility include cellulose acetate phthalate, polyvinyl acetate phthalate, hydroxypropyl methylcellulose phthalate and methacrylic acid copolymer. Some of these coating agents may require a plasticizer such as triethyl citrate, polyethylene glycol or triacetin.

Oral formulations for treatment of diabetes and related conditions may be suitable for disintegration prior to leaving the stomach, having no coating or an immediate release coating, such as hydroxypropyl methylcellulose or sucrose possibly including plasticizers.

Enteric and immediate release coatings may also contain materials to make them opaque such as titanium dioxide, dyes to color, or talc to make less tacky. The coatings are typically applied as a solution or dispersion in either organic or aqueous media. On a production scale, both types coating are typically applied by spraying it onto the dosage form using a coating pan or a fluid bed coater.

The compounds according to the invention may also be formulated for parental administration (e.g. by injection, for example bolus injection or continuous infusion) and may be presented in unit dose form in ampules, pre-filled syringes, small volume in fusion or in multi-dose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by aseptic isolation of sterile solid or by lyophilization from solution, for constitution with a suitable vehicle, e.g. sterile, pyrogen free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthishes comprising the active ingredient in a suitable liquid carrier. For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are possibly presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams, or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation the compounds according to the invention are conveniently delivered from an insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin of blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example antiinfective agents such as bactericidal or fugicidal agents, antiinflammatory agents or anticancer agents.

The invention thus provides, in a further aspect, a combination comprising a compound of formula (I) or a physiologically acceptable derivative thereof together with another therapeutically active agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician or veterinarian. In general, however, a suitable dose will be in the range of from about 0.1 to 300 mg/kg of bodyweight per day, particularly from about 1 to 100 mg/kg of bodyweight per day. An appropriate dosage unit involved in oral administration may generally contain from about 1 to 250 mg, particularly from about 25 to 250 mg, of a compound of formula (I). The dosage employed for the topical administration will, of course, depend on the size of the area being treated. For the eyes each dose will be typically in the range of from 10 to 100 mg of the compound of formula (I).

For use in the treatment of CCK related disorders the compounds of the invention can be administered by any of the aforementioned routes, particularly by the oral route or by injection. The daily non-toxic dosage for a 70 kg mammal will be in the range of about 10 mg to 5 g of a compound of formula (I).

EXAMPLES

The following examples illustrate aspects of this invention but should not be construed as limitations thereto.

| Pharmacy Example A | |
|---|---|
| Active Ingredient: | 50 mg |
| Lactose anhydrous USP: | 163 mg |
| Microcrystalline Cellulose NF: | 69 mg |
| Pregelatinized starch Ph. Eur. | 15 mg |
| Magnesium stearate USP | 3 mg |
| Compression weight: | 300 mg |

The active ingredient, microcrystaline cellulose, lactose and preglelatinized starch are sieved through a 500 micron sieve and blended in a suitable mixer. The magnesium stearate is sieved through a 250 micron sieve and blended with the active blend. The blend is compressed into tablets using suitable punches, then coated with cellulose acetate phthalate.

Intermediate 1

2-(2,4-Dioxo-5-phenyl-2,3,4,5-tetrahydro-benzo[b] [1,4]diazepin-1-yl)-N-isopropyl-N-phenyl acetamide To 20 mL of THF at 0° C. is added dropwise over 10 min simultaneously a solution of 1.97 g (5.48 mmol) of N-isopropyl-N-phenyl-2-(2-phenylamino-phenylamino) acetamide in 20 mL of THF and 0.53 mL (5.48 mmol) of malonyl dichloride in 20 mL of THF. The resulting red-brown solution is stirred at RT for 5.5 h and the solvent removed in vacuo. Purification of the resulting brown oil by silica gel flash chromatography (50 to 75% ethyl acetate/ petroleum ether) followed by recrystallization from ethyl acetate/petroleum ether gave 0.84 g of the title compound as a white powder: mp. 199°–200° C.; $^1$H NMR (CDCl$_3$, 300 MHz) δ7.6–7.2 (m, 12H), 7.09 (t, 1H, J=8), 6.90 (d, 1H, J=8), 5.05 (m, 1H), 4.38 (d, 1H, J=17), 4.04 (d, 1H, J=17), 3.54 (dd, 2H, J=5, 22), 1.10 (d, 6H, J=7); low resolution MS (FAB) m/e 428 (MH$^+$).

Intermediate 2

2-[2,4-Dioxo-5-(4-chlorophenyl)-3-methyl-3-(3-propenyl)-2,3,4,5-tetrahydro-benzo[b][1,4]diazepin-1-yl]-N-isopropyl-N-(4-methoxy)-phenyl acetamide 2.0 mL (23 mmol) of oxalyl chloride is added to a solution of 1.1 g (4.7 mmol) of 2-methyl-2-(3-propenyl)-malonic acid and 0.022 mL of DMF in 80 mL of CH$_2$Cl$_2$ at 0° C. The solution is stirred at RT for 2 h and subsequently concentrated in vacuo to a yellow liquid. The crude acid chloride is dissolved in 60 mL of THF, added dropwise to 2.0 g (4.7 mmol) of N-isopropyl-N-(4-methoxy-phenyl)-2-[2-(4-chlorophenylamino)-phenylamino]acetamide in 140 mL of THF and the solution heated at reflux for 18 h. After removal of the solvent in vacuo, the residue is diluted with 1N HCl and extracted with EtOAc (x3). The organic extract is washed with 1N HCl, sat NaHCO$_3$ and brine, dried over MgSO$_4$ and concentrated in vacuo. Purification by silica gel flash chromatography (30% EtOAc/petroleum ether) followed by recrystallisation from methanol/H$_2$O gave 1.9 g of the title compound as a white powder: $^1$H NMR (CDCl$_3$, 300 MHz, mixture of conformations) δ7.4–6.7 (m, 12H), 5.7 (m, 1H), 5.05 (m, 2H), 4.71 (d, 1H, J=17), 4.39 (d, 1H, J=17), 3.84 (s, 3H), 2.09 (d, 2H, J=7), 1.57 (s, 3H), 1.09 (t, 3H, J=7); low resolution MS (FAB) m/e 546 (MH$^+$).

Intermediate 3

[1-(Isopropyl-(4-methoxy-phenyl)-carbamoylmethyl)-3-methyl-2,4-dioxo-5-(4-chloro-phenyl)-2,3,4,5-tetrahydro-1H-benzo[b][1,4] diazepin-3-yl]-acetic acid 7.2 g (34 mmol) of NaIO$_4$ is added to a biphasic mixture of 1.8 g (3.4 mmol) of 2-[2,4-Dioxo-5-(4-chlorophenyl)-3-methyl-3-(3-propenyl)-2,3,4,5-tetrahydro-benzo[b][1,4] diazepin-1-yl]-N-isopropyl-N-(4-methoxy-phenyl) acetamide, prepared as in Intermediate 2, in 120 mL of CCl$_4$ and 0.07 g (0.34 mmol) of RuCl$_3$.H2O in 60 mL of H$_2$O. The mixture is vigorously stirred at RT for 18 h. After removal of the CCl$_4$ in vacuo, the residue is diluted with H$_2$O and extracted with EtOAc (x3). The organic extract is washed with aq. NaHSO$_3$ (x3), dried over MgSO$_4$ followed by decolorizing charcoal, filtered and concentrated in vacuo to give 1.8 g of the title compound as a grey foam: $^1$H NMR (CDCl$_3$, 300 MHz) δ7.4–6.7 (m, 12H), 4.95 (m, 1H), 4.3 (m, 2H), 3.85 (s, 3H), 3.24 (d, 1H, J=16), 3.04 (d, 1H, J=16), 1.28 (s, 3H), 1.08 (dd, 6H, 6.12); R$_f$=0.25 (silica gel, 50% EtOAc/petroleum ether).

Intermediate 4

2-(2,4-Dioxo-5-phenyl-2,3,4,5-tetrahydro-benzo[b] [1,4]diazepin-1-yl)-N-isopropyl-N-(4-methoxy-phenyl) acetamide To 100 mL of THF at 0° C. is added dropwise over 20 min simultaneously a solution of 8.0 g (20.5 mmol) of N-isopropyl-N-(4-methoxy-phenyl)-2-(2-phenylamino-phenylamino) acetamide, prepared as in Intermediate 43, in 100 mL of THF and 2.40 mL (24.6 mmol, 1.2 equiv) of malonyl dichloride in 100 mL of THF. The resulting solution is stirred at RT for 20 h and the solvent removed in vacuo. Purification of the resulting brown oil by silica gel flash column chromatography afforded 7.5 g of the title compound as a light tan solid: $^1$H NMR (CDCl$_3$, 300 MHz) δ7.44–6.86 (m, 13H), 5.02 (m, 1H), 4.38 (d, 1H, J=16.6), 4.04 (d, 1H, J=16.6), 3.84 (s, 3H), 2.55 (m, 2H), 1.10 (d, 6H, J=6.8); R$_f$=0.15 in hexane/EtOAc 1/1.

Intermediate 5

2-(2,4-dioxo-3-Allyl-5-phenyl-2,3,4,5-tetrahydro-benzo[b]1,4]diazepin-1-yl)-N-isopropyl-N-phenyl acetamide To a stirring solution of 4.43 g (10.4 mmol) of 2-(2,4-Dioxo-5-phenyl-2,3,4,5-tetrahydro-benzo[b][1,4]diazepin-1-yl)-N-isopropyl-N-phenyl acetamide, prepared as in Intermediate 1, in 20 mL of DMF at 0° C. is added in one portion 456 mg (11.4 mmol, 1.1 equiv) of sodium hydride (60% dispersion in oil). The resulting solution is stirred at 0° C. for 20 min, during which time gas evolution is observed, and then a solution of 0.90 mL (10.4 mmol) of allyl bromide in 10 mL of DMF is added dropwise over 20 min. The resulting brown solution is stirred 30 min at 0° C. and then at RT for 18 h. The reaction is quenched by careful addition of 10 mL of H$_2$O and the solvent is removed in vacuo. The residue is poured into 30 mL of H$_2$O and extracted with EtOAc (3×30 mL). The organic layers are washed with brine (1×30 mL), dried (MgSO$_4$) and the solvent is removed in vacuo. Purification of the brown residue by silica gel flash column chromatography using petroleum ether/EtOAc 7/3 as eluent afforded 2.91 g of the title compound as an off-white solid: $^1$H NMR (CDCl$_3$, 300 MHz) δ7.46–7.08 (m, 13H), 6.94 (d, 1H, J=8.1), 5.92 (m, 1H), 5.02 (m, 2H), 4.34 (d, 1H, 4.04 (d, 1H), 3.43 (t, 1H), 2.78 (m, 2H), 1.11 (m, 6H); low resolution MS (FAB) m/e 468 (MH$^+$).

Intermediate 6

2-(3-Allyl-3-methyl-2,4-dioxo-5-phenyl-2,3,4,5-tetrahydro-benzo[b][1,4]diazepin-1-yl)-N-isopropyl-N-phenyl acetamide To a stirring solution of 1.50 g (3.20 mmol) of 2-(2,4-Dioxo-5-phenyl-2,3,4,5-tetrahydro-benzo[b][1,4]diazepin-1-yl)-N-isopropyl-N-phenyl acetamide, prepared as in Intermediate 1, in 15 mL of DMF at 0° C. is added 192 mg (4.81 mmol, 1.5 equiv) of sodium hydride (60% dispersion in mineral oil). The resulting solution is stirred 15 min, then 360 μL (5.76 mmol, 1.8 equiv) of methyl iodide is added. The reaction mixture is stirred 3 h at RT then quenched with 10 mL H$_2$O. The DMF is removed in vacuo, and the residue is dissolved in 100 mL Et$_2$O and washed with 100 mL H$_2$O. The organic layer is dried (MgSO$_4$) and the solvents removed in vacuo to afford 1.61 g of the title compound as a white solid which is used without further purification: $^1$H NMR (DMSO-d$_6$, 300 MHz, mixture of conformers) δ7.56–7.11 (m, 13H), 6.74 (m, 1H), 5.85 (m, 0.34 H), 5.61 (m, 0.66H), 5.10–4.69 m, 2.34H), 4.20 (m, 1.66H), 1.94 (d, 2H, J=7.3), 1.21 (s, 2H), 0.98 (m, 6H), 0.82 (s, 1H). R$_f$=0.66 in hexane/EtOAc 1/1.

Intermediate 7

[1-(isopropyl-phenyl-carbamoylmethyl)-3-methyl-2,4-dioxo-5-phenyl-2,3,4,5-tetrahydro-1H-benzo[b][1,4]diazepin-3-yl]-acetic acid To a rapidly stirring biphasic solution of 1.03 g (2.14 mmol) of 2-(3-Allyl-3-methyl-2,4-dioxo-5-phenyl-2,3,4,5-tetrahydro-benzo[b][1,4]diazepin-1-yl)-N-isopropyl-N-phenyl acetamide, prepared as in Intermediate 6, in 50 mL of CCl$_4$ and 25 mL of H$_2$O is added 44 mg (0.21 mmol, 0.1 equiv) of ruthenium (III) chloride hydrate, followed by 4.58 g (21.40 mmol, 10.0 equiv) of sodium periodate. The resulting black solution is stirred rapidly at RT for 24 h, then diluted with 100 mL of H$_2$O and extracted with EtOAc (3×200 mL). The organics are washed with brine (1×150 mL), sat. NaHSO$_3$ (1×150 mL), dried (MgSO$_4$), and the solvent removed in vacuo. Purification of the residue by silica gel flash column chromatography using dichloromethane/methanol 15/1 as eluent afforded 982 mg of the title compound as a grey solid: $^1$H NMR (CDCl$_3$, 300 MHz, mixture of conformations) δ7.53–7.09 (m, 13H), 6.86 (m, 1H), 5.02 (m, 1H), 4.34 (d, 1H), 4.41 (m, 1H), 4.08 (m, 1H), 3.27 (d, 1H ), 3.03 (d, 1H), 1.24 (s, 3H), 1.11 (m, 6H); low resolution MS (FAB) m/e 500 (MH$^+$), 482, 365.

Intermediate 8

[1-(Isopropyl-(4-methoxy-phenyl)-carbamoylmethyl)-3-methyl-2,4-dioxo-5-phenyl-2,3,4,5-tetrahydro-1H-benzo[b][1,4]diazepin-3-yl]-acetic acid To a rapidly stirring biphasic solution of 12.0 g (23.45mmol) of 2-(3-Allyl-3-methyl-2,4-dioxo-5-phenyl-2,3,4,5-tetrahydro-benzo[b][1,4]diazepin-1-yl)-N-isopropyl-N-(4-methoxy-phenyl) acetamide in 600 mL of CCl$_4$ and 300 mL of H$_2$O is added 500 mg (2.34 mmol, 0.1 equiv) of ruthenium (III) chloride hydrate, followed by 50.0 g (0.23 mol, 10.0 equiv) of sodium periodate portionwise over 15 min. The resulting black solution is stirred rapidly at RT for 22 h, filtered through a pad of Celite, then diluted with 100 mL of H$_2$O and extracted with EtOAc (3×600 mL). The organics are washed with brine (1×450 mL), sat. NaHSO$_3$ (1×450 mL), dried (MgSO$_4$), and the solvent removed in vacuo. Purification of the residue by silica gel flash column chromatography using dichloromethane/methanol 15/1 as eluent afforded 6.58 g of the title compound as a grey solid: $^1$H NMR (CDCl$_3$, 300 MHz, mixture of conformations) δ7.46–6.85 (m, 13H), 5.02 (m, 1H), 4.54–4.25 (m, 1H), 4.10 (m, 1H), 3.91 (s, 3H), 3.27 (d, 1H), 3.00 (d, 1H), 1.27 (s, 3H), 1.11 (m, 6H); R$_f$=0.30 in CH$_2$Cl$_2$/MeOH 9/1.

Intermediate 9

N-Isopropyl-2-[3-methyl-2,4-dioxo-3-(2-oxoethyl)-5-phenyl-2,3,4,5-tetrahydro-benzo[b][1,4]diazepin-1-yl]-N-phenyl acetamide To a stirring solution of 200 mg (0.42 mmol) of 2-(3-Allyl-3-methyl-2,4-dioxo-5-phenyl-2,3,4,5-tetrahydro-benzo[b][1,4]diazepin-1-yl)-N-isopropyl-N-phenyl acetamide, prepared as in Intermediate 6, in 10 mL of 1,4-dioxane and 3 mL of H$_2$O is added 0.5 mL of a 4% solution of osmium tetraoxide in H$_2$O. The resulting solution is stirred 1 min, then 220 mg (1.03 mmol, 2.5 equiv) of sodium periodate is added. The reaction mixture is stirred 3 h at RT then poured into 25 mL of EtOAc and extracted with H$_2$O (1×25 mL), sat. NaHSO$_3$ (1×25 mL), dried (MgSO$_4$), and the solvents removed in vacuo. Purification of the crude material by silica gel flash column chromatography using hexane/EtOAc 1/1 as eluent afforded 141 mg of the title compound as a white foam: $^1$H NMR (CDCl$_3$, 300 MHz, mixture of conformations) δ9.65 (s, 0.8H), 9.40 (s, 0.2H), 7.50–7.03 (m, 13H), 6.83 (d, 0.8H), 6.75 (d, 0.2H), 5.07 (m, 0.8H), 4.96 (m, 0.2H), 4.41 (d, 1H), 4.02 (d, 1H), 2.96 (dd, 2H), 1.62 (s, 0.6H), 1.17 (s, 2.4H), 1.09 (m, 6H); low resolution MS (FAB) m/e 619 (MH$^+$), 574.

Intermediate 10

2-(3-Allyl-3-methoxy-2,4-dioxo-5-phenyl-2,3,4,5-tetrahydro-benzo[b][1,4]diazepin-1-yl)-N-isopropyl-N-(4-methoxy-phenyl) acetamide To a stirring solution of 1.50 g (7.10 mmol) of 2-allyl-2-methoxy-propandioyl dichloride in 50 mL of THF at 0° C. is added dropwise over 2 min a solution of 1.85 g (4.74 mmol) of N-isopropyl-N-(4-methoxy-phenyl)-2-(2-phenylamino-phenylamino) acetamide, prepared as in Intermediate 43, in 20 mL of THF. The resulting solution is stirred at RT for 15 min then refluxed for 18 h. After cooling to RT the solvent is removed in vacuo and the crude product purified by silica gel flash column chromatography using hexane/EtOAc 3/1 as eluent to afford 1.46 g of the title compound as a clear, colorless oil: $^1$H NMR (CDCl$_3$, 300 MHz) δ7.40–6.88 (m, 12H), 6.78 (d, 1H), 5.92 (m, 1H), 5.10 (m, 2H), 4.46 (d, 1H), 3.80 (s, 3H), 3.64 (m, 1H), 3.02 (s, 3H), 1.88 (m, 1H), 1.75 (m, 1H), 1.13 (m, 6H); low resolution MS (FAB) m/e 528 (MH$^+$).

Intermediate 11

[1-(Isopropyl-(4-methoxy-phenyl)-carbamoylmethyl)-3-methoxy-2,4-dioxo-5-phenyl-2,3,4,5-tetrahydro-1H-benzo[b][1,4]diazepin-3-yl]-acetic acid To a rapidly stirring biphasic solution of 700 mg (1.33 mmol) of 2-(3-Allyl-3-methoxy-2,4-dioxo-5-phenyl-2,3,4,5-tetrahydro-benzo[b][1,4]diazepin-1-yl)-N-isopropyl-N-(4-methoxy-phenyl) acetamide, prepared as in Intermediate 10, in 30 mL of CCl$_4$ and 15 mL of H$_2$O is added 28 mg (0.13 mmol, 0.1 equiv) of ruthenium (III) chloride hydrate, followed by 2.84 g (13.3 mmol, 10.0 equiv) of sodium periodate portionwise over 5 min. The resulting black solution is stirred rapidly at RT for 16 h, filtered through a pad of Celite, then diluted with 20 mL of H$_2$O and extracted with EtOAc (3×60 mL). The organics are washed with brine (1×50 mL), sat. NaHSO$_3$ (1×50 mL), dried (MgSO$_4$), and the solvent removed in vacuo. Purification of the residue by silica gel flash column chromatography using dichloromethane/methanol 15/1 as eluent afforded 500 mg of the title compound as a grey solid: $^1$H NMR (CDCl$_3$, 300 MHz) δ7.42–6.91 (m, 13H), 5.04 (m, 1H), 4.42 (d, 1H), 4.00 (d, 1H), 3.82 (s, 3H), 3.43 (dd, 2H), 3.17 (s, 3H), 1.15 (m, 6H); R$_f$=0.33 in CH$_2$Cl$_2$/MeOH 9/1.

Intermediate 12

2-(N-tert-butoxycarbonyl)-indolylmethanol

To a stirring solution of 2.5 g (13.21 mmol) of Ethyl indolyl-2-carboxylate in 50 mL of THF at 0° C. is added 580 mg (14.53 mmol, 1.1 equiv) of sodium hydride (60% in oil) in portions. The reaction mixture is stirred 10 min at 0° C., during which time gas evolution is observed, and then a solution of 3.17 g (14.53 mmol, 1.1 equiv) of di-tert-butylpyrocarbonate in 10 mL of THF is added. The resulting solution is stirred 2 h at RT and then poured into 100 mL of Et$_2$O and extracted with H$_2$O (1×100 mL). The organics are dried (MgSO$_4$) and the solvent is removed in vacuo. The resulting crude ester is dissolved in 50 mL of dichloromethane and cooled to −78° C., and 33.0 mL (33.0 mmol, 2.5 equiv) of 1.0M solution of DIBAL-H in hexane is added dropwise over 10 min. The resulting solution is allowed to slowly warm to RT over 1 h, then quenched by careful addition of 5 mL of methanol. The reaction mixture is poured into 200 mL of Et$_2$O and extracted with H$_2$O (2×100 mL). The organic layer is separated, dried (MgSO$_4$), and the solvent removed in vacuo. Purification of the crude material by silica gel flash column chromatography using hexane/EtOAc 5/1 as eluent afforded 1.64 g of the title compound as a light golden oil: $^1$H NMR (CDCl$_3$, 300 MHz) δ7.96(d, 1H), 7.52 (d, 1H), 7.25 (m, 2H), 6.59 (s, 1H), 4.80 (d, 2H), 3.73 (t, 1H), 1.77 (s, 9H); R$_f$=0.20 in hexane/EtOAc 2/1.

Intermediate 13 2-Bromomethyl (N-tert-butoxycarbonyl) indole

To a stirring solution of 964 mg (3.66 mmol, 1.1 equiv) of triphenylphosphine in 15 mL of acetonitrile at 0° C. is added 180 mL (3.48 mmol, 1.05 equiv) of Br$_2$. The resulting orange-yellow suspension is stirred 10 min at 0° C., then a solution of 860 mg (3.30 mmol) of 2-(N-tert-butoxycarbonyl)-indolylmethanol, prepared as in Intermediate 12, in 5 mL of acetonitrile is added over 2 min. The resulting solution is stirred 20 min at RT, and then the reaction mixture is poured into 50 mL of Et$_2$O and extracted with sat. NaHCO$_3$ (1×50 mL). The organic layer is separated, dried (MgSO$_4$), and the solvent is removed in vacuo. Purification of the residue by silica gel flash column chromatography using hexane/EtOAc 20/1 as eluent afforded 596 mg of the title compound as a clear, tannish oil: $^1$H NMR (CDCl$_3$, 300 MHz) δ8.18 (d, 1H), 7.50 (d, 1H), 7.28 (m, 2H), 6.72 (s, 1H), 4.95 (s, 2H), 1.77 (s, 9H); R$_f$=0.62 in hexane/EtOAc 5/1.

Intermediate 14

1-Benzyl-1H-indazole-3-carboxylic acid benzyl ester

To a stirring solution of 750 mg (4.62 mmol) of 1H-Indazole-3-carboxylic acid (Snyder, H. R.; Thompson, C. B.; Hinman, R. L. *J. Am. Chem. Soc.* 1952, 74, 2009) in 20 mL of DMF is added 1.92 g (13.86 mmol, 3.0 equiv) of K$_2$CO$_3$, followed by 1.43 mL of benzyl bromide. The reaction mixture is stirred 15 min at RT then heated at 60° C. for 16 h. The reaction is cooled to RT, poured into 100 mL 1N HCl, and extracted with EtOAc (2×100 mL). The organic layers are washed with H$_2$O (2×100 mL), dried (MgSO$_4$), and the solvent removed in vacuo. Purification of the crude material by silica gel flash column chromatography using a gradient elution of hexane/EtOAc 20/1 to 2/1 afforded 735 mg of the title compound as a yellow oil which later solidified: $^1$H NMR (CDCl$_3$, 300 MHz) δ8.20 (d, 1H), 7.55 (d, 2H), 7.40–7.18 (m, 11H), 5.70 (s, 2H), 5.57 (s, 2H); R$_f$=0.15 in hexane/EtOAc 10/1.

Intermediate 15

(1-Benzyl-1H-indazol-3-yl) methanol

To a stirring solution of 735 mg (2.15 mmol) of 1-Benzyl-1H-indazole-3-carboxylic acid benzyl ester, prepared as in Intermediate 14, in 15 mL dichloromethane at −78° C. is added dropwise over 5 min a solution of 5.4 mL (5.4 mmol, 2.5 equiv) of a 1.0M solution of DIBAL-H in hexane. The resulting solution is allowed to slowly warm to RT over a 4 h period then quenched by careful addition of 5 mL of H$_2$O. The reaction mixture is poured into 100 mL of EtOAc and extracted with 1N HCl (1×100 mL), dried (MgSO$_4$), and the solvent removed in vacuo. Purification of the crude material by silica gel flash column chromatography using hexane/EtOAc 1/1 as eluent afforded 448 mg of the title compound as a pale yellow solid: $^1$H NMR (CDCl$_3$, 300 MHz) δ7.80

(d, 1H), 7.40–7.08 (m, 8H), 5.50 (s, 2H), 5.04 (d, 2H), 2.24 (m, 1H); $R_f$=0.50 in hexane/EtOAc 1/1.

Intermediate 16

1-Benzyl-3-bromomethyl-1H-indazole

To a stirring solution of 550 mg (2.09 mmol, 1.3 equiv) of triphenylphosphine in 10 mL of acetonitrile at 0° C. is added 0.1 mL (1.93 mmol, 1.2 equiv) of $Br_2$. The resulting orange-yellow suspension is stirred 10 min at 0° C., then a solution of 383 mg (1.61 mmol) of (1-Benzyl-1H-indazol-3-yl) methanol, prepared as in Intermediate 15, in 5 mL of acetonitrile is added over 2 min. The resulting solution is stirred 1 h at RT, and the solvent is removed in vacuo. Purification of the residue by silica gel flash column chromatography using hexane/EtOAc 5/1 as eluent afforded 305 mg of the title compound as a white solid: $^1$H NMR (CDCl$_3$, 300 MHz) δ7.82 (d, 1H), 7.40–7.16 (m, 8H), 5.59 (s, 2H), 4.90 (s, 2H); $R_f$=0.75 in hexane/EtOAc 2/1.

Intermediate 17

3-(2-Bromo-phenoxy)-acrylic acid methyl ester

To a stirring solution of 972 mg (11.56 mmol) of ethyl propiolate in 20 mL of THF at 0° C. is added a solution of 1.61 mL (11.56 mmol) of triethylamine in 5 mL of THF, followed by a solution of 2.0 g (11.56 mmol) of 2-Bromophenol in 5 mL of THF. The resulting clear orange-brown solution is stirred 5 h at 0° C., then poured into 100 mL of Et$_2$O and extracted with H$_2$O (1×100 mL). The organic layer is separated and washed with sat. Na$_2$CO$_3$ (1×100 mL), dried (MgSO$_4$), and the solvent removed in vacuo to provide 2.97 g of the title compound as an orange oil which is used without any further purification: $^1$H NMR (CDCl$_3$, 300 MHz) δ7.71 (d, 1H, J=12.3), 7.61 (d, 1H, J=7.4), 7.37–7.08 (m, 3H), 5.47 (d, 1H, J=12.3), 3.72 (s, 3H); $R_f$=0.40 in hexane/EtOAc 5/1.

Intermediate 18

Benzofuran-3-carboxylic acid methyl ester

A stirring solution of 2.43 g (9.45 mmol) of 3-(2-Bromo-phenoxy) acrylic acid methyl ester, prepared as in Intermediate 17, 1.98 g (7.56 mmol, 0.8 equiv) of triphenylphosphine, 794 mg (9.45 mmol, 1.0 equiv) of NaHCO$_3$, and 848 mg (3.78 mmol, 0.4 equiv) of palladium (II) acetate in 25 mL of DMF is heated to 110° C. for 16 h. After cooling to RT, the reaction mixture is diluted with 100 mL of Et$_2$O and extracted with H$_2$O (1×100 mL), dried (MgSO$_4$), and the solvents removed in vacuo. Purification of the crude material by silica gel flash column chromatography afforded 650 mg of the title compound as a yellow oil: $^1$H NMR (CDCl$_3$, 300 MHz) δ8.22 (s, 1H), 8.06 (m, 1H), 7.55 (m, 1H), 7.37 (m, 2H), 3.95 (s, 3H); $R_f$=0.50 in hexane/EtOAc 5/1.

Intermediate 19

3-Hydroxymethylbenzofuran

To a stirring solution of 650 mg (3.69 mmol) of Benzofuran-3-carboxylic acid methyl ester, prepared as in Intermediate 18, in 25 mL dichloromethane at −78° C. is added dropwise over 5 min a solution of 9.22 mL (9.22 mmol, 2.5 equiv) of a 1.0M solution of DIBAL-H in hexane. The resulting solution is allowed to slowly warm to RT over a 4 h period then quenched by careful addition of 5 mL of H$_2$O. The reaction mixture is poured into 100 mL of EtOAc and extracted with 1N HCl (1×100 mL), dried (MgSO$_4$), and the solvent removed in vacuo. Purification of the crude material by silica gel flash column chromatography using hexane/EtOAc 4/1 as eluent afforded 444 mg of the title compound as a pale yellow oil: $^1$H NMR (CDCl$_3$, 300 MHz) δ7.66 (d, 1H), 7.60 (s, 1H), 7.49 (d, 1H), 7.29 (m, 2H), 4.82 (d, 2H), 1.70 (m, 1H); $R_f$=0.17 in hexane/EtOAc 5/1.

Intermediate 20

3-Bromomethylbenzofuran

To a stirring solution of 912 mg (3.48 mmol, 1.2 equiv) of triphenylphosphine in 5 mL of CCl$_4$ at 0° C. is added 165 μL (3.19 mmol, 1.1 equiv) of Br$_2$. The resulting orange-yellow suspension is stirred 10 min at 0° C., then a solution of 430 mg (2.90 mmol) of 3-hydroxymethylbenzofuran, prepared as in Intermediate 19, in 5 mL of CCl$_4$ is added over 2 min. The resulting solution is stirred 1.5 h at RT, and the solvent is removed in vacuo. Purification of the residue by silica gel flash column chromatography using hexane/EtOAc 20/1 as eluent afforded 500 mg of the title compound as a clear, colorless oil: $^1$H NMR (CDCl$_3$, 300 MHz) δ7.71 (m, 2H), 7.50 (m, 1H), 7.37 (m, 2H), 4.62 (s, 2H); $R_f$=0.67 in hexane/EtOAc 5/1.

Intermediate 21

1-Bromomethylnaphthalene

To a stirring solution of 912 mg (3.48 mmol, 1.2 equiv) of triphenylphosphine in 10 mL of CCl$_4$ at 0° C. is added 180 μL (3.48 mmol, 1.2 equiv) of Br$_2$. The resulting orange-yellow suspension is stirred 10 min at 0° C., then a solution of 500 mg (3.16 mmol) of 1-Naphthalenemethanol in 5 mL of CCl$_4$ is added over 2 min. The resulting solution is stirred 1.5 h at RT, and the solvent is removed in vacuo. Purification of the residue by silica gel flash column chromatography using hexane/EtOAc 10/1 as eluent afforded 670 mg of the title compound as a clear, colorless oil: $^1$H NMR (CDCl$_3$, 300 MHz) δ8.18 (d, 1H), 7.83 (m, 2H), 7.63–7.38 (m, 4H), 4.98 (s, 2H); $R_f$=0.65 in hexane/EtOAc 5/1.

Intermediate 22

2-(1-Benzyl-1H-indazol-3-ylmethyl)-2-methoxy-propanedioc acid dimethyl ester To a stirring solution of 183 mg (1.13 mmol) of Dimethyl methoxymalonate in 5 mL of DMF at 0° C. is added 1.35 mL (1.35 mmol, 1.2 equiv) of a 1.0M solution of NaN(TMS)$_2$ in THF. The resulting solution is stirred 5 min, then a solution of 340 mg (1.13 mmol, 1.0 equiv) of 1-Benzyl-3-bromomethyl-1H-indazole in 2 mL of DMF is added. The reaction mixture is stirred 1 h at RT, then poured into 50 mL of Et$_2$O and extracted with H$_2$O (2×50 mL). The organic layer is separated, dried (MgSO$_4$) and the solvent removed in vacuo. Purification of the crude material by silica gel flash column chromatography using hexane/EtOAc 4/1 as eluent afforded 350 mg of the title compound as a clear, colorless oil: $^1$H NMR (CDCl$_3$, 300 MHz) δ7.68 (d, 1H, J=8.0), 7.31–7.07 (m, 8H), 5.54 (s, 2H), 3.80 (s, 2H), 3.72 (s, 6H), 3.51 (s, 3H); $R_f$=0.18 in hexane/EtOAc 5/1.

Intermediate 23

2-(1-Benzyl-1H-indazol-3-ylmethyl)-2-methoxy-propanedioc acid

A solution of 350 mg (0.92 mmol) of 2-(1-Benzyl-1H-indazol-3-ylmethyl)-2-methoxy-propanedioc acid dimethyl ester, prepared as in Intermediate 22, and 0.6 mL of 6N NaOH in 10 mL of a 9/1/1 mixture of absolute EtOH/$H_2O$/THF is stirred 22 h at RT. The solvent is removed in vacuo and the residue dissolved in 15 mL $H_2O$, cooled to 0° C., and acidified to pH 1 with 1N HCl. The reaction mixture is then extracted with EtOAc (2×30 mL) and the organic layers are washed with brine (1×30 mL), dried ($MgSO_4$), and the solvent removed in vacuo to afford 324 mg of the title compound as a light pink solid which is used without further purification: $^1$H NMR ($CDCl_3$, 300 MHz) δ7.62 (d, 1H, J=8.0), 7.31–6.86 (m, 8H), 5.51 (s, 2H), 3.70 (s, 2H), 3.19 (s, 3H); $R_f$=0.62 in $MeCN/H_2O$ 3/2.

Intermediate 24

(1-Methyl-1H-indazol-3-yl) methanol

To a stirring solution of 440 mg (2.31 mmol) of 1-Methyl-1H-indazole-3-carboxylic acid methyl ester (Fludzinski, P. et. al. *J. Med. Chem.* 1987, 30, 1535) in 10 mL dichloromethane at −78° C. is added dropwise over 5 min a solution of 5.8 mL (5.8 mmol, 2.5 equiv) of a 1.0M solution of DIBAL-H in hexane. The resulting solution is allowed to slowly warm to RT over a 3 h period then quenched by careful addition of 5 mL of $H_2O$. The reaction mixture is poured into 100 mL of EtOAc and extracted with 1N HCl (1×100 mL), dried ($MgSO_4$), and the solvent removed in vacuo. Purification of the crude material by silica gel flash column chromatography using hexane/EtOAc 1/1 as eluent afforded 340 mg of the title compound as a pale yellow oil: $^1$H NMR ($CDCl_3$, 300 MHz) δ7.80 (d, 1H), 7.42–7.12 (m, 3H), 5.02 (d, 2H), 4.00 (s, 3H), 2.27 (m, 1H); $R_f$=0.25 in hexane/EtOAc 1/1.

Intermediate 25

1-Methyl-3-bromomethyl-1H-indazole

To a stirring solution of 692 mg (2.64 mmol, 1.3 equiv) of triphenylphosphine in 10 mL of acetonitrile at 0° C. is added 125 μL (2.44 mmol, 1.2 equiv) of $Br_2$. The resulting orange-yellow suspension is stirred 10 min at 0° C., then a solution of 330 mg (2.03 mmol) of (1-Methyl-1H-indazol-3-yl) methanol, prepared as in Intermediate 24, in 5 mL of acetonitrile is added over 2 min. The resulting solution is stirred 1.5 h at RT, and the solvent is removed in vacuo. Purification of the residue by silica gel flash column chromatography using hexane/EtOAc 5/1 as eluent afforded 185 mg of the title compound as a yellow solid: $^1$H NMR ($CDCl_3$, 300 MHz) δ7.82 (d, 1H), 7.40 (m, 2H), 7.22 (m, 1H), 4.82 (s, 2H), 4.03 (s, 3H); $R_f$=0.87 in hexane/EtOAc 1/1.

Intermediate 26

{1-[Isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid A solution of 500 mg (1.0 equiv, 0.0011 mol) 2-(2,4-dioxo-5-phenyl-2,3,4,5-tetrahydro-benzo[b][1,4]diazepin-1-yl)-N-isopropyl-N-(4-methoxy-phenyl)-acetamide, prepared as in Intermediate 4, in 2 mL of dry DMF is cooled to 0° C. with an ice water bath. 48 mg (1.1 equiv, 0.0012 mol) of solid NaH (60% in oil) is added and the mixture is stirred at 0° C. for 20 min. To the resulting solution is added dropwise 0.095 mL (1.0 equiv, 0.0011 mol) of allyl bromide in 1.3 mL of dry DMF. The reaction is stirred at 0° C. for 30 min, allowed to warm to RT and stirred 3.5 h. To the resulting solution is added 50 mL of $H_2O$, acidified with 1N HCl and extracted with ethyl acetate (2×100 mL). The organic layer is dried over $MgSO_4$ and concentrated in vacuo to yield 490 mg (90%) of a yellow solid. The crude product is dissolved in 30 mL of $CCl_4$, 15 mL of $H_2O$ is added followed by 20 mg (0.1 equiv, 0.098 mmol) of $RuCl_3$ and 2.1 g (10 equiv, 9.8 mmol) of solid $NaIO_4$. The reaction is stirred rapidly for 16 h at RT. The resulting solution is filtered through celite and $H_2O$ (20 mL) is added. The layers are separated and the aqueous layer is extracted with ethyl acetate (2×30 mL). The organics are washed with sat. sodium bisulfite (1×10 mL) and brine (1×10 mL), dried over $MgSO_4$ and the solvent is removed in vacuo. The resulting brown oil is purified by silica gel flash chromatography using methylene chloride/methanol 9/1 as eluent to yield 130 mg (26%) of the title compound as a white solid: $^1$H NMR ($CDCl_3$, 300 MHz) δ7.25–6.82 (m, 13H), 5.20–4.34 (m, 3H), 3.88–3.78 (m, 4H), 2.79 (m, 2H), 1.20–0.86 (m, 6H); $R_f$=0.21 in $CH_2Cl_2$/MeOH 9/1.

Intermediate 27

{3-(Benzyloxycarbonyl-methyl)-1-[isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid benzyl ester 1.23 mL (14.1 mmol, 4.9 equiv) of oxalyl chloride is added dropwise to a suspension of 1.16 g (2.89 mmol, 1.0 equiv) of bis-(benzyloxycarbonyl-methyl)-malonic acid and 14 mL (0.18 mmol, 0.06 equiv) of DMF in 40 mL of $CH_2Cl_2$. The mixture is stirred at RT for 100 min to give a yellow solution, and then concentrated in vacuo to a light brown oil. The crude product is dissolved in 60 mL of THF, cooled in an ice/water bath, and a solution of 0.94 g (2.41 mmol, 0.83 equiv) of N-isopropyl-N-(4-methoxy-phenyl)-2-(2-phenylamino-phenylamino) acetamide, prepared as in Intermediate 43, in 25 mL of THF is added dropwise over 5 min. The resulting brown solution is heated at reflux for 20 h, and then concentrated in vacuo. The residue is diluted with 100 mL of 1N HCl and extracted with EtOAc (×3). The organic extract is washed with 1N HCl and brine, dried over $MgSO_4$ and concentrated in vacuo. Purification by silica gel flash chromatography using 30–50% EtOAc/hexane as eluent followed by recrystallization from 1:1 EtOAc/hexane gave 0.54 g of the title compound as a white powder: $^1$H NMR ($CDCl_3$, 300 MHz) δ7.4–6.9 (m, 23H), 6.96 (d, 1H, J=9), 5.2–4.9 (m, 6H), 4.4 (m, 1H), 4.12 (m, 1H), 3.86 (s, 3H), 4.43 (d, 1H, J=18), 3.18 (dd, 2H, J=6, 17), 2.80 (d, 1H, J=18), 1.02 (dd, 6H, J=6.5, 11); low resolution MS (FAB) m/e 646 (MH$^+$).

Intermediate 28

{3-(Benzyloxycarbonyl-methyl)-1-[isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid (7)

450 mg (0.6 mmols) of {3-(Benzyloxycarbonyl-methyl)-1-[isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid benzyl ester, prepared as in Intermediate 27, is dissolved in 100 mL of ethyl acetate and 45 mg of 10% Pd/C is added. The reaction mixture is then kept under a hydrogen atmosphere with stirring for 2.5 h. The solution is then filtered through celite and the solvent is removed in vacuo. The resulting white solid is purified by reverse phase MPLC in methanol/water 70/30 as eluent to afford 130 mg (32%) of the title compound as a white solid: $^1$H NMR (CDCl$_3$, 300 MHz) δ7.38–6.54 (m, 18H), 5.29–4.88 (m, 4H), 4.23 (m, 1H), 3.83 (d, J=7.5, 3H), 3.23–2.69 (m, 4H), 1.08–1.02 (m, 6H); low resolution MS m/e 664.

Intermediate 29

[1-(Isopropyl-phenyl-carbamoylmethyl)-3-ethyl-2,4-dioxo-5-phenyl-2,3,4,5-tetrahydro-1H-benzo[b][1,4]diazepin-3-yl]acetic acid 500 mg (1.0 equiv, 1.1 mmol) 2-(2,4-dioxo-3-allyl-5-phenyl-2,3,4,5-tetrahydro-benzo[b][1,4]diazepin-1-yl)-N-isopropyl-N-phenyl-acetamide, prepared as in Intermediate 5, is dissolved in 4 mL of dry DMF and cooled to 0° C. with an ice/water bath. 66 mg (1.5 equiv, 1.7 mmol) of solid NaH (60% in oil) is added and the mixture is stirred for 20 min at 0° C. 0.16 mL (1.8 equiv, 2.0 mmol) of ethyl iodide is added dropwise at 0° C. The reaction is allowed to warm to RT and stirred 2.5 h. To the resulting solution is added 50 mL of H$_2$O, and the solvent is removed in vacuo. The aqueous residue is acidified with 1N HCl and extracted with ethyl acetate (2×100 mL). The organic layer is dried over MgSO$_4$ and concentrated in vacuo. The crude product is dissolved in 30 mL of CCl$_4$ and 15 mL of H$_2$O, 23 mg (0.1 equiv, 0.11 mmol) of RuCl3 and 2.35 g (10 equiv, 11 mmol) of solid NaIO$_4$ are added. The reaction is stirred rapidly for 4h at RT. The resulting mixture is filtered through celite and H$_2$O (20 mL) is added. The layers are separated and the aqueous layer is extracted with ethyl acetate (2×30 mL). The combined organics are washed with sat. sodium bisulfite (1×10 mL) and brine (1×10 mL), dried over MgSO$_4$ and the solvent is removed in vacuo. The resulting solid is purified by silica gel flash chromatography using methylene chloride/methanol 9/1 as eluent to yield 290 mg (51%) of the title compound as a solid: $^1$H NMR (CDCl$_3$, 300 MHz) δ7.47–6.09 (m, 13H), 6.84 (d, J=7.8, 1H) 5.06–5.00 (m, 1H), 4.39–4.03 (m, 2H), 3.25–3.12 (m, 2H), 1.55–1.51 (m, 2H), 1.12–1.08 (t, J=6.5, 6H), 0.91–0.86 (t, J=7.3, 3H); low resolution MS (FAB) m/e 514 (MH$^+$).

Intermediate 30

[1-(Isopropyl-phenyl-carbamoylmethyl)-3-benzyl-2,4-dioxo-5-phenyl-2,3,4,5-tetrahydro-1H-benzo[b][1,4]diazepin-3-yl]acetic acid 500 mg (1.0 equiv, 1.1 mmol) 2-(2,4-dioxo-3-allyl-5-phenyl-2,3,4,5-tetrahydro-benzo[b][1,4]diazepin-1-yl)-N-isopropyl-N-phenyl-acetamide, prepared as in Intermediate 5, is dissolved in 4 mL of dry DMF and cooled to 0° C. with an ice/water bath. 66 mg (1.5 equiv, 1.7 mmol) of solid NaH (60% in oil) is added and the mixture is stirred for 20 min at 0° C. 0.23 mL (1.8 equiv, 2.0 mmol) of benzyl bromide is added dropwise at 0° C. The reaction is allowed to warm to RT and stirred 3 h. To the resulting solution is added 50 mL of H$_2$O, and then the solvent is removed in vacuo. The aqueous residue is acidified with 1N HCl and extraction with ethyl acetate (2×100 mL). The organic layer is dried over MgSO$_4$ and concentrated in vacuo to a pale yellow solid; low resolution MS (FAB) m/e 558 (MH$^+$). The crude product is dissolved in 20 mL of CCl$_4$, 10 mL of H$_2$O, 15 mg (0.1 equiv, 0.07 mmol) of RuCl$_3$ and 1.5 g (10 equiv, 7 mmol) of solid NaIO$_4$ are added. The reaction is stirred rapidly for 16 h at room temperature. The resulting mixture is filtered through celite and H$_2$O (20 mL) is added. The layers are separated and the aqueous layer is extracted with ethyl acetate (2×30 mL). The combined organics are washed with sat. sodium bisulfite (1×10 mL) and brine (1×10 mL), dried over MgSO$_4$ and the solvent is removed in vacuo. The resulting brown solid is purified by silica gel flash chromatography using methylene chloride/methanol 9/1 as eluent to yield 135 mg the title compound as a white solid: $^1$H NMR (CDCl$_3$, 300 MHz) δ7.49–7.12 (m, 18H), 6.89 (d, J=8.1, 1H) 5.09–5.04 (m, 1H), 4.43–4.10 (m, 2H), 3.03–3.01 (m, 4H), 1.14–1.10 (t, J=6.8, 6H); low resolution MS (FAB) m/e 576 (MH$^+$).

Intermediate 31

2-(3-allyl-2,4-dioxo-5-phenyl-3-methoxymethyl-2,3,4,5-tetrahydro-benzo[b][1,4]diazepin-1-yl)-N-isopropyl-N-(4-methoxy-phenyl)-acetamide A solution of 1.0 mL (1.0 equiv, 0.005 mol) of diethyl allylmalonate in 15 mL of dry THF is cooled to 0° C. with an ice/water bath. 210 mg (1.05 equiv, 0.0052 mol) of solid NaH (60% in oil) is added and the mixture stirred for 20 min at 0° C. To the resulting solution is added dropwise 0.305 mL (1.05 equiv, 0.0052 mols) of methoxymethyl chloride at 0° C. The reaction is stirred at 0° C. for 20 min., allowed to warm to RT and stirred 16 h. the reaction mixture is filtered to remove solids and the solvent from the filtrate in vacuo. 50 mL of H$_2$O is added and the mixture extracted with ethyl acetate (2×80 mL). The organic layer is dried over MgSO$_4$ and concentrated in vacuo. The crude product is dissolved in 20 mL of ethanol/water 9/1 and cooled to 0° C. with an ice/water bath. To this solution is added dropwise 695 mg (6.0 equiv, 0.024 mol) of potassium hydroxide dissolved in 10 mL of ethanol/water 9/1. The solution is stirred at RT for 3 days, and then the solvent is removed in vacuo 10 mL of H$_2$O is added and the mixture was extracted with ethyl acetate (2×80 mL). The organic layer is dried over MgSO$_4$ and concentrated in vacuo to yield 500 mg of 2-allyl-2-methoxymethyl malonic acid. 350 mg (1.0 equiv, 0.0019 mol) of 2-allyl-2-methoxymethyl malonic acid is dissolved in 30 mL of CH$_2$Cl$_2$ and cooled in a salt/ice/water bath to –5° C. 0.65 mL (4.0 equiv, 0.0075 mols) of oxalyl chloride is added dropwise at –5° C. The reaction mixture is allowed to stir at RT for 2 h, and then the solvent is removed in vacuo. The crude product is dissolved in 20 mL of dry THF and added dropwise to a solution of 592 mg (0.8 equiv, 0.0015 mol) of N-isopropyl-N-phenyl-2-(2-phenylamino-phenylamino)-acetamide in dry 20 mL of dry THF cooled to 0° C. The reaction mixture is heated at reflux for 22 h, cooled to RT and the solvent is removed in vacuo. 60 mL of brine/ethyl acetate 1/1 are added and the mixture is extracted with ethyl acetate (2×30 mL). The organic extract is dried over MgSO$_4$ and the solvent removed in vacuo. Purification by silica gel flash chromatography with hexane/ethyl acetate 2/1 as eluent gave 550 mg of the title compound as a brown gum: $^1$H NMR (CDCl$_3$, 300 MHz) δ7.39–6.78 (m, 13H), 6.20–5.65 (m, 1H), 5.04–5.00 (m, 2H), 4.73 (d, J=17.1, 1H), 3.98–3.84 (2s, 3H), 3.43 (s, 3H), 2.80 (s, 2H), 2.33–2.27 (m, 2H), 1.10–1.03 (m, 6H); R$_f$=0.30 in hexane/EtOAc 2/1.

Intermediate 32

[1-(Isopropyl-phenyl-carbamoylmethyl)-2,4-dioxo-5-phenyl-2,3,4,5-tetrahydro-1H-benzo[b][1,4]diazepin-3-yl]acetic acid 1.0 g (1.0 equiv, 2.0 mmol) of 2-(2,4-dioxo-3-allyl-5-phenyl-2,3,4,5-tetrahydro-benzo[b][1,4]diazepin-1-yl)-N-isopropyl-N-phenyl-acetamide is dissolved in 60 mL of CCl$_4$. 30 mL of H$_2$O is added followed by 42 mg (0.1 equiv, 0.2 mmol) of RuCl$_3$ and 4.3 g (10 equiv, 20 mmol) of solid NaIO$_4$. The reaction is stirred rapidly for 3 days at RT. The resulting mixture is filtered through celite and H$_2$O (60 mL) is added. The layers are separated and the aqueous layer is extracted with ethyl acetate (2×200 mL). The organics are washed with sat. sodium bisulfite (1×60 mL) and brine (1×60 mL), dried over MgSO$_4$ and the solvent is removed in vacuo. The resulting solid is purified by silica gel MPLC using methylene chloride/methanol 9/1 as eluent to yield 550 mg the title compound as a solid: $^1$H NMR (CDCl$_3$, 300 MHz) δ7.43–7.05 (m, 13H), 6.89 (d, J=8.0, 1H), 5.01–4.96 (m, 1H), 4.32–4.07 (m, 2H), 3.92–3.87 (m, 1H), 2.92–2.90 (m, 2H), 1.07–1.01 (m, 6H); low resolution MS (FAB) m/e 486 (MH$^+$).

Intermediate 33

1-Phenyl-1,5-dihydro-1H-benzo[b][1,4]diazepine-2, 4-dione 100 g (1.0 equiv, 0.47 mol) of 2-nitrophenylene diamine is dissolved in 1 L of dry toluene and cooled to 0° C. with a ice/water bath. 55 mL (1.1 equiv, 0.51 mol) of methyl malonylchloride is added dropwise over 20 min. The reaction mixture is allowed to warm to RT and stirred 1 h, and at 80° C. for 2 days. The solvent is removed in vacuo, and the resulting solid is recrystallized from Et$_2$O/CH$_2$Cl$_2$/hexane afford 110.6 g of N-(2-nitro-phenyl)-N-phenyl-malonamic acid methyl ester. 55.6 g (1.0 equiv, 0.17 mol) of the above product is dissolved it in 4 L of ethanol and 200 mL of ethyl acetate. 5 g of 10% Pd/C is added, and the reaction mixture is stirred under a atmosphere of hydrogen for 7 hours, then filtered through celite and the solvent is removed in vacuo to afford 43.7 g of N-(2-amino-phenyl)-N-phenyl-malonamic acid methyl ester. 10 g (1.0 equiv, 0.035 mol) of the above amine is dissolved in 220 mL of ethanol, cooled to 0° C., and 1.2 g (1.6 equiv) of Na dissolved in 180 mL of ethanol is added. The reaction mixture is warmed slowly to room temperature and stirred 1 h followed by the removal of solvent in vacuo. The residue is acidified with 1N HCl and extracted with ethyl acetate (2×500 mL). The organic layer is dried over MgSO$_4$ and the solvent is removed in vacuo. Trituration with Et$_2$O afforded 2.75 g of the title compound as a white solid: $^1$H NMR (DMSO, 300 MHz) δ10.60 (s, 1H), 7.64–7.08 (m, 8H), 6.81 (d, J=8.0, 1H), 3.61–3.11 (m, 2H); R$_f$=0.44 in hexane/EtOAc 1/2.

Intermediate 34

[1-(Isopropyl-phenyl-carbamoylmethyl)-3-methyl-2, 4-dioxo-5-phenyl-2,3,4,5-tetrahydro-1H-benzo[b][1, 4]diazepin-3-yl]butyric acid A mixture of 0.15 g (0.41 mmol, 1.25 equiv) of (tert-butoxycarbonylmethylene) triphenylphosphorane and 0.20 g (0.323 mmol, 1.0 equiv) of N-Isopropyl-2-[3-methyl-2,4-dioxo-3-(2-oxoethyl)-5-phenyl-2,3,4,5-tetrahydro-benzo[b] [1,4]diazepin-1-yl]-N-phenyl acetamide, prepared as in Intermediate 9, in 2 mL of methylene chloride is stirred at RT for 4h. The solvents are removed in vacuo and the residue purified by silica gel flash column chromatography (20% ethyl acetate in hexane) to afford 96 mg of a white foam. The compound is dissolved in 5 mL of EtOH, 10 mg of 10% palladium on carbon added and the mixture is stirred under an atmosphere of hydrogen for 1 h. The solids are removed by filtration through celite and the filtrate concentrated in vacuo to afford 96 mg of a colorless glass. The compound is dissolved in 1 mL of 4N HCl in dioxane and stirred at RT for 6 h. The solvents are removed in vacuo and the residue triturated with ether to afford 91 mg of the titled compound as a glassy foam: $^1$H NMR (300 MHz, CDCl$_3$) δ6.8–7.7 (m, 14H), 5.06 (sept, 1H, J=7), 4.44 (d, 1H, J=9), 3.97 (d, 1H, J=9), 2.03 (m, 2H), 1.77 (m, 2H), 1.59 (s, 3H), 1.4 (t, 2H, J=7), 1.07 (dd, 6H, J=7); R$_f$=0.25 in CH$_2$Cl$_2$/MeOH 9/1.

Intermediate 35

1-(2-Pyridyl)-1,5-dihydro-1H-benzo[b][1,4] diazepine-2,4-dione

A mixture of 15 g (85.1 mmol, 1.0 equiv) of 1,5-dihydro-1H-benzo[b][1,4]diazepine-2,4-dione, 10 g (157 mmol, 1.8 equiv) of powdered copper 8.4 g (85.6 mmol, 1.0 equiv) of potassium acetate in 250 mL of DMSO is heated to 100° C. A solution of 5.4 mL (56.7 mmol, 0.67 equiv) of 2-bromopyridine in 10 mL of DMSO is added dropwiseover 12 h by syringe pump. The resulting mixture is heated for an additional 5 h at 100° C., and then poured into 500 mL of ice/water. 500 mL of DCM is added and the mixture filtered through celite. The layers were separated and the aqueous extracted with DCM. The combined organic extracts were washed with 200 mL of 2% ammonium hydroxide (×3), dried (MgSO$_4$) and concentrated to a pale yellow solid. Trituration with ether gave 5.3 g of the title compound as a white solid: mp 245°–6° C.; $^1$H NMR (CDCl$_3$, 300 MHz) δ8.75 (s, 1H, NH), 8.48 (m, 1H), 8.0–7.0 (m, 7H), 3.70 (s, 2H).

Intermediate 36

2-(2,4-dioxo-5-pyrid-2-yl-2,3,4,5-tetrahydro-benzo [b][1,4]diazepin-1-yl)-N-isopropyl-N-(4-methoxy-phenyl) acetamide 1.6 mL (1.6 mmol, 1.0 equiv) of 1M NaN(TMS)$_2$ in THF is added dropwise to a solution of 0.40 g (1.6 mmol, 1.0 equiv) of 2,4-dioxo-5-pyrid-2-yl-2,3,4,5-tetrahydro-benzo [b][1,4]diazepine in 20 mL of DMF at 0° C. After 15 min, a solution of 0.47 g (1.6 mmol, 1.0 equiv) of 2-bromo-N-isopropyl-N-(4-methoxy-phenyl) acetamide in 3 mL of DMF is added dropwise and the resulting green solution is stirred at 0° C. for 25 min. The reaction mixture is poured into 100 mL of H$_2$O and extracted with EtOAc (×2). The organic extract is washed with H$_2$O and brine, dried over MgSO$_4$ and concentrated to a brown oil. Purification by silica gel flash chromatography using EtOAc as eluent gave 0.35 g of the title compound as a light yellow foam: $^1$H NMR (CDCl$_3$, 300 MHz) δ8.4–6.8 (m, 12H), 5.04 (m, 1H), 4.44 (d, 1H, J=17), 3.94 (d, 1H, J=17), 3.80 (s, 3H), 3.65 (d, 1H, J=12), 3.49 (d, 1H, J=12), 1.11 (d, 6H, J=7); low resolution MS (FAB) m/e 459 (MH$^+$).

Intermediate 37

2-[3-(N-tert-butoxycarbonyl-indol-2-ylmethyl)-2,4-dioxo-5-phenyl-2,3,4,5-tetrahydro-benzo[b][1,4] diazepin-1-yl]-N-isopropyl-N-phenyl acetamide To a stirring solution of 200 mg (0.47 mmol) of 2-(2,4-Dioxo-5-phenyl-2,3,4,5-tetrahydro-benzo[b][1,4]diazepin-1-yl)-N-isopropyl-N-phenyl acetamide, prepared as in Intermediate 1, in 2 mL of DMF is added 21 mg (0.51 mmol, 1.1 equiv) of sodium hydride (60% in mineral oil). The resulting solution is stirred 5 min, then a solution of 166 mg (0.51 mmol, 1.1 equiv.) of 2-Bromomethyl (N-tert-butoxycarbonyl) indolyl in 1 mL of DMF is added. The resulting solution is stirred at RT for 1 h then heated to 40° C. for 1 h. The solution is cooled to RT, poured into 40 mL of EtOAc and extracted with H$_2$O (1×40 mL), dried (MgSO$_4$), and the solvent removed in vacuo. Purification of the resulting material by silica gel flash chromatography with hexane/ethyl acetate 2/1 as eluent gave 193 mg of the title compound as a clear oil: $^1$H NMR (300 MHz, CDCl$_3$) δ8.10 (d, 1H), 7.52–7.09 (m, 16H), 6.92 (d, 1H), 6.51 (s, 1H), 5.02 (m, 1H), 4.24 (m, 3H), 3.80 (m, 2H), 1.53 (s, 9H), 1.04 (m, 6H); R$_f$=0.40 in hexane/ethyl acetate 2/1.

Intermediate 38

2-[3-(N-tert-butoxycarbonyl-indol-3-ylmethyl)-2,4-dioxo-5-phenyl-2,3,4,5-tetrahydro-benzo[b][1,4]diazepin-1-yl]-N-isopropyl-N-phenyl acetamide To a stirring solution of 200 mg (0.47 mmol) of 2-(2,4-Dioxo-5-phenyl-2,3,4,5-tetrahydro-benzo[b][1,4]diazepin-1-yl)-N-isopropyl-N-phenyl acetamide, prepared as in Intermediate 1, in 2 mL of DMF is added 1.0 mL (0.51 mmol, 1.1 equiv) of a 0.5M solution of KN(TMS)$_2$. The resulting solution is stirred 5 min, then a solution of 160 mg (0.51 mmol, 1.1 equiv.) of 3-Bromomethyl (N-tert-butoxycarbonyl) indolyl in 1 mL of DMF is added. The resulting solution is stirred at RT for 1 h then heated to 40° C. for 1 h. The solution is cooled to RT, poured into 40 mL of EtOAc and extracted with H$_2$O (1×40 mL), dried (MgSO$_4$), and the solvent removed in vacuo. Purification of the resulting material by silica gel flash chromatography with hexane/ethyl acetate 3/1 as eluent gave 216 mg of the title compound as an off-white solid: $^1$H NMR (300 MHz, CDCl$_3$) δ8.10 (d, 1H), 7.52–7.09 (m, 16H), 6.87 (d, 1H), 5.02 (m, 1H), 4.24 (m, 2H), 3.72 (m, 1H), 3.58 (m, 1H), 3.40 (dd, 1H), 1.62 (s, 9H), 1.09 (m, 6H); R$_f$=0.66 in hexane/ethyl acetate 1/1.

Intermediate 39

2-[3-(1-Benzyl-1H-indazol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide To a stirring solution of 200 mg (0.30 mmol) of 2-[3-(1-Benzyl-1H-indazol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide in 5 mL of DMF is added 0.45 mL (0.45 mmol, 1.5 equiv) of a 1.0M solution of NaN(TMS)$_2$. The resulting solution is stirred 5 min, then 76 mg (0.54 mmol, 1.8 equiv) of methyl iodide is added. The resulting solution is stirred at RT for 1 h then heated to 50° C. for 16 h. The solution is cooled to RT, poured into 40 mL of EtOAc and extracted with H$_2$O (1×40 mL), dried (MgSO$_4$), and the solvent removed in vacuo. Purification of the resulting material by silica gel flash chromatography with hexane/ethyl acetate 3/2 as eluent gave 127 mg of the title compound as an off-white solid, contaminated with starting material, which is inseparable, in a ratio of approximately 1/1: $^1$H NMR (300 MHz, CDCl$_3$) δ7.86 (d, 1H, J=8.1), 7.33–6.88 (m, 21H), 5.58 (s, 2H), 5.43 (s, 2H), 5.05 (m, 1H), 5.00 (m, 1H), 4.50 (d, 1H), 4.25 (m, 3H), 3.85 (s, 3H), 3.58 (dd, 1H, J=5.1, 16.0), 1. 59 (s, 3H), 1.06 (2×d, 6H, J=6.6); R$_f$=0.15 in hexane/ethyl acetate 2/1.

Intermediate 40

2-[2,4-Dioxo-5-phenyl-3-(5-phenyl-[1,2,4]oxadiazol-3-ylmethyl)-2,3,4,5-tetrahydro-benzo[b][1,4]diazepin-1-yl]-N-isopropyl-N-phenyl acetamide To a stirring solution of 200 mg (0.47 mmol) of 2-(2,4-Dioxo-5-phenyl-2,3,4,5-tetrahydro-benzo[b][1,4]diazepin-1-yl)-N-isopropyl-N-phenyl acetamide in 4 mL DMF at 0° C. is added dropwise 0.98 mL (0.49 mmol, 1.05 equiv) of a 0.5N solution of KN(TMS)$_2$ in toluene. The resulting solution is stirred 5 min, then 100 mg (0.51 mmol, 1.1 equiv) of 3-chloromethyl-5-phenyl-[1,2,4]oxadiazole is added. The reaction mixture is stirred 30 min at 0° C. then 14 h at RT. The reaction mixture is quenched with 1 mL of H$_2$O and the solvent removed in vacuo. The residue is dissolved in 40 mL EtOAc, washed with 40 mL H2O, and the organic layer is dried (MgSO$_4$) and the solvent removed in vacuo. The resulting oil is purified by silica gel flash column chromatography using hexane/EtOAc 2/1 as eluent followed by further purification via reverse phase MPLC using a C-18 column and 60% acetonitrile/40% H$_2$O with 0.1% TFA as eluent followed by lyophilization to afford 116 mg of 2-[2,4-Dioxo-5-phenyl-3-(5-phenyl-[1,2,4]oxadiazol-3-ylmethyl)-2,3,4,5-tetrahydro-benzo[b][1,4]diazepin-1-yl]-N-isopropyl-N-phenyl acetamide as a white amorphous solid: $^1$H NMR (CDCl$_3$, 300 MHz) δ8.07 (d, 2H, J=6.9), 7.59–7.13 (m, 16H), 7.00 (dd, 1H, J=1.3, 8.1), 5.01 (m, 1H), 4.27 (s, br, 2H), 4.1 (t, 1H, J=6.1), 3.66 (dd, 1H, J=7.8, 17.1), 3.50 (dd, 1H, J=6.1, 17.1) 1.08 (t, 6H, J=6.9); low resolution MS (FAB) m/e 586 (MH$^+$), 451, 277, 227, 195.

Intermediate 41

2-[2,4-Dioxo-5-phenyl-3-(3-phenyl-allyl)-2,3,4,5-tetrahydro-benzo[b][1,4]diazepin-1-yl]-N-isopropyl-N-phenyl acetamide To a stirring solution of 250 mg (0.58 mmol) of 2-(2,4-Dioxo-5-phenyl-2,3,4,5-tetrahydro-benzo[b][1,4]diazepin-1-yl)-N-isopropyl-N-phenyl acetamide in 3 mL of DMF at 0° C. is added 127 mg (0.70 mmol, 1.2 equiv) of sodium hydride (60% dispersion in mineral oil). The resulting solution is stirred 10 min, then 95 mL (0.64 mmol, 1.1 equiv) of trans-cinnamyl bromide is added. The reaction mixture is stirred 10 min at 0° C. then 2 h at RT and quenched with 1 mL H$_2$O. The reaction mixture is diluted with 40 mL EtOAc and washed with 40 mL H$_2$O. The organic layer is dried (MgSO$_4$) and the solvents removed in vacuo. Purification of the resulting oil by silica gel flash column chromatography using hexane/EtOAc 4/1 as eluent followed by lyophilization of the product afforded 262 mg of the 2-[2,4-Dioxo-5-phenyl-3-(3-phenyl-allyl)-2,3,4,5-tetrahydrobenzo[b][1,4]diazepin-1-yl]-N-isopropyl-N-phenyl acetamide as a white amorphous solid: $^1$H NMR (CDCl$_3$, 300 MHz) δ7.46–7.07 (m, 18H), 6.92 (dd, 1H, J=1.2, 8.1), 6.46 (d, H, J=15.9), 6.25 (m, 1H), 5.04 (m, 1H), 4.31 (d, 1H, J=16.6), 4.13 (d, 1H, J=16.6), 3.46 (dd, 1H, J=6.1, 7.8), 2.93 (m, 2H), 1.10 (2×d, 6H, J=6.9); low resolution MS (FAB) m/e 544 (MH$^+$), 409, 223.

Intermediate 42

3-Bromomethyl-1-tert-butoxycarbonyl indazole
A. 3-Methylindazole

To a stirring solution of 36.2 g (0.26 mol) of 2-Fluoroacetophenone in 120 mL of ethylene glycol is added 8.6 mL (0.27 mol, 1.05 equiv.) of hydrazine. The resulting solution is stirred 2 h at RT and then heated at 165° C. for 40 h. The solution is cooled to RT, poured into CH$_2$Cl$_2$ (200 mL) and extracted with H$_2$O (2×200 mL). The organic layers were combined, dried (MgSO$_4$), and the solvent removed in vacuo. Purification of the crude material by recrystallization form hexane/CHCl$_3$ afforded 26 g of 3-Methylindazole as a light tan solid: $^1$H NMR (CDCl$_3$, 300 MHz) δ7.73 (d, 1H, J=8.1), 7.44 (m, 2H), 7.19 (dd, 1H, J=7.0,7.0), 2.67 (s, 3H).

B. 1-tert-butoxycarbonyl-3-methylindazole

To a stirring solution of 30.3 g (0.23 mol) of 3-methylindazole, prepared as in Part A, in 300 mL of $CH_3CN$ is added 35.0 mL (0.25 mol, 1.1 equiv) of $Et_3N$ and 5.77 g (47.2 mmol, 0.2 equiv) of DMAP, and the mixture is cooled to 0° C. 60.5 g (0.28 mol, 1.2 equiv) of $(BOC)_2O$ in 200 mL $CH_3CN$ is added dropwise with stirring at 0° C. and the resultant reaction mixture stirred 3 h at RT. The solvent is removed in vacuo and the crude material partitioned between $Et_2O$ (300 mL) and $H_2O$ (100 mL). The pH is adjusted to 2.0 with 1N HCl, the organic phase separated, dried ($MgSO_4$), filtered and concentrated in vacuo to an orange oil which is purified by filtration through a pad of silica gel using Hexane/EtOAc 4/1 as eluent. The filtrate is concentrated in vacuo to give 53.4 g of 1-tert-butoxycarbonyl-3-methylindazole as a white solid: $^1H$ NMR ($CDCl_3$, 300 MHz) δ8.15 (d, 1H, J=7.8), 7.67 (d, 1H, J=7.8), 7.56 (dd, 1H, J=7.3, 7.3), 7.35 (dd, 1H, J=7.3, 7.3), 2.62 (s, 3H), 1.77 (s, 9H); TLC $R_f$=0.66 (EtOAc/Hexane 1/2).

C. 3-Bromomethyl-1-tert-butoxycarbonyl indazole

A stirring solution of 53.4 g (0.23 mol) of 1-tert-butoxycarbonyl-3-methylindazole, prepared as in Part B, in 1.0 L of $CCl_4$ is heated to reflux, and then a mixture of 45.1 g (0.25 mol, 1.1 equiv) of N-bromosuccinimide and 5.7 g (23.5 mmol, 0.1 equiv) of benzoyl peroxide is added portionwise over 5 min as a solid. The resulting solution is heated at reflux for 4.5 h, then cooled to RT. The reaction mixture is filtered through a pad of Celite to remove the precipitated succinimide, and the solvent is removed in vacuo. Purification of the crude material by gradient silica gel flash column chromatography using hexane/EtOAc 15/1 to hexane/EtOAc 3/1 as eluent afforded 43.2 of the title compound as a white solid: $^1H$ NMR ($CDCl_3$, 300 MHz) δ8.20 (d, 1H, J=7.8), 7.88 (d, 1H, J=7.8), 7.60 (dd, 1H, J=7.3, 7.3), 7.41 (dd, 1H, J=7.3, 7.3), 4.91 (s, 2H), 1.77 (s, 9H); ;TLC $R_f$=0.56 (EtOAc/Hexane 1/5).

Intermediate 43

N-Isopropyl-N-(4-methoxy-phenyl)-2-(2-phenylamino-phenylamino) acetamide

To a stirring solution of 21.8 g (0.12 mol) of N-phenyl-o-phenylene diamine in 300 mL of DMF is added 18.0 g (0.13 mol, 1.1 equiv.) of $K_2CO_3$ and 33.9 g (0.12 mol) of bromomethyl-N-isopropyl-N-(4-methoxy-phenyl) acetamide. The resulting mixture is heated to 60° C. for 16 h then cooled to RT. The mixture is filtered to remove the $K_2CO_3$ and then diluted with 800 mL of EtOAc and 200 mL of $Et_2O$. This solution is washed successively with $H_2O$ (2×400 mL), brine (1×400 mL), 1N HCl (2×400 mL), and $H_2O$ (1×400 mL), and the organics dried ($MgSO_4$) and concentrated to give a greenish-black oil. Trituration of this material with $Et_2O$/petroleum ether 1/4 gave a light grey solid which is dried under vacuum to afford 37.2 g of the title compound: $^1H$ NMR ($CDCl_3$, 300 MHz) δ7.24–6.71 (m, 12H), 6.43 (d, 1H, J=8.3), 4.96 (m, 1H), 3.92 (s, 3H), 3.44 (s, 2H), 1.05 (d, 6H, J=6.9).

Intermediate 44

N-Isopropyl-N-(4-methoxy-phenyl)-2-phenylamino acetamide

A mixture of N-Isopropyl-N-(4-methoxy-phenyl) bromoacetamide (257.6 g, 924 mmol), 1,2-phenylene diamine (100 g, 924 mmol) and potassium carbonate (128 g, 924 mmol) in DMF (1200 mL) is stirred at 0° C. for 2 h and then allowed to stir at RT for 20 h. The reaction mixture is filtered through celite and the filtrate concentrated in vacuo The resultant residue is dissolved in EtOAc (1200 mL), washed with water (3×200 mL), brine (200 mL), dried ($MgSO_4$) and concentrated in vacuo. After removal of about 70% of the solvent a precipitate formed which is removed by filtration and washed with cold EtOAc and dried to afford the desired product (67.1 g) as a beige solid. The combined filtrates were concentrated in vacuo to afford a dark oil (88 g). Two recrystallisations from ethanol afforded a second batch (29.6 g) of the desired product as a beige solid: $^1H$ NMR (300 MHz, DMSO-$d_6$), δ7.22 (m, 2H), 7.05 (m, 2H), 6.47 (m, 1H), 6.34 (m, 2H), 5.95 (m, 1H), 4.81 (m., 1H, J=6.8), 4.59 (dt, 1H, J=27.2, 6.1), 4.4 (s, 2H), 3.77 (s, 3H), 3.30 (s, 2H), 0.96 (d, 6H, J=6.8).

Intermediate 45

2-(2-Aminophenylamino)-N-isopropyl-N-phenyl acetamide

To a stirred solution of 40 g (385 mmol) of phenylenediamine is added 75 g (543 mmol, 1.4 equiv.) of potassium carbonate. The suspension is stirred at RT and a solution of 99 g (386.5 mmol, 1 equiv.) of 2-Bromo-N-isopropyl-N-phenyl acetamide in 15 mL THF is added dropwise. The resulting suspension is stirred at RT for 16 h and diluted with 1 L $H_2O$ and 1 L EtOAc. The Organics were washed with $H_2O$ (3×500 mL), brine (500 mL), dried ($MgSO_4$), and the solvents removed in vacuo. Purification by silica gel flash column chromatography using hexane/EtOAc 8/2 as eluent afforded 71 g of a yellow solid: mp. 110°–112° C.; $^1H$ NMR ($CDCl_3$, 300 MHz) δ7.48–7.44 (m, 4H), 7.18– 7.15 (m, 2H), 6.69–6.59 (m, 3H), 6.21–6.19 (m, 1H), 5.11–4.98 (m, 1H), 3.4 (s, 2H), 1.09 (d, 6H, J=7).

Intermediate 46

2-(2,4-dioxo-2,3,4,5-tetrahydro-benzo[b][1,4] diazepin-1-yl)-N-isopropyl-N-(4-methoxy-phenyl)-acetamide To a stirring solution of 300 mL THF at RT is added 5 g (16 mmol) N-Isopropyl-N-(4-methoxy-phenyl)-2-phenylamino acetamide, prepared as in Intermediate 44, as a solution in 50 mL THF and 1.55 mL (16 mmol, 1 equiv) malonyl dichloride as a solution in 50 mL THF simultaneously and dropwise via addition funnel. After addition is complete, the reaction is allowed to stir an additional 2 h at RT. The reaction is then concentrated in vacuo, and the resulting oil is purified by flash chromatography to afford 4.21 g of the title compound as an off-white solid: $^1H$ NMR ($CDCl_3$, 400 MHz) δ8.68 (s, 1H), 7.39 (d, 1H, J=1.7), 7.24–7.15 (m, 2H), 7.04 (dd, 2H, J=1.7, 7.5), 6.9 (m, br, 2H), 5.0 (q, 1H, J=6.8), 4.39 (d, 1H, J=16.5), 3.8 (s, 3H), 3.74 (d, 1H, J=17), 3.36 (d, 2H, J=6.8), 1.06 (d, 6H, J=6.8); low resolution MS (FAB)m/e 382 ($MH^+$).

Intermediate 47

2-(2,4-Dioxo-2,3,4,5-tetrahydro benzo[b][1,4] diazepin-1-yl)-N-isopropyl-N-phenyl acetamide To a stirred solution of 10 g (37.14 mmol) of 2-(2-Aminophenylamino)-N-isopropyl-N-phenyl acetamide, prepared as in Intermediate 45, in 100 mL of THF is added 5.2 g (37.14 mmol, 1 equiv.) of malonyl dichloride. The resulting solution is stirred at RT for 2 h and the solvent removed in vacuo. Purification by silica gel flash column chromatography using hexane/EtOAc 1/1 as eluent afforded 6.1 g of the title compound as an oil: ¹H NMR (CDCl₃, 300 MHz) δ9.65 (s, 1H), 7.4 (bd, 1H, J=9), 7.30–6.93 (m, 7H), 5.09–4.95 (m, 1H), 4.42 (d, 1H, J=16), 3.68 (d, 1H, J=17), 3.36 (d, 2H, J=4), 1.09 (d, 6H, J=7).

Intermediate 48

2-(2,4-Dioxo-5-pyridin-3-yl-2,3,4,5-tetrahydro-benzo[b][1,4]diazepin-1-yl)-N-isopropyl-N-(4-methoxy-phenyl)-acetamide To a stirring solution of 26.6 g (69.7 mmol) 2-(2,4-Dioxo-2,3,4,5-tetrahydro-benzo[b][1,4]diazepin-1-yl)-N-isopropyl-N-(4-methoxy-phenyl)-acetamide, prepared as in Intermediate 46, in 1 L DMF is added 13.3 g (209 mmol, 3 equiv) of Cu powder, 13.7 g (139 mmol, 2 equiv) of potassium acetate and 13.4 mL (139 mmol, 2 equiv) of 3-bromopyridine. The reaction is heated to 120° C. After 5 h, an additional 13 g (133 mmol) of potassium acetate and 15 mL (156 mmol) of 3-bromopyridine were added, and the reaction is allowed to stir overnight. After ca. 18 h, an additional 15 g (236 mmol) Cu and 5 g (51 mmol) potassium acetate were added, and stirring is continued for an additional 24 h. The reaction is then allowed to cool, and is filtered through celite, rinsing with ethyl acetate. The organics were extracted with 10% NH₄OH, the twice with water. The aqueous layer is extracted with EtOAc/ethyl ether. The combined organics were dried (MgSO₄) filtered and concentrated in vacuo to afford an oil. This is purified by silica gel flash chromatography to afford 15.8 g of the title compound as a white powder as well as 1.5 g of recovered unreacted starting material: ¹H NMR (CDCl₃, 400 MHz) δ8.68 (s, br, 2H), 7.86 (d, 1H, J=7.8), 7.36 (d, 2H, J=7.6) 7.27–7.10 (m, 6H ) 6.95 (t, 2H, J=7.6) 6.84 (d, 1H, J=7.1) 4.95 (m, 1H), 4.23 (s, br, 2H) 3.82 (s, 3H) 3.53 (dd, 2H, J=12.2, 44) 1.04 (dd, 6H, J=2.4, 6.8); low resolution MS (FAB)m/e (MH⁺).

Intermediate 49

2-(2,4-dioxo-5-pyridin-3-yl-2,3,4,5-tetrahydro benzo[b][1.4]diazepin-1-yl)-N-isopropyl-N-phenylacetamide To a stirring solution of 3.3 g (9.39 mmol) of 2-(2,4-Dioxo-2,3,4,5-tetrahydro benzo[b][1,4]diazepin-1-yl)-N-isopropyl-N-phenyl acetamide, prepared as in Intermediate 47, in 25 mL of DMF is added 2.97 g (18.78 mmol, 2 equiv.) of 3-bromopyridine, 1.84 g (18.78 mmol, 2 equiv.) of potassium acetate, and 1.19 g (18.78 mmol, 2 equiv.) of copper powder. The suspension is heated to 125° C. for 8 h and then cooled to RT. It is diluted with 500 mL EtOAc and filtered through a bed of celite. The filtrate is washed with H₂O (2×500 mL), conc. NH₄OH (2×350 mL) and then dried (MgSO₄), and the solvents removed in vacuo. Purification by silica gel flash column chromatography using hexane/EtOAc 1/1 as eluent afforded 2.61 g of the title compound as an oil: ¹H NMR (CDCl₃, 300 MHz) δ8.50 (m, 1H), 7.78 (d, 1H, J=9), 7.48–7.25 (m, 7H), 7.14 (t, 1H, J=8), 6.88 (d, 1H, J=10), 5.06–4.95 (m, 1H), 4.30–4.09 (m, 3H), 3.54 (q, 1H, J=13, 6), 1.7 (s, 1H), 1.42 (d, 2H, J=6), 1.10 (dd, 6H, J=9,2).

Intermediate 50

3-Bromomethyl-1 tert-butoxycarbonyl-pyrazolo[3,4-b]pyridine

A. 3-Methyl-1H-pyrazolo[3,4-b]pyridine

To a stirring suspension of 5.0 g (51.5 mmol) of 3-Amino-5-methyl pyrazole in 10.1 g (61.8 mmol, 1.2 equiv) of malonaldehyde dimethyl acetal is added approx. 8 g of polyphosphoric acid, and the resulting mixture is heated to 100° C. for 2 h. The resulting black oil is poured onto crushed ice and made basic by the addition of 3N NaOH, then extracted with EtOAc (2×100 mL). The organic layers were combined, dried (MgSO₄), and the solvent removed in vacuo. Purification of the crude material by silica gel flash column chromatography using hexane/EtOAc 1/1 as eluent afforded 160 mg of 3-Methyl-1H-pyrazolo[3,4-b]pyridine as a white solid: ¹H NMR (CDCl₃, 400 MHz) δ8.57 (dd, 1H, J=1.1, 4.7), 8.04 (dd, 1H, J=1.1, 8.0), 7.12 (dd, 1H, J=4.7, 8.0), 2.60 (s, 3H); low resolution MS (FAB)m/e 134 (MH⁺).

B. 3-Methyl-1 tert-butoxycarbonyl-pyrazolo[3,4-b]pyridine

To a stirring solution of 160 mg (1.20 mmol) of 3-Methyl-1H-pyrazolo[3,4-b]pyridine, prepared as in Part A, in 5 mL of acetonitrile at 0° C. is added 167 μL (1.20 mmol) of Et₃N and 145 mg (1.20 mmol) of DMAP. The resulting solution is stirred 2 min., then a solution of 315 mg (1.44 mmol, 1.2 equiv) of di-tert-butyl dicarbonate in 1 mL of acetonitrile is added. The resulting solution is warmed to RT and stirred 30 min. The reaction mixture is poured into 10 mL of EtOAc and extracted with brine (1×10 mL), dried (MgSO₄), and the solvent removed in vacuo. Purification of the crude material by silica gel flash column chromatography using hexane/EtOAc 1/1 as eluent afforded 253 mg of 3-Methyl-1 tert-butoxycarbonyl-pyrazolo[3,4-b]pyridine as a pale yellow oil: ¹H NMR (CDCl₃, 400 MHz) δ8.72 (dd, 1H, J=1.5, 4.7), 7.99 (dd, 1H, J=1.5, 8.0), 7.26 (dd, 1H, J=4.7, 8.0), 2.59 (s, 3H), 1.71 (s, 9H).

C. 3-Bromomethyl-1 tert-butoxycarbonyl-pyrazolo[3,4-b]pyridine

A stirring solution of 240 mg (1.03 mmol) of 3-Methyl-1 tert-butoxycarbonyl-pyrazolo[3,4-b]pyridine, prepared as in Part B, in 10 mL of CCl₄ is heated to reflux, and then a mixture of 220 mg (1.23 mmol, 1.2 equiv) of N-bromosuccinimide and 25 mg (0.10 mmol, 0.1 equiv) of benzoyl peroxide is added all at once as a solid. The resulting solution is heated at reflux for 3.5 h, then cooled to RT. The reaction mixture is filtered through a pad of Celite to remove the precipitated succinimide, and the solvent is removed in vacuo. Purification of the crude material by silica gel flash column chromatography using hexane/EtOAc 3/1 as eluent afforded 170 mg of the title compound as a white solid: ¹H NMR (CDCl₃, 400 MHz) δ8.75 (dd, 1H, J=1.4, 4.6), 8.21 (dd, 1H, J=1.4, 8.0), 7.32 (dd, 1H, J=4.6, 8.0), 4.74 (s, 2H), 1.70 (s, 9H).

Intermediate 51

1-Benzyl-3-bromomethyl-4,5,6,7-tetrahydro-1H-indazole

A. 4,5,6,7-Tetrahydro-1-Benzyl-1H-indazole-3-carboxylic acid ethyl ester

To a stirring solution of 2.0 g (10.30 mmol) of 4,5,6,7-Tetrahydro-1H-indazole-3-carboxylic acid ethyl ester (Ainsworth, C. J. Am. Chem. Soc. 1957, 79, 5242) in 50 mL of DMF is added 1.85 g (13.838 mmol, 1.3 equiv) of K₂CO₃, followed by 1.35 mL (11.33 mmol, 1.1 equiv) of benzyl bromide. The reaction mixture is stirred 15 min at RT then heated at 60° C. for 16 h. The reaction is cooled to RT, poured into 100 mL 1N HCl, and extracted with Et₂O (2×100 mL). The organic layers were washed with H₂O (2×100 mL), dried (MgSO₄), and the solvent removed in vacuo. Purification of the crude material by silica gel flash column chromatography using a gradient elution of hexane/EtOAc 6/1 to 3/1 afforded 1.05 g of 4,5,6,7-Tetrahydro-1-Benzyl-1H-indazole-3-carboxylic acid ethyl ester as a yellow oil which later solidified: ¹H NMR (CDCl₃, 300 MHz)

δ 7.37–7.23 (m, 3H), 7.13 (m, 2H), 5.31 (s, 2H), 4.39 (q, 2H, J=7.2), 2.74 (m, 2H), 2.40 (m, 2H), 1.72 (m, 4H), 1.39 (t, 3H, J=7.2).

B. (4,5,6,7-Tetrahydro-1-benzyl-1H-indazol-3-yl) methanol

To a stirring solution of 1.0 g (3.52 mmol) of 4,5,6,7-Tetrahydro-1-Benzyl-1H-indazole-3-carboxylic acid ethyl ester, prepared as in Part A, in 15 mL of THF at 0° C. is added dropwise over 5 min a solution of 5.3 mL (5.3 mmol, 1.5 equiv) of a 1.0M solution of $LiAlH_4$ in THF. The resulting solution is stirred at RT for 30 min then heated to 50° C. for 1 h. The reaction mixture is cooled to 0° C. and worked up by carefully quenching first with 0.22 mL of $H_2O$, then 0.22 mL of 15% NaOH, then 0.66 mL of $H_2O$. The resulting slurry is filtered and the filter cake triturated with 20 mL EtOAc and refiltered. The filtrates were combined, dried ($MgSO_4$), and the solvent removed in vacuo. Purification of the crude material by Kugelrohr distillation gave 740 mg of (4,5,6,7-Tetrahydro-1-benzyl-1H-indazol-3-yl) methanol as a pale yellow thick oil: bp 225° C. at 0.8 mm; $^1$H NMR ($CDCl_3$, 300 MHz) δ7.32–7.24 (m, 3H), 7.10 (m, 2H), 5.17 (s, 2H), 4.62 (s, 2H), 2.46 (m, 4H), 1.72 (m, 4H); low resolution MS (FAB)m/e 243 ($MH^+$).

C. 1-Benzyl-3-bromomethyl-4,5,6,7-tetrahydro-1H-indazole

To a stirring solution of 752 mg (2.87 mmol, 1.3 equiv) of triphenylphosphine in 10 mL of $CCl_4$ at 0° C. is added 135 μL (2.63 mmol, 1.2 equiv) of $Br_2$. The resulting orange-yellow suspension is stirred 10 min at 0° C., then a solution of 580 mg (2.39 mmol) of (4,5,6,7-Tetrahydro-1-benzyl-1H-indazol-3-yl) methanol in 3 mL of $CCl_4$ is added over 2 min. The resulting solution is stirred 2.5 h at RT, and the solvent is removed in vacuo. Purification of the residue by silica gel flash column chromatography using hexane/EtOAc 5/1 as eluent afforded 76 mg of the title compound as a clear oil: $^1$H NMR ($CDCl_3$, 300 MHz) δ7.32–7.24 (m, 3H), 7.10 (m, 2H), 5.17 (s, 2H), 4.49 (s, 2H), 2.48 (m, 4H), 1.74 (m, 4H); low resolution MS (FAB)m/e 305 ($MH^+$).

Intermediate 52

2-[2,4-Dioxo-5-phenyl-3-(4,5,6,7-tetrahydro-1-benzyl-1H-indazol-3-ylmethyl)-2,3,4,5-tetrahydro-benzo[b][1,4]diazepin-1-yl]-N-isopropyl-N-(4-methoxyphenyl)-acetamide To a stirring solution of 164 mg (0.36 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide in 5 mL of DMF at 0° C. is added 0.430 mL (0.78 mmol, 1.2 equiv) of a 1.0M solution of $NaN(TMS)_2$ in THF. The resulting solution is stirred 5 min, and a solution of 120 mg (0.39 mmol, 1.1 equiv.) of 3-Bromomethyl-4,5,6,7-tetrahydro-1-benzyl-1H-indazole in 2 mL of DMF is added. The resulting solution is stirred for 3 h at RT then quenched with 5 mL of $H_2O$. The reaction mixture is poured into 50 mL of EtOAc and extracted with $H_2O$ (2×50 mL). The organic layer is separated, dried ($MgSO_4$), and the solvents removed in vacuo. Purification by silica gel flash column chromatography using hexane/EtOAc 1/1 as eluent afforded 175 mg of the title compound as a white solid: mp 173°–176° C.; $^1$H NMR ($CDCl_3$, 400 MHz) δ7.37–6.84 (m, 18H), 5.02 (s, 2H), 4.99 (m, 1H), 4.22 (s, br, 2H), 4.10 (dd, 1H, J=5.3, 8.7), 3.823 (s, 3H), 3.36 (dd, 1H, J=8.6, 15.6), 3.09 (dd, 1H, J=5.3, 15.6), 2.54–2.38 (m, 4H), 1.67 (m, 4H), 1.04 (d, 6H, J=6.6); low resolution MS (FAB)m/e 682 ($MH^+$).

Intermediate 53

2-Bromo-N-(4-trifluoromethyl-phenyl)-N-isopropyl-acetamide

To a stirring solution of 8.0 g (49.6 mmol) of 4-trifluoromethylaniline in 80 mL of 1,2-dichloroethane at RT is added 4.0 mL (54.6 mmol, 1.1 equiv) of acetone, 5 drops of glacial acetic acid, and 13.7 g (64.5 mmol, 1.3 equiv) of sodium triacetoxyborohydride. The solution is stirred at RT for 72 h, cooled to 0° C., and then quenched by addition of $H_2O$ (200 mL). The organic layer is separated, washed with brine (1×200 mL), dried ($MgSO_4$) and the solvents removed in vacuo to afford 10.1 g of crude (4-trifluoromethyl-phenyl)-isopropyl amine. A solution of 2.0 g (9.5 mmol) of this material in 50 mL of DCM is cooled to 0° C. and 1.5 mL (10.8 mmol, 1.5 equiv) of triethylamine is added, followed by dropwise addition of 0.90 mL (10.3 mmol, 1.05 equiv) of bromoacetyl bromide. The solution is stirred at RT for 4 h and then poured into $Et_2O$ (200 mL). The organics were washed with 1N HCl (2×50 mL), brine (1×50 mL), dried ($MgSO_4$) and the solvents removed in vacuo. Purification of the material by silica gel flash column chromatography using EtOAc/hexane 1/10 as eluent afforded 2.09 g of the title compound: $^1$HNMR ($CDCl_3$, 300 MHz) δ7.78 (d, 2H, J=8.5), 7.40 (d, 2H, J=8.5), 5.01 (m, 1H), 3.51 (s, 2H), 1.08 (d, 6H, J=6.9).

Intermediate 54

2-(2,4-Dioxo-5-phenyl-2,3,4,5-tetrahydro-benzo[b][1,4]diazepin-1-yl)-N-isopropyl-N-(4-trifluoromethyl-phenyl)-acetamide A. N-Isopropyl-2-(2-phenylamino-phenylamino)-N-(4-trifluoromethyl-phenyl)-acetamide To a stirred solution of 1.16 g (6.32 mmol) of N-Phenyl phenylenediamine in 15 mL of DMF is added 1.05 g (7.58 mmol, 1.2 equiv) of $K_2CO_3$ and 2.05 g (6.32 mmol) of Bromomethyl-N-isopropyl-N-(4-trifluoromethyl-phenyl) acetamide. The resulting mixture is stirred 1 h at RT then is heated to 50° C. for 16 h. The reaction mixture is then cooled to RT, poured into 100 mL $H_2O$ and extracted with $Et_2O$ (2×100 mL). The organic layers were washed in series with 1N HCl (2×80 mL), $NaHCO_3$ (1×80 mL), and $H_2O$ (1×80 mL), dried ($MgSO_4$), and the solvent removed in vacuo. Purification of the crude material by silica gel flash column chromatography using hexane/EtOAc 5/1 as eluent afforded 2.05 g of N-Isopropyl-2-(2-phenylamino-phenylamino)-N-(4-trifluoromethyl-phenyl)-acetamide as a light tan solid: $^1$H NMR ($CDCl_3$, 400 MHz) δ7.72 (d, 2H, J=8.2), 7.26 (d, 2H, J=8.2), 7.15 (m, 3H), 6.95 (dd, 1H, J=7.7, 7.7), 6.80 (dd, 1H, J=7.1, 7.1), 6.74 (d, 2H, J=7.9), 6.68 (dd, 1H, J=7.4, 7.4), 6.29 (d, 1H, J=7.9), 5.20 (s, 1H), 5.00 (m, 1H), 3.40 (s, 2H), 1.06 (d, 6H, J=6.6); low resolution MS (FAB)m/e 427 ($MH^+$); high resolution MS ($C_{24}H_{24}F_3N_3O$) Calc. 427.1871 Found 427.1871.

B. 2-(2,4-Dioxo-5-phenyl-2,3,4,5-tetrahydro-benzo[b][1,4]diazepin-1-yl)-N-isopropyl-N-(4-trifluoromethyl-phenyl)-acetamide To 60 mL of THF at 0° C. is added dropwise over 20 min simultaneously a solution of 2.0 g (4.68 mmol) of N-Isopropyl-2-(2-phenylamino-phenylamino)-N-(4-trifluoromethyl-phenyl) acetamide, prepared as in Part A, in 30 mL of THF and 590 μL (6.08 mmol, 1.3 equiv) of malonyl dichloride in 30 mL of THF. The resulting solution is stirred at RT for 20 h and the solvent removed in vacuo. Purification of the resulting brown oil by silica gel flash column chromatography using hexane/EtOAc 3/2 as eluent afforded 1.35 g of the title compound as a light tan solid: mp 186°–188° C.; $^1$H NMR ($CDCl_3$, 400 MHz) δ7.74 (d, 2H, J=8.1), 7.42 (d, 2H, J=8.1), 7.36 (m, 3H), 7.25 (m, 4H), 7.08 (ddd, 1H, J=1.4, 8.4, 8.4), 6.90 (dd, 1H, J=1.2, 8.2), 5.06 (m, 1H), 4.12 (dd, 2H, J=14.4, 95.5), 3.52 (dd, 2H, J=12.0, 34.5), 1.11 (d, 6H, J=6.6); low resolution MS (FAB)m/e 496 ($MH^+$), 293, 265; Anal. ($C_{27}H_{24}F_3N_3O_3$) Calcd. C, 65.45; H, 4.88; N, 8.48; Found C, 65.16; H, 4.95; N, 8.33.

Intermediate 55

2-[3-(1-Benzyl-1H-indazol-3-ylmethyl)-3-methoxy-2,4-dioxo-5-pyridin-3-yl-2,3,4,5-tetrahydro-benzo[b][1,4]diazepin-1-yl]-N-isopropyl-N-(4-methoxy-phenyl)-acetamide A. 2-[3-(1-Benzyl-1H-indazol-3-ylmethyl)-3-methoxy-2,4-dioxo-2,3,4,5-tetrahydro-benzo[b][1,4]diazepin-1-yl]-N-isopropyl-N-(4-methoxy-phenyl)-acetamide To a stirring solution of 720 mg (2.03 mmol) of 2-(1-Benzyl-1H-indazol-3-ylmethyl)-2-methoxy-propanedioc acid and 10 mL of DMF in 10 mL of dichloromethane at 0° C. is added dropwise 530 μL (6.09 mmol, 3.0 equiv) of oxalyl chloride. The resulting solution is stirred 2 h at RT, then the solvent and excess oxalyl chloride were removed in vacuo to yield the crude diacid chloride as an orange-red oil. The crude acid chloride is dissolved in 10 mL of THF and is added dropwise over 10 min simultaneously along with a solution of 637 mg (2.03 mmol) of N-Isopropyl-2-(2-amino-phenylamino)-N-(4-methoxy-phenyl) acetamide in 10 mL of THF to 30 mL of THF at 0° C. The resulting solution is stirred at RT for 30 min and then refluxed for 16 h. The solution is then cooled to RT and the solvent removed in vacuo. Purification of the resulting brown oil by silica gel flash column chromatography using hexane/EtOAc 3/2 as eluent afforded 570 mg of 2-[3-(1-Benzyl-1H-indazol-3-ylmethyl)-3-methoxy-2,4-dioxo-2,3,4,5-tetrahydro-benzo[b][1,4]diazepin-1-yl]-N-isopropyl-N-(4-methoxy-phenyl)-acetamide as a light tan solid: mp 202°–204° C.; $^1$H NMR (CDCl$_3$, 400 MHz) δ8.09 (s, br, 1H), 8.04 (d, 1H, J=8.0), 7.34–6.83 (m, 16H), 5.46 (dd, 2H, J=16.0, 19.1), 5.03 (m, 1H), 4.52 (d, 1H, J=16.5), 4.14 (d, 1H, J=15.5), 3.89 (d, 1H, J=15.5), 3.81 (s, 3H), 3.81 (d, 1H, J=16.5), 3.23 (s, 3H), 1.10 (2×d, 6H, J=7.8); low resolution MS (FAB)m/e 633 (MH$^+$), 632 (M$^+$); Anal. (C$_{37}$H$_{37}$N$_5$O$_5$) Calcd. C, 70.35; H, 5.90; N, 11.09; Found C, 70.44; H, 5.88; N, 11.12.

B. 2-[3-(1-Benzyl-1H-indazol-3-ylmethyl)-3-methoxy-2,4-dioxo-5-pyridin-3-yl-2,3,4,5-tetrahydro-benzo[b][1,4]diazepin-1-yl]-N-isopropyl-N-(4-methoxy-phenyl)-acetamide To a stirring suspension of 570 mg (0.90 mmol) of 2-[3-(1-Benzyl-1H-indazol-3-ylmethyl)-3-methoxy-2,4-dioxo-2,3,4,5-tetrahydro-benzo[b][1,4]diazepin-1-yl]-N-isopropyl-N-(4-methoxy-phenyl)-acetamide, prepared as in Part A, and 172 mg (2.71 mmol, 3.0 equiv) of Cu$^0$ powder in 10 mL of DMF is added 117 mg (1.80 mmol, 2.0 equiv of potassium acetate, followed by 285 mg (1.80 mmol, 2.0 equiv) of 3-bromopyridine). The resulting mixture is heated to 120° C. for 4 h, then an additional 285 mg of 3-bromopyridine is added and the reaction heated to 120° C. for an additional 15 h. The reaction mixture is then cooled to RT and filtered through a pad of Celite to remove the Cu$^0$ powder. The reaction mixture is then poured into 100 mL of EtOAc-Et$_2$O (1:1) and extracted with H$_2$O (2×100 mL), dried (MgSO$_4$), and the solvent removed in vacuo. Purification of the crude material by silica gel flash column chromatography using hexane/EtOAc 1/1 as eluent afforded 450 mg of the title compound as a light tan solid: mp 223°–224° C.; $^1$H NMR (CDCl$_3$, 400 MHz) δ8.47 (d, 1H, J=3.8), 8.31 (s, br, 1H), 8.04 (d, 1H, J=8.2), 7.51 (d, 1H, J=7.3), 7.38 (d, 1H, J=7.7), 7.31–6.93 (m, 15H), 6.64 (d, 1H, J=7.5), 5.52 (s, 2H), 5.04 (m, 1H), 4.46 (d, 1H, J=15.9), 4.26 (d, 1H, J=15.8), 4.00 (m, 2H), 3.84 (s, 3H), 3.15 (s, 3H), 1.11 (2×d, 6H, J=6.7); low resolution MS (FAB)m/e 709 (MH$^+$), 293, 265; Anal. (C$_{42}$H$_{40}$N$_6$O$_5$) Calcd. C, 71.17; H, 5.69; N, 11.86; Found C, 70.90; H, 5.74; N, 11.65.

Intermediate 56

1-Benzyl-5-bromomethyl-3-methyl-1H-pyrazole

A. 5-methyl-2H-pyrazole-3-carboxylic acid methyl ester

To a stirring solution of 2.0 g (13.87 mmol) of methyl acetopyruvate in 40 mL of absolute ethanol at 0° C. is added 0.48 mL (15.27 mmol, 1.1 equiv) of hydrazine. The resultion solution is stirred for 1 h at RT then heated to reflux for 3 h. The solution is then cooled to RT and the solvent removed in vacuo to give 5-methyl-2H-pyrazole-3-carboxylic acid methyl ester as a clear yellow oil which is used without further purification: $^1$H NMR (CDCl$_3$, 300 MHz) δ6.61 (s, 1H), 3.97 (s, 3H), 2.40 (s, 3H).

B. 2-Benzyl-5-methyl-2H-pyrazole-3-carboxylic acid methyl ester

To a stirring solution of 21.91 g (13.63 mmol) of 5-methyl-2H-pyrazole-3-carboxylic acid methyl ester, prepared as in Part A, in 50 mL of DMF is added 2.88 g (20.44 mmol, 1.5 equiv) of K$_2$CO$_3$, followed by 1.95 mL (16.35 mmol, 1.2 equiv) of benzyl bromide. The reaction mixture is stirred 15 min at RT then heated at 50° C. for 20 h. The reaction is cooled to RT, poured into 100 mL 1N HCl, and extracted with Et$_2$O (2×100 mL). The organic layers were washed with H$_2$O (2×100 mL), dried (MgSO4), and the solvent removed in vacuo. Purification of the crude material by silica gel flash column chromatography using a gradient elution of hexane/EtOAc 10/1 to 1/1 afforded 833 mg of 2-Benzyl-5-methyl-2H-pyrazole-3-carboxylic acid methyl ester as a yellow oil: $^1$H NMR (CDCl$_3$, 300 MHz) δ7.42–7.25 (m, 5H), 6.68 (s, 21H), 5.74 (s, 2H), 3.86 (s, 3H), 2.34 (s, 3H).

C. (2-Benzyl-5-methyl-2H-pyrazol-3yl) methanol

To a stirring solution of 833 mg (3.61 mmol) of 2-Benzyl-5-methyl-2H-pyrazole-3-carboxylic acid methyl ester, prepared as in Part B, in 5 mL of THF at 0° C. is added dropwise over 5 min a solution of 5.5 mL (5.5 mmol, 1.5 equiv) of a 1.0M solution of LiAlH$_4$ in THF. The resulting solution is stirred at RT for 48 h. The reaction mixture is cooled to 0° C. and worked up by carefully quenching first with 0.20 mL of H$_2$O, then 0.20 mL of 15% NaOH, then 0.60 mL of H$_2$O. The resulting slurry is filtered and the filter cake triturated with 20 mL EtOAc and refiltered. The filtrates were combined, dried (MgSO$_4$), and the solvent removed in vacuo. Purification of the crude material by Kugelrohr distillation gave 710 mg of (2-Benzyl-5-methyl-2H-pyrazol-3yl) methanol as a clear oil: $^1$H NMR (CDCl$_3$, 300 MHz) δ7.41–7.29 (m, 3H), 7.16 (m, 2H), 6.07 (s, 1H), 5.37 (s, 2H), 4.55 (s, 2H), 2.30 (s, 3H); low resolution MS (FAB)m/e 203 (MH$^+$).

D. 1-Benzyl-5-bromomethyl-3-methyl-1H-pyrazole

To a stirring solution of 1.10 g (4.21 mmol, 1.2 equiv) of triphenylphosphine in 15 mL of CCl$_4$ at −5° C. is added 200 μL (3.86 mmol, 1.1 equiv) of Br$_2$. The resulting orange-yellow suspension is stirred 10 min at 0° C., then a solution of 710 mg (3.51 mmol) of (2-Benzyl-5-methyl-2H-pyrazol-3yl) methanol, prepared as in Part C, in 5 mL of CCl$_4$ is added over 2 min. The resulting solution is stirred 0.5 h at RT, and then poured into 25 mL NaHCO$_3$ and extracted with Et$_2$O (2×25 mL), dried (MgSO$_4$), and the solvent removed in vacuo. Purification of the residue by silica gel flash column chromatography using hexane/EtOAc 5/1 as eluent afforded 576 mg of the title compound as a clear oil: $^1$H NMR (CDCl$_3$, 300 MHz) δ7.32 (m, 3H), 7.19 (m, 2H), 6.16 (s, 1H), 5.42 (s, 2H), 4.32 (s, 2H), 2.31 (s, 3H); low resolution MS (FAB)m/e 265 (M$^+$).

Intermediate 57

2-(3-Hydroxymethyl-2,4-dioxo-5-phenyl-2,3,4,5-tetrahydro-benzo[b][1,4]diazepin-1-yl]-N-isopropyl-N-(4-methoxy-phenyl)-acetamide To a stirring solution of 460 mg (0.80 mmol) of 2-[3-(Benzyloxymethyl)-2,4-dioxo-5-phenyl-2,3,4,5-tetrahydrobenzo[b][1,4]diazepin-1-yl]-N-isopropyl-N-(4-methoxy-phenyl)-acetamide in 10 mL of DMF/CHCl₃ 1/1 is added 200 mg of 10% Pd/C. The resulting mixture is stirred at RT over an atmosphere of H₂ gas (balloon) for 6 h. The reaction mixture is filtered through a pad of Celite to remove the catalyst, rinsing with EtOAc. The filtrate is diluted further with 20 mL of EtOAc and extracted with H₂O (2×40 mL). The organic layer is separated, dried (MgSO₄), and the solvents removed in vacuo. Purification by trituration with EtOAc/Et₂O 1/1 afforded 365 mg of the title compound as a white solid: mp 136°–139° C.; $^1$H NMR (CDCl₃, 400 MHz) δ7.40–7.19 (m, 8H), 7.10 (m, 2H), 6.94 (m, 3H), 4.99 (m, 1H), 4.28 (m, 2H), 4.15 (m, 2H), 3.84 (s, 3H), 3.65 (t, 1H, J=6.9), 2.37 (t, 1H, J=7.3), 1.06 (2×d, 6H, J=6.3); low resolution MS (FAB)m/e 488 (MH⁺), 323, 277; Anal. ($C_{28}H_{29}N_3O_5$) Calcd. C, 68.98; H, 6.00; N, 8.62 Found C, 67.05; H, 5.99; N, 8.33.

Intermediate 58

2-[3-(1-tert-butoxycarbonyl-1H-indazol-3-ylmethyl)-2,4-dioxo-5-phenyl-2,3,4,5-tetrahydro-benzo[b][1,4]diazepin-1-yl]-N-(4-fluoro-phenyl)-N-isopropyl-acetamide A. 2-Bromo-N-(4-fluoro-phenyl)-N-isopropyl-acetamide To a stirring solution of 17 mL (180 mmol) of 4-fluoroaniline in 550 mL of THF at RT is added 26.7 mL (180 mmol, 1.0 equiv) of acetone, 10.3 mL (180 mmol, 1.0 equiv) acetic acid, and 57.22 g (270 mmol, 1.5 equiv) of sodium triacetoxyborohydride. The solution is stirred at RT for 15 h, cooled to 0° C., and then quenched by addition of H₂O. The reaction mixture warmed to RT and is poured into EtOAc, the organic layer is separated, washed with brine (1×200 mL), dried (MgSO₄) and the solvents removed in vacuo. Purification of the material by silica gel flash column chromatography using EtOAc/hexane 1:1 as eluent afforded 14.9 g (54%) of (4-Fluoro-phenyl)-isopropyl amine. A solution of 6.68 g (43.6 mmol) of (this material in 50 mL of DCM is cooled to 0° C. and 6 mL (43.6 mmol, 1.0 equiv) triethyl amine is added, followed by dropwise addition of 2.27 mL (43.6 mmol, 1.0 equiv) of bromoacetyl bromide. The solution is stirred at RT for 15 h and then poured into DCM (200 mL). The organic layer is separated, washed with saturated aq NaHCO₃ (4×50 mL), 1N HCl (6×50 mL), brine (1×50 mL), dried (MgSO₄) and the solvents removed in vacuo. Purification of the material by silica gel flash column chromatography using EtOAc/hexane (3:17) as eluent afforded 5.32 g of 2-Bromo-N-(4-fluoro-phenyl)-N-isopropyl-acetamide: $^1$HNMR (CDCl₃, 300 MHz) δ7.26–7.09 (m, 4 H), 4.85 (m,1H), 3.51 (s, 2H), 1.05 (d, 6H, J=6.9); low resolution MS(FAB) m/e 274 (MH⁺).

B. 2-(2,4-Dioxo-5-phenyl-2,3,4,5-tetrahydro-benzo[b][1,4]diazepin-1-yl)-N-(4-fluoro-phenyl)-N-isopropyl-acetamide To a stirring solution of 1.5 g (5.95 mmol) of intermediate 33 in 15 mL of DMF at RT is added 2.47 g (17.9 mmol, 1.5 equiv) of potassium carbonate, 100 mg (0.6 mmol, 0.1 equiv) potassium iodide, and 1.04 g (5.95 mmol, 1 equiv) of 2-bromo-N-(4-fluoro-phenyl)-N-isopropyl-acetamide, prepared as in Part A. The resulting solution is stirred for 16 h and then poured into 200 mL of EtOAc and washed with H₂O (1×100 mL), saturated aq NaHCO₃ (1×100 mL), and 1N HCl (2×100 mL). The organic layer is separated, dried (MgSO₄) and the solvents removed in vacuo to afford 1.94 g (74%) of the crude 2-(2,4-Dioxo-5-phenyl-2,3,4,5-tetrahydro-benzo[b][1,4]diazepin-1-yl)-N-(4-fluoro-phenyl)-N-isopropyl-acetamide: $^1$H NMR (CDCl₃, 300 MHz) δ7.98 (s, 1H), 7.40–7.06 (m, 11H), 6.90 (m, 1H), 5.45 (m, 1H), 4.30 (d, 1H, J=16.2), 4.00 (d, 1H, J=16.2), 3.55 (m, 2H), 1.08 (d, 6H, J=6.7); low resolution MS (FAB) m/e 446 (MH⁺).

C. 2-[3-(1-tert-butoxycarbonyl-1H-indazol-3-ylmethyl)-2,4-dioxo-5-phenyl-2,3,4,5-tetrahydro-benzo[b][1,4]diazepin-1-yl]-N-(4-fluoro-phenyl)-N-isopropyl-acetamide To a stirring solution of 500 mg (1.12 mmol) of 2-(2,4-dioxo-5-phenyl-2,3,4,5-tetrahydro-benzo[b][1,4]diazepin-1-yl)-N-(4-fluoro-phenyl)-N-isopropyl-acetamide, prepared as in Part B, in 10 mL DMF at 0° C. is added 2.68 mL (1.34 mmol, 1.2 equiv) of NaN(TMS)₂ in toluene. The resulting solution is stirred 5 min, and 417 mg (1.34 mmol, 1.2 equiv) of 3-bromomethyl-1-tert-butoxycarbonyl-1H-indazole is added. The resulting solution is stirred 4.5 h, poured into 100 mL Et₂O/EtOAc (1:1), washed with H₂O (2×50 mL). The organic layer is separated, dried (MgSO₄), and the solvents removed in vacuo to afford 890 mg of the crude title compound: low resolution MS (FAB) m/e 676 (MH⁺).

Intermediate 59

2-[3-(1-tert-butoxycarbonyl-1H-indazol-3-ylmethyl)-2,4-dioxo-5-thiophen-3-yl-2,3,4,5-tetrahydro-benzo[b][1,4]diazepin-1-yl]-N-isopropyl-N-(4-methoxy-phenyl)-acetamide A. 2-(2,4-Dioxo-5-thiophen-3-yl-2,3,4,5-tetrahydro-benzo[b][1,4]diazepin-1-yl)-N-isopropyl-N-(4-methoxy-phenyl)-acetamide To a stirring solution of 500 mg (1.31 mmol) of 1-[isopropyl-(4-methoxy-phenyl)-amino]-1,5-dihydro-benzo[b][1,4]diazepine-2,4-dione in 20 mL of DMF is added 257 mg (2.62 mmol, 2.0 equiv) of potassium acetate, 249 mg (3.93 mmol, 3.0 equiv) copper dust, and 245 mg (2.62 mmol, 2 equiv) of 3-bromothiophene. The resulting solution is heated at 122° C. for 1.5 h, an additional 320 mg (1.95 mmol, 1.5 equiv) 3-bromothiophene is then added followed by continued heating for 1.5 h. The reaction mixture is filtered hot through a pad of celite, the pad is washed with 10 mL of methanol and the filtrate concentrated in vacuo. The residue is diluted with EtOAc (100 mL) and washed with 5% aq ammonium hydroxide (5×25 mL). The organic layer is separated, dried (MgSO₄) and the solvents removed in vacuo. Purification of the material by silica gel flash column chromatography using EtOAc/hexane 2/1 as eluent afforded 345.5 mg (62%) of 2-(2,4-Dioxo-5-thiophen-3-yl-2,3,4,5-tetrahydro-benzo[b][1,4]diazepin-1-yl)-N-isopropyl-N-(4-methoxy-phenyl)-acetamide: $^1$H NMR (CDCl₃, 300 MHz) δ7.42 (s, 1H), 7.39 (m, 3H), 7.28–6.90 (m, 7H), 5.01 (m, 1H), 4.31 (d, 1H, J=16.6), 4.10 (d, 1H, J=16.6), 3.81 (s, 3H), 3.50 (ABq, 2H, J=12.0, 26.9), 1.07 (d, 6H, J=6.9); low resolution MS (FAB) m/e 464 (MH⁺).

B. 2-[3-(1-tert-butoxycarbonyl-1H-indazol-3-ylmethyl)-2,4-dioxo-5-thiophen-3-yl-2,3,4,5-tetrahydro-benzo[b][1,4]diazepin-1-yl]-N-isopropyl-N-(4-methoxy-phenyl)-acetamide To a stirring solution of 340 mg (0.80 mmol) of 2-(2,4-dioxo-5-thiophen-3-yl-2,3,4,5-tetrahydro-benzo[b][1,4]diazepin-1-yl)-N-isopropyl-N-(4-methoxy-phenyl)-acetamide, prepared as in Part A, in 10 mL DMF at 0° C. is added 1.93 mL (0.96 mmol, 1.2 equiv) of NaN(TMS)₂ in toluene. The resulting solution is stirred 5 min and 299 mg (0.96 mmol, 1.2 equiv) of 3-bromomethyl-1-tert-butoxycarbonyl-1H-indazole is added. The resulting solution is stirred 4.5 h, poured into 100 mL Et₂O/EtOAc (1:1), washed with H₂O (2×50 mL). The organic layer is separated, dried (MgSO₄), and the solvents removed in vacuo to afford 590 mg of the crude title compound: low resolution MS (FAB) m/e 694 (MH⁺).

Intermediate 60

2-[3-(1-tert-butoxycarbonyl-1H-indazol-3-ylmethyl)-2,4-dioxo-5-thiophen-2-yl-2,3,4,5-tetrahydro-benzo[b][1,4]diazepin-1-yl]-N-isopropyl-N-(4-methoxy-phenyl)-acetamide A. 2-(2,4-Dioxo-5-thiophen-2-yl-2,3,4,5-tetrahydro-benzo[b][1,4]diazepin-1-yl)-N-isopropyl-N-(4-methoxy-phenyl)-acetamide To a stirring solution of 500 mg (1.31 mmol) of 1-[isopropyl-(4-methoxy-phenyl)-amino]-1,5-dihydro-benzo[b][1,4]diazepine-2,4-dione in 20 mL of DMF is added 257 mg (2.62 mmol, 2.0 equiv) of potassium acetate, 249 mg (3.93 mmol, 3.0 equiv) copper dust, and 245 mg (2.62 mmol, 2 equiv) of 2-bromothiophene. The resulting solution is heated at 122° C. for 1.5 h, an additional 320 mg (1.95 mmol, 1.5 equiv) 2-bromothiophene is then added followed by continued heating for 1.5 h. The reaction mixture is filtered hot through a pad of celite, the pad is washed with 10 mL of methanol and the filtrate concentrated in vacuo. The residue is diluted with EtOAc (100 mL) and washed with 5% aq ammonium hydroxide (5×25 mL). The organic layer is separated, dried (MgSO$_4$) and the solvents removed in vacuo. Purification of the material by silica gel flash column chromatography using EtOAc as eluent afforded 210 mg (46%) of 2-(2,4-Dioxo-5-thiophen-2-yl-2,3,4,5-tetrahydro-benzo[b][1,4]diazepin-1-yl)-N-isopropyl-N-(4-methoxy-phenyl)-acetamide: $^1$H NMR (CDCl$_3$, 300 MHz) δ7.43 (d, 1H, J=8.3), 7.29–6.74 (m, 10H), 5.01 (m, 1H), 4.36 (d, 1H, J=16.7), 3.85 (d, 1H, J=16.6), 3.83 (s, 3H), 3.50 (ABq, 2H, J=12.2, 28.3), 1.09 (d, 6H, J=6.8); low resolution MS (FAB) m/e 464 (MH$^+$).

B. 2-[3-(1-tert-butoxycarbonyl-1H-indazol-3-ylmethyl)-2,4-dioxo-5-thiophen-2-yl-2,3,4,5-tetrahydro-benzo[b][1,4]diazepin-1-yl]-N-isopropyl-N-(4-methoxy-phenyl)-acetamide To a stirring solution of 200 mg (0.43 mmol) of 2-(2,4-dioxo-5-thiophen-2-yl-2,3,4,5-tetrahydro-benzo[b][1,4]diazepin-1-yl)-N-isopropyl-N-(4-methoxy-phenyl)-acetamide, prepared as in Part A, in 5 mL DMF at 0° C. is added 1.04 mL (0.52 mmol, 1.2 equiv) of NaN(TMS)$_2$ in toluene. The resulting solution is stirred 5 min and 162 mg (0.52 mmol, 1.2 equiv) of 3-bromomethyl-1-tert-butoxycarbonyl-1H-indazole is added. The resulting solution is stirred 16 h at RT, poured into 100 mL Et$_2$O/EtOAc (1:1), washed with H2O (3×50 mL). The organic layer is separated, dried (MgSO$_4$), and the solvents removed in vacuo to afford 280 mg of the crude title compound: low resolution MS (FAB) m/e 694 (MH$^+$).

Intermediate 61

6-Fluoro-3-[1-Isopropyl-p-tolyl-carbamoylmethyl)-2,4-dioxo-5-phenyl-2,3,4,5,-tetrahydro-1H-benzo[b][1,4]diazepin-3-ylmethyl]-indazole-1-carboxylic acid tert butyl ester A. Isopropyl-p-tolyl-amine To a stirred solution of 5.65 g (52.7 mmol) p-Toluidine and 3.21 g (55.4 mmol, 1.05 equiv) Acetone in 50 mL DCE is added 14.52 g (68.5 mmol, 1.3 equiv) Sodium triacetoxyborohydride and stirred 18 h at ambient temperature. The reaction mixture is diluted with DCM (200 mL), washed successively with H$_2$O (75 mL), satd. NaHCO$_3$ (75 mL), and brine (75 mL), dried (MgSO$_4$), filtered and concentrated in vacuo to give 7.67 g (51.4 mmol) of Isopropyl-p-tolyl-amine as a pale amber oil: $^1$H NMR (CDCl$_3$, 300 MHz) δ7.00 (d, 2H, J=8.3), 6.54 (d, 2H, J=8.4), 3.61 (m, 1H), 2.25 (s, 3H), 1.21 (d, 6H, J=6.3); TLC R$_f$=0.50 (EtOAc/Hexanes, 1:9).

B. 2-Bromo-N-isopropyl-N-p-tolyl-acetamide

To a stirred solution of 6.07 g (40.7 mmol) Isopropyl-p-tolyl-amine, prepared as in Part A, and 4.12 g (40.7 mmol, 1 equiv) Et$_3$N in 50 mL DCM is added 8.22 g (40.7 mmol, 1 equiv) Bromoacetyl bromide in 25 mL DCM dropwise over 30 minutes at 0° C. The reaction mixture is stirred 1 h at 0° C. followed by warming to ambient temperature and stirring 18 h. The reaction mixture is washed with 1N HCl (3×50 mL), dried (MgSO$_4$), filtered through a pad of 20 g silica gel eluted with 400 mL DCM, and concentrated in vacuo to give 9.39 g (34.5 mmol) of 2-Bromo-N-isopropyl-N-p-tolyl-acetamide as an amber oil: $^1$H NMR (CDCl$_3$, 300 MHz) δ7.25 (d, 2H, J=8.1), 7.09 (d, 2H, J=8.3), 4.96 (m, 1H), 3.55 (s, 2H), 2.42 (s, 3H), 1.07 (d, 6H, J=6.8); TLC R$_f$=0.23 (EtOAc/Hexanes, 1:9).

C. 6-Fluoro-3-methyl-indazole-1-carboxylic acid tert-butyl ester

In a sealed flask were combined 12.99 g (83.2 mmol) 2,4-Difluoroacetophenone, 8.80 g (274 mmol, 3.3 equiv) Hydrazine and 8.7 mL EtOH and heated at 150° C. for 18 h. The resultant solid is dissolved in 150 mL EtOH, precipitated with 500 mL H$_2$O, cooled, filtered, air and pump dried to give 8.56 g (57.0 mmol) 6-Fluoro-3-methyl-1H-indazole which is used without characterization. The material thus obtained is combined with 6.35 g (62.7 mmol, 1.1 equiv) Et$_3$N and 1.39 g (11.4 mmol, 0.2 equiv) DMAP in 110 mL CH$_3$CN cooled to 0° C. 14.93 g (68.4 mmol, 1.2 equiv) (BOC)$_2$O in 80 mL CH$_3$CN is added dropwise with stirring at 0° C. and the resultant reaction mixture stirred 2 h at 0° C. followed by 18 h at ambient temperature. The solvent is removed in vacuo and the crude material partitioned between EtOAc (200 mL) and H$_2$O (100 mL). The pH is adjusted to 2.0 with 1N HCl, the organic phase separated, dried (MgSO$_4$), filtered and concentrated in vacuo to an orange solid which is purified by filtration through a pad of 60 g silica gel eluted with 1.2 L DCM. The filtrate is concentrated in vacuo to give 12.68 g (50.7 mmol) of 6-Fluoro-3-methyl-indazole-1-carboxylic acid tert-butyl ester as a tan crystalline solid: $^1$H NMR (CDCl$_3$, 300 MHz) δ7.78 (d, 1H, J=9.8), 7.57 (m, 1H), 7.07 (m, 1H), 2.57 (s, 3H), 1.72 (s, 9H); TLC R$_f$=0.52 (DCM).

D. 3-Bromomethyl-6-fluoro-1-tert-butoxycarbonyl-1H-indazole 12.68 g (50.7 mmol) 6-Fluoro-3-methyl-indazole-1-carboxylic acid tert-butyl ester, prepared as in Part C, is combined with 9.92 g (55.7 mmol, 1.1 equiv) N-Bromosuccinimide and 1.23 g (5.1 mmol, 0.1 equiv) Benzoyl peroxide in 600 mL CCl$_4$ and refluxed 10 h. The reaction mixture is filtered and the filtrate concentrated in vacuo and purified by flash chromatography on 300 g silica gel eluted successively with DCM/Hexanes (1:2, 3 L), (1:1, 3 L). Appropriate fractions were combined and concentrated in vacuo to give 10.18 g (30.9 mmol) of 3-Bromomethyl-6-fluoro-1-tert-butoxycarbonyl-1H-indazole as an amber oil: $^1$H NMR (CDCl$_3$, 300 MHz) δ7.82 (m, 2H), 7.13 (m, 1H), 4.76 (s, 2H), 1.72 (s, 9H); TLC R$_f$=0.17 (EtOAc/Hexanes, 1:19).

E. 2-(2,4-Dioxo-5-phenyl-2,3,4,5,-tetrahydro-benzo[b][1,4]diazepin-1-yl)-N-isopropyl-N-p-tolyl-acetamide To a stirred solution of 700 mg (2.78 mmol) 1-Phenyl-2,3,4,5-tetrahydro-benzo[b][1,4]diazepin-2,4-dione in 15 mL DMF is added 144 mg (3.61 mmol, 1.3 equiv) 60 wt % NaH at ambient temperature and stirred 0.5 h. To this solution is added 750 mg (2.78 mmol, 1.0 equiv) 2-Bromo-N-isopropyl-N-p-tolyl-acetamide, prepared as in Part B, in 1 mL DMF and stirred 18 h at ambient temperature. The solvent is removed in vacuo and the residue taken into 50 mL EtOAc and washed successively with H$_2$O (30 mL), 1N HCl (30 mL), satd. NaHCO$_3$ (30 mL), and brine (30 mL), dried (MgSO$_4$), filtered and concentrated in vacuo to a yellow oil. The crude product is purified by flash chromatography on 27 g silica gel eluted successively with EtOAc/Hexanes (2:3, 500 mL), (1:1, 100 mL). Appropriate fractions were combined and concentrated in vacuo to give 554 mg (1.25 mmol) of 2-(2,4-Dioxo-5-phenyl-2,3,4,5,-tetrahydro-benzo[b][1,4]diazepin-1-yl)-N-isopropyl-N-p-tolylacetamide as a white foam: $^1$H NMR (CDCl$_3$, 300 MHz) δ7.43–7.07 (m, 12H), 6.90 (d, 1H, J=8.3), 5.03 (m, 1H), 4.37 (d, 1H, J=16.6), 4.04 (d, 1H, J=16.6), 3.58 (d, 1H, J=11.9), 3.49 (d, 1H, J=11.7), 2.41 (s, 3H), 1.10 (d, 6H, J=6.6); TLC R$_f$=0.27 (EtOAc/Hexanes, 1:1).

F. 6-Fluoro-3-[1-Isopropyl-p-tolyl-carbamoylmethyl)-2,4-dioxo-5-phenyl-2,3,4,5,-tetrahydro-1H-benzo[b][1,4]diazepin-3-ylmethyl]-indazole-1-carboxylic acid tert butyl ester To a stirred solution of 394 mg (0.893 mmol) 2-(2,4-Dioxo-5-phenyl-2,3,4,5,-tetrahydro-benzo[b][1,4]diazepin-1-yl)-N-isopropyl-N-p-tolyl-acetamide, prepared as in Part E, in 10 mL DMF cooled to 0° C. is added 47 mg (1.16 mmol, 1.3 equiv) 60 wt % NaH and stirred 0.5 h. To this solution is added 294 mg (0.893 mmol, 1.0 equiv) 3-Bromomethyl-6-fluoro-1-tert-butoxycarbonyl-1H-indazole, prepared as in Part D, and the resultant reaction mixture stirred 1 h at 0° C. followed by 18 h at ambient temperature. The solvent is removed in vacuo and the residue taken into EtOAc (50 mL), washed with H$_2$O (30 mL) and brine (30 mL), dried (MgSO$_4$), filtered and concentrated in vacuo. The crude product is purified by flash chromatography on 26 g silica gel eluted with EtOAc/Hexanes (1:3, 500 mL) Appropriate fractions were combined and concentrated in vacuo to give 431 mg (0.625 mmol) of the title compound as a white foam: $^1$H NMR (CDCl$_3$, 300 MHz) δ7.87 (m, 1H), 7.76 (d, 1H, J=9.5), 7.55–6.96 (m, 14H), 5.05 (m, 1H), 4.30 (m, 3H), 3.85 (m, 1H), 3.55 (m, 1H), 2.45 (s, 3H), 1.69 (s, 9H), 1.12 (d, 6H, J=6.8); TLC R$_f$=0.15 (EtOAc/Hexanes, 1:3).

Intermediate 62

3-[1-(Cyclopropyl-phenyl-carbamoylmethyl)-2,4-dioxo-5-phenyl-2,3,4,5,-tetrahydro-1H-benzo[b][1,4]diazepin-3-ylmethyl]-indazole-1-carboxylic acid tert-butyl ester A. 2-Bromo-N-cyclopropyl-N-phenyl-acetamide To a stirred solution of 908 mg (6.83 mmol) Cyclopropyl-phenyl-amine (Kang, Sung, Kim, *J. Chem. Soc., Chem. Commun.*, 1987, 897–898) and 690 mg (6.83 mmol, 1 equiv) Et$_3$N in 10 mL DCM is added 1.38 g (6.83 mmol, 1 equiv) Bromoacetyl bromide in 4 mL DCM dropwise over 15 minutes at 0° C. The reaction mixture is stirred 3 h at 0° C., diluted with 30 mL DCM, washed with 1N HCl (30 mL), dried (MgSO$_4$), and concentrated in vacuo. The crude product is purified by flash chromatography on 30 g silica gel eluted successively with EtOAc/Hexanes (1:9, 100 mL), (3:17, 300 mL). Appropriate fractions were combined and concentrated in vacuo to give 948 mg (3.73 mmol) of 2-Bromo-N-cyclopropyl-N-phenyl-acetamide as an amber oil: $^1$H NMR (CDCl$_3$, 300 MHz) δ7.39 (m, 3H), 7.15 (m, 2H), 3.62 (s, br, 2H), 3.24 (m, 1H), 0.83 (m, 2H), 0.52 (m, 2H); TLC R$_f$=0.18 (EtOAc/Hexanes, 3:17).

B. N-Cyclopropyl-2-(2,4-dioxo-5-phenyl-2,3,4,5-tetrahydro-benzo[b][1,4]diazepin-1-yl)-N-phenyl-acetamide To a stirred solution of 500 mg (1.98 mmol) 1-Phenyl-2,3,4,5-tetrahydro-benzo[b][1,4]diazepin-2,4-dione in 15 mL DMF is added 103 mg (2.58 mmol, 1.3 equiv) 60 wt % NaH at ambient temperature and stirred 0.5 h. To this solution is added 504 mg (1.98 mmol, 1.0 equiv) 2-Bromo-N-cyclopropyl-N-phenyl-acetamide, prepared as in Part A, in 1 mL DMF and stirred 18 h at ambient temperature. The solvent is removed in vacuo and the residue taken into 50 mL EtOAc, washed successively with H$_2$O (30 mL), 1N HCl (30 mL), satd. NaHCO$_3$ (30 mL), and brine (30 mL), dried (MgSO$_4$), filtered and concentrated in vacuo to a brown oil. The crude product is purified by flash chromatography on 15 g silica gel eluted with EtOAc/Hexanes (1:1, 450 mL). Appropriate fractions were combined and concentrated in vacuo to give 572 mg (1.34 mmol) of N-Cyclopropyl-2-(2,4-dioxo-5-phenyl-2,3,4,5,tetrahydro-benzo[b][1,4]diazepin-1-yl)-N-phenyl-acetamide as a white foam: $^1$H NMR (CDCl$_3$, 300 MHz) δ7.50–7.07 (m, 13H), 6.92 (d, 1H, J=7.3), 3.60 (d, 1H, J=11.9), 3.51 (d, 1H, J=12.0), 3.30 (m, 1H), 0.86 (m, 2H), 0.60 (m, 2H); TLC R$_f$=0.35 (EtOAc/Hexanes, 2:1).

C. 3-[1-(Cyclopropyl-phenyl-carbamoylmethyl)-2,4-dioxo-5-phenyl-2,3,4,5-tetrahydro-1H-benzo[b][1,4]diazepin-3-ylmethyl]-indazole-1-carboxylic acid tert-butyl ester To a stirred solution of 572 mg (1.34 mmol) N-Cyclopropyl-2-(2,4-dioxo-5-phenyl-2,3,4,5-tetrahydro-benzo[b][1,4]diazepin-1-yl)-N-phenyl-acetamide in 4 mL DMF cooled to 0° C. is added 75 mg (1.75 mmol, 1.3 equiv) 60 wt % NaH and stirred 0.5 h. To this solution is added 439 mg (1.41 mmol, 1.05 equiv) 3-bromomethyl-1-tert-butoxycarbonyl-1H-indazole and the resultant reaction mixture stirred 1 h at 0° C. followed by 18 h at ambient temperature. The solvent is removed in vacuo and the residue taken into EtOAc (50 mL), washed with H$_2$O (30 mL) and brine (30 mL), dried (MgSO$_4$), filtered and concentrated in vacuo. The crude product is purified by flash chromatography on 15 g silica gel eluted successively with EtOAc/Hexanes (2:5, 200 mL), (1:2, 250 mL). Appropriate fractions were combined and concentrated in vacuo to give 543 mg (0.828 mmol) of the title compound as a white foam: $^1$H NMR (CDCl$_3$, 300 MHz) δ8.06 (d, 1H, J=8.2), 7.87 (d, 1H, J=8.0), 7.52–7.21 (m, 14H), 7.12 (m, 1H), 6.97 (d, 1H, J=7.9), 4.36 (m, 3H), 3.88 (m, 1H), 3.54 (m, 1H), 3.29 (m, 1H), 1.66 (s, 9H), 0.83 (m, 2H), 0.58 (m, 2H); TLC R$_f$=0.19 (EtOAc/Hexanes, 1:2).

Intermediate 63

3-{1-[Cyclopentyl-(4-methoxy-phenyl)-carbamoylmethyl]-2,4-dioxo-5-phenyl-2,3,4,5,-tetrahydro-1H-benzo[b][1,4]diazepin-3-ylmethyl}-indazole-1-carboxylic acid tert-butyl ester A. 2-Bromo-N-cyclopentyl-N-(4-methoxy-phenyl)-acetamide To a stirred solution of 7.00 g (56.8 mmol) p-Anisidine, 9.56 g (114 mmol, 2.0 equiv) Cyclopentanone, and 4.10 g (68.2 mmol, 1.2 equiv) Acetic acid in 145 mL Methanol is added 125 mL (125 mmol, 2.2 equiv) 1N Sodium cyanoborohydride in THF and stirred 18 h at ambient temperature. The reaction mixture is concentrated in vacuo and the residue taken into 200 mL EtOAc, washed with H$_2$O (150 mL), dried (MgSO$_4$), filtered and concentrated in vacuo to give crude Cyclopentyl-(4-methoxy-phenyl)-amine as a brown oil. To a stirred solution of this material and 6.03 g (58.6 mmol, 1.05 equiv) Et$_3$N in 70 mL DCM is added 11.47 g (56.8 mmol, 1 equiv) Bromoacetyl bromide in 50 mL DCM dropwise over 30 minutes at 0° C. The reaction mixture is stirred 1 h at 0° C. followed by warming to ambient temperature and stirring 18 h. The reaction mixture is washed with 1N HCl (3×50 mL), dried (MgSO$_4$), filtered through a pad of 100 g silica gel eluted with EtOAc/Hexanes (3:17, 1.5 L), and concentrated in vacuo to give 10.22 g (32.7 mmol) of 2-Bromo-N-cyclopentyl-N-(4-methoxy-phenyl)-acetamide as an orange oil: $^1$H NMR (CDCl$_3$, 300 MHz) δ7.09 (d, 2H, J=9.0), 6.90 (d, 2H, J=9.0), 4.84 (m,1H), 3.83 (s, 3H), 3.54 (s, 2H), 1.87 (m, 2H), 1.49 (m, 4H), 1.25 (m, 2H); TLC R$_f$=0.65 (EtOAc/Hexanes, 3:17).

B. N-Cyclopentyl-N-(4-methoxy-phenyl)-2-(6-phenylamino-cyclohexa-2,4-dienylamino)-acetamide 2.03 g (10.7 mmol) N-Phenyl-o-phenylene diamine, 3.50 g (11.2 mmol, 1.05 equiv) 2-Bromo-N-cyclopentyl-N-(4-methoxy-phenyl)-acetamide, prepared as in Part A, 1.62 g (11.7 mmol, 1.1 equiv) Potassium carbonate, and 177 mg (1.1 mmol, 0.1 equiv) Potassium Iodide were combined in 35 mL DMF and stirred 18 h at 60° C. The reaction mixture is filtered and the solvent removed in vacuo. The residue is taken into EtOAc (150 mL), washed with 1N HCl (2×50 mL), H$_2$O (50 mL), dried (MgSO$_4$), filtered and concentrated in vacuo. The crude product is purified by flash chromatography on 50 g silica gel eluted with EtOAc/Hexanes (3:17, 1 L). Appropriate fractions were combined and concentrated in vacuo to give 2.53 g (6.09 mmol) of N-Cyclopentyl-N-(4-methoxy-phenyl)-2-(6-phenylamino-cyclohexa-2,4-dienylamino)-acetamide as a yellow oil: $^1$H NMR (Acetone-d$_6$, 300 MHz) δ7.26–6.50 (m, 13H), 6.22 (d, 1H, J=7.9), 5.29 (s, br, 1H), 4.82 (m, 1H), 3.87 (s, 3H), 3.41 (d, 2H, J=4.4), 1.83 (m, 2H), 1.48 (m, 4H), 1.33 (m, 2H); TLC R$_f$=0.14 (EtOAc/Hexanes, 3:17).

C. N-Cyclopentyl-2-(2,4-dioxo-5-phenyl-2,3,4,5,-tetrahydro-benzo[b][1,4]diazepin-1-yl)-N-(4-methoxy-phenyl)-acetamide To a stirred solution of 419 mg (1.01 mmol) N-Cyclopentyl-N-(4-methoxy-phenyl)-2-(6-phenylamino-cyclohexa-2,4-dienylamino)-acetamide, prepared as in Part B, in 5 mL THF is added 170 mg (1.21 mmol, 1.2 equiv) Malonyl dichloride dissolved in 2 mL THF dropwise at 0° C. The reaction is stirred 1 h at 0° C. followed by 18 h at ambient temperature. The solvent is removed in vacuo and the residue purified by flash chromatography on 15 g silica gel eluted with EtOAc/Hexanes (1:1, 300 mL). Appropriate fractions were combined and concentrated in vacuo to give 249 mg (0.515 mmol) of N-Cyclopentyl-2-(2,4-dioxo-5-phenyl-2,3,4,5-tetrahydro-benzo[b][1,4]diazepin-1-yl)-N-(4-methoxy-phenyl)-acetamide as a clear glass: $^1$H NMR (CDCl$_3$, 300 MHz) δ7.43–7.20 (m, 8H), 7.09 (m, 2H), 6.97 (m, 3H), 4.95 (m, 1H), 4.38 (d, 1H, J=16.4), 4.06 (d, 1H, J=16.3), 3.84 (s, 3H), 3.59 (d, 1H, J=12.0), 3.49 (d, 1H, J=11.9), 1.90 (m, 2H), 1.52 (m, 4H), 1.35 (m, 2H); TLC R$_f$=0.16 (EtOAc/Hexanes, 1:1).

D. 3-{1-[Cyclopentyl-(4-methoxy-phenyl)-carbamoylmethyl]-2,4-dioxo-5-phenyl-2,3,4,5,-tetrahydro-1H-benzo[b][1,4]diazepin-3-ylmethyl}-indazole-1-carboxylic acid tert-butyl ester To a stirred solution of 186 mg (0.385 mmol) N-Cyclopentyl-2-(2,4-dioxo-5-phenyl-2,3,4,5,-tetrahydro-benzo[b][1,4]diazepin-1-yl)-N-(4-methoxy-phenyl)-acetamide in 6 mL DMF cooled to 0° C. is added 0.462 mL of 1M Sodium bis(trimethyl silyl)amide in THF and stirred 0.5 h. To this solution is added 132 mg (0.423 mmol, 1.1 equiv) 3-Bromomethyl-indazole-1-carboxylic acid tert-butyl ester and the resultant reaction mixture stirred 1 h at 0° C. followed by 18 h at ambient temperature. The solvent is removed in vacuo and the residue taken into EtOAc (50 mL), washed with H$_2$O (30 mL) and brine (30 mL), dried (MgSO$_4$), filtered and concentrated in vacuo. The crude product is purified by flash chromatography on 10 g silica gel eluted with EtOAc/Hexanes (1:2, 250 mL). Appropriate fractions were combined and concentrated in vacuo to give 129 mg (0.181 mmol) of the title compound as a white glass: $^1$H NMR (CDCl$_3$, 300 MHz) δ8.05 (d, 1H, J=8.3), 7.87 (d, 1H, J=8.0), 7.51–6.93 (m, 15H), 4.94 (m, 1H), 4.30 (m, 3H), 3.90 (m, 1H), 3.84 (s, 3H), 3.56 (m, 1H), 1.87 (m, 2H), 1.66 (s, 9H), 1.51 (m, 4H), 1.30 (m, 2H); TLC R$_f$=0.25 (EtOAc/Hexanes, 1:2).

Intermediate 64

6-Fluoro-3-{1-[(4-fluoro-phenyl)-isopropyl-carbamoylmethyl]-2,4-dioxo-5-phenyl-2,3,4,5,-tetrahydro-1H-benzo[b][1,4]diazepin-3-ylmethyl}-indazole-1-carboxylic acid tert-butyl ester To a stirred solution of 800 mg (1.79 mmol) 2-(2,4-Dioxo-5-phenyl-2,3,4,5,-tetrahydro-benzo[b][1,4]diazepin-1-yl)-N-(4-fluoro-phenyl)-N-isopropyl-acetamide in 15 mL DMF cooled to 0° C. is added 86 mg (2.16 mmol, 1.2 equiv) 60 wt % NaH and stirred 0.5 h. To this solution is added 591 mg (1.79 mmol, 1.0 equiv) 3-Bromomethyl-6-fluoro-1-tert-butoxycarbonyl-1H-indazole and the resultant reaction mixture stirred 1 h at 0° C. followed by 18 h at ambient temperature. The solvent is removed in vacuo and the residue taken into EtOAc (80 mL), washed with H$_2$O (30 mL) and brine (30 mL), dried (MgSO$_4$), filtered and concentrated in vacuo. The crude product is purified by flash chromatography on 40 g silica gel eluted with EtOAc/Hexanes (1:3, 800 mL) Appropriate fractions were combined and concentrated in vacuo to give 730 mg (1.05 mmol) of the title compound as a white glass: $^1$H NMR (CDCl$_3$, 300 MHz) δ7.83 (m, 1H), 7.72 (d, 1H, J=9.2), 7.41–7.03 (m, 13H), 6.95 (d, 1H, J=7.4), 5.02 (m, 1H), 4.26 (m, 1H), 4.22 (s, 2H), 3.82 (m, 1H), 3.51 (m, 1H), 1.65 (s, 9H), 1.07 (d, 6H, J=6.9); TLC R$_f$=0.36 (EtOAc/Hexanes, 2:3).

Intermediate 65

3-[1-(tert-Butyl-phenyl-carbamoylmethyl)-2,4-dioxo-5-phenyl-2,3,4,5,-tetrahydro-1H-benzo[b][1,4] diazepin-3-ylmethyl]-indazole-1-carboxylic acid tert-butyl ester A. 2-Bromo-N-tert-butyl-N-phenyl-acetamide To a stirred solution of 7.91 g (53.0 mmol) tert-Butyl-phenyl-amine (Biehl, Smith, Reeves, *J. Org. Chem.*, 1971, 13, 1842) and 5.36 g (58.3 mmol, 1.1 equiv) Et$_3$N in 60 mL DCM is added 11.77 g (58.3 mmol, 1.1 equiv) Bromoacetyl bromide in 40 mL DCM dropwise over 45 minutes at 0° C. The reaction mixture is stirred 3 h at 0° C., diluted with 200 mL DCM, washed with 1N HCl (2×150 mL), dried (MgSO$_4$), and concentrated in vacuo. The crude product is filtered through a pad of 15 g silica gel eluted with 300 mL DCM. The filtrate is concentrated in vacuo to give 12.40 g (45.9 mmol) of 2-Bromo-N-tert-butyl-N-phenyl-acetamide as an amber oil: $^1$H NMR (CDCl$_3$, 300 MHz) δ7.45–7.21 (m, 12H), 7.08 (t, 1H), 6.90 (m, 1H), 4.30 (d, 1H, J=16.4), 3.85 (d, 1H, J=16.6), 3.59 (d, 1H, J=12.0), 3.49 (d, 1H, J=11.9), 1.43 (s, 9H); TLC R$_f$=0.24 (EtOAc/Hexanes, 1:1).

B. N-tert-Butyl-2-(2,4-dioxo-5-phenyl-2,3,4,5,-tetrahydro-benzo[b][1,4]diazepin-1-yl)-N-phenyl-acetamide To a stirred solution of 600 mg (2.38 mmol) 1-Phenyl-2,3,4,5-tetrahydro-benzo[b][1,4]diazepin-2,4-dione in 16 mL DMF is added 2.62 mL (2.62 mmol, 1.1 equiv) of 1M Sodium bis(trimethylsilyl)amide in THF at ambient temperature and stirred 0.5 h. To this solution is added 707 mg (2.62 mmol, 1.1 equiv) 2-Bromo-N-tert-butyl-N-phenyl-acetamide, prepared as in Part A, in 4 mL DMF and stirred 18 h at ambient temperature. The solvent is removed in vacuo and the residue taken into 50 mL EtOAc, washed successively with H$_2$O (30 mL), 1N HCl (30 mL), satd. NaHCO$_3$ (30 mL), and brine (30 mL), dried (MgSO$_4$), filtered and concentrated in vacuo to a brown oil. The crude product is purified by flash chromatography on 40 g silica gel eluted successively with EtOAc/Hexanes (2:3, 500 mL), (1:1, 750 mL). Appropriate fractions were combined and concentrated in vacuo to give 748 mg (1.69 mmol) of N-tert-Butyl-2-(2,4-dioxo-5-phenyl-2,3,4,5,-tetrahydro-benzo[b][1,4]diazepin-1-yl)-N-phenyl-acetamide as a white foam: $^1$H NMR (CDCl$_3$, 300 MHz) δ7.45–7.21 (m, 12H), 7.08 (t, 1H), 6.90 (m, 1H), 4.30 (d, 1H, J=16.4), 3.85 (d, 1H, J=16.6), 3.59 (d, 1H, J=12.0), 3.49 (d, 1H, J=11.9), 1.43 (s, 9H); TLC R$_f$=0.24 (EtOAc/Hexanes, 1:1).

C. 3-[1-(tert-Butyl-phenyl-carbamoylmethyl)-2,4-dioxo-5-phenyl-2,3,4,5,-tetrahydro-1H-benzo[b][1,4]diazepin-3-ylmethyl]-indazole-1-carboxylic acid tert-butyl ester To a stirred slurry of 514 mg (1.17 mmol) N-tert-Butyl-2-(2,4-dioxo-5-phenyl-2,3,4,5-tetrahydro-benzo[b][1,4]diazepin-1-yl)-N-phenyl-acetamide, prepared as in Part B, in 15 mL THF cooled to 0° C. is added 1.28 mL (1.28 mmol, 1.1 equiv) of 1M Sodium bis(trimethylsilyl)amide in THF at ambient temperature and stirred 0.5 h. To this solution is added 381 mg (1.22 mmol, 1.05 equiv) 3-bromomethyl-1-tert-butoxycarbonyl-1H-indazole and the resultant reaction mixture stirred 1 h at 0° C. followed by 18 h at ambient temperature. The solvent is removed in vacuo and the residue taken into EtOAc (50 mL), washed with $H_2O$ (30 mL) and brine (30 mL), dried ($MgSO_4$), filtered and concentrated in vacuo. The crude product is purified by flash chromatography on 20 g silica gel eluted with EtOAc/Hexanes (1:3, 350 mL). Appropriate fractions were combined and concentrated in vacuo to give 263 mg (0.392 mmol) of the title compound as a white foam: $^1$H NMR ($CDCl_3$, 300 MHz) δ8.04 (d, 1H, J=8.4), 7.89 (d, 1H, J=7.9), 7.51–7.20 (m, 14H), 7.10 (m, 1H), 6.94 (m, 1H), 4.28 (m, 1H), 4.20–4.06 (m, 2H), 3.84 (m, 1H), 3.56 (m,1H), 1.66 (s, 9H), 1.39 (s, 9H); TLC $R_f$=0.16 (EtOAc/Hexanes, 1:3).

Intermediate 66

2-[7-Fluoro-3-(1-tert-butoxycarbonyl-indazol-3-ylmethyl)-2,4-dioxo-5-pyridin-3-yl-2,3,4,5-tetrahydro-benzo[b][1,4]diazepin-1-yl]-N-isopropyl-N-(4-methoxy-phenyl)-acetamide A. 2-Amino-N-isopropyl-N-(4-methoxy-phenyl)-acetamide A solution of 2.86 g of 2-bromo-N-isopropyl-N-(4-methoxy-phenyl)-acetamide (10 mmol) in 100 mL methanol is saturated with ammonia at 0° C. and left for 3 days at ambient temperature in a sealed flask. Methanol and ammonia were removed in vacuo and the residue is dissolved in 100 mL of chloroform and washed with water (2×50 mL). The organic layer is dried over anhydrous $MgSO_4$, filtered, concentrated in vacuo and dried under high vacuum to afford 2.7 g of 2-Amino-N-isopropyl-N-(4-methoxy-phenyl)-acetamide as an oil: $^1$H NMR (300 MHz, $CDCl_3$) δ6.96 (m, 4H), 4.99 (m, 1H), 3.84 (s, 3H), 2.97 (s, 2H), 1.58 (s, 2H), 1.05 (d, 6H, J=6.6); low resolution MS (ESI)m/e 223 (MH$^+$).

B. 2-(4-Fluoro-2-nitro-phenylamino)-N-isopropyl-N-(4-methoxy-phenyl)-acetamide

A mixture of 9.06 g of 2,5-difluoro-nitrobenzene (60 mmol) and 12.64 g of 2-amino-N-isopropyl-N-(4-methoxy-phenyl)-acetamide, prepared as in Part A, (60 mmol, 1.0 equiv) were combined in 225 mL of 2:1 ethanol/water and heated to reflux under nitrogen and stirred vigorously overnight (approx. 16 hrs.). The resulting slurry is cooled to ambient temperature, filtered and washed with 2:1 water/ethanol. The wet solid is dissolved in methylene chloride, dried over anhydrous sodium sulfate, and evaporated in vacuo. The residue is triturated with hexane, filtered and washed with hexane. The product is dried under high vacuum to provide 9.32 g of 2-(4-Fluoro-2-nitro-phenylamino)-N-isopropyl-N-(4-methoxy-phenyl)-acetamide as an orange solid: $^1$H NMR (300 MHz, $CDCl_3$) δ7.89 (dd, 1H, J=3.1, 9.3), 7.12 (m, 3H), 6.99 (m, 2H), 6.35 (dd, 1H, J=4.8, 9.2), 5.03 (m, 1H), 3.89 (s, 3H), 3.57 (s, 2H), 1.09 (d, 6H, J=6.8); low resolution MS (ESI)m/e 362 (MH$^+$).

C. 2-(2-Amino-4-fluoro-phenylamino)-N-isopropyl-N-(4-methoxy-phenyl)-acetamide

A solution of 30 mL ethyl acetate, 175 mL ethanol, and 2.50 g of 2-(4-Fluoro-2-nitro-phenylamino)-N-isopropyl-N-(4-methoxy-phenyl)-acetamide, prepared as in Part B, (6.92 mmol) is combined with 0.25 g of palladium on carbon (10 wt %) and hydrogenated under a hydrogen balloon over 16 hrs. The reaction mixture is filtered and evaporated in vacuo to provide 1.91 g of 2-(2-Amino-4-fluoro-phenylamino)-N-isopropyl-N-(4-methoxy-phenyl)-acetamide as a solid: $^1$H NMR (300 MHz, $CDCl_3$) δ7.03 (m, 2H), 6.94 (m, 2H), 6.36 (m, 3H), 4.99 (m, 1H), 4.37 (b, 3H), 3.86 (s, 3H), 3.39 (s, 2H), 1.07 (d, 6H, J=6.8); low resolution MS (FAB)m/e 332 (MH$^+$).

D. 2-(7-Fluoro-2,4-dioxo-2,3,4,5-tetrahydro-benzo[b][1,4]diazepin-1-yl)-N-isopropyl-N-(4-methoxy-phenyl)-acetamide A solution of 1.72 g of 2-(2-amino-4-fluoro-phenylamino)-N-isopropyl-N-(4-methoxy-phenyl)-acetamide, prepared as in Part C, (5.20 mmol) in 15 mL of tetrahydrofuran is transferred to an addition funnel. A solution of 0.506 mL of malonyl dichloride (5.20 mmol, 1.0 equiv) in 15 mL tetrahydrofuran is transferred to a separate addition funnel. Each solution of each reagent is simultaneously added dropwise over 30 min. to 100 mL of tetrahydrofuran at ambient temperature under nitrogen with vigorous agitation. After stirring for 20 min. at ambient temperature, an additional 0.506 mL of malonyl dichloride (5.20 mmol, 0.1 equiv) is added in a single portion. The reaction is allowed to stir an additional 2.5 hrs. and then evaporated in vacuo to a residue. The residue is purified on flash grade silica gel with 1:3 ethyl acetate/hexane followed by 3:1 ethyl acetate/hexane. The appropriate fractions were combined, evaporated in vacuo to a residue and triturated with hexane. The hexane is removed in vacuo and the residual solid is dried under high vacuum to provide 1.06 g of 2-(7-Fluoro-2,4-dioxo-2,3,4,5-tetrahydro-benzo[b][1,4]diazepin-1-yl)-N-isopropyl-N-(4-methoxy-phenyl)-acetamide as a tan solid: $^1$H NMR (300 MHz, $CDCl_3$) δ8.14 (s, br, 1H), 7.45 (dd, 1H, J=5.5. 9.2), 7.29 (m, 1H), 7.05 (m, 1H), 6.94 (m, 3H), 6.78 (m, 1H), 4.99 (m, 1H), 4.37 (d, 1H, J=16.4), 3.82 (s, 3H), 3.69 (d, 1H, J=16.0), 3.40 (m, 2H), 1.09 (d, 6H, J=6.8); low resolution MS (FAB)m/e 400 (MH$^+$).

E. 2-(7-Fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide A mixture of 0.880 g of 2-(7-Fluoro-2,4-dioxo-2,3,4,5-tetrahydro-benzo[b][1,4]diazepin-1-yl)-N-isopropyl-N-(4-methoxy-phenyl)-acetamide, prepared as in Part D, (2.20 mmol), 420 mg of copper powder (6.61 mmol, 3 equiv), 476 mg of potassium acetate (4.85 mmol, 2.2 equiv), and 0.290 mL of 3-bromopyridine (4.85 mmol, 2.2 equiv) in 10 mL of dimethylformamide is heated at 100° C. under nitrogen for 3 hrs. An additional 0.132 mL of 3-bromopyridine (2.43 mmol, 1.1 equiv) is added and the reaction is maintained for an additional 2 hrs. The reaction mixture is cooled to ambient temperature, filtered through a sintered glass funnel and then evaporated in vacuo to a residue. The residue is partitioned between ethyl acetate and aqueous ammonium hydroxide (5 mL conc. diluted to 100 mL). After separating the layers, the organic layer is washed with aqueous ammonium hydroxide (5 mL conc. diluted to 100 mL), and then saturated aqueous brine. The organic phase is then extracted three times with aqueous HCl (1N). The acid layers were combined and neutralized with aqueous sodium hydroxide (1N). The neutralized mixture is extracted twice with methylene chloride. The methylene chloride layers were combined, dried over anhydrous sodium sulfate, filtered and evaporated in vacuo to a residue. The residue is triturated with hexane and then concentrated in vacuo to provide 0.705 g of 2-(7-Fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide as a tan solid: H NMR (300 MHz, $CDCl_3$) δ8.60 (m, 2H), 8.08 (s, br, 1H), 7.54 (s, 1H), 7.39 (m, 1H), 7.15 (m, 2H), 7.00 (m, 3H), 6.57 (dd, 1H, J=2.7, 9.2), 4.95 (m, 1H), 4.32 (d, 1H, J=17.9), 4.14 (d, 1H, J=17.8), 3.85 (s, 3H), 3.61 (d, 1H, J=12.1), 3.52 (d, 1H, J=12.1), 1.06 (d, 6H, J=6.8); low resolution MS (FAB)m/e 477 (MH+).

F. 2-[7-Fluoro-3-(1-tert-butoxycarbonyl-indazol-3-ylmethyl)-2,4-dioxo-5-pyridin-3-yl-2,3,4,5-tetrahydro-benzo[b][1,4]diazepin-1-yl]-N-isopropyl-N-(4-methoxy-phenyl)-acetamide To a solution of 0.400 g of 2-(7-fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide, prepared as in Part E, (0.839 mmol) in 5 mL dimethylformamide at 0° C. under nitrogen is added 2.01 mL (1.01 mmol, 1.2 equiv) potassium bis(trimethylsilyl)amide (0.5M in toluene) dropwise over 5 min. After stirring 10 min., 287 mg of 3-bromomethyl-1-tert-butoxycarbonyl-1H-indazole (0.923 mmol, 1.1 equiv) is added. After 15 min., the reaction is added to a mixture of ethyl acetate, saturated aqueous brine, and water with vigorous agitation. The mixture is transferred to a separatory funnel and the layers were separated. The organic layer is washed with 1:1 water/saturated aqueous brine, saturated aqueous brine, and then dried over anhydrous sodium sulfate, filtered and evaporated in vacuo to a residue. The residue is purified on flash grade silica with 2:3 ethyl acetate/hexane (500 mL) followed by 3:2 ethyl acetate/hexane (1000 mL). The appropriate fractions were combined, evaporated in vacuo to a residue, and triturated with hexane. Hexane is removed in vacuo to provide 388 mg of the title compound as a white solid: $^1$H NMR (300 MHz, CDCl$_3$) δ8.69 (s, br, 1H), 8.58 (d, 1H, J=4.6), 8.20 (s, br, 1H), 8.02 (d, 1H, J=8.2), 7.84 (d, 1H, J=7.9), 7.57 (s, 1H), 7.50 (m, 1H), 7.32 (m, 2H), 7.14 (d, 2H, J=8.8), 7.05 (m, 1H), 6.97 (m, 2H), 6.61 (dd, 1H, J=2.8, 9.2), 4.92 (m, 1H), 4.52 (d, 1H, J=18.4), 4.40 (dd, 1H, J=5.1, 8.7), 4.04 (d, 1H, J=18.4), 3.85 (s, 3H), 3.81 (m, 1H), 3.53 (dd, 1H, J=5.2, 16.7), 1.66 (s, 9H), 1.03 (m, 6H). TLC R$_f$=0.50 (ethyl acetate/hexane 7/3).

Intermediate 67

2-[7,8-Difluoro-3-(1-tertbutoxycarbonyl-indazol-3-ylmethyl)-2,4-dioxo-5-phenyl-2,3,4,5-tetrahydro-benzo[b][1,4]diazepin-1-yl]-N-isopropyl-N-(4-methoxy-phenyl)-acetamide A. 2-(4,5-Difluoro-2-phenylamino-phenylamino)-N-isopropyl-N-(4-methoxy-phenyl)-acetamide A mixture of 3.004 g of 4,5-difluoro-N-phenyl-benzene-1,2-diamine (J. Gen. Chem. USSR (Engl. Transl.), 1964, 34), 1.910 g of potassium carbonate (13.82 mmol, 1.0 equiv), and 3.956 g of 2-bromo-N-isopropyl-N-(4-methoxy-phenyl)-acetamide (13.82 mmol, 1.0 equiv) in 20 mL of dimethylformamide is stirred under nitrogen at ambient temperature for 16 h. An additional 3.00 g of 2-bromo-N-isopropyl-N-(4-methoxy-phenyl)-acetamide (10.5 mmol, 0.75 equiv) is added and the reaction is heated at 50° C. for 2 h. The mixture is cooled to ambient temperature and then partitioned between diethyl ether and 1:1 water/saturated aqueous brine. The layers were separated and the aqueous layer is back-extracted twice with diethyl ether. The ether layers were combined, washed with saturated aqueous brine, dried over anhydrous sodium sulfate and then evaporated in vacuo to a residue. The residue is purified on flash grade silica gel using 10–20% ethyl acetate in hexane. The appropriate fractions were combined, evaporated in vacuo and dried under vacuum to provide 5.62 g of 2-(4,5-Difluoro-2-phenylamino-phenylamino)-N-isopropyl-N-(4-methoxy-phenyl)-acetamide as a solid: Low resolution MS (FAB)m/e 425 (M+); TLC R$_f$=0.43 (ethyl acetate/hexane 3:7).

B. 2-(7,8-Difluoro-2,4-dioxo-5-phenyl-2,3,4,5-tetrahydro-benzo[b][1,4]diazepin-1-yl)-N-isopropyl-N-(4-methoxy-phenyl)-acetamide A solution of 5.62 g 2-(4,5-difluoro-2-phenylamino-phenylamino)-N-isopropyl-N-(4-methoxy-phenyl)-acetamide, prepared as in Part A, (13.2 mmol) in 50 mL of tetrahydrofuran is transferred to an addition funnel. A solution of 1.60 mL of malonyl dichloride (16.53 mmol, 1.25 equiv) in 50 mL tetrahydrofuran is transferred to a separate addition funnel. Each solution of each reagent is simultaneously added dropwise over 20 min. to 250 mL of tetrahydrofuran at ambient temperature under nitrogen with vigorous agitation. After stirring 16 hrs. at ambient temperature, the reaction mixture is concentrated in vacuo. The residue is purified on flash grade silica gel using 40–50% ethyl acetate in hexane. The appropriate fractions were combined, evaporated in vacuo, dried under high vacuum for 2 hrs., and then triturated with hexane. The hexane is removed in vacuo and the residual solid is dried under high vacuum to provide 2.340 g of 2-(7,8-Difluoro-2,4-dioxo-5-phenyl-2,3,4,5-tetrahydro-benzo[b][1,4]diazepin-1-yl)-N-isopropyl-N-(4-methoxy-phenyl)-acetamide as an off-white solid: $^1$H NMR (300 MHz, CDCl$_3$) δ7.37 (m, 7H), 7.15 (m, 1H), 7.01 (m, 2H), 6.76 (dd, 1H, J=7.8, 11.1), 5.04 (m, 1H), 4.36 (d, 1H, J=16.3), 4.00 (d, 1H, J=16.5), 3.89 (s, 3H), 3.62 (d, 1H, J=12.2), 3.54 (d, 1H, J=12.2), 1.14 (m, 6H); low resolution MS (FAB)m/e 494 (MH+).

C. 2-[7,8-Difluoro-3-(1-tert-butoxycarbonyl-indazol-3-ylmethyl)-2,4-dioxo-5-phenyl-2,3,4,5-tetrahydro-benzo[b][1,4]diazepin-1-yl]-N-isopropyl-N-(4-methoxy-phenyl)-acetamide To a solution of 0.500 g of 2-(7,8-difluoro-2,4-dioxo-5-phenyl-2,3,4,5-tetrahydro-benzo[b][1,4]diazepin-1-yl)-N-isopropyl-N-(4-methoxy-phenyl)-acetamide, prepared as in Part B, (1.013 mmol) in 5 mL dimethylformamide at 0° C. under nitrogen is added 2.43 mL (1.22 mmol, 1.2 equiv) potassium bis(trimethylsilyl)amide (0.5M in toluene) dropwise over 5 min. After stirring 5 min., 346 mg of 3-bromomethyl-1-tert-butoxycarbonyl-1H-indazole (1.11 mmol, 1.1 equiv) is added. After 1 h at 0° C., the reaction is quenched by addition to a stirring mixture of ethyl acetate, water and saturated aqueous brine. The mixture is transferred to a separatory funnel and the layers were separated. The organic layer is washed with 1:1 water/saturated aqueous brine. The aqueous layers were combined and washed twice with ethyl acetate. The organic layers were combined, washed with saturated aqueous brine, dried over anhydrous sodium sulfate, and then evaporated in vacuo to an oil. The crude product is purified on flash grade silica gel using 25–30% ethyl acetate in hexane. The appropriate fractions were combined, evaporated in vacuo and triturated with hexane. The hexane is evaporated in vacuo and the residual solid is dried under high vacuum to provide 525 mg of the title compound as a white solid: $^1$H NMR (300 MHz, CDCl$_3$) δ8.06 (d, 1H, J=8.3), 7.84 (d, 1H, J=7.9), 7.49 (m, 1H), 7.38 (m, 2H), 7.29 (m, 6H), 7.12 (m, 1H), 6.98 (m, 2H), 6.78 (dd, 1H, J=8.5, 10.6), 4.99 (m, 1H), 4.36 (dd, 1H, J=4.6, 8.7), 4.20 (s, br, 2H), 3.85 (s, 3H), 3.84 (m, 1H), 3.52 (dd, 1H, J=4.6 16.8), 1.67 (s, 9H), 1.08 (m, 6H); low resolution MS (FAB)m/e 724 (MH+).

Intermediate 68

2-[3-(1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-phenyl-acetamide To a solution of 427 mg of 2-(2,4-Dioxo-5-phenyl-2,3,4,5-tetrahydro-benzo[b][1,4]diazepin-1-yl)-N-isopropyl-N-

(4-methoxy-phenyl) acetamide in 5 mL of dry DMF at 0° C. is added 2.2 mL of a 0.5M solution of potassium bis(trimethylsilyl)amide in toluene. The reaction mixture is stirred for 30 min at 0° C. and a solution of 311 mg of 3-Bromomethyl-1-tert-butoxycarbonyl indazole, prepared as in Intermediate 1, in 2 mL of dry DMF is added dropwise. The reaction mixture is stirred overnight at rt, poured into water and the product extracted with ethyl acetate (2×15 mL). The solvent is removed in vacuo and the residue is purified by silica gel flash column chromatography (MeOH 1% CHCl$_3$ 99%) to afford 420 mg of the title compound: $^1$H NMR (400 MHz, CDCl$_3$) δ8.03 (d, 1H, J=8.3), 7.86 (d, 1H, J=8.0), 7.51–7.18 (m, 14H), 7.10 (m, 1H), 6.94 (m, 1H), 5.02 (m, 1H,J=6.8), 4.32 (dd, 1H, J=8.9, 4.7), 4.24 (d, 1H, J=16.4), 4.22 (d, 1H, J=16.4), 3.85 (dd, 1H, J=16.5, 8.9), 3.53 (dd, 1H, J=16.5, 4.7), 1.64 (s, 9H), 1.07 (d, 6H, J=6.8).

Intermediate 69

2-[3-(6-Fluoro-1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-phenyl-acetamide To a solution of 427 mg of 2-(2,4-Dioxo-5-phenyl-2,3,4,5-tetrahydro-benzo[b][1,4]diazepin-1-yl)-N-isopropyl-N-(4-methoxy-phenyl) acetamide in 5 mL of dry DMF at 0° C. is added 2.2 mL of a 0.5M solution of potassium bis(trimethylsilyl)amide in toluene. The reaction mixture is stirred for 30 min at 0° C. and a solution of 329 mg of 3-Bromomethyl-6-fluoro-1-tert-butoxycarbonyl indazole in 2 mL of dry DMF is added dropwise. The reaction mixture is stirred overnight at RT, poured into water and the product extracted with ethyl acetate (2×15 mL). The solvent is removed in vacuo and the residue is purified by silica gel flash column chromatography (MeOH 1%:CHCl$_3$ 99%) to afford 410 mg of the title compound: $^1$H NMR (400 MHz, CDCl$_3$) δ7.85–6.91 (m, 17H), 5.01 (m, 1H,J=6.8), 4.22 (m, 3H), 3.81 (dd, 1H, J=16.5, 8.9), 3.51 (dd, 1H, J=16.5, 4.7), 1.68 (s, 9H), 1.07 (d, 6H, J=6.8).

Intermediate 70

2-[3-(6-Fluoro-1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-(4-trifluoromethoxy-phenyl)-acetamide A. Isopropyl-(4-trifluoromethoxy-phenyl)-amine A solution of 9.33 g of p-trifluoromethoxyaniline, 4.1 mL of acetone, and 14.53 g of sodium triacetoxyborohydryde in 50 mL of 1,2-dichloroethane were stirred overnight at RT. The reaction mixture is then poured onto ice-water and product extracted with 100 mL of dichloromethane. The organic layer is washed with water, sat NaHCO$_3$, dried with Na$_2$SO$_4$ and solvent evaporated to afford 12 g of Isopropyl-(4-trifluoromethoxy-phenyl)-amine: $^1$H NMR (300 MHz, CDCl$_3$) δ7.06 (d, 2H, J=8.5), 6.56 (d, 2H, J=8.5), 3.63(m, 1H), 1.25 (d, 6H, J=6.8).

B. 2-Bromo-N-isopropyl-(4-trifluoromethoxy-phenyl)-acetamide

To a solution of 12 g of isopropyl-(4-trifluoromethoxy-phenyl)-amine, prepared as in Part A, and 9 mL of triethylamine in 150 mL of methylene chloride stirred at 0° C. is added dropwise 11 g of bromoacetyl bromide and the resulting reaction mixture is stirred overnight at RT. The organic solution is washed successively with 1N HCl, NaHCO$_3$ and dried with Na$_2$SO$_4$. The solvent is removed in vacuo and the residue is purified by silica gel flash column chromatography using hexane/EtOAc 80:20 to afford 10 g of 2-Bromo-N-isopropyl-(4-trifluoromethoxy-phenyl)-acetamide: $^1$H NMR (300 MHz, CDCl$_3$) δ7.31(m, 4H), 5.00 (m, 1H), 3.54 (s, 2H), 1.10 (d, 6H, J=6.8).

C. 2-(2,4-Dioxo-5-phenyl-2,3,4,5-tetrahydro-benzo[b][1,4]diazepin-1-yl)-N-isopropyl-N-(4-trifluoromethoxy-phenyl) acetamide To a solution of 252 mg of intermediate 33 in dry 3 mL of DMF at 0° C. is added 2.2 mL of a 0.5M solution of potassium bis(trimethylsilyl)amide in toluene. The reaction mixture is stirred for 30 min at 0° C. then a solution of 340 mg of 2-Bromo-N-isopropyl-(4-trifluoromethoxy-phenyl)-acetamide, prepared as in Part B, in 3 mL of dry DMF is added dropwise. The reaction mixture is stirred overnight at RT, poured into water and the product extracted with ethyl acetate (2×15 mL). The solvent is removed in vacuo and the residue is purified by silica gel flash column chromatography using hexane/EtOAc 85:15 as eluent to afford 260 mg of 2-(2,4-Dioxo-5-phenyl-2,3,4,5-tetrahydro-benzo[b][1,4]diazepin-1-yl)-N-isopropyl-N-(4-trifluoromethoxy-phenyl) acetamide: $^1$H NMR (400 MHz, CDCl$_3$) δ7.48–6.95 (m,13H), 5.10 (m, 1H), 4.35 (d, 1H, J=16.2), 4.08 (d, 1H, J=16.2), 3.63 (d, 1H, J=12.0), 3.53 (d, 2H, J=12.0), 1.15 (d, 6H, J=6.8).

D. 2-[3-(6-Fluoro-1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-(4-trifluoromethoxy-phenyl)-acetamide To a solution of 250 mg of 2-(2,4-Dioxo-5-phenyl-2,3,4,5-tetrahydro-benzo[b][1,4]diazepin-1-yl)-N-isopropyl-N-(4-trifluoromethoxy-phenyl) acetamide, prepared as in Part C, in 5 mL of dry DMF at 0° C. is added 1.5 mL of a 0.5M solution of potassium bis(trimethylsilyl)amide in toluene. The reaction mixture is stirred for 30 min at 0° C. and a solution of 170 mg of 3-Bromomethyl-6-fluoro-1-tert-butoxycarbonyl-indazole in 3 mL of dry DMF is added dropwise. The reaction mixture is stirred overnight at RT, poured into water and the product extracted with ethyl acetate (2×15 mL). The solvent is removed in vacuo and the residue is purified by silica gel flash column chromatography using hexane/EtOAc 1/1 as eluent to afford 100 mg of the title compound: $^1$H NMR (300 MHz, CDCl$_3$) δ7.98–6.95 (m,16H) 5.07 (m, 1H), 4.30 (m, 3H), 3.86 (dd, 1H, J=16.5, 6.4), 3.65 (dd, 1H,J=16.5,6.4), 1.69 (s, 9H), 1.13 (d, 6H, J=6.8).

Intermediate 71

2-[3-Methyl-3-(1-tert-butoxycarbonyl-1H-indazol-3-ylmethyl)-2,4-dioxo-5-pyridin-3-yl-2,3,4,5-tetrahydro-benzo[b][1,4]diazepin-1-yl]-N-isopropyl-N-(4-methoxy-phenyl)-acetamide A. 2-(3-Methyl-2,4-dioxo-5-pyridin-3-yl-2,3,4,5-tetrahydro-benzo[b][1,4]diazepin-1-yl)-N-isopropyl-N-(4-methoxy-phenyl)-acetamide To a stirring solution of 2.65 g (5.78 mmol) of 2-(2,4-Dioxo-5-pyridin-3-yl-2,3,4,5-tetrahydro-benzo[b][1,4]diazepin-1-yl)-N-isopropyl-N-(4-methoxy-phenyl) acetamide in 80 mL of DMF at 0° C. is added 6.36 mL (6.36 mmol) of a 1.0M solution of NaN(TMS)$_2$ in THF. The resulting solution is stirred 10 min, then 400 mL (6.36 mmol) of methyl iodide is added neat. The resulting solution is stirred at RT for 45 min then poured into 100 mL NH$_4$Cl. The reaction mixture is concentrated to remove the DMF, diluted with 500 mL of H$_2$O and extracted with EtOAc (3×200 mL). The organics were dried (MgSO$_4$), and the solvents removed in vacuo. Purification by silica gel flash chromatography using EtOAc as eluent afforded 2.52 g of 2-(3-Methyl-2,4-dioxo-5-pyridin-3-yl-2,3,4,5-tetrahydro-benzo[b][1,4]diazepin-1-yl)-N-isopropyl-N-(4-methoxy-phenyl)-acetamide as a white foam: $^1$H NMR (CDCl$_3$, 400 MHz) δ8.50 (s, br, 2H), 7.79 (d, 1H, J=8.1), 7.43 (d, 1H, J=8.1), 7.36–6.94 (m, 8H), 6.88 (d, 1H, J=8.8), 4.98 (m, 1H), 4.26 (m, 2H), 3.85 (s, 3H), 3.54 (q, 1H, J=7.1), 1.42 (d, 3H, J=7.1), 1.07 (m, 6H); low resolution MS (FAB)m/e 473 (MH$^+$); Anal. (C$_{27}$H$_{28}$N$_4$O$_4$) Calcd. C, 68.63; H, 5.97; N, 11.86 Found C, 66.91; H, 6.13; N, 11.29.

B. 2-[3-Methyl-3-(1-tert-butoxycarbonyl-1H-indazol-3-ylmethyl)-2,4-dioxo-5-pyridin-3-yl-2,3,4,5-tetrahydro-benzo[b][1,4]diazepin-1-yl]-N-isopropyl-N-(4-methoxy-phenyl)-acetamide To a stirring solution of 2.33 g (4.93 mmol) of 2-(3-Methyl-2,4-dioxo-5-pyridin-3-yl-2,3,4,5-tetrahydro-benzo[b][1,4]diazepin-1-yl)-N-isopropyl-N-(4-methoxy-phenyl)-acetamide, prepared as in Part A, in 50 mL of DMF at 0° C. is added 5.42 mL (5.42 mmol) of a 1.0M solution of NaN(TMS)$_2$ in THF. The resulting solution is stirred 10 min, then a solution of 1.69 g (5.42 mmol) of 3-bromomethyl-1-tert-butoxycarbonyl-1H-indazole in 10 mL of DMF is added. The resulting solution is stirred at RT for 2 h then poured into 100 mL NH$_4$Cl. The reaction mixture is concentrated to remove the DMF, diluted with 300 mL of H$_2$O and extracted with EtOAc (3×200 mL). The organics were dried (MgSO$_4$), and the solvents removed in vacuo. Purification by silica gel flash chromatography using hexane/EtOAc 3/1 as eluent afforded 2.41 g of the title compound as a light yellow foam: $^1$H NMR (CDCl$_3$, 400 MHz) δ8.53 (m, 2H), 8.06 (m, 2H), 7.50–6.96 (m, 12H), 5.03 (m,1H), 4.58 (d, 1H), 4.06 (d, 1H), 3.85 (s, 3H), 3.02 (dd, AB quartet, 2H, J=16.8), 1.72 (s, 9H), 1.55 (s, 3H), 1.14 (d, 6H, J=6.8); low resolution MS (FAB)m/e 703 (MH$^+$), 603, 438; Anal. (C$_{40}$H$_{42}$N$_6$O$_6$) Calcd. C, 68.36; H, 6.02; N, 11.96 Found C, 67.11; H, 6.15; N, 11.48.

Intermediate 72

2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(3,4-methylenedioxy-phenyl) acetamide A. N-Isopropyl-N-(3,4-methylenedioxy-phenyl) aniline Sodium triacetoxyborohydride (27.9 g, 134 mmol) is added poRTionwise over 45 minutes to a 0° C. solution of 3,4-methylenedioxy aniline (13.8 g, 101 mmol) in THF (100 mL), acetone (7.82 mL, 106 mmol) and acetic acid (5.9 mL) and the resultant mixture is allowed to attain RT overnight. The reaction mixture is cooled to 0° C. and then water (50 mL) is added slowly followed by 50% aqueous sodium hydroxide solution (20 mL) and the resultant mixture stirred for 1.5 h. The organics were removed and the residual aqueous phase diluted with water (30 mL) and extracted into ethyl acetate (3×50 mL). The combined organics were washed with water (2×100 mL), brine (50 mL), dried (MgSO$_4$) and concentrated in vacuo to afford crude N-Isopropyl-N-(3,4-methylenedioxy-phenyl) aniline (12.0 g) as a dark oil which is used without further purification. $^1$H NMR (300 MHz, CDCl$_3$) δ6.72 (d, 1H, J=8.3), 6.43 (s, 1H), 6.29 (s, br, 1H), 5.91 (s, 2H), 3.53 (m, 1H, J=6.8), 1.17 (m, 6H).

B. N-Isopropyl-N-(3,4-methylenedioxy-phenyl) bromoacetamide

Bromoacetyl bromide (6.0 mL) in methylene chloride (100 mL) is added dropwise to a 0° C. solution of N-Isopropyl-N-(3,4-methylenedioxy-phenyl) aniline, prepared as in Part A, (12.0 g) in methylene chloride (100 mL) and triethylamine (9.41 mL) and the resultant mixture is allowed to attain RT overnight. The reaction mixture is washed with 1N hydrochloric acid (3×80 mL), water (2×80 mL), brine (80 mL), dried, (MgSO$_4$) and concentrated in vacuo to afford crude N-Isopropyl-N-(3,4-methylenedioxy-phenyl) bromoacetamide (16.3 g) as a black mobile oil which is used without further purification: $^1$H NMR (300 MHz, CDCl$_3$) δ6.82 (d, 1H, J=8.2), 6.61 (m, 2H), 4.90 (m, 1H, J=6.8), 3.58 (s, 2H), 1.07 (m, 6H).

C. 2-(-2,4-dioxo-5-phenyl-2,3,4,5-tetrahydrobenzo[b][1,4]diazepin-1-yl)-N-isopropyl-N-(3,4-methylenedioxy-phenyl) acetamide Sodium hydride (63 mg, 1.59 mmol) is added to a 0° C. solution of Intermediate 33 (400 mg, 1.58 mmol) in DMF and the resultant mixture stirred at 0° C. for 0.5 h prior to the addition of N-Isopropyl-N-(3,4-methylenedioxy-phenyl) bromoacetamide, prepared as in Part B, (476 mg, 1.59 mmol) in DMF (25 mL). The resultant mixture is allowed to attain RT overnight. The mixture is then poured into water (50 mL) and extracted into ethyl acetate (3×50 mL) and the combined organics then washed with water (3×50 mL), brine (50 mL) dried (MgSO$_4$) and concentrated in vacuo to afford 2-(-2,4-dioxo-5-phenyl-2,3,4,5-tetrahydrobenzo[b][1,4]diazepin-1-yl)-N-isopropyl-N-(3,4-methylenedioxy-phenyl) acetamide (760 mg) as a brown glass which is used without further purification: $^1$H NMR (300 MHz, CDCl$_3$) δ8.03 (s, 1H), 7.5–6.6 (m, 11H), 6.09 (s, 2H), 5.03 (m, 1H, J=6.9), 4.46 (dd, 1H, J=27.2, 12.6), 4.16 (dd, 1H, J=27.2, 5.6), 3.58 (d, 1H, J=15.8), 3.48 (d, 1H, J=15.8), 1.08 (m, 6H).

D. 2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(3,4-methylenedioxy-phenyl) acetamide 31 mg of Sodium Hydride (60% in oil) is added to a solution of 2-(-2,4-dioxo-5-phenyl-2,3,4,5-tetrahydrobenzo[b][1,4]diazepin-1-yl)-N-isopropyl-N-(3,4-methylenedioxy-phenyl) acetamide (300 mg. 0.636 mmol) in DMF (10 mL) and the resultant mixture stirred at RT for 0.5 h prior to the addition of 3-bromomethyl-1-tert-butoxycarbonyl-1H-indazole (197 mg, 0.636 mmol) to the reaction mixture. After 22 h, 10 mL of water is added and the resultant mixture extracted into ethyl acetate (3×10 mL). The combined organics were washed with water (3×10 mL), brine (10 mL), dried (MgSO$_4$), and concentrated in vacuo to afford the crude product (460 mg) as a brown foam. Purification by silica gel flash column chromatography using 2% methanol in methylene chloride as eluent gave the desired product (123 mg) as a beige solid: $^1$H NMR (300 MHz, CDCl$_3$) δ8.10 (d, 1H, J=8.6), 7.91 (d, 1H, J=8.0), 6.8–7.6 (m, 14H), 6.09 (s, 2H), 5.01 (m, 1H, J=6.9), 4.36 (m, 3H), 3.90 (dd, 1H, J=16.4, 8.8), 3.58 (m, 1H), 1.67 (s, 9H), 1.08 (m, 6H).

Intermediate 73

2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(2-methoxy-phenyl) acetamide A. N-Isopropyl-N-(2-methoxy-phenyl) aniline Sodium triacetoxyborohydride (27.9 g, 134 mmol) is added portionwise over 45 minutes to a 0° C. solution of 2-methoxyaniline (12.5 g, 101 mmol) in THF (100 mL), acetone (7.82 mL, 106 mmol) and acetic acid (5.9 mL) and the resultant mixture is allowed to attain RT overnight. The reaction mixture is cooled to 0° C. and then water (50 mL) is added slowly followed by 50% aqueous sodium hydroxide solution (20 mL) and the resultant mixture stirred for 1.5 h. The organics were removed and the residual aqueous phase diluted with water (30 mL) and extracted into ethyl acetate (3×50 mL). The combined organics were washed with water (2×100 mL), brine (50 mL), dried (MgSO$_4$) and concentrated in vacuo to afford N-Isopropyl-N-(2-methoxy-phenyl) aniline (14.51 g) as an amber oil which is used without further purification: $^1$H NMR (300 MHz, CDCl$_3$) δ6.91 (t, 1H, J=7.6), 7.01 (d, 1H, J=7.6), 6.68 (t, 2H, J=7.9), 3.88 (s, 3H), 3.66 (m, 1H, J=6.8), 1.28 (d, 6H, J=6.8).

B. N-Isopropyl-N-(2-methoxy-phenyl) bromoacetamide

Bromoacetyl bromide (7.8 mL) in methylene chloride (125 mL) is added dropwise to a 0° C. solution of N-Isopropyl-N-(2-methoxy-phenyl) aniline, prepared as in Part A, (14.51 g, 87.9 mmol) in methylene chloride (125 mL) and triethylamine (12.3 mL) and the resultant mixture is allowed to attain RT overnight. After 18 h an additional 2.0 mL of bromoacetyl bromide is added and the resultant reaction mixture stirred at RT for 4 h. The reaction mixture is washed with 1N hydrochloric acid (3×100 mL), water (2×100 mL), brine (100 mL), dried, (MgSO$_4$) and concentrated in vacuo to afford N-Isopropyl-N-(2-methoxy-phenyl) bromoacetamide(20.3 g) as a dark mobile oil which is used without further purification: $^1$H NMR (300 MHz, CDCl$_3$) δ7.45 (dt, 1H, J=7.8, 1.4), 7.20 (dd, 1H, J=7.8, 1.4), 7.04 (m, 2H), 4.90 (m, 1H, J=6.8), 3.85 (s, 3H), 3.60 (dd, 2H, J=32.9, 11.5), 1.20 (d, 3H, J=6.8), 0.97 (d, 3H, J=6.8).

C. N-Isopropyl-N-(2-methoxy-phenyl)-2-(2-phenylamino-phenylamino) acetamide

A mixture of N-Isopropyl-N-(2-methoxy-phenyl) bromoacetamide, prepared as in Part B, (10.0 g 34.9 mmol), N-phenyl phenylenediamine (6.41 g, 34.9 mmol) and potassium carbonate (4.82 g) in DMF (100 mL) is stirred at RT for 48 h. The reaction mixture is filtered through celite and the filtrate concentrated in vacuo. Purification by silica gel flash column chromatography using 20% ethyl acetate in hexane as eluent gave N-Isopropyl-N-(2-methoxy-phenyl)-2-(2-phenylamino-phenylamino) acetamideas a light brown foam (4.50 g): $^1$H NMR (300 MHz, CDCl$_3$) δ7.46 (t, 1H, J=7.9), 7.030–7.05 (m, 8H), 6.98 (t, 1H, J=6.8), 6.84 (m, 2H), 6.70 (t, 1H, J=7.6), 6.37 (d, 1H, J=8.0), 5.4 (s, br, 1H), 4.95 (m, 1H, J=6.8), 3.84 (s, 3H), 3.45 (dd, 2H, J=23.2, 6.6), 1.20 (d, 3H, J=6.8), 1.01 (d, 3H, J=6.8).

D. 2-(-2,4-dioxo-5-phenyl-2,3,4,5-tetrahydrobenzo[b][1,4] diazepin-1-yl)-N-isopropyl-N-(2-methoxy-phenyl) acetamide Malonyl dichloride (0.50 mL) in THF (22 mL) is added dropwise over 35 min to a 0° C. solution of N-Isopropyl-N-(2-methoxy-phenyl)-2-(2-phenylamino-phenylamino) acetamide, prepared as in Part C, (1.90 g, 4.87 mmol) in THF (45 mL) and the resultant mixture allowed to attain RT overnight. The solvents were removed in vacuo and the residue purified by silica gel flash column chromatography using 2% methanol in methylene chlorideas eluent to afford 2-(-2,4-dioxo-5-phenyl-2,3,4,5-tetrahydrobenzo[b][1,4] diazepin-1-yl)-N-isopropyl-N-(2-methoxy-phenyl) acetamide (770 mg) as a cream foam, which exists as 3:2 mixture of rotamers (major rotamer recorded): $^1$H NMR (300 MHz, CDCl$_3$) δ7.60–6.90 (m, 13H), 5.05 (m, 1H, J=6.9), 4.60–3.40 (m, 7H), 1.12 (m, 6H).

E. 2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(2-methoxy-phenyl) acetamide 45 mg of Sodium Hydride (60% in oil, 1.12 mmol) is added to a solution of 2-(-2,4-dioxo-5-phenyl-2,3,4,5-tetrahydrobenzo[b][1,4]diazepin-1-yl)-N-isopropyl-N-(2-methoxy-phenyl) acetamide, prepared as in Part D, (430 mg. 0.934 mmol) in DMF (10 mL) and the resultant mixture stirred at RT for 0.5 h prior to the addition of 3-Bromomethyl-1-tert-butoxycarbonyl-1H-indazole (291 mg, 0.934 mmol) to the reaction mixture. After stirring 22 h at RT, water (10 mL) is added and the resultant mixture extracted into ethyl acetate (3×10 mL). The combined organics were washed with water (3×10 mL), brine (10 mL), dried (MgSO$_4$), and concentrated in vacuo to afford the crude product which is purified by silica gel flash column chromatography using 3% methanol in methylene chlorideas eluent to give the desired product (260 mg) as a beige solid, which exists as 3:2 mixture of rotamers (major rotamer recorded): $^1$H NMR (300 MHz, CDCl$_3$) δ8.1 (t, 1H, J=8.0), 7.90 (m, 1H), 7.60–6.90 (m, 15H), 5.05 (m, 1H, J=6.9), 4.60–3.40 (m, 8H), 1.7 (s, 9H), 1.16 (m, 6H).

Intermediate 74

2-[3-(1-tert-butoxycarbonyl-1H-indazol-3-ylmethyl)-2,4-dioxo-5-phenyl-2,3,4,5-tetrahydrobenzo[b][1,4] diazepin-1-yl]-N-isopropyl-N-(3-methoxy-phenyl) acetamide A. N-Isopropyl-N-(3-methoxy-phenyl) aniline Sodium triacetoxyborohydride (27.9 g, 134 mmol) is added portion wise over 45 minutes to a 0° C. solution of 3-methoxyaniline (12.5 g, 101 mmol) in THF (100 mL), acetone (7.82 mL, 106 mmol) and acetic acid (5.9 mL) and the resultant mixture is allowed to attain RT overnight. The reaction mixture is cooled to 0° C. and then water (50 mL) is added slowly followed by 50% aqueous sodium hydroxide solution (20 mL) and the resultant mixture stirred for 1.5 h. The organics were removed and the residual aqueous phase diluted with water (30 mL) and extracted into ethyl acetate (3×50 mL). The combined organics were washed with water (2×100 mL), brine (50 mL), dried (MgSO$_4$), and concentrated in vacuo to afford N-Isopropyl-N-(3-methoxy-phenyl) aniline (16.22 g) as a brown oil which is used without further purification: $^1$H NMR (300 MHz, CDCl$_3$) δ7.13 (t, 1H, J=8.0), 7.01 (dt, 2H, J=9.7, 1.9), 6.19 (s, 1H), 3.80 (s, 3H), 3.62 (m, 1H, J=6.8), 1.06 (d, 6H, J=6.8).

B. N-Isopropyl-N-(3-methoxy-phenyl) bromoacetamide

Bromoacetyl bromide (8.76 mL) in methylene chloride (100 mL) is added dropwise to a 0° C. solution of N-Isopropyl-N-(3-methoxy-phenyl) aniline, prepared as in Part A, (16.22 g, 98.3 mmol) in methylene chloride (200 mL) and triethylamine (13.8 mL) and the resultant mixture is allowed to attain RT overnight. The reaction mixture is washed with 1N hydrochloric acid (3×100 mL), water (2×100 mL), brine (100 mL), dried (MgSO$_4$), and concentrated in vacuo to afford N-Isopropyl-N-(3-methoxy-phenyl) bromoacetamide(23.16 g) as a dark mobile oil which is used without further purification: $^1$H NMR (300 MHz, CDCl$_3$) δ7.38 (t, 1H, J=8.0), 7.01 (dd, 1H, J=8.1, 2.2), 6.81(d, 1H, J=7.6), 6.79 (s, 1H), 4.95 (m, 1H, J=6.8), 3.88 (s, 3H), 3.60 (s, 2H), 1.06 (d, 6H, J=6.8).

C. N-Isopropyl-N-(3-methoxy-phenyl)-2-(2-phenylamino-phenylamino) acetamide

A mixture of N-Isopropyl-N-(3-methoxy-phenyl) bromoacetamide, prepared as in Part B, (12.0 g 41.9 mmol), N-phenyl phenylenediamine (7.7 g, 41.9 mmol) and potassium carbonate (5.79 g) in DMF (100 mL) is stirred at RT for 20 h. The reaction mixture is filtered through celite and the filtrate diluted with ethyl acetate (150 mL) and washed with water (2×100 mL), 2N hydrochloric acid (2×100 mL), 1N aqueous sodium hydrogen carbonate (100 mL), dried (K$_2$CO$_3$/MgSO$_4$), and concentrated in vacuo. Purification by silica gel flash column chromatography using 20% ethyl acetate in hexane as eluent gave 8.2 g of N-Isopropyl-N-(3-methoxy-phenyl)-2-(2-phenylamino-phenylamino) acetamide as a light brown foam: $^1$H NMR (300 MHz, CDCl$_3$)

δ 7.43 (t, 1H, J=8.0), 7.3–7.1 (m, 3H), 7.02 (m, 2H), 6.9–6.6 (m, 7H), 6.36 (d, 1H, J=7.8), 5.3 (s, br, 1H), 4.95 (m, 1H, J=6.8), 3.88 (s, 3H), 3.53 (s, 2H), 1.06 (m, 6H).

D. 2-(-2,4-dioxo-5-phenyl-2,3,4,5-tetrahydrobenzo[b][1,4] diazepin-1-yl)-N-isopropyl-N-(3-methoxy-phenyl) acetamide Malonyl dichloride (1.48 mL) in THF (50 mL) is added dropwise over 35 min to a 0° C. solution of N-Isopropyl-N-(3-methoxy-phenyl)-2-(2-phenylamino-phenylamino) acetamide, prepared as in Part C, (5.45 g, 14.1 mmol) in THF (140 mL) and the resultant mixture allowed to attain RT overnight. The solvents were removed in vacuo and the residue diluted with ethyl acetate (100 mL) and washed with saturated aqueous sodium hydrogen carbonate (100 mL), water (100 mL), brine (100 mL), dried (MgSO$_4$), and concentrated in vacuo. The resulting oil is purified by silica gel flash column chromatography using 3% methanol in methylene chlorideas eluent to afford 2-(-2,4-dioxo-5-phenyl-2,3,4,5-tetrahydrobenzo[b][1,4]diazepin-1-yl)-N-isopropyl-N-(3-methoxy-phenyl) acetamide (2.4 g) as an amber foam: $^1$H NMR (300 MHz, CDCl$_3$) δ 7.3–7.1 (m, 10H), 7.02 (t, 1H, J=7.2), 6.92 (dd 1H, J=8.6,2.4), 6.83 (d, 1H, J=7.2), 4.95 (m, 1H, J=6.8), 4.38 (m, 1H), 4.02 (m, 1H), 3.78 (s, 3H), 3.48 (dd, 2H, J=39.3, 11.9), 1.06 (m, 6H).

E. 2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(3-methoxy-phenyl) acetamide 52 mg of Sodium hydride (60% in oil, 1.31 mmol) is added to a solution of 2-(-2,4-dioxo-5-phenyl-2,3,4,5-tetrahydrobenzo[b][1,4]diazepin-1-yl)-N-isopropyl-N-(3-methoxy-phenyl) acetamide, prepared as in Part D, (500 mg, 1.09 mmol) in DMF (10 mL ) and the resultant mixture stirred at RT for 0.5 h prior to the addition of 3-Bromomethyl-1-tert-butoxycarbonyl-1H-indazole (339 mg, 1.09 mmol) to the reaction mixture. After stirring 18 h at RT, water (50 mL) is added and the resultant mixture extracted into ethyl acetate (3×50 mL). The combined organics were washed with water (3×20 mL), brine (20 mL), dried (MgSO$_4$) and concentrated in vacuo to afford the crude product which is purified by silica gel flash column chromatography using 5% methanol in methylene chloride as eluent to give the desired product (252 mg) as a cream foam: $^1$H NMR (300 MHz, CDCl$_3$) δ 8.07 (d, 1H, J=8.6), 7.91 (d, 1H, J=8.5), 7.5–6.8 (m, 15H), 5.03 (m, 1H, J=6.9), 4.39 (m, 3H), 3.94 (m, 2H), 3.84 (s, br, 4H), 3.60 (dd, 1H, J=10.1, 2.1), 1.6 (s, 9H), 1.16 (d, 6H, J=6.9).

Intermediate 75

2-[3-(1-tert-butoxycarbonyl-1H-indazol-3-ylmethyl)-2,4-dioxo-5-pyridin-3-yl-2,3,4,5-tetrahydrobenzo[b][1,4]diazepin-1-yl]-N-isopropyl-N-(4-methoxy-phenyl) acetamide To a stirring solution of 597.8 mg (1.3 mmol) 2-(2,4-Dioxo-5-pyridin-3-yl-2,3,4,5-tetrahydro-benzo[b][1,4] diazepin-1-yl)-N-isopropyl-N-(4-methoxy-phenyl)-acetamide, prepared as in Intermediate 48, in 15 mL DMF at 0° C. is added 3.13 mL (1.57 mmol, 1.2 equiv) of a 0.5M solution of KN(TMS)$_2$ in toluene. The reaction is allowed to warm to RT over 20 min, then is cooled back to 0° C., and 445.4 mg (1.43 mmol, 1.1 equiv) of 3-bromomethyl-1-tert-butoxycarbonyl-1H-indazole is added in one portion. The reaction is allowed to warm to RT., and after 20 min is concentrated in vacuo. The residue is taken up in water-ethyl acetate, and is poured into a separatory funnel containing water and ethyl acetate. The layers were separated, and the aqueous layer is extracted with ethyl acetate. The combined organics were dried (Na$_2$SO$_4$) filtered and concentrated in vacuo to afford an amber oil, which is purified by silica gel flash column chromatography to afford 561 mg of the title compound as a viscous, glassy oil: $^1$H NMR (CDCl$_3$, 400 MHz) δ 8.52 (d, br, 2H, J=18.8), 8.01 (d, 1H, J=8.4), 7.78 (m, 2H), 7.46 (t, 1H, J=20), 7.36–7.23 (m, 6H), 7.13 (m, 2H), 6.93 (m, 2H), 4.95 (m, 1H), 4.41 (d, br, 1H), 4.34 (dd, 1H, J=5.2, 8.4), 3.83 (s, 3H), 3.83 (dd, 1H), 3.55 (dd, 1H, J=5.1, 16.6), 1.64 (s, 9H), 1.03 (dd, 6H, J=2.0, 6.5); low resolution MS (FAB)m/e 689 (MH$^+$).

Intermediate 76

2-[3-(1-tert-butoxycarbonyl-1H-indazol-3-ylmethyl)-2,4-dioxo-5-pyridin-4-yl-2,3,4,5-tetrahydrobenzo[b][1,4]diazepin-1-yl]-N-isopropyl-N-(4-methoxy-phenyl) acetamide A. 2-(2,4-Dioxo-5-pyridin-4-yl-2,3,4,5-tetrahydro-benzo[b][1,4]diazepin-1-yl)-N-isopropyl-N-(4-methoxy-phenyl)-acetamide To a stirring solution of 700 mg (1.89 mmol) 2-(2,4-Dioxo-2,3,4,5-tetrahydro-benzo[b][1,4]diazepin-1-yl)-N-isopropyl-N-(4-methoxy-phenyl)-acetamide in DMSO is added 370 mg of Cu powder (5.8 mmol, 3 equiv), 380 mg of potassium acetate (3.88 mmol, 2 equiv) and 500 mg of 4-bromopyridine (3.16 mmol, 1.7 equiv, freshly free-based from the hydrochloride salt). The reaction is heated to 100° C. for 16 h then poured onto ice. Dichloromethane is added, and the mixture is filtered through celite. The filtrate is poured into a separatory funnel containing 100 mL of H$_2$O, and the layers separated. 2 mL of a 30% solution of NH$_4$OH were added to the aqueous layer, and the resulting blue solution is extracted with dichloromethane. The combined organics were dried (Na$_2$SO$_4$), filtered and concentrated. The residue is purified by silica gel flash column chromatography to afford 437 mg of 2-(2,4-Dioxo-5-pyridin-4-yl-2,3,4,5-tetrahydro-benzo[b][1,4]diazepin-1-yl)-N-isopropyl-N-(4-methoxy-phenyl)-acetamide as a white solid: mp. 211°–213° C.; $^1$H NMR (CDCl$_3$, 400 MHz) δ 8.61 (d, br, 2H, J=5.4), 7.43 (d, 1H, J=8.1), 7.36–7.14 (m, 5H), 6.99–6.22 (m, 4H), 5.03 (m, 1H), 4.26 (dd, br, 2H, J=16.6, 28.5), 3.87 (s, 3H), 3.55 (dd, 2H, J=12.0, 36.4), 1.09 (d, 6H, J=6.8); low resolution MS (FAB)m/e 459 (MH$^+$).

B. 2-[3-(1-tert-butoxycarbonyl-1H-indazol-3-ylmethyl)-2,4-dioxo-5-pyridin-4-yl-2,3,4,5-tetrahydrobenzo[b][1,4] diazepin-1-yl]-N-isopropyl-N-(4-methoxy-phenyl) acetamide To a stirring solution of 437.3 mg 2-(2,4-Dioxo-5-pyridin-4-yl-2,3,4,5-tetrahydro-benzo[b][1,4]diazepin-1-yl)-N-isopropyl-N-(4-methoxy-phenyl)-acetamide (0.95 mmol) in 10 mL DMF at 0° C. is added 2.09 mL (1.04 mmol, 1.1 equiv) of a 0.5M solution of KN(TMS)$_2$. The reaction is allowed to warm to RT, then cooled back down to 0° C., and 325 mg (1.04 mmol, 1.1 equiv) 3-bromomethyl-1-tert-butoxycarbonyl-1H-indazole is then added in one portion. The reaction is allowed to warm to RT, and is stirred an additional 20 min. The reaction is then concentrated, diluted with H$_2$O, and the aqueous layer is extracted with ethyl acetate (3×100 mL). The combined organics were dried (Na$_2$SO$_4$), filtered and concentrated. The residue is purified by silica gel flash column chromatography (gradient 1:1–2:1 ethyl acetate:hexanes) to afford 487 mg of the title compound as a pale yellow foam: $^1$H NMR (CDCl$_3$, 400 MHz) δ 8.58 (s, br, 2H), 8.01 (d, 1H, J=8.4), 7.93 (d, 1H, J=7.8), 7.47 (t, 1H, J=7.5), 7.38–7.26 (m, 4H) 7.26–7.11 (m, 4H), 6.94 (dd, 2H, J=8.7, 11.8), 4.94 (m, 1H), 4.39 (s, br, 1H), 4.32 (dd, 1H, J=4.9, 8.5), 4.16 (d, 1H, J=16.6), 3.83 (s, 3H), 3.80 (m, 1H), 3.52 (dd, 1H, J=5.1, 16.5), 1.62 (s, 9H), 1.03 (d, 6H, J=6.9); low resolution MS (FAB)m/e 689 (MH$^+$).

73

Intermediate 77

2-[5-(3-Fluoro-phenyl)-3-(1-tert-butoxycarbonyl-1H-indazol-3-ylmethyl)-2,4-dioxo-2,3,4,5-tetrahydrobenzo[b][1,4]diazepin-1-yl]-N-isopropyl-N-(4-methoxy-phenyl) acetamide A. 2-[5-(3-Fluoro-phenyl)-2,4-dioxo-2,3,4,5-tetrahydro-benzo[b][1,4]diazepin-1-yl]-N-isopropyl-N-(4-methoxyphenyl)-acetamide To a stirring solution of 500 mg (1.3 mmol) 2-(2,4-Dioxo-2,3,4,5-tetrahydro-benzo[b][1,4]diazepin-1-yl)-N-isopropyl-N-(4-methoxy-phenyl)-acetamide in 5 mL DMF is added 248 mg (3.9 mmol, 3 equiv) of Cu powder, 255 mg (2.6 mmol, 2 equiv) of potassium acetate, and 289 μL (2.6 mmol, 2 equiv) of 1-bromo-3-fluorobenzene. The reaction is heated to 100° C., and after 3 h an additional 289 μL (2.6 mmol, 2 equiv) of 1-bromo-3-fluorobenzene and 248 mg (3.9 mmol, 3 equiv) of Cu powder were added. The reaction is heated at 100° C. for 20 h then is poured onto ice. Dichloromethane is added, and the mixture is filtered through celite. The filtrate is poured into a separatory funnel, and the layers separated. 2 mL of a 30% solution of $NH_4OH$ were added to the aqueous layer, and the resulting blue solution is extracted with dichloromethane. The combined organics were dried ($Na_2SO_4$), filtered and concentrated. The residue is purified by silica gel flash column chromatography (gradient 2:1–1:1 hexanes:ethyl acetate) to afford 497 mg of 2-[5-(3-Fluoro-phenyl)-2,4-dioxo-2,3,4,5-tetrahydro-benzo[b][1,4]diazepin-1-yl]-N-isopropyl-N-(4-methoxy-phenyl)-acetamide as an off-white solid: $^1H$ NMR ($CDCl_3$, 400 MHz) δ7.45–7.25 (m, 4H), 7.18–6.93 (m, 8H), 5.04 (m, 1H), 4.35 (d, 1H, J=16.3), 4.17 (d, 1H, J=16.1), 3.88 (s, 3H), 3.56 (dd, 2H, J=12.0, 29.8), 1.12 (d, 6H, J=6.8); low resolution MS (FAB)m/e 476 ($MH^+$).

B. 2-[5-(3-Fluoro-phenyl)-3-(1-tert-butoxycarbonyl-1H-indazol-3-ylmethyl)-2,4-dioxo-2,3,4,5-tetrahydrobenzo[b][1,4]diazepin-1-yl]-N-isopropyl-N-(4-methoxy-phenyl) acetamide To a stirring solution of 260 mg (0.55 mmol) 2-[5-(3-Fluorophenyl)-2,4-dioxo-2,3,4,5-tetrahydro-benzo[b][1,4]diazepin-1-yl]-N-isopropyl-N-(4-methoxy-phenyl)-acetamide, prepared as in Part A, in 4 mL DMF at 0° C. is added 1.3 mL (0.66 mmol, 1.2 equiv) KN(TMS)$_2$ via syringe under $N_2$. The reaction is allowed to warm to RT, and is stirred at RT for 20 min. The reaction is cooled to 0° C., and 200 mg (0.66 mmol, 1.2 equiv) 3-bromomethyl-1-tert-butoxycarbonyl-1H-indazole is added in one portion. The reaction is allowed to warm to RT, and after 20 min is concentrated. The reaction is then transferred to a separatory funnel containing water and ethyl acetate. The layers were separated, and the aqueous layer is extracted with ethyl acetate. The combined organics were dried ($Na_2SO_4$), filtered and concentrated. The residue is purified by silica gel flash column chromatography (gradient 3:1–2:1 hexanes:ethyl acetate) to afford 248 mg of the title compound as a pale yellow foam: $^1H$ NMR ($CDCl_3$, 400 MHz) δ8.03 (d, br, 1H, J=8.4), 7.84 (d, 1H, J=8.0), 7.46 (t, 1H, J=7.7), 7.38–7.11 (m, 6H), 6.99–6.93 (m, 3H), 4.97 (m, 1H), 4.19 (d, 1H, J=16.6), 3.83 (s, 3H), 3.83 (m, 1H) 3.52 (dd, 1H, J=4.8, 16.6), 1.64 (s, 9H), 1.04 (d, 6H, J=6.7); low resolution MS (FAB)m/e 706 ($MH^+$).

Intermediate 78

{1-[Isopropyl-(4-methoxyphenyl)-carbamoylmethyl]-3-methyl-2,4-dioxo-5-pyridin-3-yl-2,3,4,5-tetrahydro-1H benzo[b][1,4]diazepin-3-yl}acetic acid A. 2-Allyl-2-methylmaolnic acid To a slurry of 14.9 g (0.37 mol) of sodium hydride (60% in oil) in 450 mL of THF at 0° C. is added dropwise a solution of 50.0 g (0.29 mol) of diethyl methylmalonate in 50 mL of THF over 10 min. The reaction mixture is stirred 10 min after the addition is complete and gas evolution had ceased, and then a solution of 45.1 g (0.37 mol) of allyl bromide in 50 mL of THF is added over 10 min. The resulting solution is warmed to RT and stirred 30 min, during which time a white precipitate of sodium bromide appears. The solution is filtered thru a pad od Celite to remove the precipitates and the solvent removed in vacuo. The residue is dissolved in 900 mL of 95% ethanol, cooled to 0° C., and 240 mL of cold 6N NaOH is added. The reaction mixture is stirred 60 h at RT. The reaction mixture is then concentrated, cooled to 0° C., and acidified carefully to pH 1 with conc. HCl. The acidic solution is then extracted with EtOAc (2×500 mL), and the organics were dried over $MgSO_4$ and the solvent removed in vacuo. Trituration of the viscous yellow oil with petroleum ether afforded 34.4 g of 2-Allyl-2-methylmaolnic acid as a white solid: $^1H$ NMR ($CDCl_3$, 300 MHz) δ11.95 (s, br, 1H), 5.75 (m, 1H), 5.10 (m, 2H), 2.62 (m, 2H), 1.44 (s, 3H); low resolution MS (FAB)m/e 159 ($MH^+$).

B. 2-(3-Allyl-3-methyl-2,4-dioxo-2,3,4,5-tetrahydro benzo[b][1,4]diazepin-1-yl)-N-isopropyl-N-(4-methoxyphenyl) acetamide To a solution of 3.04 g (19.2 mmol) of 2-allyl-2-methyl malonic acid, prepared as in Part A, in 50 mL of DCM at 0° C. is added 7 mL of DMF, followed by 6.7 mL (76.8 mmol) of oxalyl chloride. The resulting solution is stirred 1 h at RT, then the solvent and excess oxalyl chloride is removed in vacuo. The residue is dissolved in 100 mL of THF and added dropwise to a stirring solution of 5.0 g (16.0 mmol) of N-Isopropyl-N-(4-methoxy-phenyl)-2-phenylamino acetamide, prepared as in Intermediate 44, in 300 mL of THF maintained at 0° C. The resulting mixture is stirred at RT for 30 min then refluxed for 16 h. The solvents were removed in vacuo and the residue poured into 200 mL of 1H HCl and extracted with EtOAc (2×100 mL). The organics were washed with $NaHCO_3$ (1×100 mL), brine (1×100 mL), dried over $MgSO_4$, and the solvent removed in vacuo. Purification of the brown oil by silica gel flash column chromatography using hexane/EtOAc 1/1 as eluent afforded 4.0 g of 2-(3-Allyl-3-methyl-2,4-dioxo-2,3,4,5-tetrahydro benzo[b][1,4]diazepin-1-yl)-N-isopropyl-N-(4-methoxyphenyl) acetamide: $^1H$ NMR ($CDCl_3$, 300 MHz) δ9.53 (s, 1H), 7.27–6.85 (m, 8H), 5.67–5.60 (m, 1H), 5.05–4.93 (m, 2H), 4.73 (d, 1H, J=17), 4.50–4.45 (d, 1H, J=16), 3.77 (s, 3H), 3.60 (d, 1H, J=17), 2.1 (s, 1H), 1.46 (s, 2H), 1.09–1.03 (m, 6H).

C. 2-(3-Allyl-3-methyl-2,4-dioxo-5-pyridin-3-yl-2,3,4,5-tetrahydro benzo[b][1,4]diazepin-1-yl)-N-isopropyl-N-[4-methoxyphenyl]acetamide To a stirring solution of 2.5 g (5.74 mmol) of 2-(3-Allyl-3-methyl-2,4-dioxo-2,3,4,5-tetrahydro benzo[b][1,4]diazepin-1-yl)-N-isopropyl-N-(4-methoxyphenyl) acetamide, prepared as in Part A, in 25 mL of DMF is added 1.81 g (11.5 mmol, 2 equiv.) of 3-bromopyridine, 1.12 g (11.5 mmol, 2 equiv.) of potassium acetate, and 364 mg (11.5 mmol) of copper powder. The suspension is heated to 125° C. for 4 h and then cooled to RT. It is diluted with 350 mL EtOAc and filtered through a bed of celite. The filtrate is washed with $H_2O$ (2×300 mL), conc. $NH_4OH$ (2×150 mL) and then dried ($MgSO_4$), and the solvents removed in vacuo. Purification by silica gel flash column chromatography using hexane/EtOAc 1/1 as eluent afforded 1.56 g of 2-(3-Allyl-3-methyl-2,4-dioxo-5-pyridin-3-yl-2,3,4,5-tetrahydro benzo[b][1,4]diazepin-1-yl)-N-isopropyl-N-[4-methoxyphenyl]acetamide as an oil: $^1$H NMR (CDCl$_3$, 300 MHz) δ8.51 (m, 2H), 7.68 (d, 1H, J=9), 7.39–6.93 (m, 8H), 6.71 (d, 1H, J=8), 5.78–5.64 (m, 1H), 5.08–5.00 (m, 2H), 4.72 (d, 1H, J=16), 4.39 (d, 1H, J=17), 4.08 (m, 1H), 3.85 (s, 3H), 3.81–3.79 (m, 1H), 2.11 (d, 1H, J=8), 1.77 (s, 1H), 1.60 (s, 2H), 1.21–1.07 (m, 6H).

D. N-Isopropyl-N-[4-methoxyphenyl]-2-[3-methyl-2,4-dioxo-3-(2-oxo-ethyl)-5-pyridin-3-yl-2,3,4,5-tetrahydro benzo[b][1,4]diazepin-1-yl]acetamide To a stirring solution of 1.5 g (2.93 mmol) of 2-(3-Allyl-3-methyl-2,4-dioxo-5-pyridin-3-yl-2,3,4,5-tetrahydro benzo[b][1,4]diazepin-1-yl)-N-isopropyl-N-[4-methoxyphenyl]acetamide, prepared as in Part C, in 10 mL of dioxane and 10 mL of H$_2$O at 0° C. is added 3.13 g (14.63 mmol, 2 equiv.) of sodium periodate followed by the addition of 2 drops of osmium tetroxide solution (4% in H$_2$O). The resulting suspension is stirred for 4 h and then diluted with 200 mL H$_2$O and 200 mL of EtOAc. The organic phase is washed with H$_2$O (2×250 mL) and a solution of Na$_2$S$_2$O$_3$ (10%) and then dried (MgSO$_4$), and the solvents removed in vacuo. Purification by silica gel flash column chromatography using hexane/EtOAc 5/1 as eluent afforded 1.56 g of N-Isopropyl-N-[4-methoxyphenyl]-2-[3-methyl-2,4-dioxo-3-(2-oxo-ethyl)-5-pyridin-3-yl-2,3,4,5-tetrahydro benzo[b][1,4]diazepin-1-yl]acetamide as an oil: $^1$H NMR (CDCl$_3$, 300 MHz) δ8.51 (m, 2H), 7.68 (d, 1H, J=9), 7.39–6.93 (m, 8H), 6.71 (d, 1H, J=8), 5.78–5.64 (m, 1H), 5.08–5.00 (m, 2H), 4.72 (d, 1H, J=16), 4.39 (d, 1H, J=17), 4.08 (m, 1H), 3.85 (s, 3H), 3.81–3.79 (m, 1H), 2.11 (d, 1H, J=8), 1.77 (s, 1H), 1.60 (s, 2H), 1.21–1.07 (m, 6H); low resolution MS (FAB)m/e 513 (MH$^+$).

E. {1-[Isopropyl-(4-methoxyphenyl)-carbamoylmethyl]-3-methyl-2,4-dioxo-5-pyridin-3-yl-2,3,4,5-tetrahydro-1H benzo[b][1,4]diazepin-3-yl}acetic acid To a stirring solution of 1.15 g (2.23 mmol) of N-Isopropyl-N-[4-methoxyphenyl]-2-[3-methyl-2,4-dioxo-3-(2-oxo-ethyl)-5-pyridin-3-yl-2,3,4,5-tetrahydro benzo[b][1,4]diazepin-1-yl]acetamide, prepared as in Part D, in 25 mL of acetone at 0° C. is added 1.0 g celite followed by dropwise addition of 1.67 mL (4.46 mmol, 2 equiv., 2.67M) of Jones reagent. The reaction is stirred at RT for 1 h and 250 mg (4.17 mmol) of 2-propanol is added. The resulting pale green suspension is filtered and the filtrate is concentrated to an oily residue. Purification by silica gel flash column chromatography using DCM/MeOH 95/5 as eluent afforded 770 mg of the title compound as an oil: MS (FAB)m/e 531 (MH$^+$).

Example 1

2-[2,4-dioxo-5-phenyl-3-(3-ethoxycarbonylphenyl)-carbamoyl-2,3,4,5-tetrahydro-benzo[b][1,4]diazepin-1-yl]-N-isopropyl-N-phenyl acetamide To a solution of 0.26 g (0.54 mmol) of [1-(isopropyl-phenyl-carbamoylmethyl)-2,4-dioxo-5-phenyl-2,3,4,5-tetrahydro-1H-benzo[b][1,4]diazepin-3-yl]acetic acid, prepared as in Intermediate 32, and 0.08 mL (0.54 mmol) of ethyl 3-aminobenzoate in 2 mL of DMF is added 0.23 g (0.54 mmol) of BOP, 72 mg (0.54 mmol) of HOBT and 63 mg (0.54 mmol) of DMAP. The black solution is stirred at RT for 21 h and subsequently poured into 20 mL of 1N HCl. The mixture is extracted with ethyl acetate (×3), washed with 1N HCl and brine, dried over MgSO$_4$ and concentrated in vacuo. The resulting yellow oil is purified by silica gel flash chromatography (40% ethyl acetate/petroleum ether) followed by recrystallization from ethyl acetate/petroleum ether to give 0.25 g of the title compound as a white powder: mp. 187°–8° C.; $^1$H NMR (CDCl$_3$, 300 MHz) δ8.01 (d, 1H, J=22), 7.77 (t, 1H, J=8), 7.5–7.2 (m, 15H), 7.12 (t, 1H, J=8), 6.94 (d, 1H, J=8), 5.02 (m, 1H), 4.36 (q, 2H, J=7), 4.26 (q, 2H, J=17), 4.04 (t, 1H, J=7), 3.10 (m, 1H), 1.39 (t, 3H, J=7), 1.08 (dd, 6H, J=4,7); low resolution MS (FAB) m/e 633 (MH$^+$); Anal. (C$_{37}$H$_{36}$N$_4$O$_6$.0.25H$_2$O) Calcd C, 69.7; H, 5.8; N, 8.8; Found: C, 69.6; H, 5.7; N, 8.8.

Example 2

2-[2,4-dioxo-5-phenyl-3-(3-carboxyphenyl)-carbamoyl-2,3,4,5-tetrahydro-benzo[b][1,4]diazepin-1-yl]-N-isopropyl-N-phenyl acetamide 0.12 g of 2-[2,4-dioxo-5-phenyl-3-(3-ethoxycarbonylphenyl)-carbamoyl-2,3,4,5-tetrahydro-benzo[b][1,4]diazepin-1-yl]-N-isopropyl-N-phenyl acetamide, prepared as in Example 1, is dissolved in 5 mL of hot ethanol. 2.5 mL of H$_2$O and 0.13 g of K$_2$CO$_3$ are added and the mixture heated at reflux for 4 h and subsequently concentrated in vacuo. The residue is poured into 20 mL of 1N HCl and extracted with ethyl acetate (×3). The organic extract is washed with brine, dried over MgSO$_4$ and concentrated in vacuo to a white solid. Purification by reverse phase C-18 MPLC (70% methanol/TFA-H$_2$O) gave 99 mg of the title compound as a white powder: mp. 165°–170° C.; $^1$H NMR (CDCl$_3$, 300 MHz) δ8.6 (s, 1H), 8.05 (s, 1H), 7.92 (d, 1H, J=7), 7.75 (d, 1H, J=7), 7.5–7.2 (m, 14H), 7.15 (t, 1H, J=7), 6.97 (d, 1H, J=7), 5.02 (m, 1H), 4.27 (s, 2H), 4.10 (t, 1H, J=7), 3.20 (d, 2H, J=7), 1.08 (d, 3H, J=7), 1.02 (d, 3H, J=7); low resolution MS (FAB) m/e 605 (MH$^+$); Anal. (C$_{35}$H$_{32}$N$_4$O$_6$.0.5 TFA.0.5 H$_2$O) Calc. C, 64.5; H, 5.0; N, 8.4; Found: C, 64.5; H, 5.0; N, 8.3.

Example 3

2-[2,4-Dioxo-5-phenyl-3-methyl-3-(3-carboxyphenyl)carbamoylmethyl-2,3,4,5-tetrahydro-benzo[b][1,4]diazepin-1-yl]-N-isopropyl-N-phenyl acetamide A solution of 0.19 g (0.38 mmol) of [1-(isopropyl-phenyl-carbamoylmethyl)-3-methyl-2,4-dioxo-5-phenyl-2,3,4,5-tetrahydro-1H-benzo[b][1,4]diazepin-3-yl]acetic acid, prepared as in Intermediate 7, 0.15 g (0.76 mmol) of t-butyl 3-aminobenzoate, 0.35 g (0.76 mmol) of PyBrOP and 0.27 mL (1.5 mmol) of N,N-diisopropyl-N-ethylamine in 2 mL of DMF is stirred at 50° C. for 17 h. The reaction mixture is diluted with 30 mL of H$_2$O and extracted with EtOAc (×3). The organic extract is washed with H$_2$O, 1N HCl, and brine, dried over MgSO4 and concentrated in vacuo to a brown foam. The crude product is dissolved in 2 mL of CH$_2$Cl$_2$ and 0.3 mL (3.8 mmol) of TFA added. After stirring at RT for 1 d, the reaction mixture is concentrated in vacuo to a brown oil. Purification by reverse phase C-18 MPLC (60–80% methanol/TFA-H$_2$O) gave 99 mg of the title compound as a white powder: $^1$H NMR (CDCl$_3$ 300 MHz, mixture of conformations) δ8.8–6.8 (m, 20H), 5.07 (m, 1H), 4.78 (d, 1H, J=12), 3.79 (d, 1H, J=12), 2.70 (q, 2H, J=10), 1.70 (s, 3H), 1.09 (m, 6H); low resolution MS (FAB) m/e 619 (MH$^+$); Anal. (C$_{36}$H$_{34}$N$_4$O$_6$.0.75 TFA.H$_2$O) Calc. C, 62.4; H, 5.1; N, 7.8; Found: C, 62.4; H, 5.2; N, 7.7.

Example 4

2-(2,4-Dioxo-5-phenyl-3-methyl-3-phenylcarbamoylmethyl-2,3,4,5-tetrahydro-benzo[b][1,4]diazepin-1-yl)-N-isopropyl-N-phenyl acetamide A solution of 35 mg (0.07 mmol) of [1-(isopropyl-phenyl-carbamoylmethyl)-3-methyl-2,4-dioxo-5-phenyl-2,3,4,5- tetrahydro-1H-benzo[b][1,4]diazepin-3-yl]acetic acid, prepared as in Intermediate 7, 0.013 mL (0.14 mmol) of aniline, 66 mg (0.14 mmol) of PyBrOP and 0.05 mL (0.23 mmol) of N,N-diisopropyl-N-ethylamine in 2 mL of DMF is stirred at RT for 2 d. The reaction mixture is diluted with 30 mL of 1N HCl and extracted with EtOAc (×3). The organic extract is washed with 1N HCl, brine, sat. NaHCO$_3$ and brine, dried over MgSO$_4$ and concentrated in vacuo to a yellow oil. Purification by reverse phase C-18 MPLC (70% methanol/ TFA-H$_2$O) gave 16 mg of the title compound as a white powder; m.p. 228°–9° C.; $^1$H NMR (d$_6$-DMSO 300 MHz, mixture of conformations) δ9.73 (s, 1H), 7.6–7.2 (m, 16H), 7.05 (m, 2H), 6.65 (d, 1H, J=8), 4.85 (m, 1H), 4.22 (m, 2H), 2.33 (m, 2H), 1.20 (s, 3H), 1.00 (m, 6H); low resolution MS (FAB) m/e 575 (MH$^+$).

Example 5

2-(2,4-Dioxo-5-phenyl-3-methyl-N-methyl-3-phenylcarbamoylmethyl-2,3,4,5-tetrahydro-benzo[b] [1,4]diazepin-1-yl)-N-isopropyl-N-phenyl acetamide A solution of 0.1 g (0.20 mmol) of [1-(isopropyl-phenyl-carbamoylmethyl)-3-methyl-2,4-dioxo-5-phenyl-2,3,4,5-tetrahydro-1H-benzo[b][1,4]diazepin-3-yl]acetic acid, prepared as in Intermediate 7, 0.043 mL (0.40 mmol) of N-methylaniline, 0.17 g (0.40 mmol) of BOP, 0.054 mL (0.40 mmol) of HOBT and 0.05 g (0.40 mmol) of DMAP in 2 mL of DMF is stirred at 65° C. for 6 d. The reaction mixture is diluted with 50 mL of 1N HCl and extracted with EtOAc (×3). The organic extract is washed with 1N HCl, brine, 1N NaOH and brine, dried over MgSO$_4$ and concentrated in vacuo to a brown oil. Purification by reverse phase C-18 MPLC (65% methanol/TFA-H$_2$O) gave 23 mg of the title compound as a white powder; m.p. 228°–9° C.; $^1$H NMR (CDCl$_3$, 300 MHz, mixture of conformations) δ7.5–6.8 (m, 19H), 5.04 (m, 1H), 4.32 (m,1H), 3.92 (m, 1H), 3.1 (m, 2H), 2.65 (br, 3H), 1.54 (s, 3H), 1.07 (m, 6H); low resolution MS (FAB) m/e 589 (MH$^+$).

Example 6

N-Isopropyl-2-[3-methyl-2,4-dioxo-5-phenyl-3-(2-phenylaminoethyl)-2,3,4,5-tetrahydro-benzo[b][1,4] diazepin-1-yl]-N-phenyl acetamide To a stirred solution of 135 mg (0.28 mmol) of N-Isopropyl-2-[3-methyl-2,4-dioxo-3-(2-oxoethyl)-5-phenyl-2,3,4,5-tetrahydro-benzo[b][1,4]diazepin-1-yl]-N-phenyl acetamide, prepared as in Intermediate 9, and 130 mg (1.40 mmol, 5.0 equiv) of aniline in 5 mL of methanol is added 18 mg (0.28 mmol, 1.0 equiv) of NaBH$_3$CN and 1 drop of glacial acetic acid. The resulting mixture is stirred 30 min at RT, then quenched by the addition of 0.1 mL H$_2$O and the solvent removed in vacuo. The residue is then dissolved in 40 mL of EtOAc and extracted with 0.5N HCl (1×40 mL); the organics are dried (MgSO$_4$) and the solvent removed in vacuo. The resulting oil is purified by silica gel flash column chromatography using hexane/EtOAc 2/1 as eluent followed by further purification by reverse phase MPLC using a C-18 column and 60% acetonitrile/40% H$_2$O with 0.1% TFA as eluent followed by lyophilization to afford 120 mg of the title compound as a white amorphous solid: $^1$H NMR (CDCl$_3$, 300 MHz, mixture of conformational isomers) δ7.54–6.73 (m, 19H), 5.04 (m, 1H), 4.54 (d, 0.5H, J=16.6), 4.24 (m, 2H), 3.80 (d, 0.5H, J=16.6), 3.62 (m,1H), 3.34 (m, 0.5H), 2.40 (s, br, 1H), 2.05 (m, 0.5H), 1.80 (m, 0.5H), 1.62 (s, 1H), 1.12 (m, 6H); low resolution MS (FAB)m/e 561 (MH$^+$), 468.

Example 7

N-Isopropyl-2-[3-methyl-2,4-dioxo-3-(2-phenyl-2-oxoethyl)-5-phenyl-2,3,4,5-tetrahydro-benzo[b][1,4] diazepin-1-yl]-N-phenyl acetamide A solution of 0.23 mL of 1.0M phenylmagnesium bromide in THF is added to a solution of 0.10 g (0.21 mmol) of N-Isopropyl-2-[3-methyl-2,4-dioxo-3-(2-oxoethyl)-5-phenyl-2,3,4,5-tetrahydro-benzo[b][1,4]diazepin-1-yl]-N-phenyl acetamide, prepared as in Intermediate 9, in 2 mL of THF at 0° C. After stirring at room temperature for 60 min the reaction is diluted with 10 mL of 1N HCl and extracted with EtOAc (×3). The organic extract is washed with sat. NaHCO$_3$ and brine, dried over MgSO$_4$ and concentrated in vacuo to a colorless oil. The crude product is dissolved in 2 mL of CH$_2$Cl$_2$ and 0.092 g (0.42 mmol) of PCC added. After stirring at RT for 90 min, the reaction mixture is passed through a short plug of silica gel and concentrated in vacuo to a dark orange oil. Purification by silica gel flash chromatography (30% ethyl acetate/petroleum ether) gave 97 mg of the title compound as a white powder; $^1$H NMR (CDCl$_3$ 300 MHz) δ8.04 (d, 2H, J=7), 7.6–7.2 (m, 15H), 7.14 (t, 1H, J=7), 7.00 (d, 1H, J=7), 5.03 (m, 1H), 4.2 (m, 2H), 3.98 (dd, 1H, J=8,18), 3.61 (dd, 1H, J=5,18), 1.09 (dd, 1H, J=2,7); low resolution MS (FAB) m/e 546 (MH$^+$).

Example 8

N-Isopropyl-2-[3-methyl-2,4-dioxo-3-(1-phenyl-1-oxoprop-2-yl)-5-phenyl-2,3,4,5-tetrahydro-benzo[b] [1,4]diazepin-1-yl]-N-phenyl acetamide 8.2 mg (0.21 mmol) of 60% sodium hydride is added to a solution of 0.075 g (0.14 mmol) of N-Isopropyl-2-[3-methyl-2,4-dioxo-3-(2-phenyl-2-oxoethyl)-5-phenyl-2,3,4, 5-tetrahydro-benzo[b][1,4]diazepin-1-yl]-N-phenyl acetamide, prepared as in Example 7, in 2 ml of DMF. After 5 min, 0.009 mL (0.15 mmol) of iodomethane is added and the solution stirred at RT for 25 min. The reaction mixture is diluted with 10 mL of 1N HCl and extracted with EtOAc (×3). The organic extracts are washed with H$_2$O and brine, dried over MgSO$_4$ and concentrated in vacuo to a bright yellow oil. Purification by reverse phase C-18 MPLC (70–75% methanol/H$_2$O) gave 17 mg of the title compound as a white powder: $^1$H NMR (CDCl$_3$ 300 MHz) δ8.04 (d, 2H, J=7), 7.6–6.9 (m, 17H), 5.03 (m, 0.5H), 4.92 (m, 0.5H), 4.8–3.9 (m, 3H), 1.26 (dd, 3H, J=7,11), 1.12 (dd, 3H, J=2,7), 0.98 (t, 3H, J=7); low resolution MS (FAB) m/e 560 (MH$^+$).

Example 9

2-[3-(2-Amino-phenylcarbamoylmethyl)-3-methyl-2,4-dioxo-5-phenyl-2,3,4,5-tetrahydro-benzo[b][1,4] diazepin-1-yl]-N-isopropyl-N-phenyl acetamide A stirring solution of 100 mg (0.20 mmol) of [1-(Isopropyl-phenyl-carbamoylmethyl)-3-methyl-2,4-dioxo-5-phenyl-2,3,4,5-tetrahydro-1H-benzo[b][1,4]diazepin-3-yl]-acetic acid, prepared as in Intermediate 7, 32 mg (0.30 mmol, 1.5 equiv) of 1,2-phenylene diamine, 187 mg (0.40 mmol, 2.0 equiv) of bromo-tris-pyrrolidino-phosphonium hexafluorophosphate (PyBroP), and 80 mg (0.60 mmol, 3.0 equiv) of diisopropylethylamine in 2 mL of DMF is heated at 50° C. for 48 h. The DMF is removed in vacuo and the residue is dissolved in 20 mL of EtOAc and extracted with 20 mL 1N HCl. The organic layer is dried (MgSO$_4$) and the solvent removed in vacuo. The resulting oil is purified by silica gel flash column chromatography using dichloromethane/MeOH 20/1 as eluent followed by further purification via reverse phase MPLC using a C-18 column and 60% acetonitrile/40% H$_2$O with 0.1% TFA as eluent followed by lyophilization to afford 30 mg of the title compound as a white amorphous solid: $^1$H NMR (CDCl$_3$, 300 MHz) δ9.38 (s, 0.7H), 9.17 (s, 0.3H), 7.53–7.04 (m, 17H), 6.81 (d, 1H, J=4.7), 4.97 (m, 1H), 4.57 (d, 0.5H, J=16.6), 4.27 (s, br, 2H), 3.87 (d, 0.5H, J=16.6), 3.36 (d, 1H, J=15.6), 3.13 (d, 1H, J=15.6), 2.60 (d, 0.5H, J=15.3), 2.42 (d, 0.5H, J=15.3), 1.61 (s, 1H), 1.22 (s, 2H), 1.09 (m, 6H); low resolution MS (FAB)m/e 590 (MH$^+$), 482.

Example 10

N-Isopropyl-2-[3-methyl-2,4-dioxo-5-phenyl-3-(5-phenyl-[1,2,4]oxadiazol-3-ylmethyl)-2,3,4,5-tetrahydro-benzo[b][1,4]diazepin-1-yl]-N-phenyl acetamide To a stirring solution of 65 mg (0.11 mmol) of 2-[2,4-Dioxo-5-phenyl-3-(5-phenyl-[1,2,4]oxadiazol-3-ylmethyl)-2,3,4,5-tetrahydro-benzo[b][1,4]diazepin-1-yl]-N-isopropyl-N-phenyl acetamide, prepared as in Intermediate 40, in 2 mL of DMF at 0° C. is added 8 mg (0.17 mmol, 1.5 equiv) of sodium hydride (60% dispersion in mineral oil). The resulting solution is stirred 5 min, then 10 mL (0.17 mmol, 1.5 equiv) of methyl iodide is added. The reaction mixture is stirred 30 min at 0° C. then 3 h at RT and quenched with 1 mL H$_2$O. The reaction mixture is diluted with 40 mL Et$_2$O and washed with 40 mL H$_2$O. The organic layer is dried (MgSO$_4$) and the solvents removed in vacuo. Purification of the resulting oil via reverse phase MPLC using a C-18 column and 70% acetonitrile/30% H$_2$O with 0.1% TFA as eluent followed by lyophilization afforded 35 mg of the title compound as a white amorphous solid: $^1$H NMR (CDCl$_3$, 300 MHz) δ8.11 (m, 2H), 7.63–6.86 (m, 17H), 5.08 (m, 1H), 4.43 (m, 0.66H), 4.03 (d, br, 0.66H, J=16.3), 3.83 (d, 0.33H, J=16.9), 3.55 (d, 0.33H, J=16.9), 2.87 (dd, 2 H, J=15.4, 33.0), 1.62 (s, 2H), 1.35 (s, 1H), 1.11 (m, 6H); low resolution MS (FAB)m/e 600 (MH$^+$), 465, 223.

Example 11

N-Isopropyl-2-[3-methyl-2,4-dioxo-5-phenyl-3-(3-phenyl-allyl)-2,3,4,5-tetrahydro-benzo[b][1,4]diazepin-1-yl]-N-phenyl acetamide To a stirring solution of 200 mg (0.37 mmol) of 2-[2,4-Dioxo-5-phenyl-3-(3-phenyl-allyl)-2,3,4,5-tetrahydro-benzo[b][1,4]diazepin-1-yl]-N-isopropyl-N-phenyl acetamide, prepared as in Intermediate 41, in 3 mL of DMF at 0° C. is added 16 mg (0.41 mmol, 1.1 equiv) of sodium hydride (60% dispersion in mineral oil). The resulting solution is stirred 5 min, then 25 mL (0.41 mmol, 1.1 equiv) of methyl iodide is added. The reaction mixture is stirred 30 min at 0° C. then 19 h at RT and quenched with 1 mL H$_2$O. The reaction mixture is diluted with 40 mL EtOAc and washed with 40 mL H$_2$O. The organic layer is dried (MgSO$_4$) and the solvents removed in vacuo. Purification of the resulting oil via reverse phase MPLC using a C-18 column and 70% acetonitrile/30% H$_2$O with 0.1% TFA as eluent followed by lyophilization afforded 107 mg of the title compound as a white amorphous solid: $^1$H NMR (CDCl$_3$, 300 MHz) δ7.53–7.05 (m, 18H), 6.79 (m, 1H), 6.15 (m, 1H), 5.97 (d, 1H, J=15.7), 5.09 (m, 1H), 4.44 (d, 1H, J=16.4), 3.95 (d, 1H, J=16.4), 3.07 (m, 2H), 2.28 (d, 1H, J=7.1), 1.61 (s, 3H), 1.14 (m, 6H); low resolution MS (FAB)m/e 558 (MH$^+$), 423, 223.

Example 12

N-Isopropyl-2-[3-methyl-2,4-dioxo-5-phenyl-3-(3-phenyl-propyl)-2,3,4,5-tetrahydro-benzo[b][1,4]diazepin-1-yl]-N-phenyl acetamide To a stirring solution of 40 mg (71.7 mmol) of N-Isopropyl-2-[3-methyl-2,4-dioxo-5-phenyl-3-(3-phenyl-allyl)-2,3,4,5-tetrahydro-benzo[b][1,4]diazepin-1-yl]-N-phenyl acetamide, prepared as in Example 11, in 3 mL absolute ethanol is added 10 mg of 10% palladium on carbon. The reaction vessel is placed on a Parr hydrogenation apparatus, evacuated, and then pressurized with H$_2$ gas to 40 psi and shaken for 2 h at RT. The reaction mixture is filtered through Celite to remove the catalyst and the solvent removed in vacuo. Purification of the resulting material via reverse phase MPLC using a C-18 column and 70% acetonitrile/30% H$_2$O with 0.1% TFA as eluent followed by lyophilization afforded 29 mg of the title compound as a white amorphous solid: $^1$H NMR (CDCl$_3$, 300 MHz) δ7.49–6.96 (m, 19H), 6.72 (d, 1H, J=8.0), 5.09 (m, 1H), 4.38 (d, 1H, J=16.3), 3.92 (d, 1H, J=16.3), 2.28 (m, 2H), 1.67–1.50 (m, 6H), 1.34 (m, 1H), 1.12 (m, 6H); low resolution MS (FAB)m/e 560 (MH$^+$), 425, 397, 223.

Example 13

2-[1-(Isopropyl-phenyl-carbamoylmethyl)-3-methyl-2,4-dioxo-5-phenyl-2,3,4,5-tetrahydro-1H-benzo[b][1,4]diazepine-3-yl]acetamide To a stirring solution of 233 mg (0.47 mmol) of [1-(Isopropyl-phenyl-carbamoylmethyl)-3-methyl-2,4-dioxo-5-phenyl-2,3,4,5-tetrahydro-1H-benzo[b][1,4]diazepin-3-yl]-acetic acid, prepared as in Intermediate 7, in 2 mL DMF is added 98 mg (0.51 mmol, 1.1 equiv) of EDC and 76 mg (0.56 mmol, 1.2 equiv) of HOBT. The resulting solution is stirred 5 min, then 75 mL (0.61 mmol, 1.3 equiv) of a 30% solution of ammonium hydroxide is added. The solution is stirred 2 h at RT, then poured into 30 mL of EtOAc and extracted H$_2$O (1×30 mL) and NaHCO$_3$ (1×30 mL). The organic layer is separated, dried (MgSO$_4$), and the solvent removed in vacuo. Purification of the resulting grey solid via reverse phase MPLC using a C-18 column and 60% acetonitrile/40% H$_2$O with 0.1% TFA as eluent followed by lyophilization afforded 35 mg of the title compound as a white amorphous solid: $^1$H NMR (CDCl$_3$, 300 MHz, mixture of conformers) δ7.47–6.80 (m, 14H), 6.70 (s, br, 0.5H), 5.84 (s, br, 0.5H), 5.03 (m, 1H), 4.63 (d, 0.5H, J=16.6), 4.35 (d, 0.5H, J=16.3), 4.08 (d, 0.5H, J=16.6), 3.74 (d, 0.5H, J=16.3), 3.10 (m, 1H), 2.46 (d, 0.5H, J=14.7), 2.23 (d, 0.5H, J=14.7), 1.65 (s, 1.5H), 1.16 (m, 7.5H); low resolution MS (FAB)m/e 499 (MH$^+$).

Example 14

N-Isopropyl-N-(4-methoxy-phenyl)-2-(3-methyl-2,4-dioxo-5-phenyl-3-phenylcarbamoylmethyl-2,3,4,5-tetrahydro-benzo[b][1,4]diazepin-1-yl) acetamide To a stirring solution of 1.5 g (2.83 mmol) of [1-(Isopropyl-(4-methoxy-phenyl)-carbamoylmethyl)-3-methyl-2,4-dioxo-5-phenyl-2,3,4,5-tetrahydro-1H-benzo[b][1,4]diazepin-3-yl]-acetic acid, prepared as in Intermediate 8, and 50 mL DMF in 25 mL of dichloromethane at −5° C. is added 0.74 mL (8.50 mmol, 3.0 equiv) of oxalyl chloride dropwise over 5 min. The resulting solution is stirred 15 min at −5° C. then 90 min at RT, during which time gas evolution is observed. The solvent and excess oxalyl chloride are then removed in vacuo, and the resulting light brown foam is dissolved in 20 mL dichloromethane and cooled to 0° C. To this solution is added 0.78 mL (8.50 mmol, 3.0 equiv) of aniline dropwise over 5 min. The resulting solution is stirred 1 h at RT and then poured into 60 mL of EtOAc and washed with 1N HCl (3×50 mL). The organic layer is separated, dried (MgSO$_4$), and the solvent removed in vacuo. Purification of the resulting brown solid by silica gel flash column chromatography using hexane/EtOAc 3/2 as eluent followed by lyophilization afforded 1.66 g of the title compound as a white amorphous solid: $^1$H NMR (DMSO-d$_6$, 300 MHz, mixture of conformers) δ9.95 (s, 0.33H), 9.72 (s, 0.66H), 7.54–6.97 (m, 18H), 6.80 (dd, 0.33H, J=1.4, 8.3), 6.63 (dd, 0.66H, J=1.3, 8.3), 4.80 (m, 1H), 4.19 (m, 2H), 3.79 (s, 3H), 3.01 (m, 0.33H), 2.31 (m, 0.66H), 1.39 (s, 2H), 1.19 (s, 1H), 0.97 (m, 6H); low resolution MS (FAB)m/e 605 (MH$^+$), 512.

Example 15

N-Isopropyl-N-phenyl-2-(3-methyl-2,4-dioxo-5-phenyl-3-phenylcarbamoylpropyl-2,3,4,5-tetrahydro-benzo[b][1,4]diazepin-1-yl) acetamide A solution of 95 mg of [1-(Isopropyl-phenyl-carbamoylmethyl)-3-methyl-2,4-dioxo-5-phenyl-2,3,4,5-tetrahydro-1H-benzo[b][1,4]diazepin-3-yl]-butyric acid, prepared as in Intermediate 34, 75.1 mg of BOP, 24.2 mg of HOBT, 21 mg of DMAP and 16.4 mg of aniline in DMF (0.5 ml) is stirred at RT overnight. The reaction mixture is diluted with 50 mL of ethyl acetate and washed with 1N aqueous sodium hydroxide solution (×2), water, 0.5N hydrochloric acid (×2), water and brine. The organic extract is dried over MgSO$_4$ and concentrated in vacuo to afford the crude product. Purification by silica gel flash column chromatography (10% MeOH in methylene chloride) gave 45 mg of the title compound as a clear glass: $^1$H NMR (300 MHz, CDCl$_3$) δ8.6 (s, 1H), 6.8–7.7 (m, 19H), 5.11 (sept, 1H, J=7.1), 4.59 (d, 1H, J=8.9), 3.71 (d, 1H, J=8.9,), 2.09 (m, 2H), 1.81 (m, 2H), 1.59 (s, 3H), 1.4 (m, 2H), 1.04 (dd, 6H, J=7.1); low resolution MS (FAB) m/e 603 (MH$^+$).

Example 16

2-(3-Ethyl-2,4-dioxo-5-phenyl-3-phenylcarbamoylmethyl-2,3,4,5-tetrahydro-benzo[b][1,4]diazepin-1-yl)-N-isopropyl-N-phenyl-acetamide 150 mg (1.0 equiv, 0.29 mmol) of [1-(isopropyl-phenyl-carbamoylmethyl)-3-ethyl-2,4-dioxo-5-phenyl-2,3,4,5-tetrahydro-1H-benzo[b][1,4]diazepin-3-yl]acetic acid, prepared as in Intermediate 29, is dissolved in 1.5 mL of DMF. To the stirring solution is added 275 mg (2.0 equiv, 0.59 mmol) of PyBroP, followed by 0.303 mL (4.0 equiv, 1.7 mmol) of ethyl diisopropyl amine and 0.053 mL (2.0 equiv, 0.59 mmol) of aniline. The reaction mixture is heated to 50° C. and stirred for 16 h. The resulting solution is poured into 40 mL of 1:1 ethyl acetate/H$_2$O, separated and extracted with ethyl acetate (×2). The organic layer is dried over MgSO$_4$ and the solvent is removed in vacuo. Purification by reverse phase C-18 MPLC with 65% acetonitrile/H$_2$O as eluent afforded 50 mg of the title compound as a white solid: $^1$H NMR (CDCl$_3$, 300 MHz) δ9.23 (s, 1H), 7.55–6.91 (m, 18H), 6.81 (d,1H, J=6.9), 5.07 (m, 1H), 4.42–4.36 (m, 2H), 4.03 (s, 2H), 3.27 (s, 2H), 1.13 (d, 6H, J=6.9), 0.92 (t, 3H, J=7.1); low resolution MS (FAB) m/e 589 (MH$^+$).

Example 17

2-(2,4-dioxo-5-phenyl-3-phenylcarbamoylmethyl-2,3,4,5-tetrahydro-benzo[b][1,4]diazepin-1-yl)-N-isopropyl-N-(4-methoxy-phenyl)-acetamide 14 mg (1.0 equiv, 0.24 mmol) of {1-[Isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid, prepared as in Intermediate 26, is dissolved in 3 mL of dry CH$_2$Cl$_2$ and cooled to −5° C. with a ice/salt/water bath. While stirring, 0.005 mL of dry DMF is added, followed by 0.063 mL (3.0 equiv, 0.72 mmol) of oxalyl chloride dropwise over 2 min. The reaction mixture is stirred at −5° C. for 15 min., then allowed to warm to RT and stirred 1 h. The solvent is removed in vacuo. The resulting oil is dissolved in 2.5 mL of dry CH$_2$Cl$_2$ and cooled to 0° C. with an ice/water bath. 0.066 mL (3.0 equiv, 0.72 mmol) of aniline is added dropwise, the ice water bath is removed and the reaction mixture is stirred at RT for 18 h. The resulting solution is poured into 20 mL of 1:1 ethyl acetate/H$_2$O, and extracted with ethyl acetate (×2). The organic layer is dried over MgSO$_4$ and the solvent is removed in vacuo. Purification by silica gel MPLC using 5% MeOH/CH$_2$Cl$_2$ as eluent followed by reverse phase C-18 MPLC with 55% acetonitrile/H$_2$O as eluent afforded 40 mg of the title compound as a white solid: $^1$H NMR (CDCl$_3$, 300 MHz) δ10.09 (s, 1H), 7.52–6.89 (m, 18H), 4.74 (m, 1H), 4.52–4.09 (m, 2H), 3.84 (t, 1H), 2.94 (d, 2H, J=6.6), 0.92 (m, 6H); low resolution MS (FAB) m/e 591 (MH$^+$).

Example 18

2-[3-(1H-indol-2-ylmethyl)-3-methyl-2,4-dioxo-5-phenyl-2,3,4,5-tetrahydro-benzo[b][1,4]diazepin-1-yl]-N-isopropyl-N-phenyl acetamide To a stirring solution of 190 mg (0.28 mmol) of 2-[3-(N-tert-butoxycarbonyl-indol-2-ylmethyl)-2,4-dioxo-5-phenyl-2,3,4,5-tetrahydro-benzo[b][1,4]diazepin-1-yl]-N-isopropyl-N-phenyl acetamide, prepared as in Intermediate 37, in 4 mL of DMF at 0° C. is added 17 mg (0.43 mmol, 1.5 equiv) of sodium hydride (60% dispersion in mineral oil). The resulting solution is stirred 5 min, then 26 μL (0.43 mmol, 1.5 equiv) of methyl iodide is added. The reaction mixture is stirred 2 h at RT and then heated to 50° C. for 3 h, then quenched with 1 mL H$_2$O. The reaction mixture is diluted with 40 mL EtOAc and washed with 40 mL H$_2$O. The organic layer is dried (MgSO$_4$) and the solvents removed in vacuo. The crude material is then dissolved in 3 mL of dichloromethane, 1 mL of TFA is added, and the reaction mixture is stirred 3 h at RT. The volatiles are removed in vacuo and the resulting crude oil purified via reverse phase MPLC using a C-18 column and 75% acetonitrile/25% H$_2$O with 0.1% TFA as eluent followed by lyophilization afforded 15 mg of the title compound as a white amorphous solid: $^1$H NMR (CDCl$_3$, 300 MHz) δ9.22 (s, 0.33H), 7.68–7.00 (m, 17H), 6.84 (m, 1H), 6.28 (s, 0.33H), 6.16 (s, 0.66H), 5.26 (m, 0.66H), 5.10 (m, 0.33H), 4.72 (d, 0.66H, J=16.3), 4.45 (d, 0.33H, J=16.6), 4.02 (m, 0.33H), 3.82 (d, 0.66H, J=16.3), 3.70 (m, 0.33H), 3.45 (d, 0.33H), 3.15 (d, 0.66H, J=14.9), 2.62 (d, 0.66H, J=14.9), 1.42 (s, 2H), 1.26 (m, 7H); low resolution MS (FAB)m/e 571 (MH$^+$).

Example 19

2-[3-(1H-indol-3-ylmethyl)-3-methyl-2,4-dioxo-5-phenyl-2,3,4,5-tetrahydro-benzo[b][1,4]diazepin-1-yl]-N-isopropyl-N-phenyl acetamide To a stirring solution of 210 mg (0.32 mmol) of 2-[3-(N-tert-butoxycarbonyl-indol-3-ylmethyl)-2,4-dioxo-5-phenyl-2,3,4,5-tetrahydro-benzo[b][1,4]diazepin-1-yl]-N-isopropyl-N-phenyl acetamide, prepared as in Intermediate 38, in 4 mL of DMF at 0° C. is added 19 mg (0.48 mmol, 1.5 equiv) of sodium hydride (60% dispersion in mineral oil). The resulting solution is stirred 5 min, then 30 mL (0.48 mmol, 1.5 equiv) of methyl iodide is added. The reaction mixture is stirred 2 h at RT and then heated to 50° C. for 14 h, then quenched with 1 mL H$_2$O. The reaction mixture is diluted with 40 mL EtOAc and washed with 40 mL H$_2$O. The organic layer is dried (MgSO$_4$) and the solvents removed in vacuo. The crude material is then dissolved in 2 mL of dichloromethane, 2 mL of TFA is added, and the reaction mixture is stirred 1 h at RT. The volatiles are removed in vacuo and the resulting crude oil purified via MPLC using a Si60 silica gel column and hexane/EtOAc 5/2 as eluent followed by lyophilization afforded 37 mg of the title compound as a white amorphous solid: $^1$H NMR (CDCl$_3$, 300 MHz) δ8.11 (s, 1H), 7.61–7.00 (m, 18H), 6.76 (d, 1H, J=5.1), 5.10 (m, 1H), 4.50 (d, 1H, J=16.4), 3.95 (d, 1H, J=16.4), 2.91 (dd, 2H), 1.58 (s, 3H), 1.14 (m, 6H); low resolution MS (FAB)m/e 571 (MH$^+$).

Example 20

2-[3-(1H-indol-2-ylmethyl)-3-methoxy-2,4-dioxo-5-phenyl-2,3,4,5-tetrahydro-benzo[b][1,4]diazepin-1-yl]-N-isopropyl-N-(4-methoxyphenyl) acetamide A solution of 0.76 g (2.0 mmol) of N-isopropyl-N-(4-methoxy-phenyl)-2-(2-phenylamino-phenylamino) acetamide, prepared as in Intermediate 43, in 10 mL of THF is added dropwise to a solution of 1.0 g (2.4 mmol) of 2-(N-tert-butoxycarbonyl-1H-indol-2-ylmethyl)-2-methoxy-malonyl dichloride in 35 mL of THF. The brown solution is heated at reflux for 1 d. After removal of THF in vacuo the residue is diluted with 100 mL of 1N HCl and extracted with EtOAc (×2). the organic extract is washed with 1N HCl, brine, sat. NaHCO$_3$ and brine, dried over MgSO$_4$ and concentrated in vacuo to a brown foam. Purification by silica gel flash chromatography (30–50% EtOAc/ petroleum ether) followed by reverse phase C-18 MPLC (70–80% methanol/H$_2$O) gave 0.15 g of the title compound as a white powder: $^1$H NMR (d$_6$-DMSO 300 MHz) δ10.78 (s,1H), 7.57 (d, 1H, J=6), 7.5–6.9 (m, 16H), 6.69 (d, 1H, J=8), 4.82 (m, 1H), 4.26 (m, 2H), 3.79 (s, 3H), 3.56 (q, 2H, J=16), 0.99 (t, 6H, J=7); low resolution MS (FAB) m/e 617 (MH$^+$).

Example 21

N-Isopropyl-2-(3-methoxy-2,4-dioxo-5-phenyl-3-phenylcarbamoylmethyl-2,3,4,5-tetrahydro-benzo[b][1,4]diazepin-1-yl)-N-(4-methoxy-phenyl)-acetamide A stirring solution of 150 mg (0.28 mmol) of [1-(Isopropyl-(4-methoxy-phenyl)-carbamoylmethyl)-3-methoxy-2,4-dioxo-5-phenyl-2,3,4,5-tetrahydro-1H-benzo[b][1,4]diazepin-3-yl]-acetic acid, prepared as in Intermediate 11, 50 mL (0.55 mmol, 2.0 equiv) of aniline, 384 mg (0.83 mmol, 3.0 equiv) of bromo-tris-pyrrolidino-phosphonium hexafluorophosphate (PyBroP), and 142 mg (1.10 mmol, 4.0 equiv) of diisopropylethylamine in 2 mL of DMF is stirred at RT for 20 h. The DMF is removed in vacuo and the residue is dissolved in 20 mL of EtOAc and extracted with H$_2$O (1×20 mL) and 1N HCl (1×20 mL). The organic layer is dried (MgSO$_4$) and the solvent removed in vacuo. The resulting oil is purified by reverse phase MPLC using a C-18 column and 55% acetonitrile/45% H$_2$O with 0.1% TFA as eluent followed by lyophilization to afford 78 mg of the title compound as a white amorphous solid: $^1$H NMR (CDCl$_3$, 300 MHz) δ8.83 (s, 1H), 7.55–6.94 (m, 17H), 6.79 (d, 1H, J=8.3), 5.04 (m, 1H), 4.47 (d, 1H, J=16.4), 4.00 (d, 1H, J=16.4), 3.85 (s, 3H), 3.58 (d, 1H, J=14.5), 3.39 (d, 1H, J=14.5), 3.21 (s, 3H), 1.12 (m, 6H); low resolution MS (FAB)m/e 622(MH$^+$), 528.

Example 22

2-[3-(1H-indol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide To a stirring solution of 750 mg (1.64 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 25 mL DMF at 0° C. is added dropwise over 5 min 3.60 mL (1.80 mmol, 1.1 equiv) of a 0.5M solution of KN(TMS)$_2$ in toluene. The resulting solution is stirred 10 min, then a solution of 560 mg (1.80 mmol, 1.1 equiv) of N-BOC-3-bromomethylindolyl (Schöllkopf et. al., *Liebigs Ann. Chem.* 1985, 413) in 2 mL DMF is added. The resulting solution is stirred 16 h at RT and then quenched with 5 mL of H$_2$O. The reaction mixture is then poured into 200 mL of EtOAc and extracted with H$_2$O (2×200 mL). The organic layer is separated, dried (MgSO$_4$), and the solvents removed in vacuo. Purification of the material by silica gel flash column chromatography afforded 927 mg of 2-[3-(N-BOC-indol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide, of which 150 mg is immediately dissolved in 4 mL of 4N HCl in dioxane and stirred 9 h at RT. The reaction mixture is poured into 30 mL EtOAc and extracted with NaHCO$_3$ (1×30 mL) and H$_2$O (1×30 mL). The organic layer is separated, dried (MgSO$_4$), and the solvents removed in vacuo. The resulting oil is purified by silica gel flash column chromatography using hexane/EtOAc 2/1 as eluent followed by further purification by reverse phase MPLC using a C-18 column and 65% acetonitrile/35% H$_2$O as eluent followed by lyophilization to afford 52 mg of the title compound as a white amorphous solid: $^1$H NMR (DMSO-d$_6$, 300 MHz) δ10.73 (s, 1H), 7.46–6.88 (m, 18H), 4.78 (m, 1H), 4.38 (d, 1H, J=16.6), 4.17 (d, 1H, J=16.6), 3.80 (s, 3H), 3.58 (t, 1H, J=6.6), 3.22 (d, 2H, J=6.6), 0.96 (m,6H); low resolution MS (FAB)m/e 587 (MH$^+$), 586 (M$^+$), 422, 293.

Example 23

2-[3-(1H-indol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide To a stirring solution of 750 mg (1.64 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 25 mL DMF at 0° C. is added dropwise over 5 min 3.60 mL (1.80 mmol, 1.1 equiv) of a 0.5M solution of KN(TMS)$_2$ in toluene. The resulting solution is stirred 10 min, then a solution of 560 mg (1.80 mmol, 1.1 equiv) of N-BOC-3-bromomethylindolyl (Schöllkopf et. al., *Liebigs Ann, Chem.* 1985, 413) in 2 mL DMF is added. The resulting solution is stirred 16 h at RT and then quenched with 5 mL of H$_2$O. The reaction mixture is then poured into 200 mL of EtOAc and extracted with H$_2$O (2×200 mL). The organic layer is separated, dried (MgSO$_4$), and the solvents removed in vacuo. Purification of the material by silica gel flash column chromatography afforded 927 mg of 2-[3-(N-BOC-indol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide. To a stirring solution of 295 mg (0.43 mmol) of 2-[3-(N-BOC-indol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide, prepared as described above, in 10 mL of DMF at 0° C. is added 690 μL (0.69 mmol, 1.6 equiv) of a 1.0M solution of NaN(TMS)$_2$ in THF. The resulting solution is stirred 10 min, then 53 μL (0.86 mmol, 2.0 equiv) of methyl iodide is added. The reaction mixture is stirred 2 h at RT and then heated to 50° C. for 14 h, then quenched with 1 mL H$_2$O. The reaction mixture is diluted with 40 mL EtOAc and washed with 40 mL H$_2$O. The organic layer is dried (MgSO$_4$) and the solvents removed in vacuo. The crude material is then resubjected to the same conditions as stated above to ensure complete alkylation. The crude material is then dissolved in 10 mL of 4N HCl in dioxane and the reaction mixture is stirred 6 h at RT. The reaction mixture is diluted with 40 mL of EtOAc and extracted with NaHCO$_3$ (1×30 mL) and H$_2$O (1×30 mL). The organic layer is dried (MgSO$_4$) and the solvents removed in vacuo. The resulting crude oil is purified via reverse phase MPLC using a C-18 column and 65% acetonitrile/35% H$_2$O as eluent followed by lyophilization to afford 82 mg of 2-[3-(1H-indol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide as a white amorphous solid: $^1$H NMR (DMSO-d$_6$, 300 MHz) δ7.56–6.84 (m, 18H), 4.83 (m,1H), 4.27 (m, 2H), 3.80 (s, 3H), 2.78 (d, 1H, J=15.1), 2.64 (d, 1H, J=15.0), 1.26 (s, 3H), 0.98 (m, 6H); low resolution MS (FAB)m/e 601 (MH$^+$), 600 (M$^+$).

Example 24

2-[3-(N-methyl-indol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide To a stirring solution of 295 mg (0.43 mmol) of 2-[3-(N-BOC-indol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide, prepared as in Example 23, in 10 mL of DMF at 0° C. is added 690 μL (0.69 mmol, 1.6 equiv) of a 1.0M solution of NaN(TMS)$_2$ in THF. The resulting solution is stirred 10 min, then 53 μL (0.86 mmol, 2.0 equiv) of methyl iodide is added. The reaction mixture is stirred 2 h at RT and then heated to 50° C. for 14 h, then quenched with 1 mL H$_2$O. The reaction mixture is diluted with 40 mL EtOAc and washed with 40 mL H$_2$O. The organic layer is dried (MgSO$_4$) and the solvents removed in vacuo. The crude material is then resubjected to the same conditions as stated above to ensure complete alkylation. The crude material is then dissolved in 10 mL of 4N HCl in dioxane and the reaction mixture is stirred 6 h at RT. The reaction mixture is diluted with 40 mL of EtOAc and extracted with NaHCO$_3$ (1×30 mL) and H$_2$O (1×30 mL). The organic layer is dried (MgSO$_4$) and the solvents removed in vacuo. The resulting crude oil is purified via reverse phase MPLC using a C-18 column and 65% acetonitrile/35% H$_2$O as eluent followed by lyophilization to afford 51 mg of 2-[3-(N-methyl-indol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide as a white amorphous solid. $^1$H NMR (DMSO-d$_6$, 300 MHz) δ7.61–6.88 (m, 18H), 4.86 (m,1H), 4.28 (m, 2H), 3.80 (s, 3H), 3.74 (s, 3H), 2.71 (dd, 2H, J=14.9, 35.4), 1.25 (s, 3H), 1.00 (m, 6H); low resolution MS (FAB)m/e 615 (MH$^+$), 614 (M$^+$).

Example 25

N-Isopropyl-N-(4-methoxy-phenyl)-2-[3-(3-fluoro-phenylcarbamoylmethyl)-3-methyl-2,4-dioxo-5-phenyl-2,3,4,5-tetrahydro-benzo[b][1,4]diazepin-1-yl]acetamide To a stirring solution of 125 mg (0.24 mmol) of [1-(Isopropyl-(4-methoxy-phenyl)-carbamoylmethyl)-3-methyl-2,4-dioxo-5-phenyl-2,3,4,5-tetrahydro-1H-benzo[b][1,4]diazepin-3-yl]-acetic acid, prepared as in Intermediate 8, and 10 mL DMF in 3 mL of dichloromethane at −5° C. is added 62 μL (0.71 mmol, 3.0 equiv) of oxalyl chloride. The resulting solution is stirred 15 min at −5° C. then 2 h at RT, during which time gas evolution is observed. The solvent and excess oxalyl chloride are then removed in vacuo, and the resulting light brown foam is dissolved in 2 mL dichloromethane and cooled to 0° C. To this solution is added 68 μL (0.71 mmol, 3.0 equiv) of 3-fluoroaniline. The resulting solution is stirred 3 h at RT and then poured into 30 mL of EtOAc and washed with 1N HCl (3×30 mL). The organic layer is separated, dried (MgSO$_4$), and the solvent removed in vacuo. Purification of the resulting brown solid by silica gel flash column chromatography using hexane/EtOAc 3/2 as eluent followed by lyophilization afforded 130 mg of the title compound as an off-white amorphous solid: $^1$H NMR (CDCl$_3$, 300 MHz) δ9.12 (s, 0.5H), 8.45 (s, 0.5H), 7.51–6.74 (m, 17H), 5.06 (m, 1H), 4.73 (d, 0.5H, J=16.6), 4.40 (m, 0.5H), 4.09 (m, 0.5H), 3.86 (s, 1.5H), 3.85 (s, 1.5H), 3.21 (d, 0.5H, J=5.6), 2.64 (d, 0.5H, J=14.4), 2.32 (d, 0.5H, J=14.4), 1.66 (s, 1.5H), 1.56 (s, 1.5H), 1.15 (m, 6H); low resolution MS (FAB)m/e 623 (MH$^+$), 513, 512.

Example 26

N-Isopropyl-2-(3-methoxymethyl-2,4-dioxo-5-phenyl-3-phenylcarbamoylmethyl-2,3,4,5-tetrahydro-benzo[b][1,4]diazepin-1-yl)-N-(4-methoxy-phenyl)-acetamide To a solution of 650 mg (1.0 equiv,1.2 mmol) of 2-(3-allyl-2,4-dioxo-5-phenyl-3-methoxymethyl-2,3,4,5-tetrahydro-benzo[b][1,4]diazepin-1-yl)-N-isopropyl-N-(4-methoxy-phenyl)-acetamide, prepared as in Intermediate 31, in 30 mL of CCl$_4$ is added 15 mL of H$_2$O followed by 25 mg (0.1 equiv, 0.12 mmol) of RuCl$_3$ and 2.6 g (10 equiv, 12 mmol) of NaIO$_4$. The mixture is stirred rapidly for 2.5 h at RT. The resulting black mixture is filtered through celite and H$_2$O (20 mL) is added. The layers are separated and the aqueous layer is extracted with ethyl acetate (2×30 mL). The combined organic extracts are washed with saturated sodium bisulfite (1×10 mL) and brine (1×10 mL), dried over MgSO$_4$ and the solvent is removed in vacuo. The resulting solid is purified by silica gel MPLC using methylene chloride/methanol 9/1 as eluent to yield 200 mg of a carboxylic acid; low resolution MS m/e 560 180 mg (1.0 equiv, 0.322 mmol) of the above acid is dissolved in 3 mL of dry CH$_2$Cl$_2$ and cooled to −5° C. with a ice/salt/water bath. 0.006 mL of dry DMF is added, followed by 0.084 mL (3.0 equiv, 0.966 mmol) of oxalyl chloride dropwise over 2 min. The reaction mixture is stirred at −5° C. for 15 min, then allowed to warm to RT and stirred for 1 h. The solvent is removed in vacuo. The resulting brown oil is dissolved in 2.5 mL of dry CH$_2$Cl$_2$ and cooled to 0° C. with an ice/water bath. 0.088 mL (3.0 equiv, 0.966 mmols) of aniline is added dropwise, the ice water bath is removed and the reaction mixture is stirred at RT for 1 h. The resulting solution is poured into ethyl acetate/1N HCl 1/1 (20 mL) and extracted with ethyl acetate (2×30 mL). The organic extract is dried over MgSO$_4$ and the solvent is removed in vacuo. Purification by silica gel flash chromatography using hexane/ethyl acetate 2/1 as eluent followed by reverse phase C18 MPLC with acetonitrile/water 55/45 as eluent afforded 32 mg of the title compound as a white solid: $^1$H NMR (CDCl$_3$, 300 MHz) δ8.97–7.97 (2s, 1H), 7.53–6.96 (m, 17H), 6.82 (d, 1H, J=8.8), 5.02 (m, 1H), 4.38–4.15 (m, 2H), 3.85 (d, 3H), 3.51–2.46 (m, 7H), 1.07 (m, 6H); low resolution MS m/e 635.

Example 27

2-[3-(1-Benzyl-1H-indazol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide

To a stirring solution of 490 mg (1.08 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 12 mL DMF at 0° C. is added dropwise over 5 min 2.35 mL (1.18 mmol, 1.1 equiv) of a 0.5M solution of KN(TMS)$_2$ in toluene. The resulting solution is stirred 10 min, then a solution of 355 mg (1.18 mmol, 1.1 equiv) of 1-Benzyl-3-bromomethyl-1H-indazole in 3 mL DMF is added. The resulting solution is stirred 4.5 h at RT and then quenched with 5 mL of H$_2$O. The reaction mixture is then poured into 50 mL of EtOAc and extracted with H$_2$O (2×50 mL). The organic layer is separated, dried (MgSO$_4$), and the solvents removed in vacuo. Purification of the material by silica gel flash column chromatography using hexane/EtOAc 3/2 as eluent followed by lyophilization in acetonitrile/H$_2$O afforded 620 mg of the title compound as a white amorphous solid: $^1$H NMR (CDCl$_3$, 300 MHz) δ7.86 (d, 1H, J=8.1), 7.40 (d, 1H, J=7.9), 7.33–6.88 (m, 20H), 5.43 (s, 2H), 5.00 (m, 1H), 4.25 (m, 3H), 3.85 (m,4H), 3.58 (dd, 1H, J=5.1, 16.0), 1.06 (d, 6H, J=6.6); low resolution MS (FAB)m/e 678 (MH$^+$), 677 (M$^+$),

Example 28

N-{1-[Isopropyl-(4-methoxy-phenyl)-carbamoylmethyl]-2,4-dioxo-5 phenyl-2,3,4,5-tetrahydro-1H-benzo[b][1,4]diazepin-3-ylmethyl}-N-methyl benzamide

To a stirring solution of of 500 mg (1.09 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 5 mL DMF at 0° C. is added dropwise 2.40 mL (1.20 mmol, 1.1 equiv) of a 0.5M solution of KN(TMS)$_2$ in toluene. The resulting solution is stirred 10 min, then added to a stirring solution of 523 mg (2.18 mmol, 2.0 equiv) of N-Bromomethylphthalimide in 5 mL DMF. The resulting solution is stirred 3 h at RT and then quenched with 5 mL of H$_2$O. The reaction mixture is then poured into 50 mL of EtOAc and extracted with H$_2$O (2×50 mL). The organic layer is separated, dried (MgSO$_4$), and the solvents removed in vacuo. Purification of the material by silica gel flash column chromatography using hexane/EtOAc 1/1 as eluent afforded 373 mg of a tan solid. 184 mg (0.30 mmol) of this material is then dissolved in 5 mL of absolute ethanol/THF 4/1, and 150 mL (1.50 mmol, 5.0 equiv.) of methylamine (33% in ethanol) is added. The resulting material is then stirred 20 h at RT, poured into 50 mL of EtOAc and washed with 1N NaOH (1×50 mL). The organic extract is dried (MgSO$_4$) and the solvents removed in vacuo. Purification of the material by silica gel flash column chromatography using dichloromethane/methanol 9/1 as eluent afforded 86 mg of a white solid. This material is then dissolved in 3 mL of dichloromethane and cooled to 0° C. To this solution is added 40 mL (0.23 mmol, 1.3 equiv.) of N-diisopropyl ethyl amine and 25 mL (0.22 mmol, 1.2 equiv.) of benzoyl chloride. The resulting solution is stirred at RT for 30 min then poured into 30 mL of 1N HCl and extracted with EtOAc (2×30 mL). The organic extract is dried (MgSO$_4$) and the solvent removed in vacuo. Purification of the material by reverse phase chromatography using a C-18 column and a gradient of 60% acetonitrile/40% H$_2$O with 0.1% TFA to 80% acetonitrile/20% H$_2$O with 0.1% TFA as eluent afforded 15 mg of the title compound as a white solid: $^1$H NMR (DMSO-d$_6$, 300 MHz) δ7.44–6.83 (m, 18H), 4.80 (m, 1H), 4.26 (m, 2H), 3.80 (s, 3H), 2.93 (s, 3H), 2.80 (m, 1H), 0.81 (m, 6H); low resolution MS (FAB) m/e 605.

Example 29

{1-[Isopropyl-(4-methoxy-phenyl)-carbamoylmethyl]-2,4-dioxo-5-phenyl-3-phenylcarbamoylmethyl-2,3,4,5-tetrahydro-1H-benzo[b][1,4]diazepin-3-yl}acetic acid

130 mg (1.0 eq, 0.196 mmol) of {3-(Benzyloxycarbonyl-methyl)-1-[isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid, prepared as in Intermediate 28, in 3 mL of dry CH$_2$Cl$_2$ is cooled to −5° C. with an ice/salt/water bath. 0.005 mL of dry DMF is added, followed by 0.051 mL (3.0 equiv, 0.59 mmol) of oxalyl chloride dropwise over 2 min. The reaction mixture is stirred at −5° C. for 15 min., then allowed to warm to RT and stirred for 1 h. The solvent is removed in vacuo. The resulting oil is dissolved in 2.5 mL of dry CH$_2$Cl$_2$ and cooled to 0° C. with an ice/water/bath. 0.054 mL (3.0 equiv, 0.59 mmol) of aniline is added dropwise, the cooling bath is removed and the reaction mixture is stirred at RT for 18 h. The resulting solution is poured into ethyl acetate/1N HCl 1/1 (20 mL) and extracted with ethyl acetate (2×30 mL). The organic layer is dried over MgSO$_4$ and the solvent is removed in vacuo. Recrystallizaton from acetonitrile (10 mL) afforded 87 mg of a white solid. The solid is dissolved in ethanol/DMF 1/1 (50 mL), 10% Pd/C is added and the reaction is placed under a hydrogen atmosphere with stirring for 9 h. The resulting mixture is filtered through celite, the solvent removed in vacuo. Purification by reverse phase C18 MPLC with acetonitrile/water 65/35 as eluent afforded 40 mg of the title compound as an amorphous white solid: $^1$H NMR (CDCl$_3$, 300 MHz) δ10.05–9.59 (2s, 1H), 7.56– 6.63 (m, 18H), 4.73 (m, 1H), 4.25 (m, 2H), 3.80 (d, 3H, J=6.9), 3.3–2.2 (m, 4H), 0.94 (m, 6H); low resolution MS (FAB) m/e 649.

Example 30

2-[3-(1H-Indazol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide

To a stirring solution of 190 mg (0.28 mmol) of 2-[3-(1-Benzyl-1H-indazol-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide, prepared as in Intermediate 39, in 15 mL of a 10% solution of formic acid in absolute ethanol is added 200 mg of 10% palladium on carbon. The resulting black suspension is heated at reflux for 6 h, then cooled to RT. The reaction mixture is filtered through Celite to remove the catalyst and the solvent removed in vacuo. Purification of the residue by silica gel flash column chromatography using hexane/EtOAc 3/2 as eluent followed by further purification via silica gel MPLC using an Si60 column and hexane/EtOAc 2/1 as eluent and lyophilization afforded 30 mg of the title compound as a white amorphous solid: $^1$H NMR (DMSO-d$_6$, 300 MHz) δ7.48–6.98 (m, 17H), 6.70 (d, 1H, J=7.8), 4.86 (m, 1H), 4.27 (m, 2H), 3.81 (s, 3H), 2.87 (dd, 2H), 1.29 (s, 3H), 1.00 (m, 6H); low resolution MS (FAB)m/e 602 (MH$^+$), 437, 279, 223.

Example 31

2-[3-(1H-Indazol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide

To a stirring solution of 110 mg (0.17 mmol) of 2-[3-(1-Benzyl-1H-indazol-3-ylmethyl)-2,4-dioxo-5-phenyl-2,3,4, 5-tetrahydro-benzo[b][1,4]diazepin-1-yl]-N-isopropyl-N-(4-methoxy-phenyl) acetamide in 15 mL of a 10% solution of formic acid in absolute ethanol is added 100 mg of 10% palladium on carbon. The resulting black suspension is heated at reflux for 24 h, then cooled to RT. The reaction mixture is filtered through Celite to remove the catalyst and the solvent removed in vacuo. Purification of the residue by gradient silica gel flash column chromatography using hexane/EtOAc 3/2 up to 2/3 as eluent followed by further purification via reverse phase MPLC using a C-18 column and 60% acetonitrile/40% $H_2O$ as eluent and lyophilization afforded 62 mg of the title compound as a white amorphous solid: $^1$H NMR ($CDCl_3$, 300 MHz) δ7.81 (d, 1H, J=8.0), 7.41–6.90 (m, 17H), 5.00 (m, 1H), 4.23 (m, 3H), 3.84 (s, 3H), 3.79 (d, 1H, J=7.9), 3.61 (dd, 1H, J=5.8, 16.1), 1.06 (m, 6H); low resolution MS (FAB)m/e 588 ($MH^+$), 423, 223; Anal. ($C_{35}H_{33}N_5O_4 \cdot H_2O$) Calcd. C, 70.45; H, 5.91; N, 11.74 Found C, 70.62; H, 5.76; N, 11.78.

HCl salt: To a stirring solution of 50 mg of 2-[3-(1H-Indazol-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide prepared above in 5 mL of $Et_2O$/methanol 1/1 is added 0.2 mL of 4N HCl in dioxane. The reaction mixture is stirred 5 min, then the solvent removed in vacuo and the residue purified by reverse phase MPLC using a C-18 column and 60% acetonitrile/40% $H_2O$ with 0.1% HCl as eluent and lyophilization afforded 20 mg of the hydrochloride salt as a white amorphous solid: $^1$H NMR (DMSO-$d_6$, 300 MHz) δ7.75 (d, 1H, J=8.0), 7.47–7.03 (m, 17H), 6.90 (dd, 1H, J=12, 8.1), 4.75 (m, 1H), 4.45 (d, 1H, J=16.6), 3.79 (s, 3H), 3.43 (m, 2H), 0.93 (m, 6H); Anal. ($C_{35}H_{34}ClN_5O_4$) Calcd. C, 67.36; H, 5.49; N, 11.22 Found C, 67.53; H, 5.62; N, 11.46.

Example 32

2-(3-Benzofuran-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL DMF at 0° C. is added dropwise over 5 min 1.45 mL (0.72 mmol, 1.1 equiv) of a 0.5M solution of KN(TMS)$_2$ in toluene. The resulting solution is stirred 10 min, then a solution of 152 mg (0.72 mmol, 1.1 equiv) of 3-Bromomethylbenzofuran in 3 mL DMF is added. The resulting solution is stirred 2 h at RT and then quenched with 5 mL of $H_2O$. The reaction mixture is poured into 50 mL of $Et_2O$ and extracted with $H_2O$ (2×50 mL). The organic layer is separated, dried (MgSO$_4$), and the solvents removed in vacuo. Purification by silica gel MPLC on an Si60 column using hexane/EtOAc 5/2 as eluent followed by lyophilization in acetonitrile/$H_2O$ afforded 292 mg of the title compound as a white amorphous solid: $^1$H NMR (CDCl$_3$, 300 MHz) δ7.56 (m, 2H), 7.43–6.86 (m, 16H), 5.05 (m, 1H), 4.40 (d, 1H, J=16.6), 4.08 (d, 1H, J=16.6), 3.85 (s,3H), 3.68 (t, 1H, J=6.4), 3.47 (m, 2H), 1.11 (m, 6H); low resolution MS (FAB)m/e 588 ($MH^+$).

Example 33

2-(3-Benzofuran-3-ylmethyl)-3-methyl-2,4-dioxo-5-phenyl-2,3,4,5-tetrahydro-benzo[b][1,4]diazepin-1-yl]-N-isopropyl-N-(4-methoxy-phenyl) acetamide To a stirring solution of 190 mg (0.32 mmol) of 2-(3-Benzofuran-3-ylmethyl)-2,4-dioxo-5-phenyl-2,3,4,5-tetrahydro-benzo[b][1,4]diazepin-1-yl]-N-isopropyl-N-(4-methoxy-phenyl) acetamide, prepared as in Example 32, in 5 mL of DMF at 0° C. is added 0.58 mL (0.58 mmol, 1.8 equiv) of a 1.0M solution of NaN(TMS)$_2$ in THF. The resulting solution is stirred 5 min, and 36 μL (0.58 mmol, 1.8 equiv) of methyl iodide is added. The resulting solution is stirred 4 h at RT, warmed to 50° C. for 16 h, and then quenched with 5 mL of $H_2O$. The reaction mixture is then poured into 50 mL of $Et_2O$ and extracted with $H_2O$ (2×50 mL). The organic layer is separated, dried (MgSO$_4$), and the solvents removed in vacuo. Purification of the material by silica gel MPLC on an Si60 column using hexane/EtOAc 3/1 as eluent followed by lyophilization in acetonitrile/$H_2O$ afforded 177 mg of the title compound as a white amorphous solid: $^1$H NMR (DMSO-$d_6$, 300 MHz) δ7.77 (s, br, 0.66H), 7.67–7.05 (m, 17.34H), 6.86 (dd, 0.66H, J=1.2, 8.0), 6.76 (dd, 0.34H, J=1.1, 8.0), 4.83 (m, 1H), 4.29 (s, br, 2H), 3.80 (s, 3H), 2.72 (dd, 2H, J=15.2, 33.7), 1.30 (s, 2H), 0.99 (m, 6H), )0.87 (s, 1H); low resolution MS (FAB)m/e 602 ($MH^+$), 601 ($M^+$), 437.

Example 34

N-Isopropyl-N-(4-methoxy-phenyl)-2-(3-naphthalen-1-ylmethyl-2,4-dioxo-5-phenyl-2,3,4,5-tetrahydro-benzo[b][1,4]diazepin-1-yl) acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL DMF at 0° C. is added dropwise over 5 min 1.45 mL (0.72 mmol, 1.1 equiv) of a 0.5M solution of KN(TMS)$_2$ in toluene. The resulting solution is stirred 10 min, then a solution of 160 mg (0.72 mmol, 1.1 equiv) of 1-bromomethylnaphthalene in 3 mL DMF is added. The resulting solution is stirred 2 h at RT and then quenched with 5 mL of $H_2O$. The reaction mixture is then poured into 50 mL of $Et_2O$ and extracted with $H_2O$ (2×50 mL). The organic layer is separated, dried (MgSO$_4$), and the solvents removed in vacuo. Purification of the material by silica gel MPLC on an Si60 column using hexane/EtOAc 2/1 as eluent followed by lyophilization in acetonitrile/$H_2O$ afforded 385 mg of the title compound as a white amorphous solid: $^1$H NMR (CDCl$_3$, 300 MHz) δ8.01 (d, 1H, J=8.0), 7.80 (d, 1H, J=7.4), 7.69 (d, 1H, J=8.0), 7.50–6.94 (m, 16H), 6.84 (dd, 1H, J=1.5, 8.3), 5.04 (m, 1H), 4.36 (d, 1H, J=16.4), 4.17 (d, 1H, J=16.4), 3.92 (m, 2H), 3.85 (s, 3H), 3.82 (m, 1H), 1.09 (t, 6H, J=7.1); low resolution MS (FAB)m/e 598 ($MH^+$), 597 ($M^+$), 433.

Example 35

N-Isopropyl-N-(4-methoxy-phenyl)-2-(3-methyl-3-naphthalen-1-ylmethyl-2,4-dioxo-5-phenyl-2,3,4,5-tetrahydro-benzo[b][1,4]diazepin-1-yl) acetamide To a stirring solution of 150 mg (0.25 mmol) of N-Isopropyl-N-(4-methoxy-phenyl)-2-(3-naphthalen-1-ylmethyl-2,4-dioxo-5-phenyl-2,3,4,5-tetrahydro-benzo[b][1,4]diazepin-1-yl) acetamide, prepared as in Example 34, in 5 mL of DMF at 0° C. is added 0.45 mL (0.45 mmol, 1.8 equiv) of a 1.0M solution of NaN(TMS)$_2$ in THF. The resulting solution is stirred 5 min, and 28 μL (0.45 mmol, 1.8 equiv) of methyl iodide is added. The resulting solution is stirred 3 h at RT, warmed to 50° C. for 16 h, and then quenched with 5 mL of $H_2O$. The reaction mixture is then poured into 50 mL of $Et_2O$ and extracted with $H_2O$ (2×50 mL). The organic layer is separated, dried (MgSO$_4$), and the solvents removed in vacuo. Purification of the material by silica gel MPLC on an Si60 column using hexane/EtOAc 3/1 as eluent followed by lyophilization in acetonitrile/H$_2$O afforded 120 mg of the title compound as a white amorphous solid: $^1$H NMR (DMSO-d$_6$, 300 MHz) δ7.93–7.86 (m, 2H), 7.77 (d, 1H, J=8.0), 7.60–7.06 (m, 16H), 6.89 (dd, 1H, J=0.8, 8.1), 4.88 (m, 1H), 4.34 (s, br, 2H), 3.81 (s, 3H), 3.20 (d, 1H, J=14.7), 3.00 (d, 1H, J=14.7), 1.01 (m, 9H); low resolution MS (FAB)m/e 612 (MH$^+$), 611 (M$^+$), 447.

Example 36

N-Isopropyl-N-(4-methoxy-phenyl)-2-(3-naphthalen-2-ylmethyl-2,4-dioxo-5-phenyl-2,3,4,5-tetrahydro-benzo[b][1,4]diazepin-1-yl) acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL DMF at 0° C. is added dropwise over 5 min 1.45 mL (0.72 mmol, 1.1 equiv) of a 0.5M solution of KN(TMS)$_2$ in toluene. The resulting solution is stirred 10 min, and then a solution of 160 mg (0.72 mmol, 1.1 equiv) of 2-bromomethylnaphthalene in 3 mL DMF is added. The resulting solution is stirred 2 h at RT and then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification of the material by silica gel MPLC on an Si60 column using hexane/EtOAc 2/1 as eluent followed by lyophilization in acetonitrile/H$_2$O afforded 310 mg of the title compound as a white amorphous solid: $^1$H NMR (CDCl$_3$, 300 MHz) δ7.80–7.70 (m, 3H), 7.45–6.93 (m, 16H), 6.84 (dd, 1H, J=1.2, 8.3), 5.04 (m, 1H), 4.35 (d, 1H, J=16.3), 4.13 (d, 1H, J=16.3), 3.85 (s, 3H), 3.68 (m, 2H), 3.48 (dd, 1H, J=4.6, 13.7), 1.09 (d, 6H, J=6.8); low resolution MS (FAB)m/e 598 (MH$^+$), 597 (M$^+$), 433.

Example 37

2-(3-Benzo[b]thiophen-3-ylmethyl-2,4-dioxo-5-phenyl-2,3,4,5-tetrahydro-benzo[b][1,4]diazepin-1-yl)-N-isopropyl-N-(4-methoxy-phenyl) acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 15 mL DMF at 0° C. is added dropwise over 5 min 1.45 mL (0.72 mmol, 1.1 equiv) of a 0.5M solution of KN(TMS)$_2$ in toluene. The resulting solution is stirred 10 min, and then a solution of 132 mg (0.72 mmol, 1.1 equiv) of 3-chloromethylbenzo[b]thiophene (Wolf, G.; Zymalkowski, F. *Arch. Pharm.* 1976, 279) in 1 mL DMF is added. The resulting solution is stirred 2 h at RT and then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification of the material by silica gel MPLC on an Si60 column using hexane/EtOAc 5/2 as eluent followed by lyophilization in acetonitrile/H$_2$O afforded 222 mg of the title compound as a white amorphous solid: $^1$H NMR (CDCl$_3$, 300 MHz) δ7.79 (m, 2H), 7.44–6.93 (m, 15H), 6.88 (dd, 1H, J=1.5, 8.1), 5.03 (m, 1H), 4.42 (d, 1H, J=16.6), 4.09 (d, 1H, J=16.6), 3.85 (s, 3H), 3.80 (t, 1H, J=6.6), 3.61 (m, 2H), 1.10 (t, 6H, J=6.8); low resolution MS (FAB)m/e 604 (MH$^+$), 439.

Example 38

N-Isopropyl-N-(4-methoxy-phenyl)-2-(3-methyl-3-naphthalen-2-ylmethyl-2,4-dioxo-5-phenyl-2,3,4,5-tetrahydro-benzo[b][1,4]diazepin-1-yl) acetamide To a stirring solution of 200 mg (0.34 mmol) of N-Isopropyl-N-(4-methoxy-phenyl)-2-(3-naphthalen-2-ylmethyl-2,4-dioxo-5-phenyl-2,3,4,5-tetrahydro-benzo[b][1,4]diazepin-1-yl) acetamide, prepared as in Example 36, in 5 mL of DMF at 0° C. is added 0.60 mL (0.60 mmol, 1.8 equiv) of a 1.0M solution of NaN(TMS)$_2$ in THF. The resulting solution is stirred 5 min, and 37 μL (0.60 mmol, 1.8 equiv) of methyl iodide is added. The resulting solution is stirred 3 h at RT, warmed to 50° C. for 16 h, and then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification of the material by silica gel MPLC on an Si60 column using hexane/EtOAc 5/2 as eluent followed by lyophilization in acetonitrile/H$_2$O afforded 180 mg of the title compound as a white amorphous solid: $^1$H NMR (DMSO-d$_6$, 300 MHz) δ7.88–7.79 (m, 3H), 7.64–7.19 (m, 14H), 7.05 (m, 2H), 6.92 (dd, 1H, J=1.0, 8.1), 4.87 (m, 1H), 4.30 (s, br, 2H), 3.80 (s, 3H), 2.76 (dd, 2H, J=13.9, 23.9), 1.22 (s, 3H), 1.00 (m, 6H); low resolution MS (FAB)m/e 612 (MH$^+$), 611 (M$^+$), 447.

Example 39

2-(2,4-dioxo-5-phenyl-3-phenylcarbamoylmethyl-2,3,4,5-tetrahydro-benzo[b][1,4]diazepin-1-yl)-N-isopropyl-N-(4-methoxy-phenyl)-acetamide (5)

14 mg (1.0 equiv, 0.24 mmol) of {1-[Isopropyl-(4-methoxy-phenyl)-carbamoylmethyl]-2,4-dioxo-5-phenyl-2,3,4,5-tetrahydro-1H-benzo[b][1,4]diazepin-3-yl}acetic acid, prepared as in Intermediate 26, is dissolved in 3 mL of dry CH$_2$Cl$_2$ and cooled to –5° C. with an ice/salt/water bath. 0.005 mL of dry DMF is added, followed by 0.063 mL (3.0 equiv, 0.72 mmol) of oxalyl chloride dropwise over 2 min. The reaction mixture is stirred at –5° C. for 15 min, allowed to warm to RT and stirred for 1 h. The solvent is removed in vacuo. The resulting oil is dissolved in 2.5 mL of dry CH$_2$Cl$_2$ and cooled to 0° C. with an ice/water/bath. 0.066 mL (3.0 equiv, 0.72 mmol) of aniline is added dropwise, the ice/water bath is removed and the reaction mixture is stirred at RT for 18 h. The resulting solution is poured into ethyl acetate/1N HCl1/1 (20 mL) and extracted with ethyl acetate (2×30 mL). The organic layer is dried over MgSO$_4$ and the solvent is removed in vacuo. Purification by silica gel MPLC using methylene chloride/methanol 95/5 as eluent followed by reverse phase C18 MPLC with acetonitrile/water 55/45 as eluent afforded 40 mg of the title compound as a white amorphous solid: $^1$H NMR (CDCl$_3$, 300 MHz) δ10.09 (s, 1H), 7.52–6.89 (m, 18H), 4.74 (m, 1H), 4.52–4.09 (m, 2H), 3.84 (t, 1H), 2.94 (d, 2H, J=6.6), 0.92 (m, 6H); low resolution MS (FAB) m/e 591.

Example 40

2-(3-Benzo[b]thiophen-3-ylmethyl-3-methyl-2,4-dioxo-5-phenyl-2,3,4,5-tetrahydro-benzo[b][1,4]diazepin-1-yl)-N-isopropyl-N-(4-methoxy-phenyl) acetamide To a stirring solution of 130 mg (0.22 mmol) of 2-(3-Benzo[b]thiophen-3-ylmethyl-2,4-dioxo-5-phenyl-2,3,4,5-tetrahydro-benzo[b][1,4]diazepin-1-yl)-N-isopropyl-N-(4-methoxy-phenyl) acetamide, prepared as in Example 37, in 5 mL of DMF at 0° C. is added 0.43 mL (0.43 mmol, 2.0 equiv) of a 1.0M solution of NaN(TMS)$_2$ in THF. The resulting solution is stirred 5 min, and 27 μL (0.43 mmol, 2.0 equiv) of methyl iodide is added. The resulting solution is stirred 4 h at RT, warmed to 50° C. for 16 h, and then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification of the material by silica gel MPLC on an Si60 column using hexane/EtOAc 3/1 as eluent followed by lyophilization in acetonitrile/H$_2$O afforded 106 mg of the title compound as a white amorphous solid: $^1$H NMR (DMSO-d$_6$, 300 MHz) δ7.92 (m, 1H), 7.66–7.05 (m, 16H), 6.81 (d, 1H, J=8.1), 4.85 (m, 1H), 4.31 (s, br, 2H), 3.80 (s, 3H), 2.97 (d, 1H, J=15.2), 2.77 (d, 1H, J=15.2), 1.20 (s, 3H), 1.00 (m, 6H); low resolution MS (FAB)m/e 618 (MH$^+$), 617 (M$^+$), 453; Anal. (C$_{37}$H$_{35}$N$_3$O$_4$S) Calcd. C, 71.71; H, 5.74; N, 6.76; S, 5.26 Found C, 71.94; H, 5.71; N, 6.80; S, 5.19.

Example 41

2-[2,4-Dioxo-5-(4-chlorophenyl)-3-methyl-3-phenylcarbamoylmethyl-2,3,4,5-tetrahydro-benzo[b][1,4]diazepin-1-yl]-N-isopropyl-N-phenyl acetamide 0.59 mL (6.7 mmol) of oxalyl chloride in 25 mL of CH$_2$Cl$_2$ is added dropwise to a solution of 1.8 g (3.4 mmol) of [1-(Isopropyl-(4-methoxy-phenyl)-carbamoylmethyl)-3-methyl-2,4-dioxo-5-(4-chloro-phenyl)-2,3,4,5-tetrahydro-1H-benzo[b][1,4]diazepin-3-yl]-acetic acid, prepared as in Intermediate 3, and 0.013 mL of DMF in 50 ml of CH$_2$Cl$_2$ cooled to 0° C. The solution is stirred at RT for 2.5 h and subsequently concentrated in vacuo to a dark grey foam. The crude acid chloride is dissolved in 60 mL of CH$_2$Cl$_2$, cooled to 0° C. and a solution of 0.92 mL (10.1 mmol) of aniline in 15 mL of CH$_2$Cl$_2$ is added dropwise. The mixture is stirred at RT for 2 h. After diluting with 200 mL of 1N HCl, the mixture is extracted with EtOAc (x2). The organic extract is washed with 1N HCl and brine, dried over MgSO$_4$ and concentrated in vacuo to a grey foam. Purification by silica gel flash chromatography (50% EtOAc/petroleum ether) followed by recrystallization from EtOAc/petroleum ether gave 1.14 g of the title compound as a white powder: m.p. 170°–6° C.; $^1$H NMR (CDCl$_3$ 300 MHz) δ7.88 (s, 1H), 7.6–6.8 (m, 17H), 5.01 (m, 1H), 4.65 (d, 1H, J=17), 3.84 (s, 3H), 3.82 (d, 1H, J=17), 2.45 (q, 2H, J=15), 1.67 (s, 3H), 1.11 (m, 6H); low resolution MS (FAB) m/e 639 (MH$^+$).

Example 42

2-[3-(1-Benzyl-1H-Indazol-3-ylmethyl)-3-methoxy-2,4-dioxo-5-phenyl-2,3,4,5-tetrahydro-benzo[b][1,4]diazepin-1-yl]-N-isopropyl-N-(4-methoxy-phenyl) acetamide To a stirring solution of 320 mg (0.90 mmol) of 2-(1-Benzyl-1H-indazol-3-ylmethyl)-2-methoxy-propanedioc acid and 7 mL of DMF in 8 mL of dichloromethane at 0° C. is added dropwise 315 μL (3.61 mmol, 4.0 equiv) of oxalyl chloride. The resulting solution is stirred 2 h at RT, then the solvent and excess oxalyl chloride are removed in vacuo to yield the crude diacid chloride as an orange-red oil. This material is immediately dissolved in 8 mL of THF and cooled to 0° C., and a solution of 296 mg (0.76 mmol) of N-isopropyl-N-(4-methoxy-phenyl)-2-(2-phenylamino-phenylamino) acetamide, prepared as in Intermediate 43 in 2 mL of THF is added dropwise over 2 min. The resulting solution is stirred 10 min at RT and then heated at reflux for 4 h. The solution is cooled to RT and the solvent removed in vacuo. Purification of the residue by silica gel flash column chromatography using hexane/EtOAc 2/1 as eluent followed by further purification by silica gel MPLC using an Si60 column and hexane/EtOAc 3/1 as eluent followed by lyophilization in acetonitrile/H$_2$O afforded 220 mg of the title compound as a white amorphous solid: $^1$H NMR (DMSO-d$_6$, 300 MHz) δ7.91 (d, 1H, J=8.1), 7.58 (d, 1H, J=8.3), 7.44–7.00 (m, 19H), 6.65 (dd, 1H, J=1.0, 8.3), 5.54 (s, 2H), 4.82 (m, 1H), 4.26 (s, br, 2H), 3.95 (d, 1H, J=15.4), 3.82 (d, 1H, J=15.4), 3.80 (s, 3H), 2.90 (s, 3H), 0.99 (m, 6H); low resolution MS (FAB)m/e 708 (MH$^+$).

Example 43

2-[3-(1H-Indazol-3-ylmethyl)-3-methoxy-2,4-dioxo-5-phenyl-2,3,4,5-tetrahydro-benzo[b][1,4]diazepin-1-yl]-N-isopropyl-N-(4-methoxy-phenyl) acetamide To a stirring solution of 80 mg (0.11 mmol) of 2-[3-(1-benzyl-1H-Indazol-3-ylmethyl)-3-methoxy-2,4-dioxo-5-phenyl-2,3,4,5-tetrahydro-benzo[b][1,4]diazepin-1-yl]-N-isopropyl-N-(4-methoxy-phenyl) acetamide in 10 mL of a 10% solution of formic acid in absolute ethanol is added 70 mg of 10% palladium on carbon. The resulting black suspension is heated at reflux for 6 h, and then cooled to RT. The reaction mixture is filtered through Celite to remove the catalyst and the solvent removed in vacuo. Purification of the residue via silica gel MPLC using an Si60 column and hexane/EtOAc 1/1 as eluent followed by lyophilization afforded 41 mg of the title compound as a white amorphous solid: $^1$H NMR (DMSO-d$_6$, 300 MHz) δ7.83 (d, 1H, J=8.3), 7.38– 6.94 (m, 16H), 6.59 (d, 1H, J=7.1), 4.76 (m, 1H), 4.19 (s, br, 2H), 3.85 (d, 1H), J=15.7), 3.73 (m, 4H), 2.88 (s, 3H), 0.93 (m, 6H); low resolution MS (FAB)m/e 618 (MH$^+$).

Example 44

N-Isopropyl-N-(4-methoxy-phenyl)-2-[3-(1-methyl-1H-indazol-3-ylmethyl)-2,4-dioxo-5-phenyl-2,3,4,5-tetrahydro-benzo[b][1,4]diazepin-1-yl]acetamide To a stirring solution of 330 mg (0.73 mmol) of 2-(2,4-dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL DMF at 0° C. is added dropwise over 5 min 1.75 mL (0.87 mmol, 1.1 equiv) of a 0.5M solution of KN(TMS)$_2$ in toluene. The resulting solution is stirred 10 min, then a solution of 180 mg (1.18 mmol, 1.1 equiv) of 1-methyl-3-bromomethyl-1H-indazole in 3 mL DMF is added. The resulting solution is stirred 3 h at RT and then quenched with 5 mL of H$_2$O. The reaction mixture is poured into 50 mL of EtOAc and extracted with H$_2$O (2×50 mL). The organic layer is separated, dried (MgSO$_4$), and the solvents removed in vacuo. Purification by silica gel flash column chromatography using hexane/EtOAc 2/1 as eluent followed by further purification via silica gel MPLC using a Si60 column and hexane/EtOAc 1/1 as eluent followed by lyophilization in acetonitrile/H$_2$O afforded 100 mg of the title compound as a white amorphous solid: $^1$H NMR (CDCl$_3$, 300 MHz) δ7.74 (d, 1H, J=8.3), 7.25–6.76 (m, 16H), 4.85 (m, 1H), 4.11 (s, br, 2H), 3.97 (dd, 1H, J=5.6, 7.8), 3.77 (s, 3H), 3.70 (s, 3H), 3.63 (dd, 1H, J=7.8, 15.9), 3.48 (dd, 1H, J=5.6, 15.9), 0.92 (d, 6H, J=6.8); low resolution MS (FAB)m/e 602 (MH$^+$), 437. Anal. (C$_{36}$H$_{35}$N$_5$O$_4$) Calcd. C, 71.86; H, 5.86; N, 11.64; Found C, 71.69; H, 5.91; N, 11.56.

Example 45

N-Isopropyl-N-(4-methoxy-phenyl)-2-[3-(1-methyl-1H-indazol-3-ylmethyl)-3-methyl-2,4-dioxo-5-phenyl-2,3,4,5-tetrahydro-benzo[b][1,4]diazepin-1-yl]acetamide To a stirring solution of 165 mg (0.27 mmol) of N-Isopropyl-N-(4-methoxy-phenyl)-2-[3-(1-methyl-1H- indazol-3-ylmethyl)-2,4-dioxo-5-phenyl-2,3,4,5-tetrahydro-benzo[b][1,4]diazepin-1-yl]acetamide, prepared as in Example 49, in 5 mL of DMF at 0° C. is added 0.82 mL (0.82 mmol, 3.0 equiv) of a 1.0M solution of NaN(TMS)$_2$ in THF. The resulting solution is stirred 5 min, and 51 μL (0.82 mmol, 3.0 equiv) of methyl iodide is added. The resulting solution is stirred for 4 h at RT, warmed to 50° C. for 16 h, and then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification by silica gel MPLC on an Si60 column using hexane/EtOAc 4/3 as eluent followed by lyophilization in acetonitrile/H$_2$O afforded 124 mg of the title compound as a white amorphous solid: $^1$H NMR (DMSO-d$_6$, 300 MHz) δ7.48–6.95 (m, 16H), 6.71 (d, 1H, J=7.3), 4.78 (m, 1H), 4.21 (s, br, 2H), 3.95 (s, 3H), 3.74 (s, 3H), 2.79 (d, 2H, J=5.9), 1.20 (s, 3H), 0.93 (m, 6H); low resolution MS (FAB)m/e 616 (MH$^+$).

Example 46

2-(2,4-Dioxo-5-phenyl-3-(1-phenyl-imidazo-2-yl) methyl-2,3,4,5-tetrahydro-benzo[b][1,4]diazepin-1-yl)-N-isopropyl-N-(4-methoxy)-phenyl acetamide 0.5 mL of 0.5N KN(TMS)$_2$ in toluene is added to a solution of 114 mg (0.25 mmol) of 2-(2,4-dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 3 mL of dry DMF cooled to 0° C. The mixture is stirred at 0° C. for 30 min and 48 mg (0.25 mmol) of 2-chloromethyl-1-phenylimidazole is added in 2 ml of dry DMF. The reaction is stirred at RT for 3 hrs. The mixture is poured onto ice/water and extracted with ethyl acetate (3×30 mL). The organic layer is dried with MgSO$_4$ and solvent evaporated in vacuo. Purification by silica gel column chromatography using 1.5% MeOH/CHCl$_3$ as eluent followed by lyophilization gave 70 mg of of the title compound: $^1$H NMR (250 MHz, CDCl$_3$) δ6.75–7.34 (m, 20H), 4.84 (q, 1H, J=6.9), 4.28 (dd, 1H, J=5, 9), 4.07(br, 2H), 3.69 (s, 3H), 3.34 (dd, 1H, J=9, 16), 2.96 (dd, 1H, J=5, 16), 0.90 (d, 3H, J=7), 0.88 (d, 3H, J=7); low resolution MS m/e 614 (MH$^+$).

Example 47

2-(3-Benzo[d]isoxazol-3-ylmethyl-2,4-dioxo-5-phenyl-2,3,4,5-tetrahydro-benzo[b][1,4]diazepin-1-yl)-N-isopropyl-N-(4-methoxy-phenyl) acetamide To a stirring solution of 390 mg (0.86 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL of DMF at 0° C. is added 1.03 mL (1.03 mmol, 1.2 equiv) of a 1.0M solution of NaN(TMS)$_2$ in THF. The resulting solution is stirred 5 min, and a solution of 200 mg (0.94 mmol, 1.1 equiv.) of 3-bromomethyl benzo[d]isoxazole (Uno, H.; Kurokawa, M.; Natsuka, K.; Yamato, Y.; Nishimura, H. *Chem. Pharm. Bull.* 1976, 24, 632)in 1 mL of DMF is added. The resulting solution is stirred for 14 h at RT then quenched with 5 mL of H$_2$O. The reaction mixture is poured into 50 mL of Et$_2$O and extracted with H$_2$O (2×50 mL). The organic layer is separated, dried (MgSO$_4$), and the solvents removed in vacuo. Purification by silica gel flash column chromatography using hexane/EtOAc 2/1 as eluent followed by lyophilization in acetonitrile/H$_2$O afforded 303 mg of the title compound as a white amorphous solid: $^1$H NMR (CDCl$_3$, 300 MHz) δ7.81 (d, 1H, J=7.8), 7.55–7.10 (m, 14H), 6.97 (m, 2H), 5.01 (m, 1H), 4.28 (m, 3H), 3.85 (m, 4H), 3.58 (dd, 1H, J=5.1, 16.6), 1.07 (d, 6H, J=6.6); low resolution MS (FAB)m/e 589 (MH$^+$), 588 (M$^+$), 424, 396; Anal. (C$_{35}$H$_{32}$N$_4$O$_5$) Calcd. C, 71.41; H, 5.48; N, 9.52 Found C, 71.48; H, 5.49; N, 9.47.

Example 48

N-Isopropyl-2-(3-isoxazolo[5,4-b]pyridin-3-ylmethyl-2,4-dioxo-5-phenyl-2,3,4,5-tetrahydro-benzo[b][1,4]diazepin-1-yl)-N-(4-methoxy-phenyl) acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 8 mL of DMF at 0° C. is added 0.78 mL (0.78 mmol, 1.2 equiv) of a 1.0M solution of NaN(TMS)$_2$ in THF. The resulting solution is stirred 5 min, and a solution of 154 mg (0.972 mmol, 1.1 equiv.) of 3-bromomethyl isoxazolo[5,4-b]pyridine (Abignente, A.; De Capraris, P.; Stein, M. L. *Farmaco Ed. Sci.* 1975, 30, 992) in 2 mL of DMF is added. The resulting solution is stirred for 2.5 h at RT then quenched with 5 mL of H$_2$O. The reaction mixture is poured into 50 mL of EtOAc and extracted with H$_2$O (2×50 mL). The organic layer is separated, dried (MgSO$_4$), and the solvents removed in vacuo. Purification by silica gel MPLC using an Si60 column and hexane/EtOAc 1/1 as eluent afforded 280 mg of the title compound as a white amorphous solid: $^1$H NMR (CDCl$_3$, 400 MHz) δ8.57 (dd, 1H, J=1.5, 4.6), 8.23 (dd, 1H, J=1.5, 7.8), 7.39–7.10 (m, 12H), 6.94 (m, 2H), 4.99 (m, 1H), 4.23 (m, 3H), 3.84 (s, 3H), 3.79 (d 1H, J=8.4), 3.57 (dd, 1H, J=5.3, 16.4), 1.06 (d, 6H, J=6.8); low resolution MS (FAB) m/e 590 (MH$^+$), 589 (M$^+$), 425; Anal. (C$_{34}$H$_{31}$N$_5$O$_5$) Calcd. C, 69.26; H, 5.30; N, 11.88 Found C, 69.13; H, 5.32; N, 11.84.

Example 49

2-[3-(1H-Indazol-3-ylmethyl)-2,4-dioxo-5-pyrid-2-yl-2,3,4,5-tetrahydro-benzo[b][1,4]diazepin-1-yl]-N-isopropyl-N-(4-methoxy-phenyl) acetamide A solution of 0.35 g (0.77 mmol, 1.0 equiv) of 2-(2,4-dioxo-5-pyrid-2-yl-2,3,4,5-tetrahydro-benzo[b][1,4] diazepin-1-yl)-N-isopropyl-N-(4-methoxy-phenyl) acetamide, prepared as in Intermediate 36, in 7 mL of DMF is cooled in an ice/water bath. 0.85 mL (0.84 mmol, 1.1 equiv) of 1M NaN(TMS)$_2$ in THF is added and the solution stirred at 0° C. for 10 min. A solution of 0.26 g (0.84 mmol, 1.1 equiv) of N-tert-butoxycarbonyl-3-bromomethyl-indazole in 3 mL of DMF is added and the resulting yellow solution stirred at RT for 1 h. The reaction is quenched with H$_2$O, extracted with EtOAc (×3), washed with H$_2$O (×2) and brine, dried over MgSO$_4$ and concentrated to a brown oil. Purification by silica gel flash chromatography using EtOAc/hexane 1/1 as eluent followed by Si60 MPLC using EtOAc/hexane 1/1 as eluent gave 0.23 g of a white powder; low resolution MS (FAB) 689 (MH$^+$). A portion of this compound is dissolved in 4N HCl in dioxane and stirred at 0° C. for 30 min, and then concentrated to a white foam. Purification by RP-18 MPLC using MeCN/H$_2$O 3/2 containing 0.1% HCl as eluent gave 33 mg of the title compound HCl salt as an amorphous white powder: $^1$H NMR (d$_6$-DMSO, 400 MHz) δ8.47 (d, 1H, J=3.5), 8.0–7.0 (m, 15H), 4.79 (m,1H), 4.20 (m, 2H), 3.79 (s, 3H), 3.51 (dd, 1H, J=7, 15), 3.39 (dd, 1H, J=5, 15), 0.97 (dd, 6H, J=7, 14); low resolution MS (FAB)m/e 589 (MH$^+$).

Example 50

2-[2,4-Dioxo-5-phenyl-3-(1H-pyrazolo[3,4-b] pyridin-3-ylmethyl)-2,3,4,5-tetrahydro-benzo[b][1,4] diazepin-1-yl]-N-isopropyl-N-(4-methoxy-phenyl)-acetamide To a stirring solution of 226 mg (0.50 mmol) of 2-(2,4-Dioxo-5-phenyl-2,3,4,5-tetrahydro-benzo[b][1,4]diazepin- 1-yl)-N-isopropyl-N-(4-methoxy-phenyl) acetamide, prepared as in Intermediate 4, in 5 mL of DMF at 0° C. is added 0.60 mL (0.60 mmol, 1.2 equiv) of a 1.0M solution of NaN(TMS)$_2$ in THF. The resulting solution is stirred 5 min, and a solution of 170 mg (0.55 mmol, 1.1 equiv.) of 3-Bromomethyl (1-tert-butoxycarbonyl) pyrazolo[3,4-b] pyridine in 2 mL of DMF is added. The resulting solution is stirred for 1 h at RT then quenched with 5 mL of H$_2$O. The reaction mixture is poured into 50 mL of EtOAc and extracted with H$_2$O (2×50 mL). The organic layer is separated, dried (MgSO$_4$), and the solvents removed in vacuo. Purification by silica gel flash column chromatography using hexane/EtOAc 1/2 as eluent afforded 254 mg of a white amorphous solid. This material is dissolved in 10 mL of 4N HCl in 1,4-dioxane and stirred at RT for 22 h. The reaction mixture is poured into 50 mL of EtOAc and washed successively with 1N NaOH (1×50 mL) and H$_2$O (1×50 mL). The organic layer is separated, dried (MgSO$_4$), and the solvents removed in vacuo. Purification by silica gel MPLC using hexane/EtOAc 1/3 as eluent afforded 89 mg of the title compound as a white solid: mp 156°–158° C.; $^1$H NMR (CDCl$_3$, 400 MHz) δ10.51 (s, br, 1H), 8.48 (dd, 1H, J=1.2, 4.6), 8.25 (d, 1H, J=7.0), 7.40–6.91 (m, 14H), 4.98 (m, 1H), 4.26 (m, 2H), 4.18 (dd, 1H, J=5.8, 7.8), 3.83 (s, 3H), 3.79 (dd 1H, J=7.8, 15.9), 3.60 (dd, 1H, J=5.7, 15.9), 1.05 (d, 6H, J=6.7); low resolution MS (FAB)m/e 589 (MH$^+$), 424; Anal. (C$_{34}$H$_{32}$N$_6$O$_4$) Calcd. C, 69.37; H, 5.48; N, 14.28 Found C, 68.69; H, 5.52; N, 14.07.

Example 51

2-[2,4-Dioxo-5-phenyl-3-(4,5,6,7-tetrahydro-1H-indazol-3-ylmethyl)-2,3,4,5-tetrahydro-benzo[b][1,4]diazepin-1-yl]-N-isopropyl-N-(4-methoxy-phenyl)-acetamide To a stirring solution of 150 mg (0.22 mmol) of 2-[2,4-Dioxo-5-phenyl-3-(4,5,6,7-tetrahydro-1-benzyl-1H-indazol-3-ylmethyl)-2,3,4,5-tetrahydro-benzo[b][1,4]diazepin-1-yl]-N-isopropyl-N-(4-methoxy-phenyl)-acetamide, prepared as in Intermediate 52, in 10 mL of a 10% solution of formic acid in absolute ethanol is added 150 mg of 10% palladium on carbon. The resulting black suspension is refluxed for 3 h, then cooled to RT. The reaction mixture is filtered through Celite to remove the catalyst and the solvent removed in vacuo. Purification of the residue via silica gel MPLC using an Si60 column and hexane/EtOAc 1/5 as eluent afforded 105 mg of the title compound as a white solid: mp 170°–173° C.; $^1$H NMR (CDCl$_3$, 400 MHz) δ7.38–6.88 (m, 13H), 5.03 (m, 1H), 4.34 (d, 1H, J=16.8), 4.14 (d, 1H, J=16.8), 3.84(s, 3H), 3.58 (dd, 1H, J=6.8, 6.8), 3.46 (dd, 1H, J=7.0, 14.0), 3.30 (dd, 1H, J=7.5, 15.2), 2.60 (m, 2H), 2.36 (m, 2H), 1.70 (m, 4H), 1.08 (2×d, 6H, J=6.6); low resolution MS (FAB)m/e 592 (MH$^+$), 591 (M$^+$), 427; Anal. (C$_{35}$H$_{37}$N$_5$O$_4$) Calcd. C, 71.05; H, 6.30; N, 11.84; Found C, 70.20; H, 6.47; N, 11.66.

Example 52

2-[3-(1H-Indazol-3-ylmethyl)-2,4-dioxo-5-phenyl-2,3,4,5-tetrahydro-benzo[b][1,4]diazepin-1-yl]-N-isopropyl-N-(4-trifluoromethyl-phenyl)-acetamide To a stirring solution of 350 mg (0.71 mmol) of 2-(2,4-Dioxo-5-phenyl-2,3,4,5-tetrahydro-benzo[b][1,4]diazepin-1-yl)-N-isopropyl-N-(4-trifluoromethyl-phenyl)-acetamide, prepared as in Intermediate 54, in 8 mL of DMF at 0° C. is added 1.7 mL (0.85 mmol, 1.2 equiv) of a 0.5M solution of KN(TMS)$_2$ in toluene. The resulting solution is stirred 5 min, and a solution of 240 mg (0.78 mmol, 1.1 equiv.) of 3-Bromomethyl 1-tert-butoxycarbonyl-1H-indazole in 2 mL of DMF is added. The resulting solution is stirred for 1 h at RT then quenched with 5 mL of H$_2$O. The reaction mixture is poured into 50 mL of EtOAc and extracted with H$_2$O (2×50 mL). The organic layer is separated, dried (MgSO$_4$), and the solvents removed in vacuo. Purification by silica gel flash column chromatography using hexane/EtOAc 3/2 as eluent afforded 440 mg of a white amorphous solid. This material is dissolved in 5 mL of 4N HCl in 1,4-dioxane and stirred at RT for 1 h. The reaction mixture is poured into 50 mL of EtOAc and washed successively with 3N NaOH (1×50 mL) and H$_2$O (1×50 mL). The organic layer is separated, dried (MgSO$_4$), and the solvents removed in vacuo. Purification by silica gel MPLC using hexane/EtOAc 3/2 as eluent afforded 189 mg of the title compound as a white solid: mp 145°–148° C.; $^1$H NMR (CDCl$_3$, 400 MHz) δ9.75 (s, br, 1H), 7.82 (d, 1H, J=8.0), 7.73 (d, 2H, J=8.0), 7.42–7.07 (m, 13H), 6.93 (d, 1H, J=7.2), 5.03 (m, 1H), 4.19 (m, 3H), 3.79 (dd 1H, J=7.5, 16.0), 3.61 (dd, 1H, J=5.8, 16.0), 1.07 (d, 6H, J=6.4); low resolution MS (FAB)m/e 626 (MH$^+$), 625 (M$^+$), 423; Anal. (C$_{35}$H$_{30}$F$_3$N$_5$O$_3$) Calcd. C, 67.19; H, 4.83; N, 11.19 Found C, 67.09; H, 4.85; N, 11.11.

Example 53

2-[3-(1H-Indazol-3-ylmethyl)-3-methoxy-2,4-dioxo-5-pyridin-3-yl-2,3,4,5-tetrahydro-benzo[b][1,4]diazepin-1-yl]-N-isopropyl-N-(4-methoxy-phenyl)-acetamide To a stirring solution of 350 mg (0.49 mmol) of 2-[3-(1-Benzyl-1H-indazol-3-ylmethyl)-3-methoxy-2,4-dioxo-5-pyridin-3-yl-2,3,4,5-tetrahydro-benzo[b][1,4]diazepin-1-yl]-N-isopropyl-N-(4-methoxy-phenyl)-acetamide, prepared as in Intermediate 55, in a 10 mL solution of 5% formic acid (v/v) in absolute ethanol/DMF 1/1 is added 350 mg of 10% palladium on carbon. The resulting mixture is heated to reflux for 3 h, then cooled to RT and filtered through a pad of Celite to remove the catalyst. The filtrate is concentrated, then poured into 50 mL of EtOAc and washed successively with 1N NaOH (1×50 mL) and H$_2$O (1×50 mL). The organic layer is separated, dried (MgSO$_4$), and the solvents removed in vacuo. Purification by silica gel flash column chromatography using hexane/EtOAc 1/2 as eluent afforded 166 mg of the title compound as a white solid: mp 207°–209° C.; $^1$H NMR (CDCl$_3$, 400 MHz) δ10.05 (s, br, 1H), 8.43 (d, 1H, J=4.6), 8.29 (s, 1H), 7.94 (d, 1H, J=8.2), 7.56 (d, 1H, J=7.2), 7.39 (d, 1H, J=7.8), 7.29 (m, 2H), 7.25–7.09 (m, 5H), 6.98 (m, 3H), 6.65 (d, 1H, J=8.1), 5.06 (m, 1H), 4.25 (dd, 2H, J=16.0, 198.0), 4.07 (dd, 2H, J=16.2, 107.8), 3.84 (s, 3H), 3.21 (s, 3H), 1.12 (2×d, 6H, J=7.2); low resolution MS (FAB)m/e 619 (MH$^+$), 618 (M$^+$); Anal. (C$_{35}$H$_{34}$N$_6$O$_5$) Calcd. C, 67.95; H, 5.54; N, 13.58 Found C, 67.85; H, 5.51; N, 13.59.

Example 54

2-[3-(2-Benzyl-5-methyl-2H-pyrazol-3ylmethyl)-2,4-dioxo-5-phenyl-2,3,4,5-tetrahydro-benzo[b][1,4]diazepin-1-yl]-N-isopropyl-N-(4-methoxy-phenyl)-acetamide To a stirring solution of 300 mg (0.66 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 5 mL of DMF at 0° C. is added 1.57 mL (0.79 mmol, 1.2 equiv) of a 0.5M solution of KN(TMS)$_2$ in toluene. The resulting solution is stirred 5 min, and a solution of 190 mg (0.72 mmol, 1.1 equiv.) of 1-Benzyl-5-bromomethyl-3-methyl-1H-pyrazole, prepared as in Intermediate 56, in 2 mL of DMF is added. The resulting solution is stirred for 18 h at RT then quenched with 5 mL of $H_2O$. The reaction mixture is poured into 50 mL of EtOAc and extracted with $H_2O$ (2×50 mL). The organic layer is separated, dried ($MgSO_4$), and the solvents removed in vacuo. Purification by silica gel flash column chromatography using hexane/EtOAc 1/2 as eluent afforded 254 mg of the title compound as a white solid: mp 117°–120° C.; $^1H$ NMR ($CDCl_3$, 400 MHz) δ7.37–7.02 (m, 15H), 6.94 (m, 2H), 6.85 (d, 1H, J=7.4), 5.80(s, 1H), 5.30 (dd, 2H, J=16.1, 30.9), 4.98 (m, 1H), 4.19 (dd, 2H, J=15.6, 76.0), 3.83 (s, 3H), 3.43 (t, 1H, J=6.7), 3.25 (ddd, 1H, J=7.1, 16.0, 40.5), 2.20 (s, 3H), 1.06 (m, 6H); low resolution MS (FAB)m/e 642 ($MH^+$), 641 ($M^+$); Anal. ($C_{39}H_{39}N_5O_4$) Calcd. C, 72.99; H, 6.13; N, 10.91 Found C, 72.86; H, 6.11; N, 10.96.

Example 55

N-Isopropyl-N-(4-methoxy-phenyl)-2-[3-(5-methyl-2H-pyrazol-3ylmethyl)-2,4-dioxo-5-phenyl-2,3,4,5-tetrahydro-benzo[b][1,4]diazepin-1-yl]-acetamide To a stirring solution of 194 mg (0.30 mmol) of 2-[3-(2-Benzyl-5-methyl-2H-pyrazol-3ylmethyl)-2,4-dioxo-5-phenyl-2,3,4,5-tetrahydro-benzo[b][1,4]diazepin-1-yl]-N-isopropyl-N-(4-methoxy-phenyl)-acetamide, prepared as in Example 54, in 10 mL of 5% formic acid (v/v) in absolute ethanol is added 190 mg of 10% palladium on carbon. The resulting mixture is heated to reflux for 2 h, then cooled to RT and filtered through a pad of Celite to remove the catalyst. The filtrate is concentrated, then poured into 50 mL of EtOAc and washed successively with 1N NaOH (1×50 mL) and $H_2O$ (1×50 mL). The organic layer is separated, dried ($MgSO_4$), and the solvents removed in vacuo. Purification by silica gel MPLC using EtOAc/chloroform 8/1 as eluent afforded 112 mg of the title compound as a white solid: mp 156°–159° C.; $^1H$ NMR ($CDCl_3$, 400 MHz) δ7.38–7.18 (m, 9H), 7.14 (d, 1H, J=8.7), 7.06 (t, 1H, J=7.3), 6.96 (m, 2H), 6.86 (d, 1H, J=7.6), 5.81 (s, 1H), 5.02 (m, 1H), 4.18 (dd, 2H, J=16.5, 86.1), 3.83 (s, 3H), 3.59 (t, 1H, J=6.8), 3.32 (ddd, 2H, J=7.5, 15.2, 34.3), 2.19 (s, 3H), 1.08 (m, 6H); low resolution MS (FAB)m/e 552 ($MH^+$), 551 ($M^+$), 387; Anal. ($C_{32}H_{33}N_5O_4$) Calcd. C, 69.67; H, 6.03; N, 12.70 Found C, 69.61; H, 6.11; N, 12.44.

Example 56

2-(3-Benzoimidazol-1-ylmethyl)-2,4-dioxo-5-phenyl-2,3,4,5-tetrahydro-benzo[b][1,4]diazepin-1-yl]-N-isopropyl-N-(4-methoxy-phenyl)-acetamide To a stirring solution of 365 mg (0.75 mmol) of 2-(3-Hydroxymethyl-2,4-dioxo-5-phenyl-2,3,4,5-tetrahydro-benzo[b][1,4]diazepin-1-yl]-N-isopropyl-N-(4-methoxy-phenyl)-acetamide, prepared as in Intermediate 57, in 8 mL of dichloromethane at −5° C. is added 125 μL (0.90 mmol, 1.2 equiv) of triethylamine, followed by 64 μL (0.82 mmol, 1.1 equiv) of methanesulfonyl chloride. The resulting solution is stirred 1 h at −5° C. then warmed to RT and stirred an additional 2 h. The reaction mixture is poured into 20 mL of $H_2O$ and extracted with 20 mL of dichloromethane. The organics were dried ($MgSO_4$) and the solvent removed in vacuo to afford the crude mesylate, which is dissolved in 5 mL of DMF. To this solution is added 144 mg (1.04 mmol) of $K_2CO_3$ and 112 mg (1.04 mmol) of 1,2-phenylene diamine, and the resulting mixture is heated to 65° C. for 1 h. The solution is cooled to RT, diluted with 50 mL of a 1:1 solution of EtOAc/$Et_2O$, and extracted with 1N HCl (1×40 mL) and $H_2O$ (2×40 mL). The organics were dried ($MgSO_4$) and the solvent removed in vacuo to afford the unstable diamine. The diamine is dissolved in 2 mL of triethyl orthoformate, 5 mg of p-toluenesulfonic acid is added, and the reaction mixture is heated to 75° C. for 1 h. The reaction mixture is cooled to RT, poured into 50 mL of EtOAc and washed successively with 1N NaOH (1×50 mL) and $H_2O$ (1×50 mL). The organic layer is separated, dried ($MgSO_4$), and the solvents removed in vacuo. Purification by silica gel MPLC using EtOAc/chloroform 5/2 as eluent afforded 152 mg of the title compound as a white solid: mp 156°–159° C.; $^1H$ NMR ($CDCl_3$, 400 MHz) δ8.19 (s, 1H), 7.75 (m, 1H), 7.39–7.13 (m, 12H), 7.05 (ddd, 1H, J=1.2, 8.2, 8.2), 6.97 (m, 2H), 6.83 (dd, 1H, J=1.0, 8.2), 5.05 (m, 2H), 4.80 (dd, 1H, J=4.7, 14.9), 4.26 (m, 2H), 3.85 (s, 3H), 3.74 (dd, 1H, J=4.7, 7.8), 0.87 (2×d, 6H, J=6.8); low resolution MS (FAB)m/e 588 ($MH^+$); Anal. ($C_{35}H_{33}N_5O_4$) Calcd. C, 71.53; H, 5.66; N, 11.92 Found C, 71.44; H, 6.00; N, 11.62.

Example 57

N-(4-Fluoro-phenyl)-2-[3-(1H-indazol-3-ylmethyl)-2,4-dioxo-5-phenyl-2,3,4,5-tetrahydro-benzo[b][1,4]diazepin-1-yl]-N-isopropyl-acetamide To 890 mg (1.3 mmol) of crude 2-[3-(1-tert-butoxycarbonyl-1H-indazol-3-ylmethyl)-2,4-dioxo-5-phenyl-2,3,4,5-tetrahydro-benzo[b][1,4]diazepin-1-yl]-N-(4-fluoro-phenyl)-N-isopropyl-acetamide, prepared as in Intermediate 58, is added 10 mL of 4N HCl in dioxane at RT. The resulting solution is stirred 4 h and 100 mL of $Et_2O$ is added. The precipitate is filtered and purified by RP-HPLC (50–60% acetonitrile/ $H_2O$ over 30 min) to afford 86.7 mg of the title compound: $^1H$ NMR ($CDCl_3$, 300 MHz) δ7.85 (d, 1H, J=8.2), 7.43–7.09 (m, 15H), 6.96 (d, 1H, J=8.3), 5.01 (m, 1H), 4.98 (m, 2H), 3.82 (m, 2H), 1.05 (m, 6H); low resolution MS (FAB) m/e 576 ($MH^+$); RP-HPLC $T_r$=5.5 min (40–60% acetonitrile/ $H_2O$).

Example 58

2-[3-(1H-Indazol-3-ylmethyl)-2,4-dioxo-5-thiophen-3-yl-2,3,4,5-tetrahydro-benzo[b][1,4]diazepin-1-yl]-N-isopropyl-N-(4-methoxy-phenyl)-acetamide To 590 mg (0.80 mmol) of crude 2-[3-(1-tert-butoxycarbonyl-1H-indazol-3-ylmethyl)-2,4-dioxo-5-thiophen-3-yl-2,3,4,5-tetrahydro-benzo[b][1,4]diazepin-1-yl]-N-isopropyl-N-(4-methoxy-phenyl)-acetamide, prepared as in Intermediate 59, is added 10 mL of 4N HCl in dioxane at RT. The resulting solution is stirred 4 h and 100 mL of $Et_2O$ is added. The precipitate is filtered and purified by RP-HPLC (30–60% acetonitrile/ $H_2O$ over 30 min) to afford 71 mg of the title compound: $^1H$ NMR (DMSO-$d_6$, 300 MHz) δ7.78 (d, 1H, J=8.1), 7.59–7.24 (m, 9H), 7.06 (m, 9H), 4.75 (m, 1H), 4.47 (d, 1H, J=17.1), 4.15 (m, 3H), 3.82 (s, 3H), 3.44 (m, 2H), 0.98 (d, 3H, J=6.9), 0.94 (d, 3H, J=6.9); low resolution MS (FAB) m/e 594 ($MH^+$); RP-HPLC $T_r$=16.2 min (30–60% acetonitrile/ $H_2O$).

Example 59

2-[3-(1H-Indazol-3-ylmethyl)-2,4-dioxo-5-thiophen-2-yl-2,3,4,5-tetrahydro-benzo[b][1,4]diazepin-1-yl]-N-isopropyl-N-(4-methoxy-phenyl)-acetamide To 280 mg (0.40 mmol) of crude 2-[3-(1-tert-butoxycarbonyl-1H-indazol-3-ylmethyl)-2,4-dioxo-5- thiophen-2-yl-2,3,4,5-tetrahydro-benzo [b][1,4]diazepin-1-yl]-N-isopropyl-N-(4-methoxy-phenyl)-acetamide, prepared as in Intermediate 60, is added 10 mL of 4N HCl in dioxane at RT. The resulting solution is stirred 3 h and 100 mL of Et₂O is added. The Et₂O is decanted away from the gum. The gum is washed with Et₂O and purified by RP-HPLC (30–60% acetonitrile/H₂O over 30 min) to afford 23.7 mg of the title compound: ¹H NMR (CDCl₃, 300 MHz) δ7.83 (d, 1H, J=8.0), 7.45–7.06 (m, 11H), 6.96–6.79 (m, 4H), 4.97 (m, 1H), 4.31 (d, 1H, J=16.6), 4.20 (m, 1H), 4.08 (d, 1H, J=16.6), 3.81 (s, 3H), 3.73 (m, 2H), 1.05 (d, 3H, J=6.8), 1.02 (d, 3H, J=6.8); low resolution MS (FAB) m/e 594 (MH⁺); RP-HPLC T$_r$=22.0 min (30–60% acetonitrile/H₂O).

Example 60

2-[3-(6-Fluoro-1H-indazol-3-ylmethyl)-2,4-dioxo-5-phenyl-2,3,4,5,tetrahydro-benzo[b][1,4]diazepin-1-yl]-N-isopropyl-N-p-tolyl-acetamide 431 mg (0.625 mmol) 6-Fluoro-3-[1-Isopropyl-p-tolyl-carbamoylmethyl)-2,4-dioxo-5-phenyl-2,3,4,5,-tetrahydro-1H-benzo[b][1,4]diazepin-3-ylmethyl]-indazole-1-carboxylic acid tert butyl ester, prepared as in Intermediate 61, is dissolved in 10 mL 4N HCl in Dioxane and stirred 4 h at ambient temperature. The solvent is removed in vacuo and the residue taken into EtOAc (50 mL), washed with satd. NaHCO₃ (30 mL) and brine (30 mL), dried (MgSO₄), filtered and concentrated in vacuo. The crude product is purified by flash chromatography on 15 g silica gel eluted with EtOAc/Hexanes (2:3, 400 mL) Appropriate fractions were combined and concentrated in vacuo to give 255 mg (0.433 mmol) of the title compound as a white foam: ¹H NMR (CDCl₃, 300 MHz) δ7.75 (m, 1H), 7.42 (d, 1H, J=7.9), 7.37–7.20 (m, 9H), 7.09 (m, 2H), 6.93 (m, 2H), 6.85 (m, 1H), 5.01 (m, 1H), 4.33–4.18 (m, 3H), 3.75 (m, 1H), 3.56 (m, 1H), 2.41 (s, 3H), 1.07 (m, 6H); low resolution MS (FAB) m/e 590.1 (MH⁺); TLC R$_f$=0.25 (EtOAc/Hexanes, 1:1).

Example 61

N-Cyclopropyl-2-[3-(1H-indazol-3-ylmethyl)-2,4-dioxo-5-phenyl-2,3,4,5,tetrahydro-benzo[b][1,4]diazepin-1-yl]-N-phenyl-acetamide 543 mg (0.828 mmol) 3-[1-(Cyclopropyl-phenyl-carbamoylmethyl)-2,4-dioxo-5-phenyl-2,3,4,5,-tetrahydro-1H-benzo[b][1,4]diazepin-3-ylmethyl]-indazole-1-carboxylic acid tert-butyl ester, prepared as in Intermediate 62, is dissolved in 10 mL 4N HCl in Dioxane and stirred 2 h at ambient temperature. The solvent is removed in vacuo and the residue taken into EtOAc (50 mL), washed with satd. NaHCO₃ (30 mL) and brine (30 mL), dried (MgSO₄), filtered and concentrated in vacuo. The crude product is purified by flash chromatography on 15 g silica gel eluted successively with EtOAc/Hexanes (1:1, 200 mL), (3:2, 200 mL). Appropriate fractions were combined and concentrated in vacuo to give 328 mg (0.590 mmol) of the title compound as a white solid: ¹H NMR (CDCl₃, 300 MHz) δ7.86 (d, 1H, J=8.1), 7.48–7.21 (m, 14H), 7.11 (m, 2H), 6.95 (m, 1H), 4.39 (m, 2H), 4.25 (m, 1H), 3.83 (m, 1H), 3.65 (m, 1H), 3.28 (m, 1H), 0.82 (m, 2H), 0.57 (m, 2H); low resolution MS (FAB) m/e 556.0 (MH⁺); TLC R$_f$=0.18 (EtOAc/Hexanes, 1:1).

Example 62

N-Cyclopentyl-2-[3-(1H-indazol-3-ylmethyl)-2,4-dioxo-5-phenyl-2,3,4,5,tetrahydro-benzo[b][1,4]diazepin-1-yl]-N-(4-methoxy-phenyl)-acetamide To a stirred solution of 129 mg (0.181 mmol) 3-{1-[Cyclopentyl-(4-methoxy-phenyl)-carbamoylmethyl]-2,4-dioxo-5-phenyl-2,3,4,5,-tetrahydro-1H-benzo[b][1,4]diazepin-3-ylmethyl}-indazole-1-carboxylic acid tert-butyl ester, prepared as in Intermediate 63, in 4 mL DCM is added 3 mL Trifluoroacetic acid and stirred 3 h at ambient temperature. The solvent is removed in vacuo and the residue taken into EtOAc (40 mL), washed with satd. NaHCO₃ (20 mL), dried (MgSO₄), filtered and concentrated in vacuo. The crude product is purified by flash chromatography on 10 g silica gel eluted with EtOAc/Hexanes (2:1, 150 mL). Appropriate fractions were combined and concentrated in vacuo to give 84 mg (0.0.137 mmol) of the title compound as a white foam: ¹H NMR (CDCl₃, 300 MHz) δ7.82 (d, 1H, J=8.0), 7.41–7.06 (m, 13H), 6.93 (m, 3H), 4.94 (m, 1H), 4.24 (m, 3H), 3.84 (s, 3H), 3.80 (m, 1H), 3.62 (m, 1H), 1.88 (m, 2H), 1.51 (m, 4H), 1.29 (m, 2H); low resolution MS (FAB) m/e 614.3 (MH⁺).

Example 63

2-[3-(6-Fluoro-1H-indazol-3-ylmethyl)-2,4-dioxo-5-phenyl-2,3,4,5,tetrahydro-benzo[b][1,4]diazepin-1-yl]-N-(4-fluoro-phenyl)-N-isopropyl-acetamide 730 mg (1.05 mmol) 6-Fluoro-3-{1-[(4-fluoro-phenyl)-isopropyl-carbamoylmethyl]-2,4-dioxo-5-phenyl-2,3,4,5,-tetrahydro-1H-benzo[b][1,4]diazepin-3-ylmethyl}-indazole-1-carboxylic acid tert butyl ester, prepared as in Intermediate 64, is dissolved in 25 mL 4N HCl in Dioxane and stirred 3 h at ambient temperature. The solvent is removed in vacuo and the residue crystalized from EtOAc (25 mL) to give 353 mg (0.560 mmol) of the HCl salt of the title compound as a white crystaline solid: ¹H NMR (CDCl₃, 300 MHz) δ7.97 (m, 1H), 7.38–7.03 (m, 14H), 6.96 (d, 1H, J=8.0), 4.99 (m 1H), 4.31 (t, 1H), 4.23 (s, 2H), 3.81 (m, 2H), 1.05 (m, 6H); low resolution MS (FAB) m/e 594.4 (MH⁺); TLC R$_f$=0.26 (EtOAc/Hexanes, 1:1).

Example 64

2-[3-(1-Acetyl-6-fluoro-1H-indazol-3-ylmethyl)-2,4-dioxo-5-phenyl-2,3,4,5,tetrahydro-benzo[b][1,4]diazepin-1-yl]-N-(4-fluoro-phenyl)-N-isopropyl-acetamide 300 mg (0.505 mmol) 2-[3-(6-Fluoro-1H-indazol-3-ylmethyl)-2,4-dioxo-5-phenyl-2,3,4,5,-tetrahydro-benzo[b][1,4]diazepin-1-yl]-N-(4-fluoro-phenyl)-N-isopropyl-acetamide, prepared as in Example 63, is dissolved in 15 mL Acetic anhydride and heated at reflux 1 h. The solvent is removed in vacuo and the residue purified by preparative HPLC on a Delta-Pak C-18 column eluted from 35% to 60% CH₃CN in H₂O with 0.1% TFA buffer over 30 minutes at 150 mL/min. The appropriate fraction is frozen and lyophilized to give 144 mg (0.226 mmol) of the title compound as a white lyophilizate: ¹H NMR (CDCl₃, 300 MHz) δ8.04 (m, 1H), 7.76 (m, 1H), 7.50 (d, 1H, J=8.0), 7.39–7.08 (m, 12H), 6.98 (d, 1H, J=7.8), 5.02 (m, 1H), 4.32 (d, 1H, J=16.6), 4.30 (t, 1H), 4.10 (d, 1H, J=16.6), 3.75 (m, 1H), 3.57 (m, 1H), 2.63 (s, 3H), 1.08 (m, 6H); low resolution MS (FAB) m/e 636.1 (MH⁺); TLC R$_f$=0.30 (EtOAc/Hexanes, 1:2).

Example 65

N-tert-Butyl-2-[3-(1H-indazol-3-ylmethyl)-2,4-dioxo-5-phenyl-2,3,4,5,tetrahydro-benzo[b][1,4]diazepin-1-yl]-N-phenyl-acetamide 263 mg (0.392 mmol) 3-[1-(tert-Butyl-phenyl-carbamoylmethyl)-2,4-dioxo-5-phenyl-2,3,4,5,-tetrahydro- 1H-benzo[b][1,4]diazepin-3-ylmethyl]-indazole-1-carboxylic acid tert-butyl ester, prepared as in Intermediate 65, is dissolved in 3 mL 4N HCl in Dioxane and stirred 1 h at ambient temperature. The solvent is removed in vacuo and the residue taken into EtOAc (50 mL), washed with satd. NaHCO$_3$ (30 mL) and brine (30 mL), dried (MgSO$_4$), filtered and concentrated in vacuo. The crude product is purified by flash chromatography on 5 g silica gel eluted successively with EtOAc/Hexanes (1:2, 50 mL), (2:3, 80 mL), (1:1, 50 mL). Appropriate fractions were combined and concentrated in vacuo to give 65 mg (0.113 mmol) of the title compound as a white foam: $^1$H NMR (CDCl$_3$, 300 MHz) δ7.82 (d, 1H, J=7.5), 7.43–7.06 (m, 16H), 4.19 (m, 2H), 4.08 (m, 1H), 3.79 (m, 1H), 3.63 (m, 1H), 1.37 (s, 9H); low resolution MS (FAB) m/e 572.2 (MH$^+$); TLC R$_f$=0.41 (EtOAc/Hexanes, 3:2).

Example 66

2-[7-Fluoro-3-(1H-indazol-3-ylmethyl)-2,4-dioxo-5-pyridin-3-yl-2,3,4,5-tetrahydro-benzo[b][1,4]diazepin-1-yl]-N-isopropyl-N-(4-methoxy-phenyl)-acetamide To a solution of 5 mL of trifluoroacetic acid under nitrogen is add 364 mg of 2-[7-fluoro-3-(1-tertbutoxycarbonyl-indazol-3-ylmethyl)-2,4-dioxo-5-pyridin-3-yl- 2,3,4,5-tetrahydro-benzo[b][1,4]diazepin-1-yl]-N-isopropyl-N-(4-methoxy-phenyl)-acetamide, prepared as in Intermediate 66. After stirring at ambient temperature for 20 min, the reaction mixture is evaporated in vacuo and the residue is partitioned between ethyl acetate and saturated aqueous sodium bicarbonate. The layers were separated and the aqueous layer is back-extracted with dichloromethane. The organic layers were combined, washed with aqueous sodium hydroxide (1N), dried over anhydrous sodium sulfate, filtered and evaporated in vacuo. The residue is triturated with hexane, the hexane is removed in vacuo, and the residual solid is dried under high vacuum to provide 286 mg of the title compound as a white solid: $^1$H NMR (300 MHz, CDCl$_3$) δ8.67 (s, br, 1H), 8.56 (dd, 1H, J=1.5, 5.2), 8.10 (d, 1H, J=8.1), 7.82 (d, 1H, J=8.1), 7.52 (dd, 1H, J=5.3, 8.3), 7.35 (m, 3H), 7.14 (m, 3H), 7.03 (m, 1H), 6.96 (m, 3H), 6.61 (dd, 1H, J=2.7, 8.9), 4.92 (m, 1H), 4.51 (d, 1H, J=15.8), 4.29 (dd, 1H, J=5.8, 7.7), 4.05 (d, 1H, J=16.0), 3.84 (s, 3H), 3.78 (dd, 1H, J=7.8, 16.4), 3.61 (dd, 1H, J=5.9, 16.2), 1.03 (d, 6H, J=6.8); low resolution MS (FAB)m/e 607 (MH$^+$).

Example 67

2-[7,8-Difluoro-3-(1H-indazol-3-ylmethyl)-2,4-dioxo-5-phenyl-2,3,4,5-tetrahydro-benzo[b][1,4]diazepin-1-yl]-N-isopropyl-N-(4-methoxy-phenyl)-acetamide To a solution of 5.0 mL trifluoroacetic acid under nitrogen is added 0.500 g of 2-[7,8-difluoro-3-(1-tertbutoxycarbonyl-indazol-3-ylmethyl)-2,4-dioxo-5-phenyl-2,3,4,5-tetrahydro-benzo[b][1,4]diazepin-1-yl]-N-isopropyl-N-(4-methoxy-phenyl)-acetamide, prepared as in Intermediate 67, (0.697 mmol). After stirring for 1.5 hrs., the trifluoroacetic acid is removed in vacuo and the residue is partitioned between methylene chloride and aqueous sodium hydroxide (1N) and transferred to a separatory funnel. The layers were separated and the organic layer is back-extracted with methylene chloride. The organic layers were combined, dried over anhydrous sodium sulfate, filtered, evaporated in vacuo to a residue and then triturated with hexane. Hexane is removed in vacuo and the remaining solid is dried under high vacuum to provide 430 mg of the title compound as an off-white solid: $^1$H NMR (300 MHz, CDCl$_3$) δ7.93 (d, 1H, J=8.2), 7.51 (m, 2H), 7.41 (m, 2H), 7.29 (m, 7H), 7.15 (m, 1H), 7.00 (m, 2H), 6.82 (m, 1H), 5.01 (m, 1H), 4.36 (m, 1H), 4.32 (d, 1H, J=17.1), 4.19 (d, 1 H, J=16.7), 3.88 (s, 3H), 3.87 (m, 1H), 3.74 (dd, 1H, J=6.0, 16.1), 1.10 (d, 6H, J=6.8); low resolution MS (FAB)m/e 624 (MH$^+$).

Example 68

2-[3-(1H-indazol-3-ylmethyl)-2,4-dioxo-5-phenyl-2,3,4,5-tetrahydro-benzo[b][1,4]diazepin-1-yl]-N-isopropyl-N-phenyl-acetamide 400 mg of 2-[3-(1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-phenyl-acetamide, prepared as in Intermediate 68, is dissolved in 10 mL of CHCl$_3$ and 5 mL of TFA is added. The reaction mixture is stirred for 6 h and the solvents were removed in vacuo and the residue is purified by flash column chromatography on silica gel (MeOH 1%:CHCl$_3$ 99%) to afford 240 mg of the title compound: $^1$H NMR (400 MHz, CDCl$_3$) δ7.93 (d, 1H, J=8.4), 7.51–7.19 (m, 16H), 6.99 (m, 1H), 5.03 (m,1H, J=6.8), 4.29 (d, 1, J=16.4), 4.26 (d, 1H, J=16.4), 4.14 (m, 1H), 3.89 (dd, 1H, J=16.5, 6.4), 3.82 (dd 1H,J=16.5, 6.4,), 1.08 (t, 6H, J=6.8); LOW RESOLUTION MS (FAB) m/e 558 (MH$^+$); T$_r$=9.90 min. (HPLC Column: Dynamax C-8 2 mL/min., 50–90% Acetonitrile in aqueous TFA (0.1% v/v) over 15 min.).

Example 69

2-[3-(6-Fluoro-1H-indazol-3-ylmethyl)-2,4-dioxo-5-phenyl-2,3,4,5-tetrahydro-benzo[b][1,4]diazepin-1-yl]-N-isopropyl-N-phenyl-acetamide 400 mg of 2-[3-(6-Fluoro-1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-phenyl-acetamide, prepared as in Intermediate 69, is dissolved in 10 mL of CHCl$_3$ and 5 mL of TFA is added. The reaction mixture is stirred for 6 h and the solvents were removed in vacuo to afford 240 mg of the title compound: $^1$H NMR (400 MHz, DMSO-d$_6$) δ7.82–6.88 (m, 18H), 4.77(m, 1H, J=6.8), 4.45 (d, 1H, J=16.8), 4.12 (m, 2H), 3.41 (m, 2H), 0.95 (t, 6H, J=6.8); low resolution MS (FAB) m/e 576 (MH$^+$); T$_r$=10.31 min. (HPLC Column: Dynamax C-8 2 mL/min., 50–90% Acetonitrile in aqueous TFA (0.1% v/v) over 15 min.).

Example 70

2-[3-(6-Fluoro-1H-indazol-3-ylmethyl)-2,4-dioxo-5-phenyl-2,3,4,5-tetrahydro-benzo[b][1,4]diazepin-1-yl]-N-isopropyl-N-(4-trifluoromethoxy-phenyl)-acetamide 70 mg of 2-[3-(6-Fluoro-1-tert-butoxycarbonyl-1H-indazol-3-ylmethyl)-2,4-dioxo-5-phenyl-2,3,4,5-tetrahydro-benzo[b][1,4]diazepin-1-yl]-N-isopropyl-N-(4-trifluoromethoxy-phenyl)-acetamide, prepared as in Intermediate 70, is dissolved in 2 mL of CHCl$_3$ and 5 mL of TFA is added. The reaction mixture is stirred for 6 h and the solvents were removed in vacuo. The residue is purified by silica gel flash column chromatography using hexane/EtOAc 40:60 as eluent to afford the 40 mg of the title compound: $^1$H NMR (400 MHz, DMSO-d$_6$) δ7.73 (dd, 1H, J=8.9, 5.1), 7.41–7.18 (m, 12H), 7.08 (dd, 1H, J=7.3, 2.0), 6.97 (dd, 1H, J=8.9, 1.7), 6.92 (dd, 1H, J=7.2, 2.0), 6.84 (dd, 1H,J=9.1, 2.0), 5.01 (m, 1H), 4.22 (m, 3H), 3.75 (dd, 1H, J=16.5, 6.4), 3.56 (dd, 1H, J=16.5, 6.4), 1.06 (t, 6H, J=6.8); low resolution MS (FAB) m/e 660 (MH$^+$); T$_r$=12.32 min. (HPLC Column: Dynamax C-8 2 mL/min., 50–90% Acetonitrile in aqueous TFA (0.1% v/v) over 15 min.).

Example 71

2-[3-(1H-indazol-3-ylmethyl)-2,4-dioxo-5-pyridin-3-yl-2,3,4,5-tetrahydrobenzo[b][1,4]diazepin-1-yl]-N-isopropyl-N-(4-methoxy-phenyl) acetamide To 561 mg (0.95 mmol) of 2-[3-(1-tert-butoxycarbonyl-1H-indazol-3-ylmethyl)-2,4-dioxo-5-pyridin-3-yl-2,3,4,5-tetrahydrobenzo[b][1,4]diazepin-1-yl]-N-isopropyl-N-(4-methoxy-phenyl) acetamide, prepared as in Intermediate 75, is added 10 mL of a 4N solution of HCl in dioxane. The reaction is stirred overnight at RT. The reaction is concentrated, then purified by silica gel flash column chromatography (gradient 2:1–4:1 ethyl acetate:hexanes) to afford an oil which is triturated from hexane to afford 284 mg of the title compound as a white powder: $^1$H NMR (CDCl$_3$, 400 MHz) δ8.49 (d, br, 2H), 7.79 (d, 2H, J=8.0), 7.29–7.07 (m, 8H) 6.95–6.85 (m, 4H ) 4.94 (m, 1H), 4.38 (d, br, 1H, J=15.6) 4.25–4.14 (m, 2H) 3.82 (s, 3H) 3.77 (m, 1H) 3.60 (dd, 1H, J=6.0, 16.1) 1.02 (t, 6H, J=7.7); low resolution MS (FAB)m/e 589 (MH$^+$); Anal. (C$_{34}$H$_{32}$N$_6$O$_4$) Calcd. C, 69.4; H, 5.5; N, 14.3 Found C, 68.4; H, 5.6; N, 14.1. To a stirred solution of 1.0 g (1.69 mmol) of the title compound in 10 mL of DCM is added 1.86 mL (2.54 mmol, 1.5 equiv.) of a 1.36M solution of 2-Oxo-4-thiazolidinecarboxylic acid chloride in DCM (prepared by stirring 1.0 g (6.8 mmol) of (−)-2-Oxo-4-thiazolidine carboxylic acid, 0.593 mL (6.8 mmol), and 0.1 mL DMF in 50.0 mL DCM until gas evolution stopped). The solution is stirred at RT for 4 h and then concentrated in vacuo. Purification by silica gel gravity column chromatography using DCM/THF 8/2 as eluent afforded 415 mg of the less polar eluting diastereomer as 2-{2,4-Dioxo-3-[1-(2-oxo-thiazolidine-4-carbonyl)-1H-indazol-3-yl methyl]-5-pyridin-3-yl-2,3,4,5-tetrahydro benzo[b][1,4]diazepin-1-yl}-N-isopropyl-N-(4-methoxyphenyl) acetamide. $^1$H NMR (CDCl$_3$, 300 MHz) δ8.53 (d, 1H, J=4), 8.45 (s, 1H), 8.33 (d, 1H, J=28), 7.82 (d, 1H, J=26), 7.72 (d, 1H, J=9), 7.62–7.57 (m, 2H), 7.45–6.94 (m, 9H), 6.72 (s, 1H), 5.62 (bt, 1H), 5.05–4.90 (m, 1H), 4.51–4.42 (m, 2H), 3.97–3.87 (m, 2H), 3.83 (s, 3H), 3.75 (dd, 1H, J=5, 18), 3.64–3.57 (m, 2H), 3.48 (dd, 1H, J=4, 22), 1.10 (d, 3H, J=7), 0.97 (d, 3H, J=7).

Example 72

(+)-2-[3-(1H-Indazol-3-yl methyl)-2,4-dioxo-5-pyridin-3-yl-2,3,4,5-tetrahydro benzo[b][1,4]diazepin-1-yl]-N-isopropyl-N-(4-methoxyphenyl) acetamide To a stirred solution of 400 mg (0.556 mmol) of 2-{2,4-Dioxo-3-[1-(2-oxo-thiazolidine-4-carbonyl)-1H-indazol-3-yl methyl]-5-pyridin-3-yl-2,3,4,5-tetrahydro benzo[b][1,4]diazepin-1-yl}-N-isopropyl-N-(4-methoxyphenyl) acetamide, prepared as in Example 71 in 10 mL methanol is added 154 mg (1.11 mmol, 2 equiv.) of potassium carbonate. The suspension is stirred for 20 min and diluted with 25 mL EtOAc and 25 mL H$_2$O. The organic phase is washed with H$_2$O (2×25 mL) and then dried (MgSO$_4$), and the solvents removed in vacuo. The resulting amorphous solid is swirled in 10 mL ether until a free flowing white solid is produced. The solid is filtered to give 258 mg of the title compound: mp. 214°–215° C.; [a]$^{25}$=+47.2; $^1$H NMR (CDCl$_3$, 400 MHz) δ8.49 (d, br, 2H), 7.79 (d, 2H, J=8.0), 7.29–7.07 (m, 8H) 6.95–6.85 (m, 4H) 4.94 (m, 1H), 4.38 (d, br, 1H, J=15.6) 4.25–4.14 (m, 2H) 3.82 (s, 3H) 3.77 (m, 1H) 3.60 (dd, 1H, J=6.0, 16.1) 1.02 (t, 6H, J=7.7); low resolution MS (FAB) m/e 589 (MH$^+$).

Example 73

(−)-2-[3-(1H-Indazol-3-yl methyl)-2,4-dioxo-5-pyridin-3-yl-2,3,4,5-tetrahydro benzo[b][1,4]diazepin-1-yl]-N-isopropyl-N-(4-methoxyphenyl) acetamide The (−) antipode is synthesized as in Examples 71 and 72 except the alternate 2-{2,4-Dioxo-3-[1-(2-oxo-thiazolidine-4-carbonyl)-1H-indazol-3-yl methyl]-5-pyridin-3-yl-2,3,4,5-tetrahydro benzo[b][1,4]diazepin-1-yl}-N-isopropyl-N-(4-methoxyphenyl) acetamide diastereomer is used to yield the title compound: m.p. 214°–215° C.; [a]$^{25}$=−52.8; low resolution MS (FAB)m/e 589 (MH$^+$).

Example 74

2-[3-(1H-Indazol-3-ylmethyl)-3-methyl-2,4-dioxo-5-pyridin-3-yl-2,3,4,5-tetrahydro-benzo[b][1,4]diazepin-1-yl]-N-isopropyl-N-(4-methoxy-phenyl)-acetamide To a stirring solution of 1.0 g of 2-[3-(1-tert-butoxycarbonyl-1H-Indazol-3-ylmethyl)-3-methyl-2,4-dioxo-5-pyridin-3-yl-2,3,4,5-tetrahydro-benzo[b][1,4]diazepin-1-yl]-N-isopropyl-N-(4-methoxy-phenyl)-acetamide, prepared as in Intermediate 75, in 10 mL of methanol is added 2.0 g of solid K$_2$CO$_3$. The reaction mixture is stirred 2 h at RT and then 15 mL H$_2$O is added and the reaction mixture stirred 15 min at RT. The resulting white precipitate is filtered, washed with 15 mL of H$_2$O, and dried under vacuum at 90° C. to afford 668 mg of the title compound as a white solid: mp 161°–5° C.; $^1$H NMR (CDCl$_3$, 400 MHz) δ10.38 (s, br, 1H), 8.55 (s, 1H), 8.48 (m, 1H), 7.74 (d, 1H, J=7.0), 7.42–6.93 (m, 13H), 6.62 (d, 1H, J=8.2), 5.09 (m, 1H), 4.49 (m, 1H), 4.08 (m, 1H), 3.85 (s, 3H), 3.05 (d, 2H, AB quartet, J=15.9), 1.67 (s, 3H), 1.13 (m, 6H); low resolution MS (FAB)m/e 603 (MH$^+$), 424; Anal. (C$_{35}$H$_{34}$N$_6$O$_4$) Calcd. C, 69.75; H, 5.69; N, 13.94 Found C, 66.54; H, 5.549; N, 13.19.

Examples 75 and 76

2-[3-(1H-indazol-3-ylmethyl)-3-methyl-2,4-dioxo-5-pyridin-3-yl-2,3,4,5-tetrahydro-benzo[b][1,4]diazepin-1-yl]-N-isopropyl-N-(4-methoxy-phenyl)-acetamide and 2-[3-(1H-indazol-3-ylmethyl)-3-methyl-2,4-dioxo-5-pyridin-3-yl-2,3,4,5-tetrahydro-benzo[b][1,4]diazepin-1-yl]-N-isopropyl-N-(4-methoxy-phenyl)-acetamide 2-[3-(1H-Indazol-3-ylmethyl)-3-methyl-2,4-dioxo-5-pyridin-3-yl-2,3,4,5-tetrahydro-benzo[b][1,4]diazepin-1-yl]-N-isopropyl-N-(4-methoxy-phenyl)-acetamide, prepared as in Example 74 (40 mg) is dissolved in 250 μL of a mixture of i-PrOH:CHCl$_3$:Hexane 32%:8%:60% and separated on Chiralpack AD column 20 mm×25 cm. using Hexane:i-PrOH:CHCl3=80%:16% :4% as eluent and a flow rate 6 mL/min. Two fractions were collected at T$_r$(1)=39.4 min and $T_r(2)$=76.6 min. The solvent is removed in vacuo to afford 18 mg of one enantiomer (ee>99.8% by analytical HPLC) and 16 mg of the other (ee>98% by analytical HPLC).

Example 77

2-[3-(1H-Indazol-3-ylmethyl)-2,4-dioxo-5-phenyl-2, 3,4,5-tetrahydrobenzo[b][1,4]diazepin-1-yl]-N-isopropyl-N-(3,4-methylenedioxy-phenyl) acetamide A mixture of 2-[3-(1-Tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(3,4-methylenedioxy-phenyl) acetamide, prepared as in Intermediate 72, (123 mg, 0.175 mmol) and 4N HCl in dioxane (1 mL) is stirred at RT for 3 h. Diethyl ether (20 mL) is added and the resultant mixture stirred vigorously for 20 min. The solids were allowed to settle and the solvent is decanted. This procedure is repeated three times and the final solid dried by concentration in vacuo to afford the titled product (106 mg) as a white solid: $^1$H NMR (300 MHz, CDCl$_3$) δ7.95 (d, 1H, J=8.3), 7.68 (d, 1H, J=8.5), 7.59 (t, 1H, J=6.8), 7.2–7.5 (m, 11H), 7.12 (t, 1H, J=8.5), 6.94 (d, 1H, J=8.2), 6.84 (dd, 1H, J=15.8, 8.3), 6.03 (s, 2H), 5.00 (m, 1H, J=6.9), 4.40 (m, 1H), 4.24 (t, 2H, J=6.1), 3.92 (dd, 1H, J=16.5, 7.7), 3.83 (dd, 1H, J=16.5, 5.8), 1.08 (m, 6H); Low resolution MS (FAB) m/e 602 (M$^+$); $T_r$=23.06 min (RP-HPLC, 70% A to 70% C, 30 min).

Example 78

2-[3-(1H-Indazol-3-ylmethyl)-2,4-dioxo-5-phenyl-2, 3,4,5-tetrahydrobenzo[b][1,4]diazepin-1-yl]-N-isopropyl-N-(2-methoxy-phenyl) acetamide A mixture of 2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(2-methoxy-phenyl) acetamide, prepared as in Intermediate 73, (260 mg, 0.377 mmol) and 4N HCl in dioxane (2 mL) is stirred at RT for 2 h. Diethyl ether (40 mL) is added and the resultant mixture stirred vigorously for 20 min. The solids were allowed to settle and the solvent is decanted. This procedure is repeated three times and the final gum dried by concentration in vacuo. Recrystallisation from 5% methanol in ethyl acetate afforded the title compound (126 mg) as a white powdery solid, which exists as 3:2 mixture of rotamers (major rotamer recorded): $^1$H NMR (300 MHz, CDCl$_3$) δ7.98 (t, 1H, J=8.0), 7.70 (m, 1H), 7.61 (s, 1H), 7.40–6.90 (m, 15H), 5.05 (m, 1H, J=6.9), 4.45 (d, 2H, J=16.4), 4.25 (d, 1H, J=17.5), 4.07 (d, 1H, J=16.4), 3.74 (m, 5H), 1.16 (m, 6H); Low resolution MS (FAB) m/e 588 (M$^+$); $T_r$=27.29 min (RP-HPLC, 100% A to 100% C, 30 min).

Example 79

2-[3-(1H-Indazol-3-ylmethyl)-2,4-dioxo-5-phenyl-2, 3,4,5-tetrahydrobenzo[b][1,4]diazepin-1-yl]-N-isopropyl-N-(3-methoxy-phenyl) acetamide A mixture of 2-[3-(1-tert-butoxycarbonyl-1H-indazol-3-ylmethyl)-2,4-dioxo-5-phenyl-2,3,4,5-tetrahydrobenzo[b][1,4]diazepin-1-yl]-N-isopropyl-N-(3-methoxy-phenyl) acetamide, prepared as in Intermediate 74, (250 mg, 0.363 mmol) and 4N HCl in dioxane (2 mL) is stirred at RT for 2 h. Diethyl ether (40 mL) is added and the resultant mixture stirred vigorously for 20 min. The solids were allowed to settle and the solvent is decanted. This procedure is repeated three times and the final solid dried by concentration in vacuo to afford the title compound (197 mg) as a white powdery solid: $^1$H NMR (300 MHz, CDCl$_3$) δ8.05 (d, 1H, J=8.6), 7.76 (d, 1H, J=8.5), 7.67 (t, 1H, J=8.8), 7.5–7.2 (m, 12H), 7.16 (t, 1H, J=6.3), 6.98 (t, 2H, J=7.3), 5.05 (m, 1H, J=6.9), 4.36 (s, br, 2H), 3.94 (t, 1H, J=7.0), 3.82 (s, br, 2H), 3.74 (s, 3H), 1.16 (m, 6H); Low resolution MS (FAB) m/e 588 (M$^+$).

Example 80

2-[3-(1H-Indazol-3-ylmethyl)-2,4-dioxo-5-pyridin-4-yl-2,3,4,5-tetrahydro-benzo[b][1,4]diazepin-1-yl]-N-isopropyl-N-(4-methoxy-phenyl)-acetamide To 487 mg (0.83 mmol) of 2-[3-(1-tert-butoxycarbonyl-1H-indazol-3-ylmethyl)-2,4-dioxo-5-pyridin-4-yl-2,3,4,5-tetrahydrobenzo[b][1,4]diazepin-1-yl]-N-isopropyl-N-(4-methoxy-phenyl) acetamide, prepared as in Intermediate 76, is added 8 mL of a 4N solution of HCl in dioxane. The reaction is stirred overnight at RT. The reaction is concentrated, then purified by silica gel flash column chromatography (gradient 3:1–4:1 ethyl acetate:hexanes) to afford 245 mg of the title compound as an oil. This oil is triturated with hexane/ethyl acetate to afford a white powder: $^1$H NMR (CDCl$_3$, 400 MHz) δ8.56 (s, br, 2H), 7.82 (d, 1H, J=8.0), 7.39–7.29 (m, 6H) 7.17–7.10 (m, 3H) 6.93 (dd, 2H, J=2.1,8.5) 4.93 (m, 1H), 4.39 (d, br, 1H, J=16.1) 4.25–4.19 (m, 2H) 3.82 (s, 3H) 3.77 (m, 1H) 3.58 (dd, 1H, J=5.8, 16.2) 1.02 (dd, 6H, J=3.9, 6.6); low resolution MS (FAB)m/e 589 (MH$^+$).

Example 81

2-[5-(3-Fluoro-phenyl)-3-(1H-indazol-3-ylmethyl)-2,4-dioxo-2,3,4,5-tetrahydro-benzo[b][1,4]diazepin-1-yl]-N-isopropyl-N-(4-methoxy-phenyl)-acetamide To 235 mg (0.33 mmol) of 2-[3-Fluoro-phenyl)-3-(1-tert-butoxycarbonyl-1H-indazol-3-ylmethyl)-2,4-dioxo-2,3,4,5-tetrahydrobenzo[b][1,4]diazepin-1-yl]-N-isopropyl-N-(4-methoxy-phenyl) acetamide, prepared as in Intermediate 77, is added 15 mL methanol. The mixture is stirred at room temperature, and to this solution is added 23 mg (0.16 mmol, 0.5 equiv) potassium carbonate. The resulting suspension is stirred ca. 20 h at RT. The reaction is then concentrated and poured into 20 mL of H$_2$O. The aqueous layer is extracted with ethyl acetate (2×30 mL). The combined organics were dried (Na$_2$SO$_4$) filtered and concentrated to afford an oil which is purified by silica gel flash column chromatography (gradient 1.5:1–1:1 hexanes:ethyl acetate) to afford 62 mg of the title compound as a white solid: $^1$H NMR (CDCl$_3$, 400 MHz) δ7.80 (d, 1H, J=8.0), 7.36–7.10 (m, 11H) 6.96–6.91 (m, 4H) 4.96 (m, 1H), 4.25 (d, br, 1H, J=31.9) 4.21–4.09 (m, 2H) 3.82 (s, 3H) 3.77 (m, 1H) 3.61 (dd, 1H, J=6.0, 16.2) 1.03 (t, 6H, J=7.2); low resolution MS (FAB)m/e 606 (MH$^+$).

Example 82

2-[3-(Benzyloxymethyl)-2,4-dioxo-5-phenyl-2,3,4,5-tetrahydro-benzo[b][1,4]diazepin-1-yl]-N-isopropyl-N-(4-methoxy-phenyl)-acetamide To a stirring solution of 1.0 g (2.18 mmol) of 2-(2,4-Dioxo-5-phenyl-2,3,4,5-tetrahydro-benzo[b][1,4]diazepin-1-yl)-N-isopropyl-N-(4-methoxy-phenyl) acetamide, prepared as in Intermediate 4, in 10 mL of DMF at −5° C. is added 2.40 mL (2.40 mmol, 1.1 equiv) of a 1.0M solution of NaN(TMS)$_2$ in THF. The resulting solution is stirred 5 min, and then 530 μL (3.05 mmol, 1.4 equiv) of chloromethyl benzyl ether (80%, tech.) is added neat. The resulting solution is stirred for 1 h at RT then quenched with 5 mL of H₂O. The reaction mixture is poured into 100 mL of EtOAc and extracted with H₂O (2×80 mL). The organic layer is separated, dried (MgSO₄), and the solvents removed in vacuo. Purification by silica gel flash column chromatography using a gradient elution of hexane/EtOAc 4/1 to hexane/EtOAc 1/2 as eluent afforded 500 mg of the title compound as a white solid, along with 320 mg of recovered starting benzodiazepine: mp. 203°–204° C.; ¹H NMR (CDCl₃, 400 MHz) δ7.37–7.18 (m, 13H), 7.10 (m, 2H), 6.92 (m, 3H), 4.98 (m, 1H), 4.56 (dd, 2H, J=11.8, 22.7), 4.25 (m, 3H), 4.08 (dd, 1H, J=5.0, 9.8), 3.83 (s, 3H), 3.67 (dd, 1H, J=5.0, 7.5), 1.06 (2×d, 6H, J=6.2); low resolution MS (FAB)m/e 578 (MH⁺), 443, 413, 277, 223; Anal. (C₃₅H₃₅N₃O₅) Calcd. C, 72.77; H, 6.11; N, 7.27 Found C, 71.62; H, 6.06; N, 7.10.

Example 83

2-[3-(1H-Indazol-3-yl methyl)-2,4-dioxo-5-pyridin-3-yl-2,3,4,5-tetrahydro benzo[b][1,4]diazepin-1-yl]-N-isopropyl-N-phenyl acetamide To a stirring solution of 2.5 g (5.84 mmol) of 2-(2,4-dioxo-5-pyridin-3-yl-2,3,4,5-tetrahydro benzo[b][1,4] diazepin-1-yl)-N-isopropyl-N-phenylacetamide, prepared as in Intermediate 49, in 15 mL of DMF at 0° C. is added 12.85 mL (6.42 mmol, 1.1 equiv) of a 0.05M solution of KN(TMS)₂ in toluene. The resulting solution is stirred 15 min, and a solution of 2.0 g (6.43 mmol, 1.1 equiv.) of 3-Bromomethyl-1-tert-butoxycarbonyl-1H-indazole in 5 mL of DMF is added. The resulting solution is stirred for 16 h at RT then quenched with 50 mL of H₂O. The reaction mixture is poured into 50 mL of EtOAc and extracted with H₂O (2×50 mL). The organic layer is separated, dried (MgSO₄), and the solvents removed in vacuo. Purification by silica gel flash column chromatography using hexane/EtOAc 1/2 as eluent afforded 3.0 g of a beige solid: ¹H NMR (CDCl₃, 300 MHz) δ8.58–8.51 (m, 2H), 8.03 (d, 1H, J=8), 7.89–7.85 (m, 2H), 7.51–6.91 (m, 12H), 5.01–4.92 (m, 1H), 4.47–4.34 (m, 2H), 4.17 (d, 1H, J=17), 3.85 (dd, 1H, J=8, 16), 3.57 (dd, 1H, J=8, 16), 1.66 (s, 9H), 1.05 (d, 6H, J=7). This material is dissolved in 25 mL of methanol and 0.5 g of solid potassium carbonate is added. The suspension stirred at RT for 2 h. The reaction mixture is poured into 50 mL of H₂O and the solid precipitate is filtered and dried to afford 2.09 g of the title compound as a white solid: ¹H NMR (CDCl₃, 300 MHz) δ8.57 (m, 1H), 7.87 (d, 1H, J=8), 7.48–7.14 (m, 15H), 6.94 (d, 1H, J=8), 5.04–4.98 (m, 1H), 4.45 (d, 1H, J=16), 4.30 (t, 1H, J=7.5), 4.20 (d, 1H, J=16), 3.83 (dd, 1H, J=8, 8), 3.66 (dd, 1H, J=6, 6), 1.10 (dd, 6H, J=7, 7); low resolution MS (FAB)m/e 559 (MH⁺).

Example 84

N-Isopropyl-N-[4-methoxyphenyl]-2-[3-methyl-2,4-dioxo-3-phenylcarbamoylmethyl-5-pyridin-3-yl-2,3,4,5-tetrahydro benzo[b][1,4]diazepin-1-yl) acetamide To a stirring solution of 750 mg (1.41 mmol) of {1-[Isopropyl-(4-methoxyphenyl)-carbamoylmethyl]-3-methyl-2,4-dioxo-5-pyridin-3-y-2,3,4,5-tetrahydro-1H benzo[b][1,4]diazepin-3-yl} acetic acid, prepared as in Intermediate 78, in 15 mL of THF at 0° C. is added 0.21 mL (1.76 mmol, 1.25 equiv.) of ethyl chloroformate followed by addition of 178 mg (1.76 mmol, 1.25 equiv.) of 4-methylmorpholine. The resulting solution is stirred for 15 min at 0° C. and then 164 mg (1.76 mmol, 1.25 equiv.) of aniline is added. The cooling bath is removed and the reaction is warmed to RT where stirring continued for 45 min. The reaction mixture is diluted with 50 mL of EtOAc and 50 mL of 1M H₃PO₄. The organic layer is washed with H₂O and 5% NaHCO₃ and then separated, dried (MgSO₄), and the solvents removed in vacuo. Purification by silica gel flash column chromatography using hexane/EtOAc 3/1 as eluent afforded 539 mg of the title compound as an oil: ¹H NMR (CDCl₃, 300 MHz) δ8.85 (s, 1H), 8.54–8.48 (m, 1H), 7.82 (dd, 1H, J=9, 25), 7.51 (t, 4H, J=8), 7.38–6.93 (m, 11H), 6.75 (dd, 2H, J=12, 28), 5.05–4.93 (m, 1H), 4.61 (d, 1H, J=16), 4.28 (s, 1H), 3.84 (d, 3H, J=5), 3.19 (s, 1H), 2.64 (q, 2H, J=7, 14), 1.66 (s, 1H), 1.21 (s, 1H), 1.13–1.07 (m, 6H); low resolution MS (FAB)m/e 606 (MH⁺).

What is claimed is:

1. Benzo[b][1,4]diazepine compounds of the following formula (I):

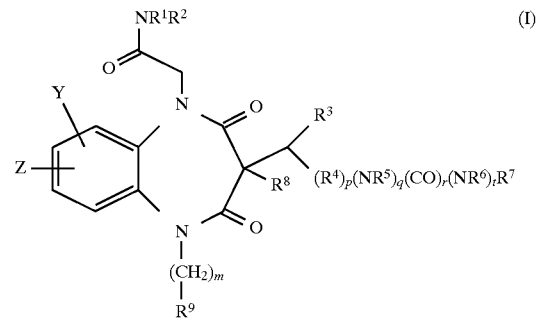

wherein:

R¹ is selected from the group consisting of C₁–C₆ alkyl, C₃–C₇cycloalkyl, phenyl, or phenyl mono-, di-, or trisubstituted independently with hydroxy, C₁₋₆alkyl, C₁₋₆alkyl substituted with 1–8 fluorine atoms, C₁₋₆alkoxy, C₁₋₆alkoxy substituted with 1–8 fluorine atoms, carboxyC₁₋₆alkoxy, halo, amino, mono- or di(C₁₋₆alkyl)amino, —COO(C₁₋₄alkyl), C₁₋₄alkylthio, carboxymethylthio, trifluoromethyl-sulfonylamino, phenylC₁₋₆alkoxy;

R² is selected from the group consisting of C₃–C₆ alkyl, C₃–C₆cycloalkyl, C₃–C₆alkenyl, benzyl, phenylC₁–C₃alkyl, phenyl mono-, di-, or trisubstituted independently in the ortho or para positions with hydroxy, C₁₋₄alkyl, C₁₋₆alkoxy, cyano, benzyloxy, pyrrolidino, morpholino, carboxyC₁₋₆alkoxy, halo, amino, mono- or di(C₁₋₆alkyl)amino, —COO(C₁₋₄alkyl), C₁₋₄alkylthio, carboxymethylthio, trifluoromethylsulfonylamino, phenylC₁₋₆alkoxy, C₁₋₄alkylsulfonyl or C₁₋₄alkylsulfinyl substituents or partially aromatic bicycloheteroaryl; or NR¹R² together form 1,2,3,4-tetrahydroquinoline or benzazepine, mono-, di-, or trisubstituted independently with C₁₋₆alkyl, C₁₋₆alkoxy or halogen substituents;

p is an integer 0 or 1;

q is an integer 0 or 1;

r is an integer 0 or 1;

t is an integer 0 or 1, provided that when r is 0 then t is 0;

$R^3$, $R^5$ and $R^6$ are independently hydrogen or $C_{1-6}$alkyl;

$R^4$ is $C_{1-6}$alkylene or $C_{2-6}$alkenylene;

$R^7$ is selected from the group consisting of hydrogen, $C_{1-6}$alkyl, $C_{1-6}$cycloalkyl, phenyl, phenyl mono-, di-, or trisubstituted independently with $C_{1-4}$alkyl, hydroxy, $C_{1-6}$alkoxy, halogen, amino, mono- or di($C_{1-6}$alkyl) amino, nitro, carboxy, —COO($C_{1-4}$alkyl), carboxy$C_{1-6}$alkoxy, carboxy$C_{1-4}$alkyl, carboxymethylthio, heteroaryl, mono- or di($C_{1-6}$alkyl)aminoalkyl, or trifluoromethyl, trifluoromethoxy, $C_{1-4}$alkylthio, —$SO_v$($C_{1-4}$alkyl), —$SO_v$NH($C_{1-4}$alkyl), —$SO_v$$CF_3$ or —$SO_v$$C_6H_5$, —$(CH_2)_v$$NO_2$, —$(CH_2)_v$CN, —$(CH_2)_v$COOH, —$(CH_2)_v$COO($C_{1-4}$alkyl), —$(CH_2)_v$$SCH_3$, —$(CH_2)_v$$SOCH_3$, —$(CH_2)_v$$SO_2CH_3$, —$(CH_2)_v$$CONH_2$, —$SCH_2COOH$, —$CONH(SO_2CH_3)$, —$CONH(SO_2CF_3)$, —$(CH_2)_v$N($C_{1-4}$alkyl)$_2$, —$(CH_2)_v$NH($SO_2CF_3$), —$(CH_2)_v$N($SO_2CF_3$)($C_{1-4}$alkyl), —$(CH_2)_v$$SO_2$NHCO($C_{1-4}$alkyl), —$(CH_2)_v$$SO_2$N($C_{1-4}$alkyl)CO($C_{1-4}$alkyl), —$(CH_2)_v$CONHSO$_2$($C_{1-4}$alkyl), —$(CH_2)_v$CON($C_{1-4}$alkyl)SO$_2$($C_{1-4}$alkyl), —$(CH_2)_v$NHR$^{10}$ or —$(CH_2)_v$OR$^{11}$ substituents, benzyloxy, heteroaryl, heteroaryl mono- or disubstituted independently with halogen, $C_{1-6}$alkyl, hydroxy, nitro, cyano, carboxy, $C_{1-6}$alkoxy, benzyloxy, —COO($C_{1-4}$alkyl), amino, mono- or di($C_{1-6}$alkyl)amino, phenyl or benzyl substituents, napthyl, bicycloheteroaryl, bicycloheteroaryl substituted independently with hydroxy, halogen, carboxyalkyl, acetyl, phenyl, heteroaryl, $C_{1-4}$alkoxy or cyano substituents, or partially aromatic bicycloheteroaryl, provided that when $R^7$ is oxadiazole then $R^8$ is not hydrogen, further provided when p is 1, q is 0, r is 0 and t is 0 then bicycloheteroaryl and substituted bicycloheteroaryl are not 2-indolyl or substituted 2-indolyl, still further provided that when p is 0, q is 1, r is 1 and t is 0 then indolyl and substituted indolyl are bound at the 2 position, even still further provided that when n, p and q are 1 and r is 0 then $R^7$ is not indolyl;

$R^{10}$ is hydrogen, $C_{1-4}$ alkyl, benzyl, —$SO_3H$, —$SO_2CH_3$, —$SO_2CF_3$, —$SO_2C_6H_5$, —COO($C_4H_9$) or —COO($CH_2C_6H_5$);

$R^{11}$ is hydrogen, $C_{1-6}$alkyl, $C_{3-6}$cycloalkyl, —$CH_2C_6H_5$, —$CH_2COOH$, —$CH_2CONH_2$, —$CH_2CONH(C_{1-4}$alkyl), —$CH_2CON(C_{1-4}$alkyl)$_2$ or

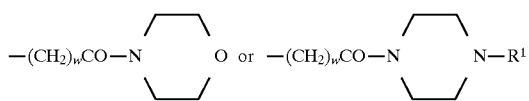

v is an integer selected from the group of 0, 1 or 2; or

NR$^6$R$^7$ together form a saturated 5, 6, or 7 membered ring optionally interrupted by 1,2,3 or 4N, S or O heteroatoms, with the proviso that any two O or S atoms are not bonded to each other;

w is an integer selected from the group of 0, 1 or 2;

$R^8$ is selected from the group consisting of hydrogen, $C_{1-6}$alkyl, $C_{1-6}$alkoxy, $C_{1-6}$alkoxy$C_{1-6}$alkyl, carboxy$C_{1-6}$alkyl, halogen, amino, cyano, amino$C_1$–$C_6$ alkyl, mono- or di($C_{1-6}$alkyl)amino, $C_1$–$C_6$alkylamino ($C_1$–$C_6$ alkyl), mono- or di($C_{1-6}$alkyl)aminoamino, $C_{1-6}$alkylmorpholino, $C_{1-6}$alkylpiperidino, $C_{1-6}$alkyltetrahydropyrrolyl, $C_{1-6}$alkylthio, $C_{1-6}$alkylthio$C_{1-6}$alkyl or $C_{1-4}$alkyoxycarbonyl$C_{1-4}$alkyl, provided that when $R^4$ is ethyl then $R^8$ is not ethyl;

m is an integer selected from the group of 0, 1, 2, 3 or 4;

$R^9$ is selected from the group consisting of hydrogen, $C_1$–$C_6$ alkyl, phenyl or phenyl mono- or disubstituted independently with halogen substituents, or a heteroaryl selected from the group consisting of pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazolyl, pyrrolidinyl, piperidinyl, morpholinyl or thiomorpholinyl, where such heteroaryl may be mono- or di-ortho-substituted independently with halogen, $C_{1-4}$alkyl, nitro, carboxyl, $C_{1-4}$alkoxycarbonyl, $C_{1-4}$alkoxy, $C_{1-4}$alkylthio, amino or mono- or di($C_{1-6}$alkyl)amino substituents;

Y and Z are independently hydrogen or halogen;

or a pharmaceutically acceptable acid-addition or base-addition salt thereof.

2. A compound as claimed in claim 1 wherein q is zero and r and t are 1.

3. A compound as claimed in claim 1 wherein q, r and t are zero.

4. A compound as claimed in claim 1 wherein p is zero.

5. A compound as claimed in claim 1 wherein and $R^1$ is isopropyl and $R^2$ is phenyl or 4-methoxyphenyl.

6. A compound as claimed in claim 1 wherein $R^3$ is hydrogen.

7. A compound as claimed in claim 1 wherein $R^8$ is hydrogen, methyl or methoxy.

8. A compound as claimed in claim 1 wherein $R^9$ is phenyl or pyridyl.

9. A compound as claimed in claim 2 wherein $R^7$ is phenyl optionally substituted by $C_{1-4}$ alkoxycarbonyl, carboxy amino or fluorine.

10. A compound as claimed in claim 3 wherein $R^7$ is a 6,6-6,5 bicycloheterocycle containing from 1 to 3 heteroatoms selected from O, N or S.

11. A compound as claimed in claim 10 wherein $R^7$ is 3-indazolyl.

12. 2-[3-(1H-indazol-3-ylmethyl)-2,4-dioxo-5-pyridin-3-yl-2,3,4,5-tetrahydrobenzo(b)[1,4]diazepin-1-yl]-N-isopropyl-N-(4-methoxyphenyl)acetamide or a physiologically acceptable salt or enantiomer thereof.

13. A compound selected from 2-[3-(1H-Indazol-3-yl)-3-methyl-2,4-dioxo-5-pyridin-3-yl-2,3,4,5-tetrahydrobenzo[b][1,4]diazepin-1-yl]-N-isopropyl-N-(4-methoxyphenyl) acetamide;

N-Isopropyl-2(3 methoxy-2,4-dioxo-5-phenyl-3-phenylcarbamoyl-methyl-2,3,4,5 tetrahydro-benzo[b][1,4]diazepinyl)-N-methoxy-phenyl acetamide;

2-[3-(1H-Indazol-3-yl-methyl)-3-methoxy-2,4-dioxo-5-pyridin-3-yl-2,3,4,5 tetrahydrobenzo[b][1,4]-diazepin-1-yl]-N-isopropyl-N(4-methoxy phenyl)acetamide;

N-Isopropyl-N(4-methoxyphenyl)-2-(3-methyl-2,4-dioxo-5-phenyl 3-phenylcarbamoylmethyl-2,3,4,5 tetrahydro-benzo(b)[1,4]-diazepin-1-yl)acetamide and physiologically acceptable salts and enantiomers thereof.

14. A method of treatment of a mammal including man for conditions where modulation of the effects of gastrin and or CCK is of a therapeutic benefit comprising administration of an effective amount of a compound according to claim 1.

15. A pharmaceutical composition comprising a compound according to claim 1 in an admixture of one or more physiologically acceptable carriers or excipients.

16. A process for the preparation of compounds of formula (I) which comprises:

(a) for the preparation compounds wherein q is zero, r and t are 1 by reacting an activated derivative of the acid (II) wherein $R^1$, $R^2$, $R^3$, $R^4$, $R^8$, $R^9$, Z, Y and P have the meanings defined in formula (I) or are protected derivatives thereof

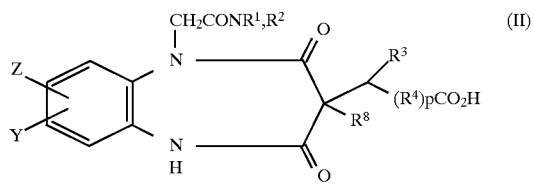

with the amine $NHR^6R^7$ wherein $R^6$ and $R^7$ have the meanings defined in formula I or are protected derivatives thereof.

* * * * *